US012692502B2

(12) United States Patent
Cuero Rengifo

(10) Patent No.: US 12,692,502 B2
(45) **Date of Patent: *Jul. 28, 2026**

(54) BIOLOGICAL DEVICES AND METHODS OF USE THEREOF TO PRODUCE STEVIOL GLYCOSIDES

(71) Applicant: Bio Capital Holdings, LLC, Houston, TX (US)

(72) Inventor: Raul Cuero Rengifo, Cypress, TX (US)

(73) Assignee: Bio Capital Holdings, LLC, Houston, TX (US)

( * ) Notice: Subject to any disclaimer, the term of this patent is extended or adjusted under 35 U.S.C. 154(b) by 561 days.

This patent is subject to a terminal disclaimer.

(21) Appl. No.: 17/806,138

(22) Filed: Jun. 9, 2022

(65) Prior Publication Data

US 2023/0212588 A1 Jul. 6, 2023

Related U.S. Application Data

(63) Continuation of application No. 16/646,217, filed as application No. PCT/US2018/050143 on Sep. 10, 2018, now Pat. No. 11,365,417.

(60) Provisional application No. 62/687,284, filed on Jun. 20, 2018, provisional application No. 62/557,220, filed on Sep. 12, 2017.

(51) Int. Cl.

| | |
|---|---|
| *C12N 15/52* | (2006.01) |
| *C12N 9/10* | (2006.01) |
| *C12N 9/12* | (2006.01) |
| *C12N 9/88* | (2006.01) |
| *C12N 9/90* | (2006.01) |
| *C12N 15/82* | (2006.01) |
| *C12P 19/18* | (2006.01) |
| *C12P 19/56* | (2006.01) |

(52) U.S. Cl.
CPC .......... *C12N 15/52* (2013.01); *C12N 9/1022* (2013.01); *C12N 9/1051* (2013.01); *C12N 9/1085* (2013.01); *C12N 9/1205* (2013.01); *C12N 9/88* (2013.01); *C12N 9/90* (2013.01); *C12N 15/8243* (2013.01); *C12P 19/18* (2013.01); *C12P 19/56* (2013.01); *C12Y 202/01007* (2013.01); *C12Y 204/01255* (2013.01); *C12Y 205/01029* (2013.01); *C12Y 207/01001* (2013.01); *C12Y 207/01036* (2013.01); *C12Y 401/01033* (2013.01); *C12Y 503/03002* (2013.01)

(58) Field of Classification Search
None
See application file for complete search history.

(56) References Cited

U.S. PATENT DOCUMENTS

| | | | |
|---|---|---|---|
| 7,183,089 B2 | 2/2007 | Keasling et al. | |
| 8,512,988 B2 | 8/2013 | Ajikumar et al. | |
| 8,927,241 B2 | 1/2015 | Ajikumar et al. | |
| 9,284,570 B2 | 3/2016 | Stephanopoulos et al. | |
| 9,353,385 B2 | 5/2016 | Park et al. | |
| 9,359,624 B2 | 6/2016 | Ajikumar et al. | |
| 9,404,130 B2 | 8/2016 | Ajikumar et al. | |
| 9,562,251 B2 | 2/2017 | Kishore et al. | |
| 9,611,498 B2 | 4/2017 | Wang et al. | |
| 9,631,215 B2 | 4/2017 | Houghton-Larsen et al. | |
| 2004/0072323 A1* | 4/2004 | Matsuda .............. | C12N 9/1085 435/166 |
| 2004/0237138 A1 | 11/2004 | Cheikh et al. | |
| 2008/0271205 A1 | 10/2008 | Yamaguchi et al. | |
| 2011/0020865 A1* | 1/2011 | Payne .................. | C07K 14/395 435/471 |
| 2012/0015416 A1* | 1/2012 | Anthony .................. | C12P 7/16 435/254.2 |
| 2013/0273601 A1 | 10/2013 | Wisselink et al. | |
| 2013/0338348 A1 | 12/2013 | Rommens et al. | |
| 2014/0329281 A1* | 11/2014 | Houghton-Larsen ....................... | C12N 15/63 435/252.33 |
| 2014/0357588 A1 | 12/2014 | Markosyan et al. | |
| 2015/0159188 A1 | 6/2015 | Ono et al. | |
| 2015/0218533 A1 | 8/2015 | Ono | |
| 2015/0361476 A1 | 12/2015 | Simon et al. | |
| 2016/0186225 A1* | 6/2016 | Mikkelsen ........... | C12N 9/1081 |
| 2016/0198748 A1 | 7/2016 | Prakash et al. | |

(Continued)

FOREIGN PATENT DOCUMENTS

| | | |
|---|---|---|
| WO | 0001649 | 1/2000 |
| WO | 0009729 | 2/2000 |

(Continued)

OTHER PUBLICATIONS

Spohner et al., Recombinant α-L-rhamnosidase from Aspergillus terreus in selectivetrimming of α-L-rhamnose from steviol glycosides, Journal of Molecular Catalysis B: Enzymatic 122 (2015) 248-254.
International Search Report and Written Opinion issued for PCT/US2018/050143, mailed Mar. 15, 2019.
Kong et al., Metabolic engineering of the Stevia rebaudiana ent-kaurenebiosynthetic pathway in recombinant *Escherichia coli*, Journal of Biotechnology 214 (2015) 95-102.
Olsson et al., Microbial production of next-generation stevia sweeteners, Olsson et al. Microb Cell Fact (2016) 15:207.

(Continued)

*Primary Examiner* — Todd M Epstein
(74) *Attorney, Agent, or Firm* — Thomas I Horstemeyer, LLP

(57) ABSTRACT

Described herein are devices and methods for increasing the production of steviol glycosides, which have industrial and economic value. The steviol glycosides produced by the devices and methods disclosed herein do not require the ultra purification that is common in conventional or commercial methods and do not have a bitter aftertaste, making them better suited as flavor-enhancing additives to food, pharmaceutical, and nutritional supplement products.

10 Claims, 16 Drawing Sheets

Specification includes a Sequence Listing.

(56)                    References Cited

U.S. PATENT DOCUMENTS

| | | |
|---|---|---|
| 2016/0213039 A1 | 7/2016 | Kumar et al. |
| 2016/0251635 A1 | 9/2016 | Mao et al. |
| 2017/0002382 A1 | 1/2017 | Ajikumar et al. |
| 2017/0081691 A1 | 3/2017 | Mao et al. |
| 2017/0218419 A1 | 8/2017 | Kishore et al. |
| 2017/0332673 A1 | 11/2017 | Philippe et al. |

FOREIGN PATENT DOCUMENTS

| | | |
|---|---|---|
| WO | 2008008256 | 1/2008 |
| WO | 2014018849 A1 | 1/2014 |
| WO | 2016038095 A2 | 3/2016 |
| WO | 2016120486 A1 | 8/2016 |
| WO | 2016196321 A1 | 12/2016 |
| WO | 2012025362 A1 | 2/2017 |

OTHER PUBLICATIONS

Brandle et al., Steviol glycoside biosynthesis, Phytochemistry 68 (2007) 1855-1863.

Kahn et al., Agrobacterium tumefaciens-mediated transgenic plant and somaclone production through direct and Indirect regeneration from leaves in Stevia rebaudiana with their glycoside profile, Protoplasma 251, 2014, 661-70. (Year: 2014).

Lenardon et al., Chitin synthase and fungal pathogenesis, Curr. Opin. Microbial. 13, 2010, 416-23. (Year: 2010).

Gen Bank, Accession No. D85029.1, 2016, www.ncbi.nlm.nih.gov (Year: 2016).

Genbank, Accession No. Z49809, 2016, www.ncbi.nlm.org. (Year: 2016).

Gen Bank, Accession No. CP010088.1, 2015, www.ncbi.nlm.nih. gov. (Year: 2015).

Invitrogen, pYes2, Cat. No. V825-20, User Manual 2008 (Year: 2008).

Genbank, Accession No. CP000423, 2016, www.ncbi.nlm.nih.gov. (Year: 2016).

Lubas etal., O-Linked GlcNAc Transferase is a Conserved Nucleocytoplasmic Protein Containing Tetratricopeptide Repeats, J. Biol Chem. 272, 1997, 9316-24. (Year: 1997).

* cited by examiner

BIOLOGICAL DEVICES AND METHODS OF USE THEREOF TO PRODUCE STEVIOL GLYCOSIDES

CROSS REFERENCE TO RELATED APPLICATIONS

This application is a Continuation Application of U.S. Nonprovisional patent application Ser. No. 16/646,217, filed on Mar. 11, 2020, which a US National Stage Application under 35 USC § 371 of International Application No. PCT/US2018/050143, filed Sep. 10, 2018, which claims priority upon U.S. Provisional Application Ser. No. 62/557,220 filed on Sep. 12, 2017 and 62/687,284 filed Jun. 20, 2018. These applications are hereby incorporated by reference in their entirety.

CROSS REFERENCE TO SEQUENCE LISTING

The genetic components described herein are referred to by sequence identifier numbers (SEQ ID NO) in a Sequence Listing. The SEQ ID NOs correspond numerically to the sequence identifiers <400>1, <400>2, etc. The Sequence Listing, in written computer readable format (CRF), was filed in electronic form as an ASCII.txt file entitled "930201-1060_Sequence_Listing" created on Mar. 11, 2020 and has 165,728 bytes, and is incorporated by reference in its entirety.

BACKGROUND

Steviol glycosides are secondary metabolites extracted from the plants *Stevia rebaudiana, Stevia phlebophylla*, and *Rubus chingii*. These compounds have been used as non-caloric sweeteners that may be useful in preventing or reducing the prevalence and/or effects of diabetes. Terpenoid or isoprenoid pathways are the main source of steviol glycoside biosynthesis. Various attempts have been made to increase the yield and production of steviol glycosides, including the employment of agronomic practices, plant tissue culture, and microbial expression, but results thus far have not been optimized to correct for the naturally low yields of most secondary metabolites. Furthermore, one of the biggest challenges for production of a high quality stevia-based sweetener incorporating steviol glycosides is the elimination of the bitter aftertaste compared to conventional sucrose-based table sugar.

Common steviol glycosides include stevioside, rebaudioside A, rebaudioside B, rebaudioside C, rebaudioside D, rebaudioside E, dulcoside A. Although these compounds are available in some crops such as, for example, *Stevia rebaudiana*, it would be desirable to have a new method of producing steviol glycosides on an abbreviated time scale, to generate large quantities of these compounds to be added to food, pharmaceuticals, and nutritional supplements. The new method would, ideally, be inexpensive, would not result in the production of genetically-modified plants, would require fewer organic solvents for extraction than traditional methods, and would result in higher steviol glycoside production using less biomass than traditional methods, thus not requiring agronomic practices and large growing fields. Furthermore, the method would lead to the production of a sweetener without a bitter aftertaste.

SUMMARY

Described herein are devices and methods for increasing the production of steviol glycosides, which have industrial and economic value. The steviol glycosides produced by the devices and methods disclosed herein do not require the ultra purification that is common in conventional or commercial methods and do not have a bitter aftertaste, making them better suited as flavor-enhancing additives to food, pharmaceutical, and nutritional supplement products.

The advantages of the invention will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below.

DETAILED DESCRIPTION

Figure 1A:
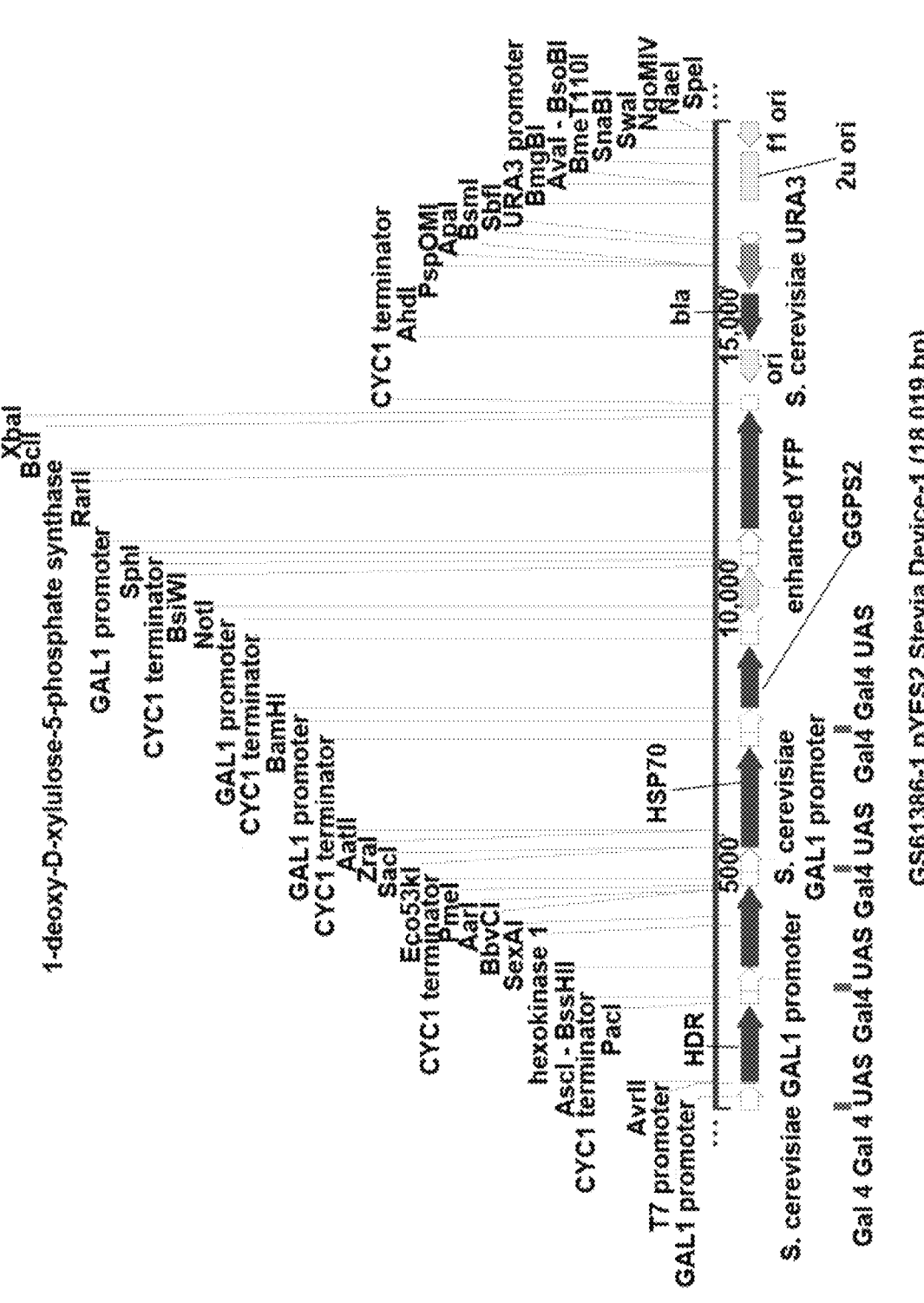
FIGS. 1A and 1B show, respectively, a linear and circular schematic of a constructed pYES2 plasmid showing the direction, placement, and size of genetic parts used of an exemplary DNA device described herein.

Before the present compounds, compositions, articles, devices, and/or methods are disclosed and described, it is to be understood that the aspects described below are not limited to specific compounds, synthetic methods, or uses, as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a," "an," and "the" include plural referents unless the context clearly dictates otherwise. Thus, for example, reference to "a plasmid" includes mixtures of two or more such plasmids, and the like.

"Optional" or "optionally" means that the subsequently described event or circumstance can or cannot occur, and that the description includes instances where the event or circumstance occurs and instances where it does not. For example, the phrase "optionally includes a reporter protein" means that the reporter protein may or may not be present.

As used herein, the term "about" is used to provide flexibility to a numerical range endpoint by providing that a given value may be "a little above" or "a little below" the endpoint without affecting the desired result.

Throughout this specification, unless the context dictates otherwise, the word "comprise," or variations such as "comprises" or "comprising," will be understood to imply the inclusion of a stated element, integer, step, or group of elements, integers, or steps, but not the exclusion of any other element, integer, step, or group of elements, integers, or steps.

As used herein, a plurality of items, structural elements, compositional elements, and/or materials may be presented in a common list for convenience. However, these lists should be construed as though each member of the list is individually identified as a separate and unique member. Thus, no individual member of any such list should be construed as a de facto equivalent of any other member of the same list based solely on its presentation in a common group, without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range was explicitly recited. As an example, a numerical range of "about 1" to "about 5" should be interpreted to include not only the explicitly recited values of about 1 to about 5, but also to include individual values and sub-ranges within the indicated range. Thus, included in this numerical range are individual values such as 2, 3, and 4, the sub ranges such as from 1-3, from 2-4, from 3-5, etc., as well as 1, 2, 3, 4, and 5, individually. The same principle applies to ranges reciting only one numerical value as a minimum or maximum. Furthermore such an interpretation should apply regardless of the breadth or range of the characters being described.

Disclosed are materials and components that can be used for, can be used in conjunction with, can be used in preparation for, or are products of the disclosed compositions and methods. These and other materials are disclosed herein, and it is understood that when combinations, subsets, interactions, groups, etc., of these materials are disclosed that while specific reference of each various individual and collective combination and permutation of these compounds may not be explicitly disclosed, each is specifically contemplated and described herein. For example, if a bacterium is disclosed and discussed and a number of different compatible bacterial plasmids are discussed, each and every combination and permutation of bacterium and bacterial plasmid that is possible is specifically contemplated unless specifically indicated to the contrary. For example, if a class of molecules, A, B, and C are disclosed as well as a class of molecules D, E, and F, and an example of a combination molecule, A-D, is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E is specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, if there are a variety of additional steps that can be performed, it is understood that each of these additional steps can be performed with any specific embodiment or combination of embodiments of the disclosed methods, and that each such combination is specifically contemplated and should be considered disclosed.

References in the specification and concluding claims to parts by weight, of a particular element or component in a composition or article, denote the weight relationship between the element or component and any other elements or components in the composition or article for which a part by weight is expressed. Thus, in a compound containing 2 parts by weight of component X and 5 parts by weight of component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

I. DNA Constructs

DNA constructs are provided herein for the production of steviol glycosides. It is understood that one way to define the variants and derivatives of the genetic components and DNA constructs described herein is in terms of homology/identity to specific known sequences. Those of skill in the art readily understand how to determine the homology of two nucleic acids. For example, the homology can be calculated after aligning two sequences so that the homology is at its highest level. Another way of calculating homology can be performed according to published algorithms (see Zuker, M., *Science,* 244:48-52, 1989; Jaeger et al., *Proc. Natl. Acad. Sci. USA,* 86:7706-7710, 1989; Jaeger et al., *Methods Enzyol.* 183:281-306, 1989, which are herein incorporated by reference for at least material related to nucleic acid alignment).

As used herein, "conservative" mutations are mutations that result in an amino acid change in the protein produced from a sequence of DNA. When a conservative mutation occurs, the new amino acid has similar properties as the wild type amino acid and generally does not drastically change the function or folding of the protein (e.g., switching isoleucine for valine is a conservative mutation since both are small, branched, hydrophobic amino acids). "Silent mutations," meanwhile, change the nucleic acid sequence of a gene encoding a protein but do not change the amino acid sequence of the protein.

It is understood that the description of mutations and homology can be combined together in any combination, such as embodiments that have at least 70%, 75%, 80%, 85%, 90%, 95%, or 99% homology to a particular sequence wherein the variants are conservative or silent mutations. It is understood that any of the sequences described herein can be a variant or derivative having the homology values listed above.

In one aspect, a database such as, for example, GenBank, can be used to determine the sequences of genes and/or regulatory regions of interest, the species from which these elements originate, and related homologous sequences.

In one aspect, provided herein is a DNA construct having the following genetic components:

(a) a gene that expresses hexokinase;

(b) a gene that expresses geranylgeranyl pyrophosphate synthase 2;

(c) a gene that expresses 1-deoxy-D-xylulose-5-phosphate synthase;

(d) a gene that expresses mevalonate-5-kinase;

(e) a gene that expresses isopentenyl pyrophosphate isomerase; and (f) a gene that expresses mevalonate pyrophosphate decarboxylase.

In one aspect, provided herein is a DNA construct having the following genetic components:

(a) a gene that expresses 4-hydroxy-3-methylbut-2-enyl diphosphate reductase;

(b) a gene that expresses hexokinase;

(c) a gene that expresses a heat shock protein;

(d) a gene that expresses a geranylgeranyl pyrophosphate synthase; and (e) a gene that expresses 1-deoxy-D-xylulose-5-phosphate synthase.

In another aspect, provided herein is a DNA construct having the following genetic components:

(a) a gene that expresses mevalonate-5-kinase;

(b) a gene that expresses isopentenyl pyrophosphate isomerase;

(c) a gene that expresses mevalonate pyrophosphate decarboxylase;

(d) a gene that expresses hexokinase;

(e) a gene that expresses a heat shock protein;

(f) a gene that expresses a geranylgeranyl pyrophosphate synthase; and (g) a gene that expresses 1-deoxy-D-xylulose-5-phosphate synthase.

In still another aspect, provided herein is a DNA construct having the following genetic components:

(a) a gene that expresses mevalonate-5-kinase;

(b) a gene that expresses isopentenyl pyrophosphate isomerase;

(c) a gene that expresses mevalonate pyrophosphate decarboxylase;

(d) a gene that expresses hexokinase;

(e) a gene that expresses a heat shock protein;

(f) a gene that expresses a geranylgeranyl pyrophosphate synthase;

(g) a gene that expresses a UDP-glycosyltransferase; and (h) a gene that expresses 1-deoxy-D-xylulose-5-phosphate synthase.

In a further aspect, provided herein is a DNA construct having the following genetic components:

(a) a gene that expresses mevalonate-5-kinase;

(b) a gene that expresses isopentenyl pyrophosphate isomerase;

(c) a gene that expresses mevalonate pyrophosphate decarboxylase;

(d) a gene that expresses hexokinase;

(e) a gene that expresses a heat shock protein;

(f) a gene that expresses a geranylgeranyl pyrophosphate synthase;

(g) a gene that expresses an O-linked acetylglucosamine transferase; and (h) a gene that expresses 1-deoxy-D-xylulose-5-phosphate synthase.

In yet another aspect, provided herein is a DNA construct having the following genetic components:

(a) a gene that expresses mevalonate-5-kinase;

(b) a gene that expresses isopentenyl pyrophosphate isomerase;

(c) a gene that expresses mevalonate pyrophosphate decarboxylase;

(d) a gene that expresses hexokinase;

(e) a gene that expresses an O-linked acetylglucosamine transferase;

(f) a gene that expresses a geranylgeranyl pyrophosphate synthase;

(g) a gene that expresses a UDP glycosyltransferase; and (h) a gene that expresses 1-deoxy-D-xylulose-5-phosphate synthase.

Each component of the DNA construct is described in detail below.

In one aspect, the nucleic acids described herein (e.g., genes that express HDR, hexokinase, a heat shock protein, GGPS, DXS, mevalonate-5-kinase, isopentenyl pyrophosphate isomerase, mevalonate pyrophosphate decarboxylase, a UDP glycosyltransferase, and/or an O-linked acetylglucosamine transferase) used in the DNA constructs described herein can be amplified using polymerase chain reaction (PCR) prior to being ligated into a plasmid or other vector. Typically, PCR-amplification techniques make use of primers, or short, chemically-synthesized oligonucleotides are complementary to regions on each respective strand flanking the DNA or nucleotide sequence to be amplified. A person having ordinary skill in the art will be able to design or choose primers based on the desired experimental conditions. In general, primers should be designed to provide for both efficient and faithful replication of the target nucleic acids. Two primers are required for the amplification of each gene, one for the sense strand (that is, the strand containing the gene of interest) and one for the antisense strand (that is, the strand complementary to the gene of interest). Pairs of primers should have similar melting temperatures that are close to the PCR reaction's annealing temperature. In order to facilitate the PCR reaction, the following features should be avoided in primers: mononucleotide repeats, complementarity with other primers in the mixture, self-complementarity, and internal hairpins and/or loops. Methods of primer design are known in the art; additionally, computer programs exist that can assist the skilled practitioner with primer design. Primers can optionally incorporate restriction enzyme recognition sites at their 5' ends to assist in later ligation into plasmids or other vectors.

PCR can be carried out using purified DNA, unpurified DNA that is integrated into a vector, or unpurified genomic DNA. The process for amplifying target DNA using PCR consists of introducing an excess of two primers having the characteristics described above to a mixture containing the sequence to be amplified, followed by a series of thermal cycles in the presence of a heat-tolerant or thermophilic DNA polymerase, such as, for example, any of Taq, Pfu, Pwo, Tfl, rTth, Tli, or Tma polymerases. A PCR "cycle" involves denaturation of the DNA through heating, followed by annealing of the primers to the target DNA, followed by extension of the primers using the thermophilic DNA polymerase and a supply of deoxynucleotide triphosphates (i.e., dCTP, dATP, dGTP, and TTP), along with buffers, salts, and other reagents as needed. In one aspect, the DNA segments created by primer extension during the PCR process can serve as templates for additional PCR cycles. Many PCR cycles can be performed to generate a large concentration of target DNA or gene. PCR can optionally be performed in a device or machine with programmable temperature cycles for denaturation, annealing, and extension steps. Further, PCR can be performed on multiple genes simultaneously in the same reaction vessel or microcentrifuge tube since the primers chosen will be specific to selected genes. PCR products can be purified by techniques known in the art such as, for example, gel electrophoresis followed by extraction from the gel using commercial kits and reagents.

In a further aspect, the plasmid can include an origin of replication, allowing it to use the host cell's replication machinery to create copies of itself.

As used herein, "operably linked" refers to the association of nucleic acid sequences on a single nucleic acid fragment so that the function of one affects the function of another. For example, if sequences for multiple genes are inserted into a single plasmid, their expression may be operably linked. Alternatively, a promoter is said to be operably linked with a coding sequence when it is capable of affecting the expression of that coding sequence.

As used herein, "expression" refers to transcription and/or accumulation of an mRNA derived from a gene or DNA fragment. Expression may also be used to refer to translation of mRNA into a peptide, polypeptide, or protein.

In one aspect, the gene that expresses 4-hydroxy-3-methylbut-2-enyl diphosphate reductase (HDR) is isolated from plants such as, for example, plants from the mustard family. In one aspect, the mustard family plant includes *Arabidopsis thaliana, Arabidopsis lyrata*, canola or rapeseed, bok choy, napa cabbage, rapini, turnip, cabbage, Savoy cabbage, red cabbage, collard greens, kale or ornamental kale, Brussels sprouts, kohlrabi, broccoli, cauliflower, or broccolini. In another aspect, the plant is wild flax or pink shepherd's purse. In a further aspect, the gene that expresses HDR has SEQ ID NO. 1 or at least 70% homology thereto, at least 75% homology thereto, at least 80% homology thereto, at least 85% homology thereto, at least 90% homology thereto, or at least 95% homology thereto. In one aspect, the gene that expresses HDR is isolated from *Arabidopsis thaliana* and can be found in GenBank with accession number NM_119600.4.

Other sequences expressing HDR or related or homologous genes can be identified in a database such as, for example, GenBank. In one aspect, sequences useful herein include those with the GI numbers listed in Table 1.

TABLE 1

| HDR Genes | | |
| --- | --- | --- |
| Source Organism | Sequence Description | GI Number |
| *Arabidopsis thaliana* | HDR | NM_119600.4 |
| *Arabidopsis thaliana* | HDR (IspH) | AY168881.1 |
| *Arabidopsis thaliana* | putative protein | AY042877.1 |
| *Arabidopsis thaliana* | putative protein | AY081454.1 |
| *Arabidopsis lyrata* | HDR | XM_002867076.2 |
| *Camelina sativa* | HDR | XM_010448794.2 |
| *Capsella rubella* | hypothetical protein | XM_006283620.1 |
| *Camelina sativa* | HDR | XM_010434124.2 |
| *Arabidopsis thaliana* | hypothetical protein | AK317707.1 |
| *Rhinolophus sinicus* | HDR | XM_019721323.1 |
| *Eutrema salsugineum* | hypothetical protein | XM_006412174.1 |
| *Thellungiela halophila* | hypothetical protein | AK352712.1 |
| *Lepidium apetalum* | 1-hydroxy-2-methyl-2-(E)-butenyl-4-diphosphate reductase | KY366217.1 |
| *Raphanus sativus* | HDR | XM_018614540.1 |
| *Brassica napus* | HDR | XM_013875339.1 |
| *Brassica oleracea* | HDR | XM_013769603.1 |
| *Brassica napus* | HDR | XM_013842177.1 |
| *Brassica oleracea* | HDR | XM_013744730.1 |
| *Brassica rapa* | HDR | XM_009110491.2 |
| *Raphanus sativus* | HDR | XM_018596045.1 |
| *Brassica rapa* | HDR | XM_009115423.2 |
| *Brassica rapa* | HDR | XR_001956406.1 |
| *Brassica napus* | HDR | XM_013800732.1 |
| *Brassica napus* | HDR | XM_013795568.1 |
| *Tarenaya hassleriana* | HDR | XM_010549745.1 |
| *Tarenaya hassleriana* | HDR | XM_010528625.2 |
| *Arabidopsis thaliana* | hypothetical protein | AK222055.1 |
| *Raphanus sativus* | HDR | XM_018592953.1 |
| *Brassica rapa* | LYTB-like protein 1 | AF398145.1 |
| *Brassica rapa* | LYTB-like protein 2 | AF398146.1 |
| *Juglans regia* | HDR | XM_019002578.1 |
| *Juglans regia* | HDR | XM_018981403.1 |

TABLE 1-continued

HDR Genes

| Source Organism | Sequence Description | GI Number |
|---|---|---|
| *Populus euphratica* | HDR | XM_011001091.1 |
| *Populus trichocarpa* | chloroplast biogenesis family protein | XM_002313780.1 |
| *Populus trichocarpa* | HDR | EU693025.1 |
| *Lonicera hypoglauca* | HDR (IspH) | JX276470.1 |
| *Lonicera dasystyla* | HDR (IspH) | JX276469.1 |
| *Lonicera japonica* | HDR (IspH) | JX276468.1 |
| *Camelina sativa* | HDR, chloroplast-like | XM_010446669.1 |
| *Erythranthe guttatus* | HDR, chloroplast-like | XM_012981553.1 |
| *Erythranthe guttatus* | HDR, chloroplast-like | XM_012981551.1 |
| *Oncidium hybrid cultivar* | HDR | EU908200.1 |
| *Isodon rubescens* | HDR | KT948058.1 |
| *Arabidopsis thaliana* | genomic DNA | CP002687.1 |
| *Arabidopsis thaliana* | genomic DNA | AL161585.2 |
| *Arabidopsis thaliana* | genomic DNA | AL035521.1 |
| *Arabidopsis thaliana* | 1-hydroxy-2-methyl-butenyl 4-diphosphate reductase | AY883838.1 |
| *Phalaenopsis equestris* | HDR, chloroplast-like | XM_020735444.1 |
| *Phalaenopsis equestris* | HDR, chloroplast-like | XM_020735443.1 |
| *Capsella rubella* | hypothetical protein | XM_006279111.1 |
| *Raphanus sativus* | HDR, chloroplast-like | XM_018596046.1 |
| *Phalaenopsis equestris* | HDR, chloroplast-like | XM_020735445.1 |
| *Camelina sativa* | genomic DNA | HE650122.1 |
| *Arabis alpina* | genomic DNA | LT669794.1 |
| *Brassica rapa* | genomic DNA | AC189325.2 |
| *Brassica napus* | uncharacterized transcript variant | XR_001280483.1 |
| *Brassica napus* | uncharacterized transcript variant | XR_001280482.1 |
| *Raphanus sativus* | proliferating cell nuclear antigen 2-like | XM_018611957.1 |
| *Raphanus sativus* | proliferating cell nuclear antigen 2-like | XM_018611956.1 |
| *Brassica oleracea* | uncharacterized transcript variant | XR_001260293.1 |
| *Brassica oleracea* | uncharacterized transcript variant | XR_001260292.1 |
| *Brassica oleracea* | uncharacterized transcript variant | XR_001260291.1 |
| *Brassica oleracea* | uncharacterized transcript variant | XR_001260290.1 |
| *Brassica oleracea* | uncharacterized transcript variant | XM_013728606.1 |
| *Calothrix* sp. 336/3 | genomic DNA | CP011382.1 |
| *Oncidium hybrid cultivar* | HDR | EU908201.1 |

In one aspect, the gene that expresses hexokinase is isolated from a microorganism. In a further aspect, the microorganism is a fungus. In one aspect, the fungus is a yeast such as, for example, *Saccharomyces cerevisiae*. In a further aspect, the gene that expresses hexokinase has SEQ ID NO. 2 or at least 70% homology thereto, at least 75% homology thereto, at least 80% homology thereto, at least 85% homology thereto, at least 90% homology thereto, or at least 95% homology thereto. In one aspect the gene that expresses hexokinase is isolated from *Saccharomyces cerevisiae* and can be found in GenBank with GI number M14410.1.

Other sequences expressing hexokinase or related or homologous genes can be identified in a database such as, for example, GenBank. In one aspect, sequences useful herein include those with the GI numbers listed in Table 2.

TABLE 2

Hexokinase Genes

| Source Organism | Sequence Description | GI Number |
|---|---|---|
| *Saccharomyces cerevisiae* | hexokinase | M14410.1 |
| *Saccharomyces cerevisiae* | chromosome VI sequence | CP020128.1 |
| *Saccharomyces cerevisiae* | chromosome VI sequence | CP014737.1 |

TABLE 2-continued

Hexokinase Genes

| Source Organism | Sequence Description | GI Number |
|---|---|---|
| *Saccharomyces cerevisiae* | chromosome VI sequence | CP011552.1 |
| *Saccharomyces cerevisiae* | hexokinase | NM_001180018.3 |
| *Saccharomyces cerevisiae* | chromosome VI sequence | BK006940.2 |
| *Saccharomyces cerevisiae* | chromosome VI sequence | D50617.1 |
| *Saccharomyces cerevisiae* | hexokinase | DQ332072.1 |
| *Saccharomyces cerevisiae* | chromosome VI sequence | CP004946.2 |
| *Saccharomyces cerevisiae* | chromosome VI sequence | CP008547.1 |
| *Saccharomyces cerevisiae* | chromosome VI sequence | CP008530.1 |
| *Saccharomyces cerevisiae* | chromosome VI sequence | CP007901.1 |
| *Saccharomyces cerevisiae* | chromosome VI sequence | CP004902.2 |
| *Saccharomyces cerevisiae* | chromosome VI sequence | CP004929.2 |
| *Saccharomyces cerevisiae* | chromosome VI sequence | CP004898.2 |
| *Saccharomyces cerevisiae* | chromosome VI sequence | CP008462.1 |
| *Saccharomyces cerevisiae* | chromosome VI sequence | CP004975.2 |
| *Saccharomyces cerevisiae* | chromosome VI sequence | CP004904.2 |
| *Saccharomyces cerevisiae* | chromosome VI sequence | CP004903.2 |
| *Saccharomyces cerevisiae* | chromosome VI sequence | CP004952.2 |
| *Saccharomyces cerevisiae* | chromosome VI sequence | CP004910.2 |
| *Saccharomyces cerevisiae* | hexokinase | JF898945.1 |
| *Saccharomyces cerevisiae* | chromosome VI sequence | CP008105.1 |
| *Saccharomyces cerevisiae* | chromosome VI sequence | CP008071.1 |
| *Saccharomyces cerevisiae* | chromosome VI sequence | CP004909.2 |

TABLE 2-continued

| Hexokinase Genes | | |
|---|---|---|
| Source Organism | Sequence Description | GI Number |
| Saccharomyces cerevisiae | chromosome VI sequence | CP004927.2 |
| Saccharomyces cerevisiae | chromosome VI sequence | CP008241.1 |
| Saccharomyces cerevisiae | chromosome VI sequence | CP008292.1 |
| Saccharomyces cerevisiae | chromosome VI sequence | CP008275.1 |
| Saccharomyces cerevisiae | chromosome VI sequence | CP008224.1 |
| Saccharomyces cerevisiae | chromosome VI sequence | CP008411.1 |
| Saccharomyces cerevisiae | chromosome VI sequence | CP008377.1 |
| Saccharomyces cerevisiae | chromosome VI sequence | CP008428.1 |
| Saccharomyces cerevisiae | chromosome VI sequence | CP008581.1 |
| Saccharomyces cerevisiae | chromosome VI sequence | CP008598.1 |
| Saccharomyces cerevisiae | chromosome VI sequence | CP008173.1 |
| Saccharomyces cerevisiae | chromosome VI sequence | CP008156.1 |
| Saccharomyces cerevisiae | chromosome VI sequence | CP008683.1 |
| Saccharomyces cerevisiae | chromosome VI sequence | CP008088.1 |
| Saccharomyces cerevisiae | chromosome VI sequence | CP008020.1 |
| Saccharomyces cerevisiae | chromosome VI sequence | CP007986.1 |
| Saccharomyces cerevisiae | chromosome VI sequence | CP007969.1 |
| Saccharomyces cerevisiae | chromosome VI sequence | CP007952.1 |
| Saccharomyces cerevisiae | chromosome VI sequence | CP007918.1 |
| Saccharomyces cerevisiae | chromosome VI sequence | CP007884.1 |
| Saccharomyces cerevisiae | chromosome VI sequence | CP007867.1 |
| Saccharomyces cerevisiae | chromosome VI sequence | CP004925.2 |
| Saccharomyces cerevisiae | chromosome VI sequence | CP004934.2 |
| Saccharomyces cerevisiae | chromosome VI sequence | CP004913.2 |
| Saccharomyces cerevisiae | chromosome VI sequence | CP004893.2 |
| Saccharomyces cerevisiae | chromosome VI sequence | CP004951.2 |
| Saccharomyces cerevisiae | chromosome VI sequence | CP004890.2 |
| Saccharomyces cerevisiae | chromosome VI sequence | CP004949.1 |
| Saccharomyces cerevisiae | chromosome VI sequence | CP004948.1 |
| Saccharomyces cerevisiae | hexokinase | CP004940.1 |
| Saccharomyces cerevisiae | hexokinase | JF898949.1 |
| Saccharomyces cerevisiae | chromosome VI sequence | JF898946.1 |
| Saccharomyces cerevisiae | chromosome VI sequence | CP008258.1 |
| Saccharomyces cerevisiae | chromosome VI sequence | CP008394.1 |
| Saccharomyces cerevisiae | chromosome VI sequence | CP008496.1 |
| Saccharomyces cerevisiae | chromosome VI sequence | CP008445.1 |
| Saccharomyces cerevisiae | chromosome VI sequence | CP008513.1 |
| Saccharomyces cerevisiae | hexokinase isoenzyme 1 | JF898948.1 |
| Saccharomyces cerevisiae | chromosome VI sequence | CP020162.1 |
| Saccharomyces cerevisiae | chromosome VI sequence | CP004979.2 |
| Saccharomyces cerevisiae | chromosome VI sequence | CP004919.2 |
| Saccharomyces cerevisiae | chromosome VI sequence | CP004918.2 |
| Saccharomyces cerevisiae | chromosome VI sequence | CP004908.2 |
| Saccharomyces cerevisiae | chromosome VI sequence | CP004917.2 |
| Saccharomyces cerevisiae | chromosome VI sequence | CP004907.2 |
| Saccharomyces cerevisiae | chromosome VI sequence | CP004897.2 |
| Saccharomyces cerevisiae | chromosome VI sequence | CP004916.2 |
| Saccharomyces cerevisiae | chromosome VI sequence | CP004906.2 |
| Saccharomyces cerevisiae | chromosome VI sequence | CP004896.2 |
| Saccharomyces cerevisiae | chromosome VI sequence | CP008326.1 |
| Saccharomyces cerevisiae | chromosome VI sequence | CP008309.1 |
| Saccharomyces cerevisiae | chromosome VI sequence | CP008360.1 |
| Saccharomyces cerevisiae | chromosome VI sequence | CP008343.1 |
| Saccharomyces cerevisiae | chromosome VI sequence | CP008479.1 |
| Saccharomyces cerevisiae | chromosome VI sequence | CP008564.1 |
| Saccharomyces cerevisiae | chromosome VI sequence | CP008666.1 |
| Saccharomyces cerevisiae | chromosome VI sequence | CP008649.1 |
| Saccharomyces cerevisiae | chromosome VI sequence | CP008615.1 |
| Saccharomyces cerevisiae | chromosome VI sequence | CP008122.1 |
| Saccharomyces cerevisiae | chromosome VI sequence | CP008054.1 |
| Saccharomyces cerevisiae | chromosome VI sequence | CP008037.1 |
| Saccharomyces cerevisiae | chromosome VI sequence | CP007935.1 |
| Saccharomyces cerevisiae | chromosome VI sequence | CP007850.1 |
| Saccharomyces cerevisiae | chromosome VI sequence | CP004915.2 |
| Saccharomyces cerevisiae | chromosome VI sequence | CP004905.2 |
| Saccharomyces cerevisiae | chromosome VI sequence | CP004944.2 |
| Saccharomyces cerevisiae | chromosome VI sequence | CP004914.2 |
| Saccharomyces cerevisiae | chromosome VI sequence | CP004963.2 |
| Saccharomyces cerevisiae | chromosome VI sequence | CP004923.2 |
| Saccharomyces cerevisiae | chromosome VI sequence | CP004932.2 |
| Saccharomyces cerevisiae | chromosome VI sequence | CP004922.2 |
| Saccharomyces cerevisiae | chromosome VI sequence | CP004972.2 |
| Saccharomyces cerevisiae | chromosome VI sequence | CP004931.2 |
| Saccharomyces cerevisiae | chromosome VI sequence | CP007833.1 |

In one aspect, the gene that expresses a heat shock protein is isolated from a microorganism. In a further aspect, the microorganism is a fungus such as, for example, yeast. In a still further aspect, the yeast is *Saccharomyces cerevisiae*. In a further aspect, the gene that expresses a heat shock protein has SEQ ID NO. 3 or at least 70% homology thereto, at least 75% homology thereto, at least 80% homology thereto, at least 85% homology thereto, at least 90% homology thereto, or at least 95% homology thereto. In one aspect, the gene that expresses a heat shock protein is isolated from *Saccharomyces cerevisiae* and can be found in GenBank with GI number X13713.

Other sequences expressing a heat shock protein or related or homologous genes can be identified in a database such as, for example, GenBank. In one aspect, sequences useful herein include those with the GI numbers listed in Table 3.

TABLE 3

| Heat Shock Protein Genes | | |
|---|---|---|
| Source Organism | Sequence Description | GI Number |
| Saccharomyces cerevisiae | chromosome IV sequence | CP020126.1 |
| Saccharomyces cerevisiae | chromosome IV sequence | CP004710.2 |
| Saccharomyces cerevisiae | chromosome IV sequence | CP011550.1 |
| Saccharomyces cerevisiae | chromosome IV sequence | BK006938.2 |
| Saccharomyces cerevisiae | HSP70 | NM_001180289.1 |
| Saccharomyces cerevisiae | chromosome IV sequence | FN393064.1 |
| Saccharomyces cerevisiae | chromosome IV sequence | Z74277.1 |
| Saccharomyces cerevisiae | heat shock cognate gene | X13713.1 |
| Saccharomyces cerevisiae | chromosome IV sequence | EF058944.1 |
| Saccharomyces cerevisiae | chromosome IV sequence | CP020228.1 |
| Saccharomyces cerevisiae | chromosome IV sequence | CP020160.1 |
| Saccharomyces cerevisiae | chromosome IV sequence | CP004738.2 |
| Saccharomyces cerevisiae | chromosome IV sequence | CP004688.2 |
| Saccharomyces cerevisiae | chromosome IV sequence | CP004678.2 |
| Saccharomyces cerevisiae | chromosome IV sequence | CP004727.2 |
| Saccharomyces cerevisiae | chromosome IV sequence | CP004717.2 |
| Saccharomyces cerevisiae | chromosome IV sequence | CP004687.2 |
| Saccharomyces cerevisiae | chromosome IV sequence | CP004667.2 |
| Saccharomyces cerevisiae | chromosome IV sequence | CP004746.2 |
| Saccharomyces cerevisiae | chromosome IV sequence | CP004716.2 |
| Saccharomyces cerevisiae | chromosome IV sequence | CP004676.2 |
| Saccharomyces cerevisiae | chromosome IV sequence | CP008239.1 |
| Saccharomyces cerevisiae | chromosome IV sequence | CP008324.1 |
| Saccharomyces cerevisiae | chromosome IV sequence | CP008273.1 |
| Saccharomyces cerevisiae | chromosome IV sequence | CP008256.1 |
| Saccharomyces cerevisiae | chromosome IV sequence | CP008222.1 |
| Saccharomyces cerevisiae | chromosome IV sequence | CP008409.1 |
| Saccharomyces cerevisiae | chromosome IV sequence | CP008392.1 |
| Saccharomyces cerevisiae | chromosome IV sequence | CP008375.1 |
| Saccharomyces cerevisiae | chromosome IV sequence | CP008358.1 |
| Saccharomyces cerevisiae | chromosome IV sequence | CP008341.1 |
| Saccharomyces cerevisiae | chromosome IV sequence | CP008494.1 |
| Saccharomyces cerevisiae | chromosome IV sequence | CP008443.1 |
| Saccharomyces cerevisiae | chromosome IV sequence | CP008579.1 |
| Saccharomyces cerevisiae | chromosome IV sequence | CP008511.1 |
| Saccharomyces cerevisiae | chromosome IV sequence | CP008647.1 |
| Saccharomyces cerevisiae | chromosome IV sequence | CP008630.1 |
| Saccharomyces cerevisiae | chromosome IV sequence | CP008596.1 |
| Saccharomyces cerevisiae | chromosome IV sequence | CP008188.1 |
| Saccharomyces cerevisiae | chromosome IV sequence | CP008171.1 |
| Saccharomyces cerevisiae | chromosome IV sequence | CP008154.1 |
| Saccharomyces cerevisiae | chromosome IV sequence | CP008681.1 |
| Saccharomyces cerevisiae | chromosome IV sequence | CP008137.1 |
| Saccharomyces cerevisiae | chromosome IV sequence | CP008120.1 |
| Saccharomyces cerevisiae | chromosome IV sequence | CP008086.1 |
| Saccharomyces cerevisiae | chromosome IV sequence | CP008052.1 |
| Saccharomyces cerevisiae | chromosome IV sequence | CP008035.1 |
| Saccharomyces cerevisiae | chromosome IV sequence | CP008001.1 |
| Saccharomyces cerevisiae | chromosome IV sequence | CP007984.1 |
| Saccharomyces cerevisiae | chromosome IV sequence | CP007950.1 |
| Saccharomyces cerevisiae | chromosome IV sequence | CP007899.1 |
| Saccharomyces cerevisiae | chromosome IV sequence | CP007882.1 |
| Saccharomyces cerevisiae | chromosome IV sequence | CP007831.1 |

TABLE 3-continued

Heat Shock Protein Genes

| Source Organism | Sequence Description | GI Number |
|---|---|---|
| *Saccharomyces cerevisiae* | chromosome IV sequence | CP004745.2 |
| *Saccharomyces cerevisiae* | chromosome IV sequence | CP004684.2 |
| *Saccharomyces cerevisiae* | chromosome IV sequence | CP004743.2 |
| *Saccharomyces cerevisiae* | chromosome IV sequence | CP004713.2 |
| *Saccharomyces cerevisiae* | chromosome IV sequence | CP004692.2 |
| *Saccharomyces cerevisiae* | chromosome IV sequence | CP004742.2 |
| *Saccharomyces cerevisiae* | chromosome IV sequence | CP004722.2 |
| *Saccharomyces cerevisiae* | chromosome IV sequence | CP004672.2 |
| *Saccharomyces cerevisiae* | chromosome IV sequence | CP004701.2 |
| *Saccharomyces cerevisiae* | chromosome IV sequence | CP004681.2 |
| *Saccharomyces cerevisiae* | chromosome IV sequence | CP004690.2 |
| *Saccharomyces cerevisiae* | chromosome IV sequence | CP004670.2 |
| *Saccharomyces cerevisiae* | chromosome IV sequence | CP011082.1 |
| *Saccharomyces cerevisiae* | chromosome IV sequence | CP004729.1 |
| *Saccharomyces cerevisiae* | HSP70 | M25395.1 |
| *Saccharomyces cerevisiae* | chromosome IV sequence | CP020211.1 |
| *Saccharomyces cerevisiae* | chromosome IV sequence | CP004748.2 |
| *Saccharomyces cerevisiae* | chromosome IV sequence | CP004697.2 |
| *Saccharomyces cerevisiae* | chromosome IV sequence | CP004677.2 |
| *Saccharomyces cerevisiae* | chromosome IV sequence | CP004726.2 |
| *Saccharomyces cerevisiae* | chromosome IV sequence | CP004706.2 |
| *Saccharomyces cerevisiae* | chromosome IV sequence | CP008307.1 |
| *Saccharomyces cerevisiae* | chromosome IV sequence | CP008290.1 |
| *Saccharomyces cerevisiae* | chromosome IV sequence | CP008477.1 |
| *Saccharomyces cerevisiae* | chromosome IV sequence | CP008460.1 |
| *Saccharomyces cerevisiae* | chromosome IV sequence | CP008426.1 |
| *Saccharomyces cerevisiae* | chromosome IV sequence | CP008562.1 |
| *Saccharomyces cerevisiae* | chromosome IV sequence | CP008664.1 |
| *Saccharomyces cerevisiae* | chromosome IV sequence | CP008613.1 |
| *Saccharomyces cerevisiae* | chromosome IV sequence | CP008103.1 |
| *Saccharomyces cerevisiae* | chromosome IV sequence | CP008069.1 |
| *Saccharomyces cerevisiae* | chromosome IV sequence | CP008018.1 |
| *Saccharomyces cerevisiae* | chromosome IV sequence | CP007967.1 |
| *Saccharomyces cerevisiae* | chromosome IV sequence | CP007933.1 |
| *Saccharomyces cerevisiae* | chromosome IV sequence | CP007916.1 |
| *Saccharomyces cerevisiae* | chromosome IV sequence | CP007865.1 |
| *Saccharomyces cerevisiae* | chromosome IV sequence | CP007848.1 |
| *Saccharomyces cerevisiae* | chromosome IV sequence | CP007814.1 |
| *Saccharomyces cerevisiae* | chromosome IV sequence | CP004695.2 |
| *Saccharomyces cerevisiae* | chromosome IV sequence | CP004675.2 |
| *Saccharomyces cerevisiae* | chromosome IV sequence | CP004744.2 |
| *Saccharomyces cerevisiae* | chromosome IV sequence | CP004724.2 |
| *Saccharomyces cerevisiae* | chromosome IV sequence | CP004714.2 |
| *Saccharomyces cerevisiae* | chromosome IV sequence | CP004704.2 |
| *Saccharomyces cerevisiae* | chromosome IV sequence | CP004674.2 |
| *Saccharomyces cerevisiae* | chromosome IV sequence | CP004733.2 |
| *Saccharomyces cerevisiae* | chromosome IV sequence | CP008205.1 |

In one aspect, the gene that expresses a geranylgeranyl pyrophosphate synthase (GGPS) is isolated from plants such as, for example, plants from the mustard family. In one aspect, the mustard family plant includes *Arabidopsis thaliana*, *Arabidopsis lyrata*, canola or rapeseed, bok choy, napa cabbage, rapini, turnip, cabbage, Savoy cabbage, red cabbage, collard greens, kale or ornamental kale, Brussels sprouts, kohlrabi, broccoli, cauliflower, or broccolini. In a further aspect, the gene that expresses GGPS has SEQ ID NO. 4 or at least 70% homology thereto, at least 75% homology thereto, at least 80% homology thereto, at least 85% homology thereto, at least 90% homology thereto, or at least 95% homology thereto. In one aspect, the gene that expresses GGPS is isolated from *Arabidopsis thaliana* and can be found in GenBank with GI number NM_127943.3.

Other sequences expressing GGPS or related or homologous genes can be identified in a database such as, for example, GenBank. In one aspect, sequences useful herein include those with the GI numbers listed in Table 4.

TABLE 4

Geranylgeranyl Pyrophosphate Synthase-2

| Source Organism | Sequence Description | GI Number |
|---|---|---|
| *Arabidopsis thaliana* | GGPS2 | NM_127943.3 |
| *Arabidopsis thaliana* | chromosome 2 sequence | CP002685.1 |
| *Arabidopsis thaliana* | chromosome 2 sequence | AC004482.3 |
| *Arabidopsis thaliana* | unknown protein | BT005328.1 |
| *Arabidopsis thaliana* | putative GGPS2 | AK117954.1 |
| *Arabidopsis thaliana* | GGPS2 | FJ172354.1 |
| *Arabidopsis thaliana* | unknown protein | AY087521.1 |
| *Arabidopsis thaliana* | GGPS2 | D85029.1 |
| *Arabidopsis thaliana* | GGPS2 | U44876.1 |
| *Arabidopsis lyrata* | GGPS2 | XM_002880482.2 |
| *Eutrema salsugineum* | hypothetical protein | XM_006404803.1 |
| *Capsella rubella* | hypothetical protein | XM_006296117.1 |
| *Arabis alpina* | chromosome 6 sequence | LT669793.1 |
| *Camelina sativa* | GGPS2 | XM_010418822.2 |
| *Camelina sativa* | GGPS2 | XM_010474073.2 |
| *Camelina sativa* | GGPS2 | XM_010431032.2 |
| *Brassica oleracea* | GGPS2 | XM_013750159.1 |
| *Brassica napus* | GGPS2 | XM_013855022.1 |
| *Brassica napus* | GGPS2 | XM_013888379.1 |
| *Brassica napus* | GGPS2 | XM_013808643.1 |
| *Brassica rapa* | GGPS2 | XM_009119018.2 |
| *Brassica napus* | GGPS2 | XM_013891548.1 |
| *Brassica napus* | GGPS2 | XM_013888378.1 |
| *Raphanus sativus* | GGPS2 | XM_018582098.1 |
| *Brassica oleracea* | GGPS2 | XM_013775753.1 |
| *Brassica rapa* | GGPS2 | XM_018658479.1 |
| *Raphanus sativus* | GGPS2 | XM_018577514.1 |
| *Arabidopsis thaliana* | GGPS2 | NM_127420.2 |
| *Arabidopsis thaliana* | unknown protein | DQ653000.1 |
| *Arabidopsis thaliana* | GGPS2/GGPP synthetase/ farnesyltranstransferase | DQ446521.1 |
| *Arabidopsis thaliana* | chromosome 2 sequence | AC006135.3 |
| *Arabidopsis thaliana* | chromosome 2 sequence | AC005724.3 |
| *Eutrema salsugineum* | hypothetical protein | XM_006409066.1 |
| *Eutrema salsugineum* | hypothetical protein | XM_006411896.1 |
| *Arabidopsis lyrata* | GGPS7 | XM_021033265.1 |
| *Arabidopsis thaliana* | terpenoid synthase superfamily | NM_127418.2 |
| *Arabidopsis thaliana* | unknown protein | DQ652999.1 |
| *Arabidopsis thaliana* | GGPS2/GGPP synthetase/ farnesyltranstransferase | DQ446520.1 |
| *Leucosceptrum canum* | GGPS4 | KT312960.1 |
| *Leucosceptrum canum* | GGPS5 | KT312961.1 |
| *Vigna radiata* | GGPS7 | XM_014665620.1 |
| *Sesamum indicum* | GGPS7 | XM_011099148.2 |
| *Jatropha curcas* | GGPS | XM_012223700.2 |
| *Populus trichocarpa* | GGPS2 family protein | XM_006383273.1 |
| *Populus euphratica* | GGPS | XM_011023075.1 |

In one aspect, the gene that expresses steviol synthase or 1-deoxy-D-xylulose-5-phosphate synthase (DXS) is isolated from a plant. In a further aspect, the plant can be *Stevia rebaudiana*, Russian dandelion, castor bean, wild tomato, Japanese morning glory, garden tomato, potato, or cacao. In a further aspect, the gene that expresses steviol synthase or DXS has SEQ ID NO. 5 or at least 70% homology thereto, at least 75% homology thereto, at least 80% homology thereto, at least 85% homology thereto, at least 90% homology thereto, or at least 95% homology thereto. In one aspect, the gene that expresses DXS is isolated from *Arabidopsis thaliana* and can be found in GenBank with GI number AEE76517.1.

Other sequences expressing steviol synthase or DXS or related or homologous genes can be identified in a database such as, for example, GenBank. In one aspect, sequences useful herein include those with the GI numbers listed in Table 5.

TABLE 5

| Steviol Synthase or DXS Genes | | |
| --- | --- | --- |
| Source Organism | Sequence Description | GI Number |
| *Stevia rebaudiana* | DXS | FJ214107.1 |
| *Stevia rebaudiana* | DXS | AJ429232.2 |
| *Stevia rebaudiana* | DXS 4 | KT276232.1 |
| *Taraxacum kok-saghyz* | DXS 1 | KT899414.1 |
| *Ricinus communis* | probable DXS 2 | XM_002532338.2 |
| *Lycopersicon hirsutum* | putative DXS 2 | AY687353.1 |
| *Ipomoea nil* | probable DXS 2 | XM_019327463.1 |
| *Ipomoea nil* | probable DXS 2 | XM_019327462.1 |
| *Solanum lycopersicum* | DXS 2 | NM_001345870.1 |
| *Solanum pennellii* | probable DXS 2 | XM_015203416.1 |
| *Stevia rebaudiana* | DXS-like protein | AY723732.1 |
| *Solanum tuberosum* | probable DXS 2 | XM_006353091.2 |
| *Tripterygium wilfordii* | DXS 2 | KM879186.1 |
| *Populus euphratica* | probable DXS 2 | XM_011012876.1 |
| *Gossypium hirsutum* | probable DXS 2 | XM_016898289.1 |
| *Gossypium arboreum* | probable DXS 2 | XM_017779849.1 |
| *Populys trichocarpa* | hypothetical protein | XM_006380518.1 |
| Gossypium hirsutum | DXS 2 | XM_016898290.1 |
| *Theobroma cacao* | DXS 2 | XM_018114317.1 |
| *Herrania umbratica* | DXS 2 | XM_021418780.1 |
| *Herrania umbratica* | DXS 2 | XM_021444875.1 |
| *Theobroma cacao* | genomic DNA | LT594788.1 |
| *Solanum pennellii* | genomic DNA | HG975450.1 |
| *Solanum lycopersicum* | genomic DNA | HG975523.1 |
| *Solanum lycopersicum* | DXS 2 | FN424052.1 |

DXP synthase, or 1-deoxy-D-xylulose-5-phosphate synthase (also abbreviated DOXP synthase or DXS) uses glycolytic pathway intermediates pyruvic acid and glyceraldehydes-3-phosphate to generate 1-deoxy-D-xylulose-5-phosphate. It is an enzyme on the non-mevalonate pathway (also known as the mevalonate-independent pathway), which is an alternative metabolic pathway for isoprenoid biosynthesis. In one aspect, DXS expressed by a gene in the DNA constructs described herein catalyzes the formation of precursor molecules to steviol glycosides.

In one aspect, the steviol glycosides are produced herein using starting materials from the non-mevalonate pathway for isoprenoid biosynthesis. In an alternative aspect, the starting materials for steviol glycoside biosynthesis used herein are generated via the mevalonate pathway. In still another aspect, the starting materials for steviol glycoside biosynthesis are generated from both the mevalonate and non-mevalonate pathways.

In one aspect, the gene that expresses mevalonate-5-kinase is isolated from a microorganism. In another aspect, the microorganism is a fungus such as, for example, a yeast. In still another aspect, the yeast is *Saccharomyces cerevisiae*. In a further aspect, the gene that expresses mevalonate-5-kinase has SEQ ID NO. 6 or at least 70% homology thereto, at least 75% homology thereto, at least 80% homology thereto, at least 85% homology thereto, at least 90% homology thereto, or at least 95% homology thereto. In one aspect, the gene that expresses mevalonate-5-kinase is isolated from *Saccharomyces cerevisiae* and can be found in GenBank with accession number NC_001145.3.

Other sequences expressing mevalonate-5-kinase or related or homologous genes can be identified in a database such as, for example, GenBank. In one aspect, sequences useful herein include those with the GI numbers listed in Table 6.

TABLE 6

| Mevalonate-5-Kinase Genes | | |
| --- | --- | --- |
| Source Organism | Sequence Description | GI Number |
| *Saccharomyces cerevisiae* | chromosome XIII sequence | CP020203.1 |
| *Saccharomyces cerevisiae* | chromosome XIII sequence | CP020135.1 |
| *Saccharomyces cerevisiae* | chromosome XIII sequence | CP005469.2 |
| *Saccharomyces cerevisiae* | chromosome XIII sequence | CP008027.1 |
| *Saccharomyces cerevisiae* | chromosome XIII sequence | CP007874.1 |
| *Saccharomyces cerevisiae* | chromosome XIII sequence | CP005464.2 |
| *Saccharomyces cerevisiae* | chromosome XIII sequence | CP005453.2 |
| *Saccharomyces cerevisiae* | chromosome XIII sequence | CP005482.2 |
| *Saccharomyces cerevisiae* | chromosome XIII sequence | CP005472.2 |
| *Saccharomyces cerevisiae* | chromosome XIII sequence | CP005411.2 |
| *Saccharomyces cerevisiae* | chromosome XIII sequence | CP005450.2 |
| *Saccharomyces cerevisiae* | chromosome XIII sequence | LN907796.1 |
| *Saccharomyces cerevisiae* | chromosome XIII sequence | CP011559.1 |
| *Saccharomyces cerevisiae* | chromosome XIII sequence | CP005456.1 |
| *Saccharomyces cerevisiae* | chromosome XIII sequence | CP005455.1 |
| *Saccharomyces cerevisiae* | chromosome XIII sequence | BK006946.2 |
| *Saccharomyces cerevisiae* | chromosome XIII sequence | Z49809.1 |
| *Saccharomyces cerevisiae* | putative RAR1 gene | X06114.1 |
| *Saccharomyces cerevisiae* | mevalonate kinase | X55875.1 |
| *Saccharomyces cerevisiae* | mevalonate kinase | NM_001182715.1 |
| *Saccharomyces cerevisiae* | chromosome XIII sequence | CP014728.1 |
| *Saccharomyces cerevisiae* | chromosome XIII sequence | CP005426.1 |
| *Saccharomyces cerevisiae* | chromosome XIII sequence | CP005406.1 |
| *Saccharomyces cerevisiae* | chromosome XIII sequence | CP005463.2 |
| *Saccharomyces cerevisiae* | chromosome X sequence | CP005403.2 |
| *Saccharomyces cerevisiae* | chromosome XIII sequence | CP020234.1 |
| *Saccharomyces cerevisiae* | chromosome XIII sequence | CP020220.1 |
| *Saccharomyces cerevisiae* | chromosome XIII sequence | CP005439.2 |
| *Saccharomyces cerevisiae* | chromosome XIII sequence | CP005458.2 |
| *Saccharomyces cerevisiae* | chromosome XIII sequence | CP005438.2 |
| *Saccharomyces cerevisiae* | chromosome XIII sequence | CP005408.2 |
| *Saccharomyces cerevisiae* | chromosome XIII sequence | CP005407.2 |
| *Saccharomyces cerevisiae* | chromosome XIII sequence | CP005415.2 |
| *Saccharomyces cerevisiae* | chromosome XIII sequence | CP005394.2 |
| *Saccharomyces cerevisiae* | chromosome XIII sequence | CP005442.2 |
| *Saccharomyces cerevisiae* | chromosome XIII sequence | CP005441.2 |
| *Saccharomyces cerevisiae* | chromosome XIII sequence | CP005470.2 |
| *Saccharomyces cerevisiae* | chromosome XIII sequence | CP005476.1 |
| *Saccharomyces cerevisiae* | chromosome XIII sequence | CP005466.1 |
| *Saccharomyces cerevisiae* | chromosome XIII sequence | CP005440.1 |
| *Saccharomyces cerevisiae* | chromosome XIII sequence | CP011822.1 |

TABLE 6-continued

Mevalonate-5-Kinase Genes

| Source Organism | Sequence Description | GI Number |
| --- | --- | --- |
| *Saccharomyces cerevisiae* | chromosome XIII sequence | CP009953.1 |
| *Saccharomyces cerevisiae* | chromosome XIII sequence | CP020186.1 |
| *Saccharomyces cerevisiae* | chromosome XIII sequence | CP020152.1 |
| *Saccharomyces cerevisiae* | chromosome XIII sequence | CP005479.2 |
| *Saccharomyces cerevisiae* | chromosome XIII sequence | CP005429.2 |
| *Saccharomyces cerevisiae* | chromosome XIII sequence | CP005419.2 |
| *Saccharomyces cerevisiae* | chromosome XIII sequence | CP005418.2 |
| *Saccharomyces cerevisiae* | chromosome XIII sequence | CP005398.2 |
| *Saccharomyces cerevisiae* | chromosome XIII sequence | CP005467.2 |
| *Saccharomyces cerevisiae* | chromosome XIII sequence | CP005417.2 |
| *Saccharomyces cerevisiae* | chromosome XIII sequence | CP005475.2 |
| *Saccharomyces cerevisiae* | chromosome XIII sequence | CP005435.2 |
| *Saccharomyces cerevisiae* | chromosome XIII sequence | CP005425.2 |
| *Saccharomyces cerevisiae* | chromosome XIII sequence | CP005395.2 |
| *Saccharomyces cerevisiae* | chromosome XIII sequence | CP008316.1 |
| *Saccharomyces cerevisiae* | chromosome XIII sequence | CP008299.1 |
| *Saccharomyces cerevisiae* | chromosome XIII sequence | CP008282.1 |
| *Saccharomyces cerevisiae* | chromosome XIII sequence | CP008418.1 |
| *Saccharomyces cerevisiae* | chromosome XIII sequence | CP008384.1 |
| *Saccharomyces cerevisiae* | chromosome XIII sequence | CP008503.1 |
| *Saccharomyces cerevisiae* | chromosome XIII sequence | CP008486.1 |
| *Saccharomyces cerevisiae* | chromosome XIII sequence | CP008469.1 |
| *Saccharomyces cerevisiae* | chromosome XIII sequence | CP008452.1 |
| *Saccharomyces cerevisiae* | chromosome XIII sequence | CP008435.1 |
| *Saccharomyces cerevisiae* | chromosome XIII sequence | CP008571.1 |
| *Saccharomyces cerevisiae* | chromosome XIII sequence | CP008673.1 |
| *Saccharomyces cerevisiae* | chromosome XIII sequence | CP008656.1 |
| *Saccharomyces cerevisiae* | chromosome XIII sequence | CP008622.1 |
| *Saccharomyces cerevisiae* | chromosome XIII sequence | CP008214.1 |
| *Saccharomyces cerevisiae* | chromosome XIII sequence | CP008180.1 |
| *Saccharomyces cerevisiae* | chromosome XIII sequence | CP008690.1 |
| *Saccharomyces cerevisiae* | chromosome XIII sequence | CP008146.1 |
| *Saccharomyces cerevisiae* | chromosome XIII sequence | CP008112.1 |
| *Saccharomyces cerevisiae* | chromosome XIII sequence | CP008095.1 |
| *Saccharomyces cerevisiae* | chromosome XIII sequence | CP007993.1 |
| *Saccharomyces cerevisiae* | chromosome XIII sequence | CP007942.1 |
| *Saccharomyces cerevisiae* | chromosome XIII sequence | CP007857.1 |
| *Saccharomyces cerevisiae* | chromosome XIII sequence | CP007823.1 |
| *Saccharomyces cerevisiae* | chromosome XIII sequence | CP005474.2 |
| *Saccharomyces cerevisiae* | chromosome XIII sequence | CP005454.2 |
| *Saccharomyces cerevisiae* | chromosome XIII sequence | CP005444.2 |
| *Saccharomyces cerevisiae* | chromosome XIII sequence | CP005434.2 |
| *Saccharomyces cerevisiae* | chromosome XIII sequence | CP005424.2 |
| *Saccharomyces cerevisiae* | chromosome XIII sequence | CP005404.2 |
| *Saccharomyces cerevisiae* | chromosome XIII sequence | CP005483.2 |
| *Saccharomyces cerevisiae* | chromosome XIII sequence | CP005473.2 |
| *Saccharomyces cerevisiae* | chromosome XIII sequence | CP005443.2 |
| *Saccharomyces cerevisiae* | chromosome XIII sequence | CP005433.2 |
| *Saccharomyces cerevisiae* | chromosome XIII sequence | CP005423.2 |
| *Saccharomyces cerevisiae* | chromosome XIII sequence | CP005393.2 |
| *Saccharomyces cerevisiae* | chromosome XIII sequence | CP005452.2 |
| *Saccharomyces cerevisiae* | chromosome XIII sequence | CP005422.2 |
| *Saccharomyces cerevisiae* | chromosome XIII sequence | CP005402.2 |
| *Saccharomyces cerevisiae* | chromosome XIII sequence | CP005461.2 |
| *Saccharomyces cerevisiae* | chromosome XIII sequence | CP005451.2 |
| *Saccharomyces cerevisiae* | chromosome XIII sequence | CP005421.2 |
| *Saccharomyces cerevisiae* | chromosome XIII sequence | CP005430.2 |
| *Saccharomyces cerevisiae* | chromosome XIII sequence | CP005420.2 |
| *Saccharomyces cerevisiae* | chromosome XIII sequence | CP005410.2 |

In one aspect, the gene that expresses isopentenyl pyrophosphate isomerase is isolated from bacteria. In another aspect, the bacteria are from the genus *Bacillus*. In still another aspect, the bacteria are *B. thuringiensis, B. anthracis,* or *B. cereus.* In a further aspect, the gene that expresses isopentenyl pyrophosphate isomerase has SEQ ID NO. 7 or at least 70% homology thereto, at least 75% homology thereto, at least 80% homology thereto, at least 85% homology thereto, at least 90% homology thereto, or at least 95% homology thereto. In one aspect, the gene that expresses isopentenyl pyrophosphate isomerase is isolated from *Bacillus thuringiensis* serovar konkukian str. 97-27 and can be found in GenBank with GI number NC_005957.1.

Other sequences expressing isopentenyl pyrophosphate isomerase or related or homologous genes can be identified in a database such as, for example, GenBank. In one aspect, sequences useful herein include those with the GI numbers listed in Table 7.

TABLE 7

Isopentenyl Pyrophosphate Isomerase Genes

| Source Organism | Sequence Description | GI Number |
| --- | --- | --- |
| *Bacillus thuringiensis* | genomic DNA | CP010088.1 |
| *Bacillus thuringiensis* | genomic DNA | AE017355.1 |
| *Bacillus anthracis* | genomic DNA | CP022044.1 |
| *Bacillus anthracis* | genomic DNA | CP019726.1 |
| *Bacillus anthracis* | genomic DNA | CP019588.1 |
| *Bacillus anthracis* | genomic DNA | CP018903.1 |
| *Bacillus anthracis* | genomic DNA | CP001974.2 |
| *Bacillus anthracis* | genomic DNA | CP001970.2 |
| *Bacillus anthracis* | genomic DNA | CP012728.1 |
| *Bacillus anthracis* | genomic DNA | CP012727.1 |
| *Bacillus anthracis* | genomic DNA | CP012726.1 |
| *Bacillus anthracis* | genomic DNA | CP012725.1 |
| *Bacillus anthracis* | genomic DNA | CP012724.1 |
| *Bacillus anthracis* | genomic DNA | CP012723.1 |
| *Bacillus anthracis* | genomic DNA | CP012722.1 |
| *Bacillus anthracis* | genomic DNA | CP012721.1 |
| *Bacillus anthracis* | genomic DNA | CP012720.1 |
| *Bacillus anthracis* | genomic DNA | CP012730.1 |
| *Bacillus anthracis* | genomic DNA | CP012729.1 |
| *Bacillus anthracis* | genomic DNA | CP015779.1 |
| *Bacillus anthracis* | genomic DNA | CP014179.1 |
| *Bacillus anthracis* | genomic DNA | CP012519.1 |
| *Bacillus anthracis* | genomic DNA | AP014833.1 |
| *Bacillus anthracis* | genomic DNA | CP010852.1 |
| *Bacillus anthracis* | genomic DNA | CP010322.1 |
| *Bacillus anthracis* | genomic DNA | CP009981.1 |
| *Bacillus anthracis* | genomic DNA | CP009902.1 |
| *Bacillus anthracis* | genomic DNA | CP009598.1 |
| *Bacillus anthracis* | genomic DNA | CP009700.1 |
| *Bacillus anthracis* | genomic DNA | CP009544.1 |
| *Bacillus anthracis* | genomic DNA | CP009541.1 |
| *Bacillus anthracis* | genomic DNA | CP009697.1 |
| *Bacillus anthracis* | genomic DNA | CP009476.1 |
| *Bacillus anthracis* | genomic DNA | CP009464.1 |
| *Bacillus anthracis* | genomic DNA | CP009341.1 |
| *Bacillus anthracis* | genomic DNA | CP009328.1 |
| *Bacillus anthracis* | genomic DNA | CP009331.1 |
| *Bacillus anthracis* | genomic DNA | CP009325.1 |
| *Bacillus anthracis* | genomic DNA | CP009315.1 |
| *Bacillus anthracis* | genomic DNA | CP010813.1 |
| *Bacillus anthracis* | genomic DNA | CP010792.1 |
| *Bacillus anthracis* | genomic DNA | CP010342.1 |
| *Bacillus anthracis* | genomic DNA | CP008854.1 |
| *Bacillus anthracis* | genomic DNA | CP008853.1 |
| *Bacillus anthracis* | genomic DNA | CP008752.1 |
| *Bacillus anthracis* | genomic DNA | CP007666.1 |
| *Bacillus anthracis* | genomic DNA | CP007704.1 |
| *Bacillus anthracis* | genomic DNA | CP007618.1 |
| *Bacillus anthracis* | genomic DNA | CP008846.1 |
| *Bacillus anthracis* | genomic DNA | CP006742.1 |
| *Bacillus anthracis* | genomic DNA | CP002091.1 |
| *Bacillus anthracis* | genomic DNA | CP001598.1 |
| *Bacillus anthracis* | genomic DNA | CP001215.1 |
| *Bacillus anthracis* | genomic DNA | AE017334.2 |
| *Bacillus anthracis* | genomic DNA | AE017225.1 |
| *Bacillus anthracis* | genomic DNA | AE016879.1 |
| *Bacillus anthracis* | genomic DNA | EF040345.1 |
| *Bacillus cereus* | genomic DNA | CP018935.1 |
| *Bacillus cereus* | genomic DNA | CP018933.1 |
| *Bacillus cereus* | genomic DNA | CP018931.1 |
| *Bacillus cereus* | genomic DNA | CP009605.1 |
| *Bacillus thuringiensis* | genomic DNA | CP009720.1 |
| *Bacillus cereus* | genomic DNA | CP009596.1 |
| *Bacillus thuringiensis* | genomic DNA | CP009335.1 |
| *Bacillus cereus* | genomic DNA | CP001283.1 |
| *Bacillus cereus* | genomic DNA | CP009968.1 |
| *Bacillus cereus* | genomic DNA | CP000001.1 |
| Bacillus cereus | genomic DNA | CP009318.1 |
| *Bacillus cereus* | genomic DNA | CP001407.1 |

TABLE 7-continued

| Isopentenyl Pyrophosphate Isomerase Genes | | |
|---|---|---|
| Source Organism | Sequence Description | GI Number |
| Bacillus cereus | genomic DNA | CP009641.1 |
| Bacillus thuringiensis | genomic DNA | CP009600.1 |
| Bacillus cereus | genomic DNA | CP009300.1 |
| Bacillus cereus | genomic DNA | CP003187.1 |
| Bacillus thuringiensis | genomic DNA | CP000485.1 |
| Bacillus thuringiensis | genomic DNA | CP020723.1 |
| Bacillus cereus | genomic DNA | AP007209.1 |
| Bacillus cereus | genomic DNA | CP000227.1 |
| Bacillus cereus | genomic DNA | CP001177.1 |
| Bacillus cereus | genomic DNA | CP001746.1 |
| Bacillus cereus | genomic DNA | CP015589.1 |
| Bacillus cereus | genomic DNA | CP009628.1 |
| Bacillus cereus | genomic DNA | CP009369.1 |
| Bacillus cereus | genomic DNA | CP020937.1 |
| Bacillus thuringiensis | genomic DNA | CP013000.1 |
| Bacillus cereus | genomic DNA | CP009590.1 |
| Bacillus cereus | genomic DNA | CP009941.1 |
| Bacillus cereus | genomic DNA | CP016316.1 |
| Bacillus cereus | genomic DNA | CP008712.1 |
| Bacillus cereus | genomic DNA | AE017194.1 |
| Bacillus thuringiensis | genomic DNA | CP002508.1 |
| Bacillus sp. ABP14 | genomic DNA | CP017016.1 |
| Bacillus cereus | genomic DNA | CP003747.1 |
| Bacillus cereus | genomic DNA | CP016595.1 |
| Bacillus thuringiensis | genomic DNA | CP019230.1 |
| Bacillus cereus | genomic DNA | CP011153.1 |
| Bacillus cereus | genomic DNA | CP011151.1 |
| Bacillus thuringiensis | genomic DNA | CP010106.1 |
| Bacillus thuringiensis | genomic DNA | CP005935.1 |
| Bacillus thuringiensis | genomic DNA | CP022345.1 |
| Bacillus thuringiensis | genomic DNA | CP020002.1 |

In one aspect, the gene that expresses mevalonate pyrophosphate decarboxylase is isolated from bacteria. In another aspect, the bacteria are from the genus *Lactobacillus*. In still another aspect, the bacteria are *L. paracasei* or *L. casei*. In a further aspect, the gene that expresses mevalonate pyrophosphate decarboxylase has SEQ ID NO. 8 or at least 70% homology thereto, at least 75% homology thereto, at least 80% homology thereto, at least 85% homology thereto, at least 90% homology thereto, or at least 95% homology thereto. In one aspect, the gene that expresses mevalonate pyrophosphate decarboxylase is isolated from *Lactobacillus paracasei* and can be found in GenBank with accession number NC_008526.1.

Other sequences expressing mevalonate pyrophosphate decarboxylase or related or homologous genes can be identified in a database such as, for example, GenBank. In one aspect, sequences useful herein include those with the GI numbers listed in Table 8.

TABLE 8

| Mevalonate Pyrophosphate Decarboxylase Genes | | |
|---|---|---|
| Source Organism | Sequence Description | GI Number |
| Lactobacillus paracasei | genomic DNA | AP012541.1 |
| Lactobacillus paracasei | genomic DNA | CP000423.1 |
| Lactobacillus paracasei | genomic DNA | CP014985.1 |
| Lactobacillus casei | genomic DNA | CP006690.1 |
| Lactobacillus paracasei | genomic DNA | CP002391.1 |
| Lactobacillus paracasei | genomic DNA | CP012148.1 |
| Lactobacillus paracasei | genomic DNA | CP012187.1 |
| Lactobacillus casei | genomic DNA | CP001084.2 |
| Lactobacillus casei | genomic DNA | CP005486.1 |
| Lactobacillus paracasei | genomic DNA | CP007122.1 |
| Lactobacillus casei | genomic DNA | HE970764.1 |
| Lactobacillus casei | genomic DNA | CP002618.1 |

TABLE 8-continued

| Mevalonate Pyrophosphate Decarboxylase Genes | | |
|---|---|---|
| Source Organism | Sequence Description | GI Number |
| Lactobacillus casei | genomic DNA | CP002616.1 |
| Lactobacillus casei | genomic DNA | FM177140.1 |
| Lactobacillus paracasei | genomic DNA | CP013921.1 |

In one aspect, the gene that expresses UDP-glycosyltransferase is isolated from a plant. In another aspect, the plant is *Stevia rebaudiana*, sunflower (*Helianthus annuus*), soy (*Glycine max*), lettuce (*Lactuca sativa*), *Gossypii arboreum*, *Gossypium hirsutum*, *Gossypium raimondii*, durian (*Durio zibethinus*), orange (*Citrus sinensis*), Clementine (*Citrus clementina*), pigeon pea (*Cajanus cajan*), grape (*Vitis vinifera*), carrot (*Daucus carota*), jujube (*Ziziphus jujube*), the common bean (*Phaseolus vulgaris*), or another common plant. In a further aspect, the gene that expresses UDP-glycosyltransferase has SEQ ID NO. 12 or at least 70% homology thereto, at least 75% homology thereto, at least 80% homology thereto, at least 85% homology thereto, at least 90% homology thereto, or at least 95% homology thereto. In one aspect, the gene that expresses UDP-glycosyltransferase is a UGT76G1 gene. In another aspect, the gene that expresses UDP-glycosyltransferase has one or more point mutations such as, for example, $UGT76G1_{His155Leu}$. In certain aspects, the constructs described herein do not include a gene that expresses UDP-glycosyltransferase.

Other sequences expressing UDP-glycosyltransferase or related or homologous genes can be identified in a database such as, for example, GenBank. In one aspect, sequences useful herein include those with the GI numbers listed in Table 9.

TABLE 9

| UDP-Glycosyltransferase Genes | | |
|---|---|---|
| Source Organism | Sequence Description | GI Number |
| Artificial sequence | UDP-glycosyltransferase 76G1 | LC037193.1 |
| Stevia rebaudiana | UDP-glycosyltransferase 76G1 | AY345974.1 |
| Stevia rebaudiana | UDP-glycosyltransferase 76G1 | GQ259127.1 |
| Artificial sequence | UDP-glycosyltransferase 76G1 | LC312448.1 |
| Stevia rebaudiana | UDP-glycosyltransferase 76G1 | KC631816.1 |
| Stevia rebaudiana | UDP-glycosyltransferase 76G2 | FJ607329.1 |
| Helianthus annuus | UDP-glycosyltransferase 76G1-like | XM_022150658.1 |
| Helianthus annuus | UDP-glycosyltransferase 76G1-like | XM_022125574.1 |
| Helianthus annuus | UDP-glycosyltransferase 76G1-like | XM_022150659.1 |
| Helianthus annuus | UDP-glycosyltransferase 76G1-like | XM_022118153.1 |
| Helianthus annuus | UDP-glycosyltransferase 76G1-like | XM_022150640.1 |
| Helianthus annuus | UDP-glycosyltransferase 76G1-like | XM_022150660.1 |
| Helianthus annuus | UDP-glycosyltransferase 76G1-like | XM_022134635.1 |
| Latuca sativa | UDP-glycosyltransferase 76G1-like | XM_023907996.1 |
| Helianthus annuus | UDP-glycosyltransferase 76G1-like | XM_022150662.1 |
| Helianthus annuus | UDP-glycosyltransferase 76G1-like | XM_022150661.1 |
| Helianthus annuus | UDP-glycosyltransferase 76G1-like | XM_022150639.1 |
| Latuca sativa | UDP-glycosyltransferase 76G1-like | XM_023915054.1 |
| Helianthus annuus | UDP-glycosyltransferase 76G1-like | XM_022118152.1 |
| Helianthus annuus | UDP-glycosyltransferase 76G1-like | XM_022118194.1 |
| Glycine max | UDP-glycosyltransferase 76F1-like | XM_006591734.2 |
| Gossypium arboreum | UDP-glycosyltransferase 76C2-like | XM_017760523.1 |
| Gossypium hirsutum | UDP-glycosyltransferase 76C2-like | XM_016892560.1 |
| Gossypium raimondii | UDP-glycosyltransferase 76C-like | XM_012604519.1 |
| Durio zibethinus | UDP-glycosyltransferase 76B1-like | XM_022908528.1 |
| Gossypium arboreum | UDP-glycosyltransferase 76F1-like | XM_017749892.1 |
| Citrus sinensis | UDP-glycosyltransferase 76F1-like | XM_006486381.2 |
| Citrus clementina | UDP-glycosyltransferase 76F1-like | XM_024185466.1 |
| Gossypium raimondii | UDP-glycosyltransferase 76F1-like | XM_012597527.1 |

TABLE 9-continued

| Source Organism | Sequence Description | GI Number |
|---|---|---|
| | UDP-Glycosyltransferase Genes | |
| Gossypium raimondii | UDP-glucose iridoid glucosyltransferase-like | XM_012619927.1 |
| Helianthus annuus | UDP-glycosyltransferase 76B1-like | XM_022157833.1 |
| Helianthus annuus | UDP-glycosyltransferase 76B1-like | XM_022157832.1 |
| Helianthus annuus | UDP-glycosyltransferase 76B1-like | XM_022157831.1 |
| Cajanus cajan | UDP-glycosyltransferase 76F1-like | XM_020349146.1 |
| Gossypium hirsutum | UDP-glycosyltransferase 76E2-like | XM_016889699.1 |
| Gossypium hirsutum | UDP-glycosyltransferase 76E2-like | XM_016889698.1 |
| Gossypium hirsutum | UDP-glycosyltransferase 76E2-like | XM_016852910.1 |
| Gossypium hirsutum | UDP-glycosyltransferase 76E2-like | XM_016852909.1 |
| Populus trichocarpa | UDP-glucuronsyl/glucosyl transferase family protein | XM_002314105.1 |
| Gossypium hirsutum | UGT2 | EF408256.1 |
| Gossypium hirsutum | UDP-glycosyltransferase 76F1-like | XM_016876371.1 |
| Hevea brasiliensis | UDP-glycosyltransferase 76B1-like | XM_021819870.1 |
| Gossypium arboreum | UDP-glucose iridoid glucosyltransferase-like | XM_017791593.1 |
| Gossypium arboreum | UDP-glucose iridoid glucosyltransferase-like | XM_017791592.1 |
| Gossypium hirsutum | UDP-glucose iridoid glucosyltransferase-like | XM_016889700.1 |
| Gossypium hirsutum | UDP-glucose iridoid glucosyltransferase-like | XM_016862869.1 |
| Gossypium raimondii | UDP-glucose iridoid glucosyltransferase-like | XM_012588601.1 |
| Helianthus annuus | UDP-glycosyltransferase 76B1-like | XM_022159431.1 |
| Helianthus annuus | UDP-glycosyltransferase 76B1-like | XM_022157847.1 |
| Helianthus annuus | UDP-glycosyltransferase 76B1-like | XM_022157834.1 |
| Gossypium hirsutum | UDP-glycosyltransferase 76F1-like | XM_016886796.1 |
| Durio zibethinus | UDP-glucose iridoid glucosyltransferase-like | XM_022875537.1 |
| Durio zibethinus | UDP-glucose iridoid glucosyltransferase-like | XM_022875536.1 |
| Vitis vinifera | UDP-glycosyltransferase 76C4 | XM_002281288.4 |
| Vitis vinifera | UDP-glycosyltransferase 76C4 | XM_010660195.2 |
| Daucus carota | UDP-glycosyltransferase 76C2-like | XM_017378693.1 |
| Ziziphus jujube | UDP-glycosyltransferase 76F1-like | XM_016021850.1 |
| Gossypium hirsutum | UDP-glucose iridoid glucosyltransferase-like | XM_016829458.1 |
| Gossypium hirsutum | UDP-glucose iridoid glucosyltransferase-like | XM_016829457.1 |
| Gossypium hirsutum | UDP-glucose iridoid glucosyltransferase-like | XM_016829456.1 |
| Gossypium hirsutum | UDP-glucose iridoid glucosyltransferase-like | XM_016829455.1 |
| Gossypium raimondii | UDP-glucose iridoid glucosyltransferase-like | XM_012588600.1 |
| Gossypium raimondii | UDP-glucose iridoid glucosyltransferase-like | XM_012588598.1 |
| Gossypium raimondii | UDP-glycosyltransferase 76E2-like | XM_012619941.1 |
| Gossypium raimondii | UDP-glycosyltransferase 76E2-like | XM_012619935.1 |
| Phaseolus vulgaris | hypothetical protein | XM_007163430.1 |
| Lobelia erinus | putative glycosyltransferase | AB221004.1 |
| Lobelia erinus | putative glycosyltransferase | AB221003.1 |
| Lobelia erinus | putative glycosyltransferase | AB221002.1 |
| Gossypium hirsutum | UDP-glucose iridoid glucosyltransferase-like | NM_001327324.1 |
| Quercus suber | UDP-glucose iridoid glucosyltransferase-like | XM_024028747.1 |
| Arachis ipaensis | UDP-glycosyltransferase 76F1-like | XM_016327036.2 |
| Arachis ipaensis | UDP-glycosyltransferase 76F1-like | XM_016326974.2 |
| Arachis ipaensis | UDP-glycosyltransferase 76F1-like | XM_016326973.2 |
| Theobroma cacao | UDP-glycosyltransferase 76F1 | XM_018128673.1 |
| Theobroma cacao | genomic DNA | LT594797.1 |
| Gossypium hirsutum | UDP-glucose iridoid glucosyltransferase-like | XM_016896239.1 |
| Populus euphratica | UDP-glycosyltransferase 76E2-like | XM_011033910.1 |
| Populus euphratica | UDP-glycosyltransferase 76E2-like | XM_011033908.1 |
| Medicago truncatula | UDP-glucosyltransferase family protein | XM_003600767.2 |
| Medicago truncatula | genomic DNA | AC229719.7 |
| Medicago truncatula | genomic DNA | CT963078.4 |
| Quercus suber | genomic DNA | XM_024015698.1 |
| Daucus carota | UDP-glycosyltransferase 76G1-like | XM_017401080.1 |
| Vigna radiata | UDP-glycosyltransferase 76B1 | XM_014640261.2 |
| Populus euphratica | UDP-glycosyltransferase 76C2-like | XM_011037728.1 |

TABLE 9-continued

| Source Organism | Sequence Description | GI Number |
|---|---|---|
| | UDP-Glycosyltransferase Genes | |
| Lobelia erinus | putative glycosyltransferase | AB220999.1 |
| Latuca sativa | UDP-glycosyltransferase 76B1-like | XM_023907991.1 |
| Helianthus annuus | UDP-glycosyltransferase 76B1-like | XM_022125894.1 |
| Helianthus annuus | UDP-glycosyltransferase 76B1-like | XM_022118156.1 |
| Manihot esculenta | UDP-glucose iridoid glucosyltransferase-like | XM_021743560.1 |
| Manihot esculenta | UDP-glucose iridoid glucosyltransferase-like | XM_021736119.1 |
| Jatropha curcas | UDP-glycosyltransferase 76F1 | XM_012232803.2 |
| Latuca sativa | UDP-glycosyltransferase 76B1-like | XM_023907995.1 |
| Latuca sativa | UDP-glycosyltransferase 76B1-like | XM_023907994.1 |
| Prunus avium | UDP-glycosyltransferase 76E2-like | XM_021973128.1 |
| Gossypium raimondii | UDP-glucose iridoid glucosyltransferase-like | XM_012586838.1 |
| Populus euphratica | UDP-glycosyltransferase 76F1-like | XM_011037730.1 |
| Lobelia erinus | putative glycosyltransferase | AB221001.1 |
| Lobelia erinus | putative glycosyltransferase | AB221000.1 |

In one aspect, the gene that expresses O-linked acetyl-glucosamine transferase (OGT) is isolated from an animal. In another aspect, the animal is a mammal such as, for example, the thirteen-lined ground squirrel, domestic cow, domestic sheep, domestic cat or dog, water buffalo, domestic yak, olive baboon, chimpanzee, human, bonobo, gorilla, polar bear, sooty mangabey, drill, giant panda, Angola colobus, crab-eating macaque, goat, rhesus macaque, Southern pig-tailed macaque, the domestic horse, or another mammal. In a further aspect, the gene that expresses O-linked acetylglucosamine transferase has SEQ ID NO. 13 or at least 70% homology thereto, at least 75% homology thereto, at least 80% homology thereto, at least 85% homology thereto, at least 90% homology thereto, or at least 95% homology thereto.

Other sequences expressing O-linked acetylglucosamine transferase or related or homologous genes can be identified in a database such as, for example, GenBank. In one aspect, sequences useful herein include those with the GI numbers listed in Table 10.

TABLE 10

| Source Organism | Sequence Description | GI Number |
|---|---|---|
| | O-Linked Acetylglucosamine Transferase Genes | |
| Ictidomys tridecemilineatus | O-linked N-acetylglucosamine transferase | XM_021719915.1 |
| Ictidomys tridecemilineatus | O-linked N-acetylglucosamine transferase | XM_005339941.2 |
| Ictidomys tridecemilineatus | O-linked N-acetylglucosamine transferase | XM_005339942.2 |
| Bubalus bubalis | O-linked N-acetylglucosamine transferase | XM_006050820.1 |
| Bos mutus | O-linked N-acetylglucosamine transferase | XM_005900810.2 |
| Bubalus bubalis | O-linked N-acetylglucosamine transferase | NM_001290907.1 |
| Bos mutus | O-linked N-acetylglucosamine transferase | XM_005900811.2 |
| Papio anubis | O-linked N-acetylglucosamine transferase | XM_003917862.3 |
| Bos taurus | O-linked N-acetylglucosamine transferase | XM_005228027.3 |
| Ursus maritimus | O-linked N-acetylglucosamine transferase | XM_008712243.1 |
| Papio Anubis | O-linked N-acetylglucosamine transferase | XM_003917863.4 |
| Ursus maritimus | O-linked N-acetylglucosamine transferase | XM_008712244.1 |

TABLE 10-continued

O-Linked Acetylglucosamine Transferase Genes

| Source Organism | Sequence Description | GI Number |
|---|---|---|
| Bos taurus | O-linked N-acetylglucosamine transferase | NM_001098070.2 |
| Bos taurus | O-linked N-acetylglucosamine transferase | BC140542.1 |
| Cercocebus atys | O-linked N-acetylglucosamine transferase | XM_012060760.1 |
| Cercocebus atys | O-linked N-acetylglucosamine transferase | XM_012060761.1 |
| Mandrillus leucophaeus | O-linked N-acetylglucosamine transferase | XM_011992070.1 |
| Mandrillus leucophaeus | O-linked N-acetylglucosamine transferase | XM_011992071.1 |
| Ailuropoda melanoleuca | O-linked N-acetylglucosamine transferase | XM_002930577.3 |
| Macaca fascicularis | O-linked N-acetylglucosamine transferase | XM_005593919.1 |
| Colobus angolensis | O-linked N-acetylglucosamine transferase | XM_011943084.1 |
| Ailuropoda melanoleuca | O-linked N-acetylglucosamine transferase | XM_002930576.3 |
| Macaca fascicularis | O-linked N-acetylglucosamine transferase | XM_005593920.2 |
| Capra hircus | O-linked N-acetylglucosamine transferase | XM_013976396.2 |
| Macaca mulatta | O-linked N-acetylglucosamine transferase | XM_015127666.1 |
| Ovis aries | O-linked N-acetylglucosamine transferase | XM_004022178.3 |
| Ovis aries | O-linked N-acetylglucosamine transferase | XM_012142301.2 |
| Macaca nemestrina | O-linked N-acetylglucosamine transferase | XM_011732741.1 |
| Colobus angolensis | O-linked N-acetylglucosamine transferase | XM_011943085.1 |
| Rhinopithecus roxellana | O-linked N-acetylglucosamine transferase | XM_010366585.1 |
| Capra hircus | O-linked N-acetylglucosamine transferase | XM_013976398.2 |
| Marmota marmota | UDP-N-acetylglucosamine-peptide N-acetylglucosaminyltransferase pseudogene | XR 001502441.1 |
| Macaca mulatta | O-linked N-acetylglucosamine transferase | XM_015127667.1 |
| Ovis aries | O-linked N-acetylglucosamine transferase | XM_004022177.3 |
| Ovis aries | O-linked N-acetylglucosamine transferase | XM_012142302.2 |
| Macaca nemestrina | O-linked N-acetylglucosamine transferase | XM_011732742.1 |
| Equus caballus | O-linked N-acetylglucosamine transferase | XM_001493372.5 |
| Canis lupus familiaris | O-linked N-acetylglucosamine transferase | XM_844299.5 |
| Rhinopithecus roxellana | O-linked N-acetylglucosamine transferase | XM_010366586.1 |
| Chlorocebus sabaeus | O-linked N-acetylglucosamine transferase | XM_007992035.1 |
| Canis lupus familiaris | O-linked N-acetylglucosamine transferase | XM_538075.6 |
| Chlorocebus sabaeus | O-linked N-acetylglucosamine transferase | XM_007992036.1 |
| Equus caballus | O-linked N-acetylglucosamine transferase | XM_005614262.3 |
| Felis catus | O-linked N-acetylglucosamine transferase | XM_004000621.5 |
| Odocoileus virgianus | O-linked N-acetylglucosamine transferase | XM_020882917.1 |
| Odocoileus virgianus | O-linked N-acetylglucosamine transferase | XM_020882916.1 |
| Panthera pardus | O-linked N-acetylglucosamine transferase | XM_019428710.1 |
| Oryctolagus cuniculus | O-linked N-acetylglucosamine transferase | XM_002720103.3 |
| Equus caballus | O-linked N-acetylglucosamine transferase | XM_001493388.5 |

O-Linked Acetylglucosamine Transferase Genes

| Source Organism | Sequence Description | GI Number |
|---|---|---|
| Felis catus | O-linked N-acetylglucosamine transferase | XM_004000622.5 |
| Odocoileus virgianus | O-linked N-acetylglucosamine transferase | XM_020882919.1 |
| Odocoileus virgianus | O-linked N-acetylglucosamine transferase | XM_020882918.1 |
| Panthera pardus | O-linked N-acetylglucosamine transferase | XM_019428712.1 |
| Oryctolagus cuniculus | O-linked N-acetylglucosamine transferase | XM_002720102.3 |
| Pongo abelii | O-linked N-acetylglucosamine transferase | XM_024240358.1 |
| Gorilla gorilla | O-linked N-acetylglucosamine transferase | XM_004064365.2 |
| Panthera tigris | O-linked N-acetylglucosamine transferase | XM_007089115.2 |
| Callithrix jacchus | O-linked N-acetylglucosamine transferase | XM_002762977.2 |
| Leptonychotes weddellii | O-linked N-acetylglucosamine transferase | XM_006749440.1 |
| Pantholops hodgsonii | O-linked N-acetylglucosamine transferase | XM_005954790.1 |
| Pongo abelii | O-linked N-acetylglucosamine transferase | XM_024240359.1 |
| Gorilla gorilla | O-linked N-acetylglucosamine transferase | XM_004064366.2 |
| Callithrix jacchus | O-linked N-acetylglucosamine transferase | XM_002762978.3 |
| Panthera tigris | O-linked N-acetylglucosamine transferase | XM_007089116.2 |
| Leptonychotes weddellii | O-linked N-acetylglucosamine transferase | XM_006749441.1 |
| Pantholops hodgsonii | O-linked N-acetylglucosamine transferase | XM_005954791.1 |
| Pan troglodytes | O-linked N-acetylglucosamine transferase | XM_016943032.1 |
| Equus asinus | O-linked N-acetylglucosamine transferase | XM_014837684.1 |
| Pan paniscus | O-linked N-acetylglucosamine transferase | XM_003820131.2 |
| Homo sapiens | clone | AL833085.2 |
| Piliocolobus tephrosceles | O-linked N-acetylglucosamine transferase | XM_023201890.1 |
| Pan troglodytes | O-linked N-acetylglucosamine transferase | XM_016943033.1 |
| Pan paniscus | O-linked N-acetylglucosamine transferase | XM_003820132.2 |
| Piliocolobus tephrosceles | O-linked N-acetylglucosamine transferase | XM_023201891.1 |
| Equus asinus | O-linked N-acetylglucosamine transferase | XM_014837686.1 |
| Orycteropus afer | O-linked N-acetylglucosamine transferase | XM_007959000.1 |
| Homo sapiens | O-linked N-acetylglucosamine transferase | NM_181672.2 |
| Pongo abelii | clone | NM_001133824.1 |
| Homo sapiens | genomic DNA | BX537844.1 |
| Homo sapiens | O-linked N-acetylglucosamine transferase | BC038180.1 |
| Equus asinus | O-linked N-acetylglucosamine transferase | XM_014837685.1 |
| Orycteropus afer | O-linked N-acetylglucosamine transferase | XM_007959001.1 |
| Homo sapiens | O-linked N-acetylglucosamine transferase | NM_181673.2 |
| Homo sapiens | O-linked N-acetylglucosamine transferase | BC014434.1 |
| Delphinapterus leucas | O-linked N-acetylglucosamine transferase | XM_022560995.1 |
| Lonchura striata | O-linked N-acetylglucosamine transferase | XM_021534535.1 |
| Ceratotherium simum | O-linked N-acetylglucosamine transferase | XM_014794874.1 |
| Ceratotherium simum | O-linked N-acetylglucosamine transferase | XM_004439842.2 |

TABLE 10-continued

| O-Linked Acetylglucosamine Transferase Genes | | |
| --- | --- | --- |
| Source Organism | Sequence Description | GI Number |
| Microcebus murinus | O-linked N-acetylglucosamine transferase | XM_012736183.1 |
| Saimiri boliviensis | O-linked N-acetylglucosamine transferase | XM_003943099.2 |
| Eptesicus fuscus | O-linked N-acetylglucosamine transferase | XM_008157607.1 |
| Synthetic construct | clone | DQ896848.2 |
| Synthetic construct | clone | DQ893623.2 |
| Peromyscus maniculatus | O-linked N-acetylglucosamine transferase | XM_006981123.2 |
| Peromyscus maniculatus | O-linked N-acetylglucosamine transferase | XM_015999616.1 |
| Delphinapterus leucas | O-linked N-acetylglucosamine transferase | XM_022560996.1 |
| Lonchura striata | O-linked N-acetylglucosamine transferase | XM_021534536.1 |
| Ceratotherium simum | O-linked N-acetylglucosamine transferase | XM_004439843.2 |
| Microcebus murinus | O-linked N-acetylglucosamine transferase | XM_012736184.1 |
| Saimiri boliviensis | O-linked N-acetylglucosamine transferase | XM_003943100.2 |
| Homo sapiens | O-linked N-acetylglucosamine transferase | EAX05286.1 |

In another aspect, the DNA construct has the following genetic components: a) a gene that expresses 4-hydroxy-3-methylbut-2-enyl diphosphate reductase, b) a gene that expresses hexokinase, c) a gene that expresses a heat shock protein, d) a gene that expresses a geranylgeranyl pyrophosphate synthase, and e) a gene that expresses 1-deoxy-D-xylulose-5-phosphate synthase.

In an alternative aspect, the DNA construct has the following genetic components: a) a gene that expresses mevalonate-5-kinase, b) a gene that expresses isopentenyl pyrophosphate isomerase, c) a gene that expresses mevalonate pyrophosphate decarboxylase, d) a gene that expresses hexokinase, e) a gene that expresses a heat shock protein, f) a gene that expresses a geranylgeranyl pyrophosphate synthase, and g) a gene that expresses 1-deoxy-D-xylulose-5-phosphate synthase.

In another aspect, the DNA construct has the following genetic components: a) a gene that expresses mevalonate-5-kinase, b) a gene that expresses isopentenyl pyrophosphate isomerase, c) a gene that expresses mevalonate pyrophosphate decarboxylase, d) a gene that expresses hexokinase, e) a gene that expresses a heat shock protein, f) a gene that expresses a geranylgeranyl pyrophosphate synthase, g) a gene that expresses a UDP glycosyltransferase, and h) a gene that expresses 1-deoxy-D-xylulose-5-phosphate synthase.

In yet another aspect, the DNA construct has the following genetic components: a) a gene that expresses mevalonate-5-kinase, b) a gene that expresses isopentenyl pyrophosphate isomerase, c) a gene that expresses mevalonate pyrophosphate decarboxylase, d) a gene that expresses hexokinase, e) a gene that expresses a heat shock protein, f) a gene that expresses a geranylgeranyl pyrophosphate synthase, g) a gene that expresses an O-linked acetylglucosamine transferase, and h) a gene that expresses 1-deoxy-D-xylulose-5-phosphate synthase.

In still another aspect, the DNA construct has the following genetic components: a) a gene that expresses mevalonate-5-kinase, b) a gene that expresses isopentenyl pyrophosphate isomerase, c) a gene that expresses mevalonate pyrophosphate decarboxylase, d) a gene that expresses hexokinase, e) a gene that expresses an O-linked acetylglucosamine transferase, f) a gene that expresses a geranylgeranyl pyrophosphate synthase, g) a gene that expresses and UDP glycosyltransferase, and h) a gene that expresses 1-deoxy-D-xylulose-5-phosphate synthase.

In another aspect, said construct further includes a) a promoter, b) a terminator or stop sequence, c) a gene that confers resistance to an antibiotic (a "selective marker"), d) a reporter protein, or a combination thereof.

In one aspect, the construct includes a regulatory sequence. In a further aspect, the regulatory sequence is already incorporated into a vector such as, for example, a plasmid, prior to genetic manipulation of the vector. In another aspect, the regulatory sequence can be incorporated into the vector through the use of restriction enzymes or any other technique known in the art.

In one aspect, the regulatory sequence is a promoter. The term "promoter" refers to a DNA sequence capable of controlling the expression of a coding sequence. In another aspect, the coding sequence to be controlled is located 3' to the promoter. In another aspect, the promoter is derived from a native gene. In an alternative aspect, the promoter is composed of multiple elements derived from different genes and/or promoters. A promoter can be assembled from elements found in nature, from artificial and/or synthetic elements, or from a combination thereof. It is understood by those skilled in the art that different promoters can direct the expression of a gene in different tissues or cell types, at different stages of development, in response to different environmental or physiological conditions, and/or in different species. In one aspect, the promoter functions as a switch to activate the expression of a gene.

In one aspect, the promoter is "constitutive." A constitutive promoter is a promoter that causes a gene to be expressed in most cell types at most times. In another aspect, the promoter is "regulated." A regulated promoter is a promoter that becomes active in response to a specific stimulus. A promoter may be regulated chemically, such as, for example, in response to the presence or absence of a particular metabolite (e.g., lactose or tryptophan), a metal ion, a molecule secreted by a pathogen, or the like. A promoter also may be regulated physically, such as, for example, in response to heat, cold, water stress, salt stress, oxygen concentration, illumination, wounding, or the like.

Promoters that are useful to drive expression of the nucleotide sequences described herein are numerous and familiar to those skilled in the art. Suitable promoters include, but are not limited to, the following: T3 promoter, T7 promoter, an iron promoter, and GAL1 promoter. In a further aspect, the promoter is a native part of the vector used herein. Variants of these promoters are also contemplated. The skilled artisan will be able to use site-directed mutagenesis and/or other mutagenesis techniques to modify the promoters to promote more efficient function. The promoter may be positioned, for example, from 10-100 nucleotides from a ribosomal binding site.

In one aspect, the promoter is a GAL1 promoter. In another aspect, the GAL1 promoter is native to the plasmid used to create the vector. In another aspect, a GAL1 promoter is positioned before the a gene that expresses hexokinase, the gene that expresses a heat shock protein, the gene that expresses geranylgeranyl pyrophosphate synthase 2, the gene that expresses 1-deoxy-D-xylulose-5-phosphate synthase, the a gene that expresses 4-hydroxy-3-methylbut-2-enyl diphosphate reductase, the gene that expresses mevalonate-5-kinase, the gene that expresses isopentenyl pyrophosphate isomerase, the gene that expresses mevalonate pyrophosphate decarboxylase, the gene that expresses a UDP-glycosyltransferase, the gene that expresses an O-linked acetylglucosamine transferase, or any combination thereof. In another aspect, the promoter is a GAL1 promoter obtained from or native to the pYES2 plasmid.

In another aspect, the regulatory sequence is a terminator or stop sequence. As used herein, a terminator is a sequence of DNA that marks the end of a gene or operon to be transcribed. In a further aspect, the terminator is an intrinsic terminator or a Rho-dependent transcription terminator. As used herein, an intrinsic terminator is a sequence wherein a hairpin structure can form in the nascent transcript that disrupts the mRNA/DNA/RNA polymerase complex. As used herein, a Rho-dependent transcription terminator requires a Rho factor protein complex to disrupt the mRNA/ DNA/RNA polymerase complex. In one aspect, the terminator is a T7 terminator. In an alternative aspect, the terminator is a CYC1 terminator obtained from or native to the pYES2 plasmid.

In a further aspect, the regulatory sequence includes both a promoter and a terminator or stop sequence. In a still further aspect, the regulatory sequence can include multiple promoters or terminators. Other regulatory elements, such as enhancers, are also contemplated. Enhancers may be located from about 1 to about 2000 nucleotides in the 5' direction from the start codon of the DNA to be transcribed, or may be located 3' to the DNA to be transcribed. Enhancers may be "cis-acting," that is, located on the same molecule of DNA as the gene whose expression they affect.

In one aspect, when the vector is a plasmid, the plasmid can also contain a multiple cloning site or polylinker. In a further aspect, the polylinker contains recognition sites for multiple restriction enzymes. The polylinker can contain up to 2, 3, 4, 5, 6, 7, 8, 9, 10, 11, 12, 13, 14, 15, 16, 17, 18, 19, 20, or more than 20 recognition sites for restriction enzymes. Further, restriction sites may be added, disabled, or removed as required, using techniques known in the art. In one aspect, the plasmid contains restriction sites for any known restriction enzyme such as, for example, HindIII, KpnI, SacI, BamHI, BstXI, EcoRI, BasBI, NotI, XhoI, SphI, XbaI, ApaI, SalI, ClaI, EcoRV, PstI, SmaI, XmaI, SpeI, EagI, SacII, or any combination thereof. In a further aspect, the plasmid contains more than one recognition site for the same restriction enzyme.

In one aspect, the restriction enzyme can cleave DNA at a palindromic or an asymmetrical restriction site. In a further aspect, the restriction enzyme cleaves DNA to leave blunt ends; in an alternative aspect, the restriction enzyme cleaves DNA to leave "sticky" or overhanging ends. In another aspect, the enzyme can cleave DNA to a distance of from 20 bases to over 1000 bases away from the restriction site. A variety of restriction enzymes are commercially available and their recognition sequences, as well as instructions for use (e.g., amount of DNA needed, precise volumes or reagents, purification techniques, as well as information about salt concentration, pH, optimum temperature, incubation time, and the like) are provided by enzyme manufacturers.

In one aspect, a plasmid with a polylinker containing one or more restriction sites can be digested with one restriction enzyme and a nucleotide sequence of interest can be ligated into the plasmid using a commercially-available DNA ligase enzyme. Several such enzymes are available, often as kits containing all reagents and instructions required for use. In another aspect, a plasmid with a polylinker containing two or more restriction sites can be simultaneously digested with two restriction enzymes and a nucleotide sequence of interest can be ligated into the plasmid using a DNA ligase enzyme. Using two restriction enzymes provides an asymmetric cut in the DNA, allowing for insertion of a nucleotide sequence of interest in a particular direction and/or on a particular strand of the double-stranded plasmid. Since RNA synthesis from a DNA template proceeds from 5' to 3', usually starting just after a promoter, the order and direction of elements inserted into a plasmid can be especially important. If a plasmid is to be simultaneously digested with multiple restriction enzymes, these enzymes must be compatible in terms of buffer, salt concentration, and other incubation parameters.

In some aspects, prior to ligation using a ligase enzyme, a plasmid that has been digested with a restriction enzyme is treated with an alkaline phosphatase enzyme to remove 5' terminal phosphate groups. This prevents self-ligation of the plasmid and thus facilitates ligation of heterologous nucleotide fragments into the plasmid.

In one aspect, different genes can be ligated into a plasmid in one pot. In this aspect, the genes will first be digested with restriction enzymes. In certain aspects, the digestion of genes with restriction enzymes provides multiple pairs of matching 5' and 3' overhangs that will spontaneously assemble the genes in the desired order. In another aspect, the genes and components to be incorporated into a plasmid can be assembled into a single insert sequence prior to insertion into the plasmid. In a further aspect, a DNA ligase enzyme can be used to assist in the ligation process.

In another aspect, the ligation mix may be incubated in an electromagnetic chamber. In one aspect, this incubation lasts for about 1 minute, about 2 minutes, about 5 minutes, about 10 minutes, about 15 minutes, about 20 minutes, about 30 minutes, or about 1 hour.

The DNA construct described herein can be part of a vector. In a further aspect, the vector is a plasmid, a phagemid, a cosmid, a yeast artificial chromosome, a bacterial artificial chromosome, a virus, a phage, or a transposon. In general, plasmid vectors containing replicon and control sequences that are derived from species compatible with the host cell are used in connection with the hosts. The vector ordinarily carries a replication site as well as marking sequences that are capable of performing phenotypic selection in transformed cells. Plasmid vectors are well known and are commercially available. Such vectors include, but are not limited to, pWLneo, pSV2cat, pOG44, pXT1, pSG, pSVK3, pBSK, pBR322, pYES, pYES2, pBSKII, pUC, and pUC19 vectors.

Plasmids are double-stranded, autonomously-replicating, genetic elements that are not integrated into host cell chromosomes. Further, these genetic elements are usually not part of the host cell's central metabolism. In bacteria, plasmids may range from 1 kilobase (kb) to over 200 kb. Plasmids can be engineered to encode a number of useful traits including the production of secondary metabolites, antibiotic resistance, the production of useful proteins, degradation of complex molecules and/or environmental toxins, and others. Plasmids have been the subject of much research in the field of genetic engineering, as plasmids are convenient expression vectors for foreign DNA in, for example, microorganisms. Plasmids generally contain regulatory elements such as promoters and terminators and also usually have independent replication origins. Ideally, plasmids will be present in multiple copies per host cell and will contain selectable markers (such as genes for antibiotic resistance) to allow the skilled artisan to select host cells that have been successfully transfected with the plasmids (for example, by growing the host cells in a medium containing the antibiotic).

Vectors capable of high levels of expression of recombinant genes and proteins are well known in the art. Vectors useful for the transformation of a variety of host cells are common and commercially available and include. The skilled practitioner will be able to choose a plasmid based on such factors as a) the amount of nucleic acid (i.e., number of genes and other elements) to be inserted, b) the host organism, c) culture conditions for the host organism, and other related factors.

In one aspect, the vector encodes a selection marker. In a further aspect, the selection marker is a gene that confers resistance to an antibiotic. In certain aspects, during fermentation of host cells transformed with the vector, the cells are contacted with the antibiotic. For example, the antibiotic may be included in the culture medium. Cells that have not been successfully transformed cannot survive in the presence of the antibiotic; only cells containing the vector which confers antibiotic resistance can survive. Optimally, only cells containing the vector to be expressed will be cultured, as this will result in the highest production efficiency of the desired gene products (e.g., peptides). Cells that do not contain the vector would otherwise compete with transformed cells for resources. In one aspect, the antibiotic is tetracycline, neomycin, kanamycin, ampicillin, hygromycin, chloramphenicol, amphotericin B, bacitracin, carbapenem, cephalosporin, ethambutol, fluoroquinolones, isoniazid, methicillin, oxacillin, vancomycin, streptomycin, quinolines, rifampin, rifampicin, sulfonamides, cephalothin, erythromycin, streptomycin, gentamycin, penicillin, other commonly-used antibiotics, or a combination thereof.

In certain aspects, the DNA construct can include a gene that expresses a reporter protein. The selection of the reporter protein can vary. For example, the reporter protein can be a yellow fluorescent protein, a red fluorescent protein, a green fluorescent protein, or a cyan fluorescent protein. In one aspect, the reporter protein is a yellow fluorescent protein and the gene that expresses the reporter protein has SEQ ID NO. 9 or at least 70% homology thereto, at least 75% homology thereto, at least 80% homology thereto, at least 85% homology thereto, at least 90% homology thereto, or at least 95% homology thereto. The amount of fluorescence that is produced by the biological device can be correlated to the amount of DNA incorporated into the plant cells. The fluorescence produced by the device can be detected and quantified using techniques known in the art. For example, spectrofluorometers are typically used to measure fluorescence. The Examples provide exemplary procedures for measuring the amount of fluorescence as a result of the expression of DNA.

Figure 1B:
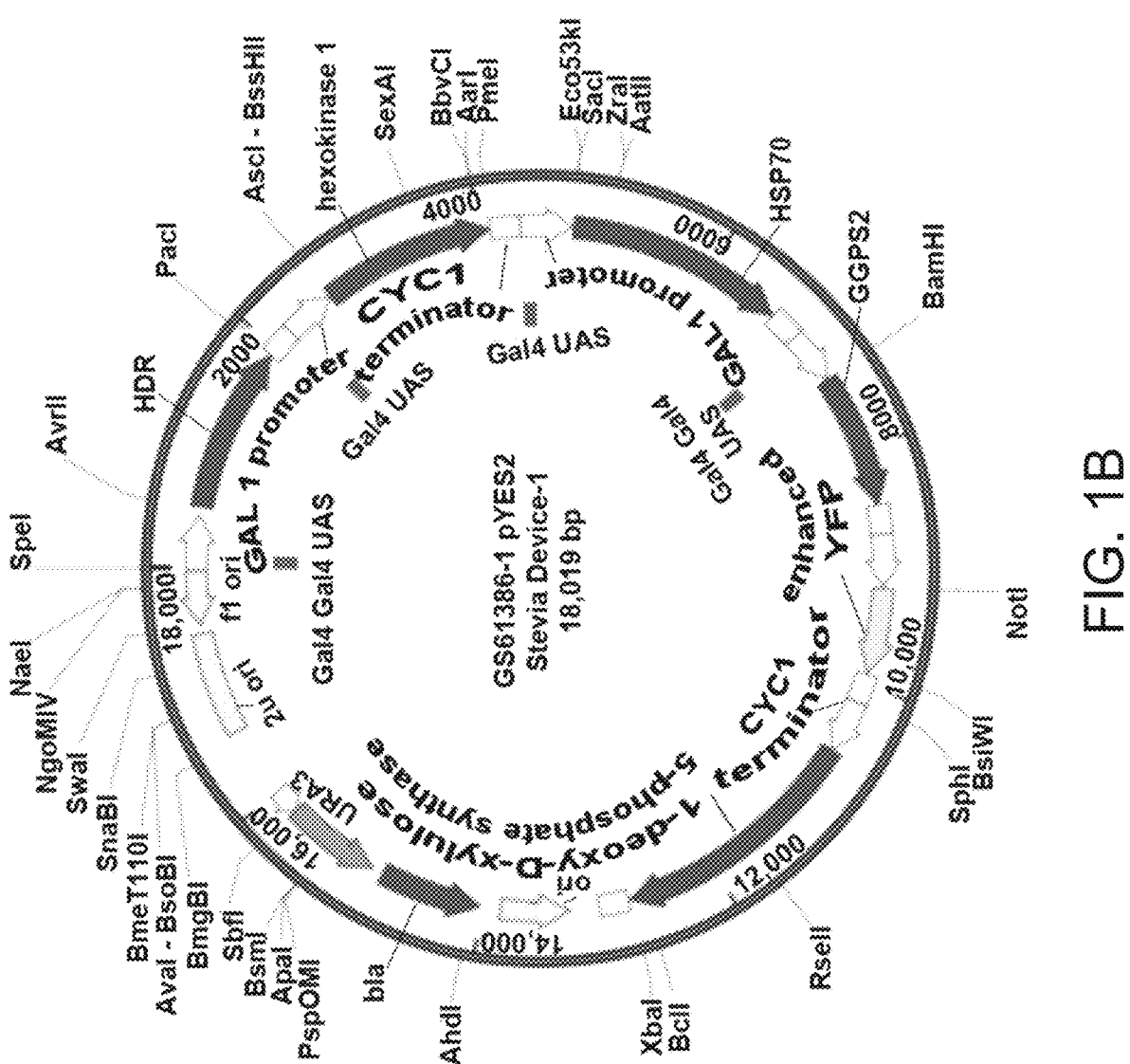

FIGS. 1A-1B provide non-limiting examples of DNA constructs described herein. In one aspect, the construct is a pYES2 plasmid having from 5' to 3' the following genetic components in the following order: (a) a gene that expresses 4-hydroxy-3-methylbut-2-enyl diphosphate reductase; (b) a gene that expresses hexokinase; (c) a gene that expresses HSP70; (d) a gene that expresses geranylgeranyl pyrophosphate synthase 2; and (e) a gene that expresses 1-deoxy-D-xylulose-5-phosphate synthase.

Figure 2A:
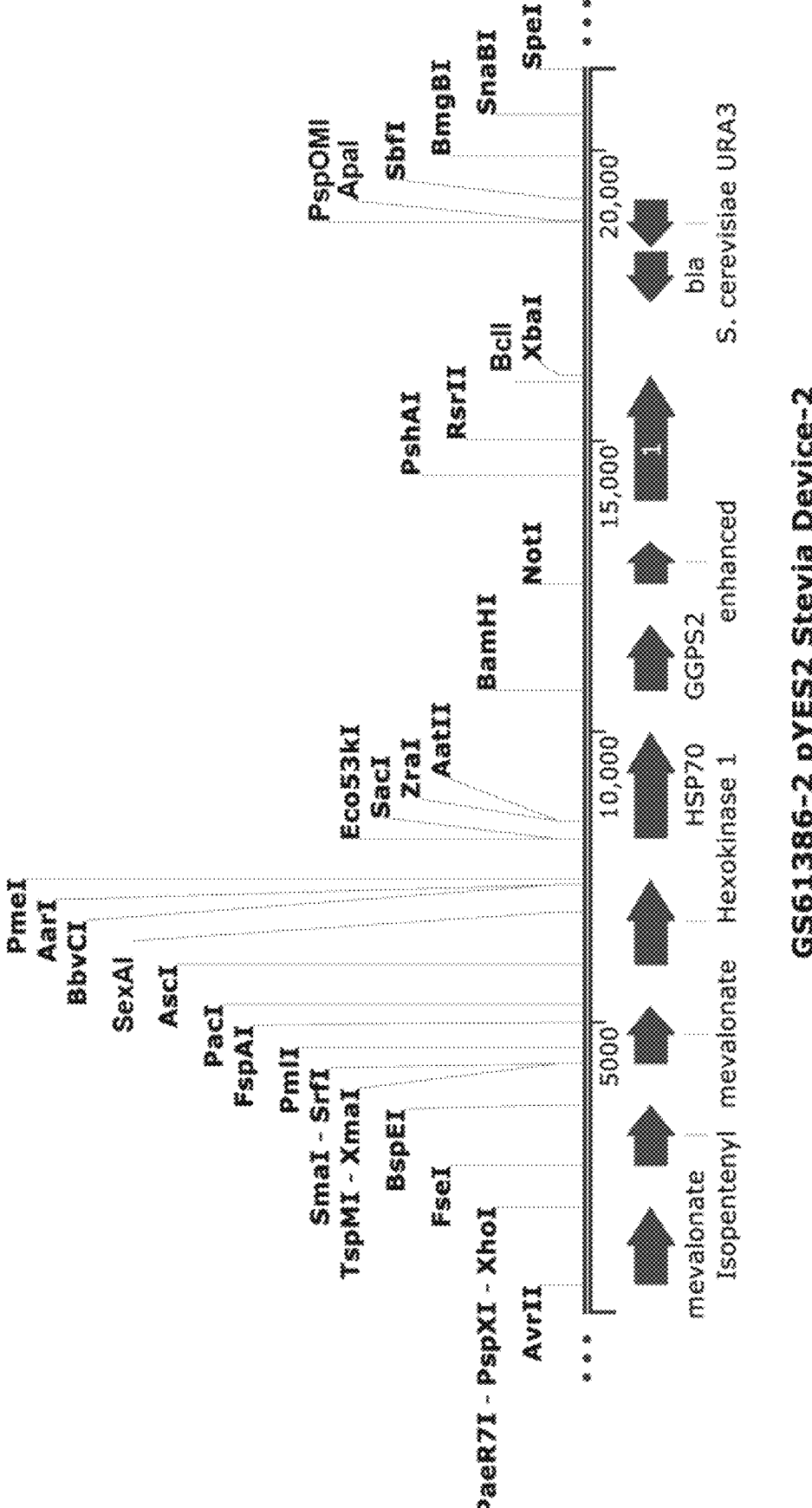
FIGS. 2A and 2B show, respectively, a linear and circular schematic of a constructed pYES2 plasmid showing the direction, placement, and size of genetic parts used of an exemplary DNA device described herein.
Figure 2B:
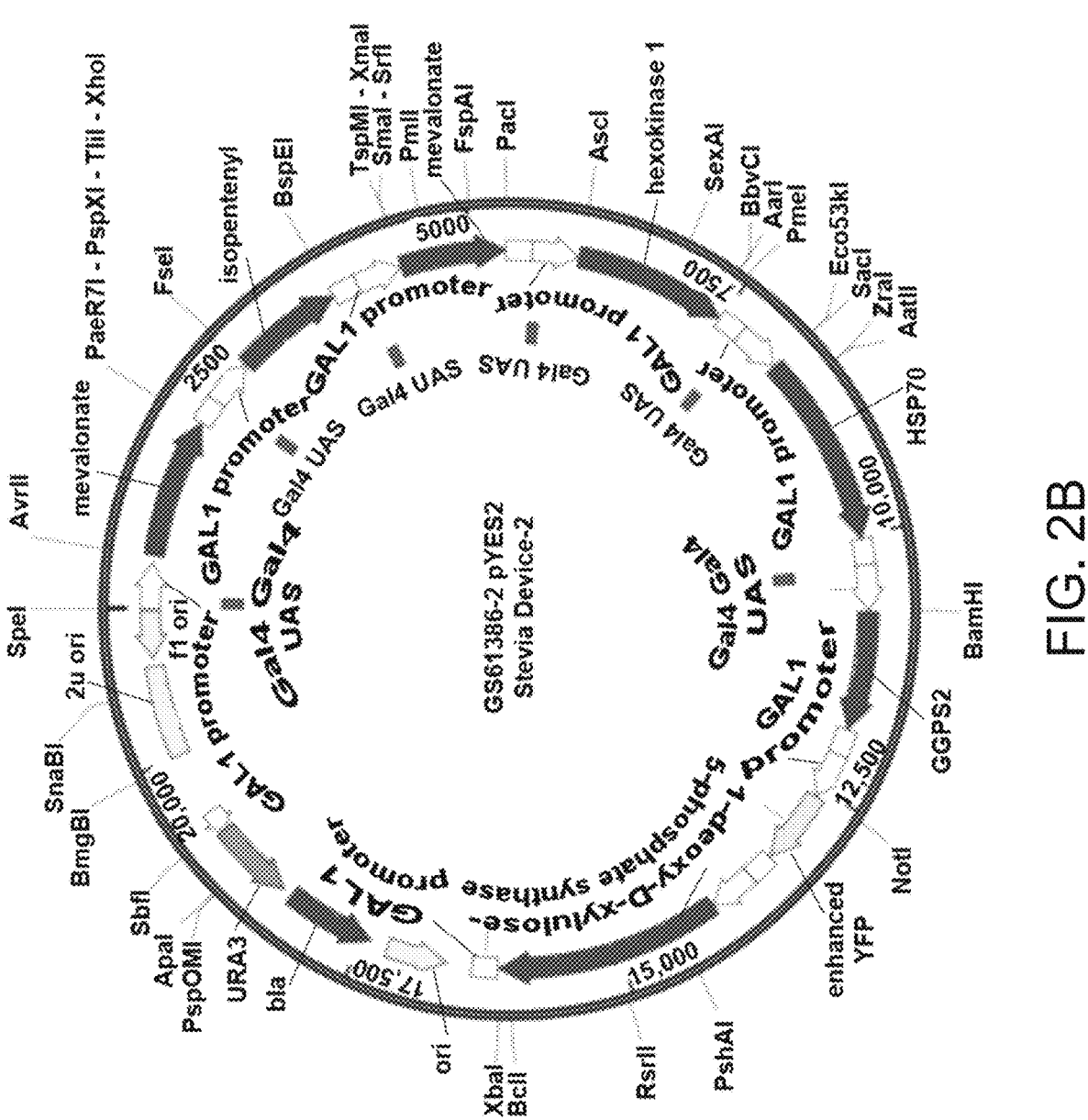

FIGS. 2A-2B provide non-limiting examples of DNA constructs described herein. In one aspect, the construct is a pYES2 plasmid having from 5' to 3' the following genetic components in the following order: (a) a gene that expresses mevalonate-5-kinase; (b) a gene that expresses isopentenyl pyrophosphate isomerase; (c) a gene that expresses mevalonate pyrophosphate decarboxylase; (d) a gene that expresses hexokinase; (e) a gene that expresses HSP70; (f)

a gene that expresses geranylgeranyl pyrophosphate synthase 2; and (g) a gene that expresses 1-deoxy-D-xylulose-5-phosphate synthase.

Figure 3A:
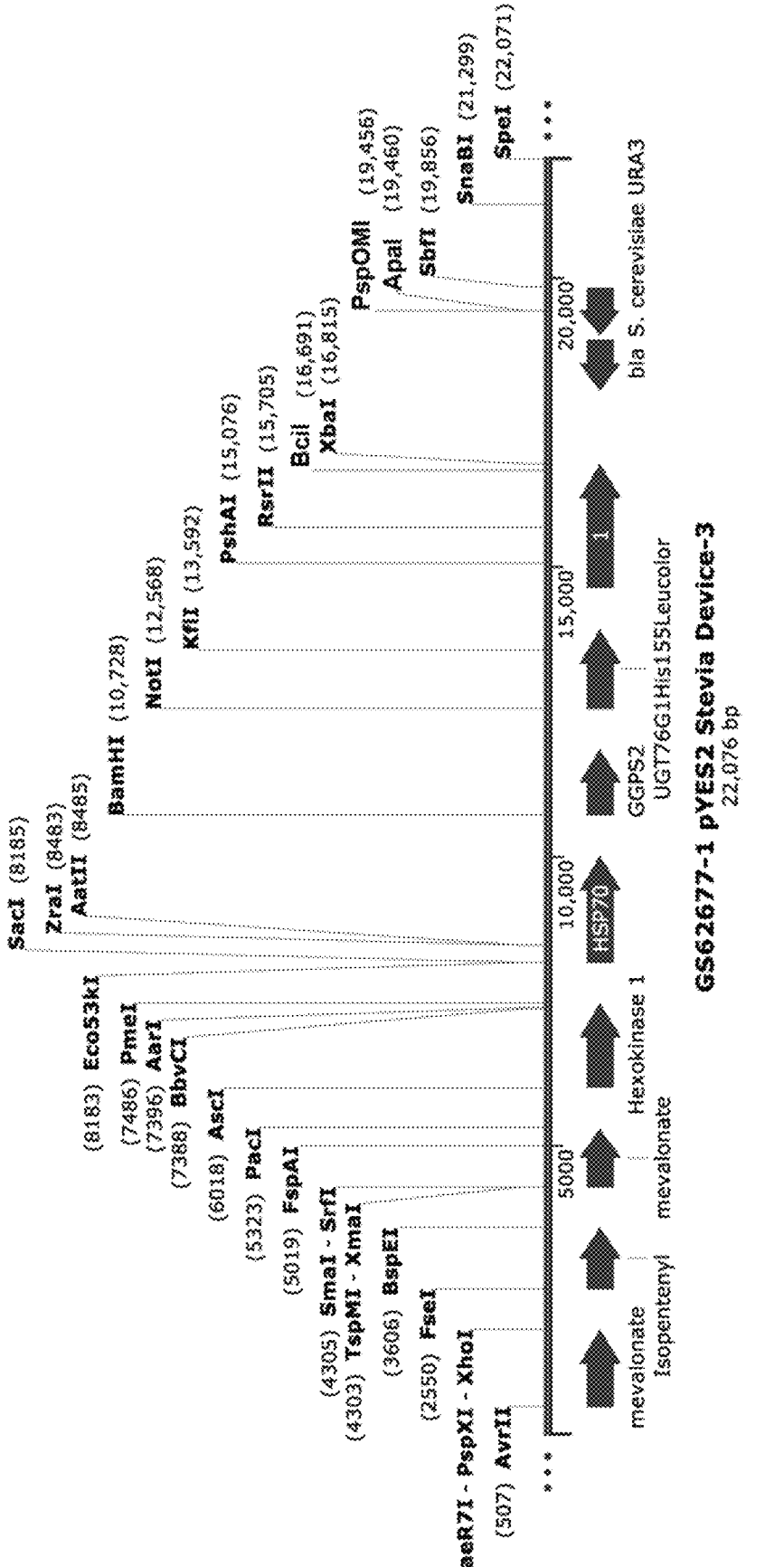
FIGS. 3A and 3B show, respectively, a linear and circular schematic of a constructed pYES2 plasmid showing the direction, placement, and size of genetic parts used of an exemplary DNA device described herein.
Figure 3B:
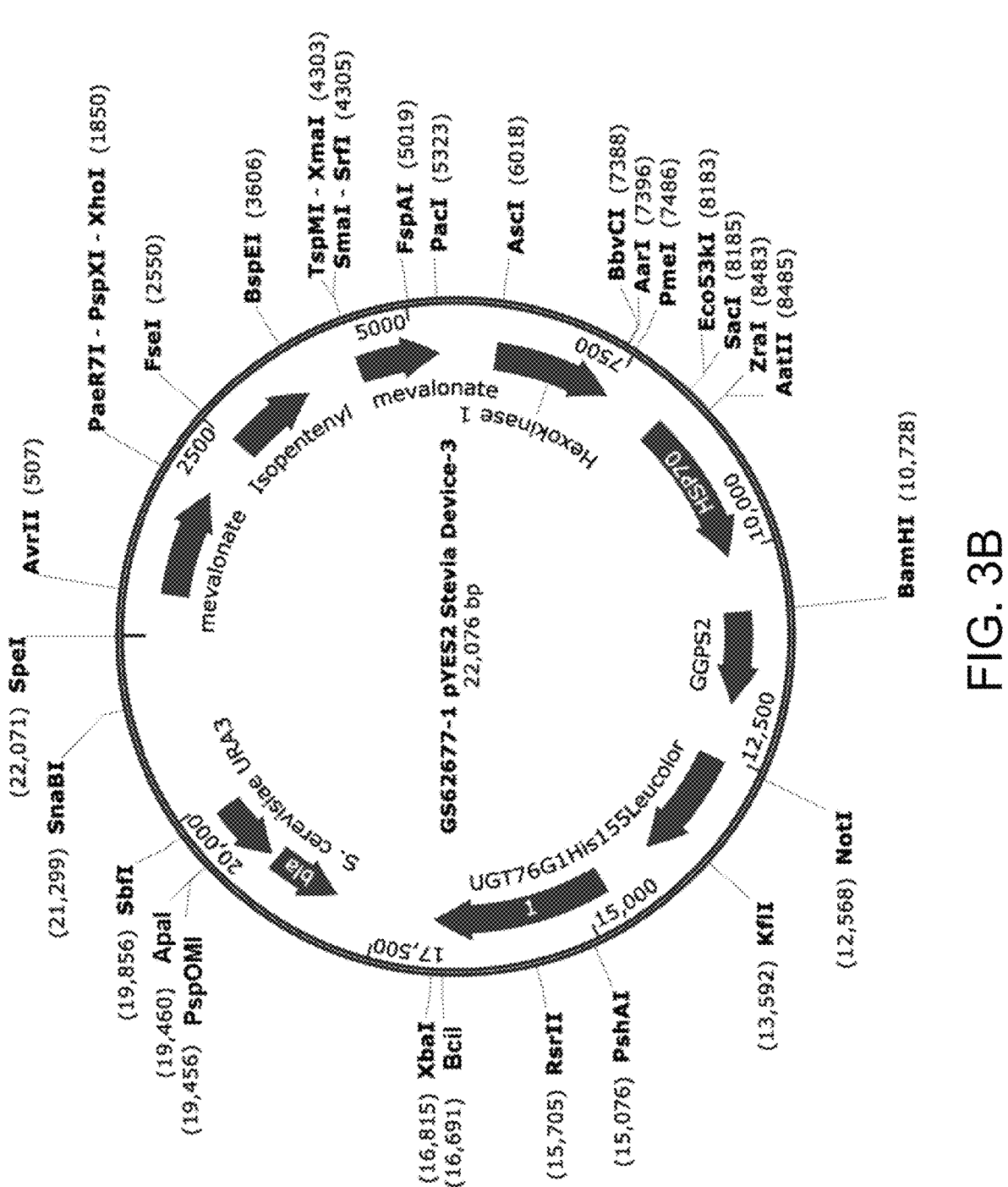

FIGS. 3A and 3B provide a non-limiting example of a DNA construct described herein. In one aspect, the construct is a pYES2 plasmid having from 5' to 3' the following genetic components in the following order: (a) a gene that expresses mevalonate-5-kinase, (b) a gene that expresses isopentenyl pyrophosphate isomerase, (c) a gene that expresses mevalonate pyrophosphate decarboxylase, (d) a gene that expresses hexokinase, (e) a gene that expresses HSP70, (f) a gene that expresses geranylgeranyl pyrophosphate synthase 2, (g) a gene that expresses $UGT76G1_{His155Leu}$, and (h) a gene that expresses 1-deoxy-D-xylulose-5-phosphate synthase.

Figure 4A:
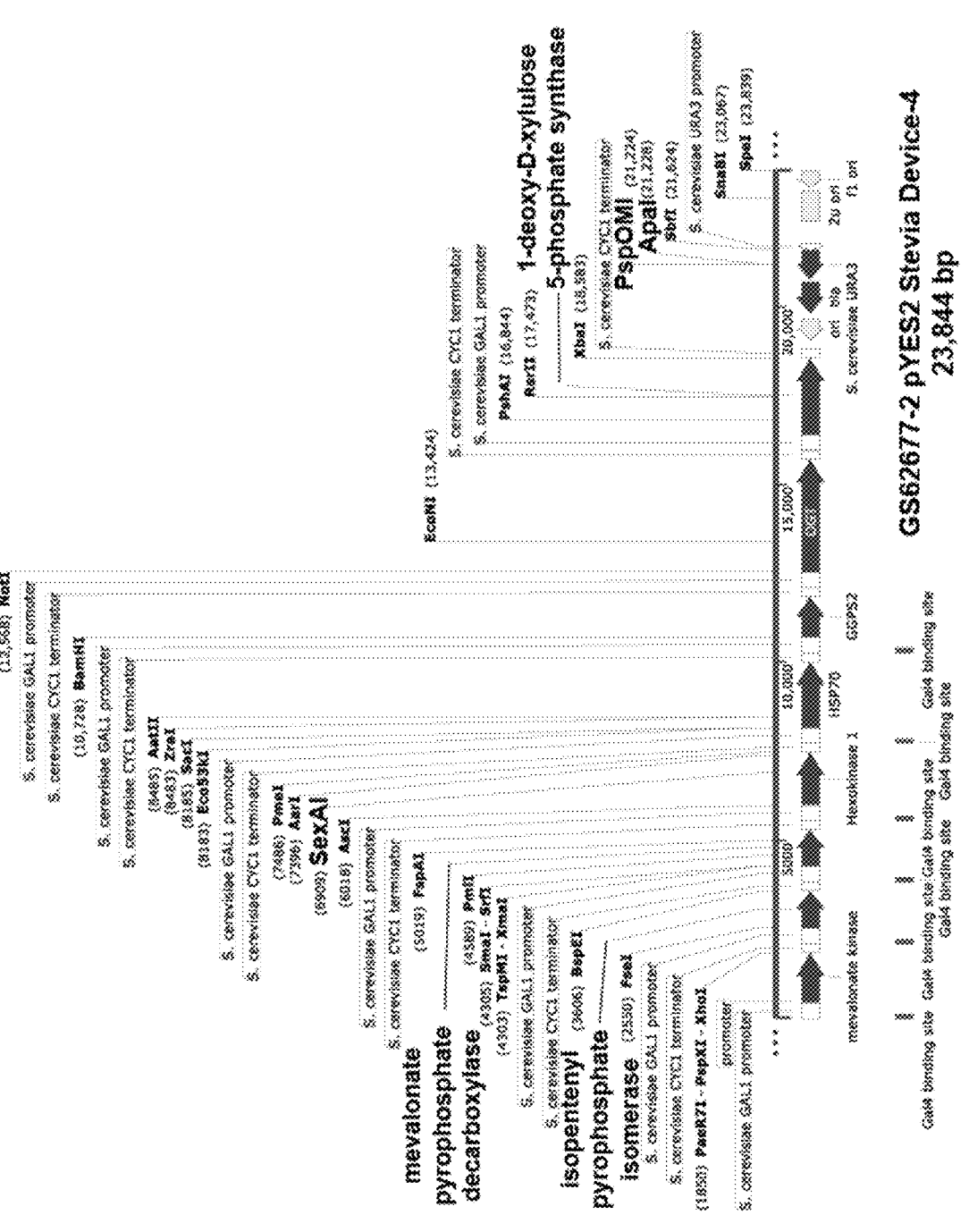
FIGS. 4A and 4B show, respectively, a linear and circular schematic of a constructed pYES2 plasmid showing the direction, placement, and size of genetic parts used of an exemplary DNA device described herein.
Figure 4B:
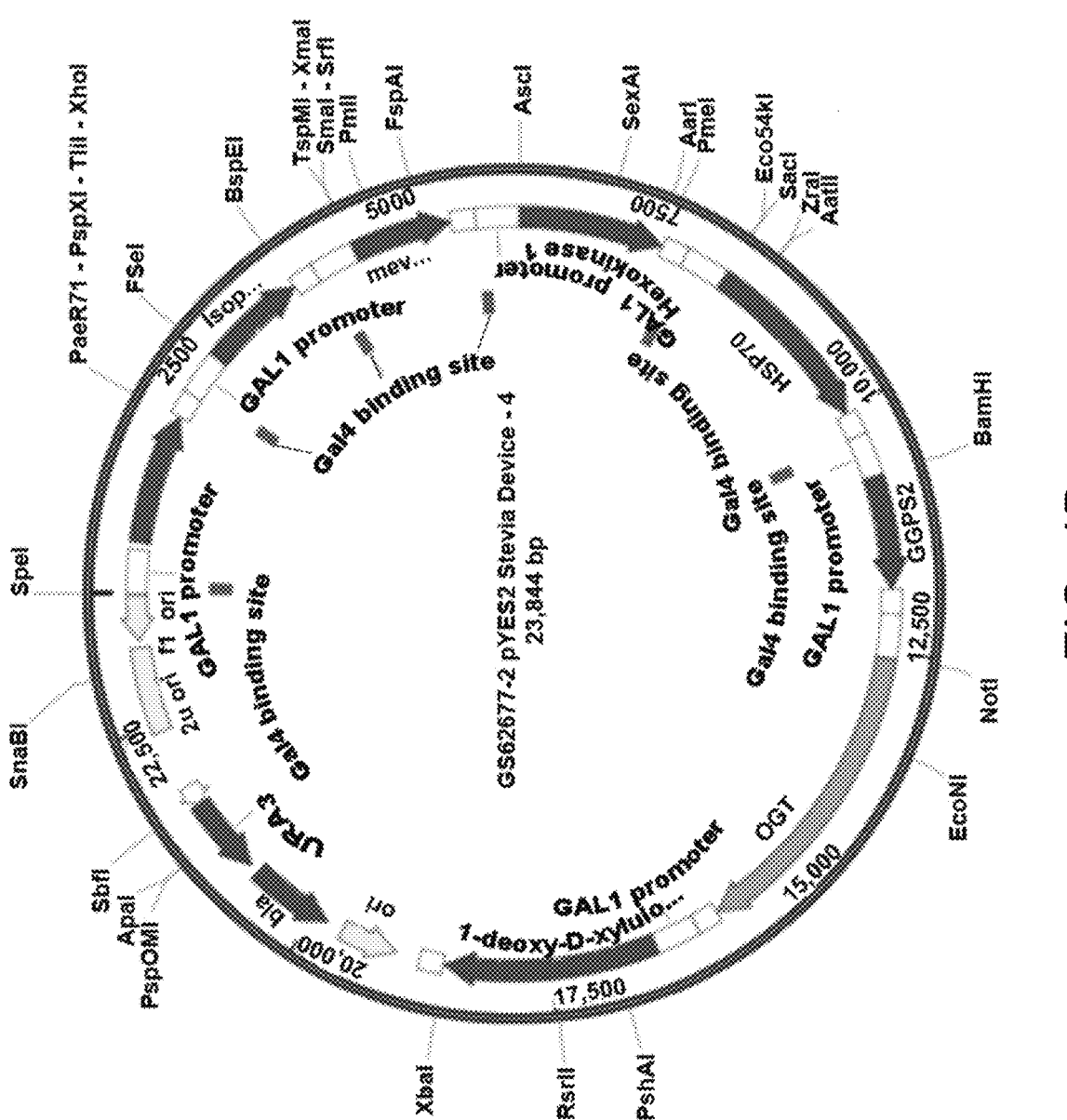

FIGS. 4A and 4B provide a non-limiting example of a DNA construct described herein. In one aspect, the construct is a pYES2 plasmid having from 5' to 3' the following genetic components in the following order: (a) a gene that expresses mevalonate-5-kinase, (b) a gene that expresses isopentenyl pyrophosphate isomerase, (c) a gene that expresses mevalonate pyrophosphate decarboxylase, (d) a gene that expresses hexokinase, (e) a gene that expresses HSP70, (f) a gene that expresses geranylgeranyl pyrophosphate synthase 2, (g) a gene that expresses OGT, and (h) a gene that expresses 1-deoxy-D-xylulose-5-phosphate synthase.

Figure 5A:
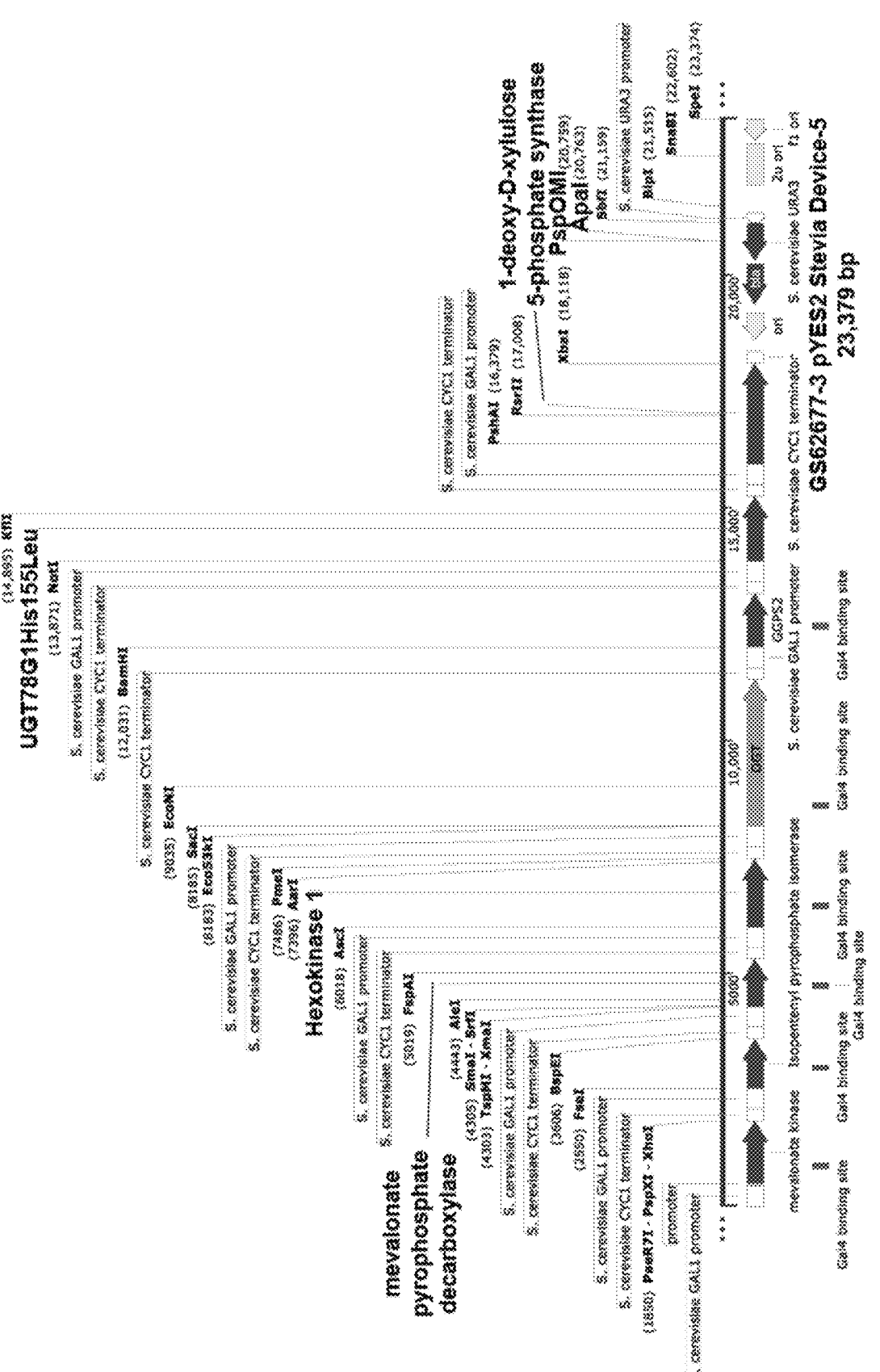
FIGS. 5A and 5B show, respectively, a linear and circular schematic of a constructed pYES2 plasmid showing the direction, placement, and size of genetic parts used of an exemplary DNA device described herein.
Figure 5B:
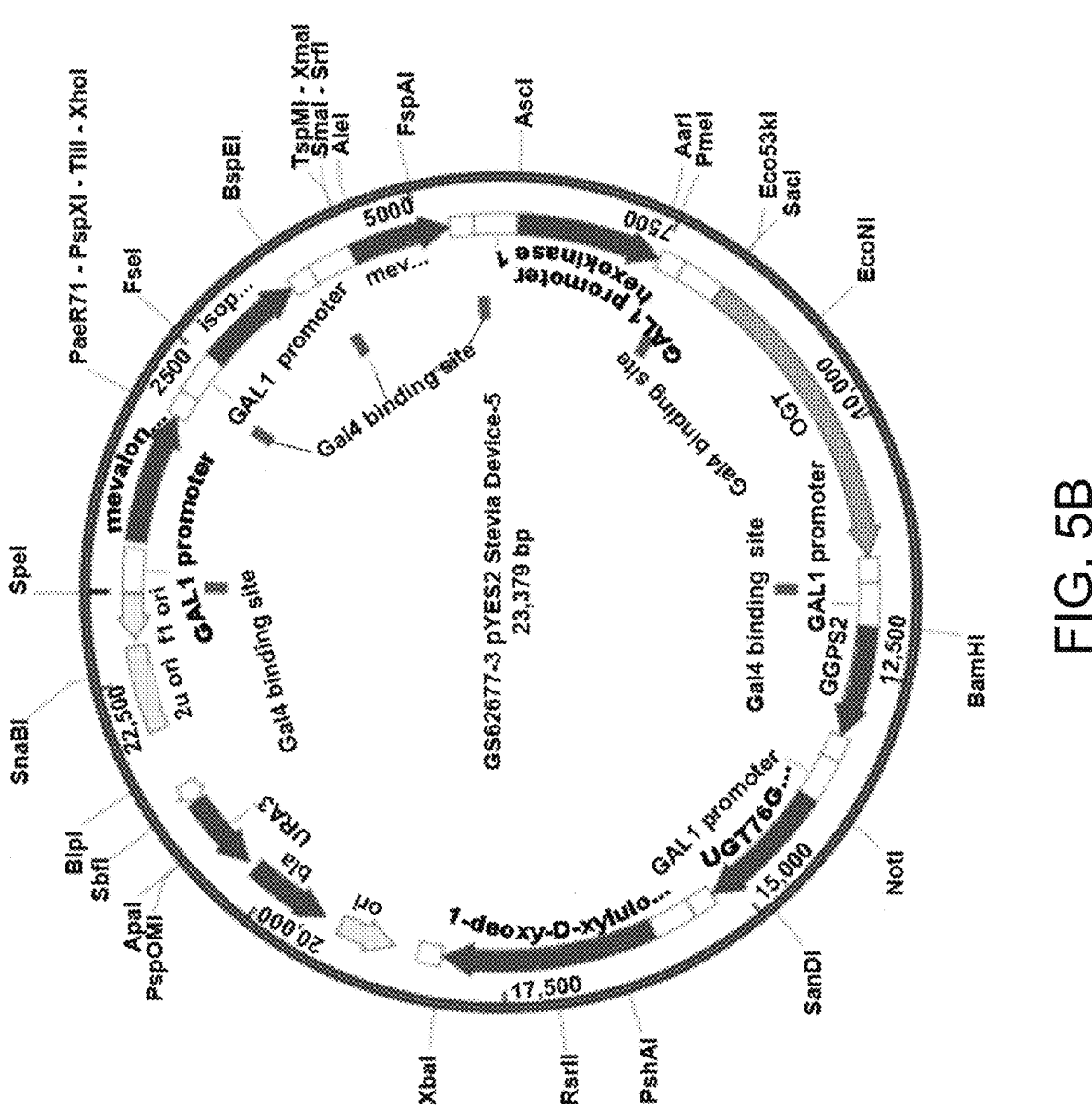

FIGS. 5A and 5B provide a non-limiting example of a DNA construct described herein. In one aspect, the construct is a pYES2 plasmid having from 5' to 3' the following genetic components in the following order: (a) a gene that expresses mevalonate-5-kinase, (b) a gene that expresses isopentenyl pyrophosphate isomerase, (c) a gene that expresses mevalonate pyrophosphate decarboxylase, (d) a gene that expresses hexokinase, (e) a gene that expresses OGT, (f) a gene that expresses geranylgeranylpyrophosphate 2, (g) a gene that expresses $UGT76G1_{His155Leu}$, and (h) a gene that expresses 1-deoxy-D-xylulose-5-phosphate synthase.

In another aspect, the construct is a pYES2 plasmid having from 5' to 3' the following genetic components in the following order: (a) a gene that expresses 4-hydroxy-3-methylbut-2-enyl diphosphate reductase having SEQ ID NO. 1 or at least 70% homology thereto; (b) a gene that expresses hexokinase having SEQ ID NO. 2 or at least 70% homology thereto; (c) a gene that expresses HSP70 having SEQ ID NO. 3 or at least 70% homology thereto; (d) a gene that expresses geranylgeranyl pyrophosphate synthase 2 having SEQ ID NO. 4 or at least 70% homology thereto; and (e) a gene that expresses 1-deoxy-D-xylulose-5-phosphate synthase having SEQ ID NO. 5 or at least 70% homology thereto.

In another aspect, the construct is a pYES2 plasmid having from 5' to 3' the following genetic components in the following order: (a) a GAL1 promoter; (b) a gene that expresses 4-hydroxy-3-methylbut-2-enyl diphosphate reductase; (c) a CYC1 terminator; (d) a GAL1 promoter; (e) a gene that expresses hexokinase; (f) a CYC1 terminator; (g) a GAL1 promoter; (h) a gene that expresses HSP70; (i) a CYC1 terminator; (j) a GAL1 promoter; (k) a gene that expresses geranylgeranyl pyrophosphate synthase 2; (l) a CYC1 terminator; (l) a GAL1 promoter; (m) a gene that expresses 1-deoxy-D-xylulose-5-phosphate synthase; (n) a CYC1 terminator.

In still another aspect, the construct is a pYES2 plasmid having from 5' to 3' the following genetic components in the following order: (a) a GAL1 promoter; (b) a gene that expresses 4-hydroxy-3-methylbut-2-enyl diphosphate reductase having SEQ ID NO. 1 or at least 70% homology thereto; (c) a CYC1 terminator; (d) a GAL1 promoter; (e) a gene that expresses hexokinase having SEQ ID NO. 2 or at least 70% homology thereto; (f) a CYC1 terminator; (g) a GAL1 promoter; (h) a gene that expresses HSP70 having SEQ ID NO. 3 or at least 70% homology thereto; (i) a CYC1 terminator; (j) a GAL1 promoter; (k) a gene that expresses geranylgeranyl pyrophosphate synthase 2 having SEQ ID NO. 4 or at least 70% homology thereto; (l) a CYC1 terminator; (l) a GAL1 promoter; (m) a gene that expresses 1-deoxy-D-xylulose-5-phosphate synthase having SEQ ID NO. 5 or at least 70% homology thereto; (n) a CYC1 terminator.

In another aspect, the construct is a pYES2 plasmid having from 5' to 3' the following genetic components in the following order: (a) a gene that expresses mevalonate-5-kinase; (b) a gene that expresses isopentenyl pyrophosphate isomerase; (c) a gene that expresses mevalonate pyrophosphate decarboxylase; (d) a gene that expresses hexokinase; (e) a gene that expresses HSP70; (f) a gene that expresses geranylgeranyl pyrophosphate synthase 2; and (g) a gene that expresses 1-deoxy-D-xylulose-5-phosphate synthase.

In another aspect, the construct is a pYES2 plasmid having from 5' to 3' the following genetic components in the following order: (a) a gene that expresses mevalonate-5-kinase having SEQ ID NO. 6 or at least 70% homology thereto; (b) a gene that expresses isopentenyl pyrophosphate isomerase having SEQ ID NO. 7 or at least 70% homology thereto; (c) a gene that expresses mevalonate pyrophosphate decarboxylase having SEQ ID NO. 8 or at least 70% homology thereto; (d) a gene that expresses hexokinase having SEQ ID NO. 2 or at least 70% homology thereto; (e) a gene that expresses HSP70 having SEQ ID NO. 3 or at least 70% homology thereto; (f) a gene that expresses geranylgeranyl pyrophosphate synthase 2 having SEQ ID NO. 4 or at least 70% homology thereto; and (g) a gene that expresses 1-deoxy-D-xylulose-5-phosphate synthase having SEQ ID NO. 5 or at least 70% homology thereto.

In another aspect, the construct is a pYES2 plasmid having from 5' to 3' the following genetic components in the following order: (a) a GAL1 promoter; (b) a gene that expresses mevalonate-5-kinase; (c) a CYC1 terminator; (d) a GAL1 promoter; (e) a gene that expresses isopentenyl pyrophosphate isomerase; (f) a CYC1 terminator; (g) a GAL1 promoter, (h) a gene that expresses mevalonate pyrophosphate decarboxylase; (i) a CYC1 terminator; (j) a GAL1 promoter; (k) a gene that expresses hexokinase; (l) a CYC1 terminator; (m) a GAL1 promoter; (n) a gene that expresses HSP70; (o) a CYC1 terminator; (p) a GAL1 promoter; (q) a gene that expresses geranylgeranyl pyrophosphate synthase 2; (r) a CYC1 terminator; (s) a GAL1 promoter; (t) a gene that expresses 1-deoxy-D-xylulose-5-phosphate synthase; and (u) a CYC1 terminator.

In another aspect, the construct is a pYES2 plasmid having from 5' to 3' the following genetic components in the following order: (a) a GAL1 promoter; (b) a gene that expresses mevalonate-5-kinase having SEQ ID NO. 6 or at least 70% homology thereto; (c) a CYC1 terminator; (d) a GAL1 promoter; (e) a gene that expresses isopentenyl pyrophosphate isomerase having SEQ ID NO. 7 or at least 70% homology thereto; (f) a CYC1 terminator; (g) a GAL1 promoter, (h) a gene that expresses mevalonate pyrophosphate decarboxylase having SEQ ID NO. 8 or at least 70% homology thereto; (i) a CYC1 terminator; (j) a GAL1 promoter; (k) a gene that expresses having hexokinase SEQ ID NO. 2 or at least 70% homology thereto; (l) a CYC1 terminator; (m) a GAL1 promoter; (n) a gene that expresses HSP70 having SEQ ID NO. 3 or at least 70% homology thereto; (o) a CYC1 terminator; (p) a GAL1 promoter; (q) a gene that expresses geranylgeranyl pyrophosphate synthase 2 having SEQ ID NO. 4 or at least 70% homology thereto; (r) a CYC1 terminator; (s) a GAL1 promoter; (t) a gene that expresses 1-deoxy-D-xylulose-5-phosphate synthase having SEQ ID NO. 5 or at least 70% homology thereto; and (u) a CYC1 terminator.

In another aspect, the construct is a pYES2 plasmid having from 5' to 3' the following genetic components in the following order: (a) a gene that expresses mevalonate-5-kinase having SEQ ID NO. 6 or at least 70% homology thereto; (b) a gene that expresses isopentenyl pyrophosphate isomerase having SEQ ID NO. 7 or at least 70% homology thereto; (c) a gene that expresses mevalonate pyrophosphate decarboxylase having SEQ ID NO. 8 or at least 70% homology thereto; (d) a gene that expresses hexokinase having SEQ ID NO. 2 or at least 70% homology thereto; (e) a gene that expresses HSP70 having SEQ ID NO. 3 or at least 70% homology thereto; (f) a gene that expresses geranylgeranyl pyrophosphate synthase 2 having SEQ ID NO. 4 or at least 70% homology thereto; (g) a gene that expresses a UDP-glycosyltransferase having SEQ ID NO. 12 or at least 70% homology thereto; and (h) a gene that expresses 1-deoxy-D-xylulose-5-phosphate synthase having SEQ ID NO. 5 or at least 70% homology thereto.

In another aspect, the construct is a pYES2 plasmid having from 5' to 3' the following genetic components in the following order: (a) a gene that expresses mevalonate-5-kinase; (b) a CYC1 terminator; (c) a GAL1 promoter; (d) a gene that expresses isopentenyl pyrophosphate isomerase; (e) a CYC1 terminator; (f) a GAL1 promoter, (g) a gene that expresses mevalonate pyrophosphate decarboxylase; (h) a CYC1 terminator; (i) a GAL1 promoter; (j) a gene that expresses hexokinase; (k) a CYC1 terminator; (l) a GAL1 promoter; (m) a gene that expresses HSP70; (n) a CYC1 terminator; (o) a GAL1 promoter; (p) a gene that expresses geranylgeranyl pyrophosphate synthase 2; (q) a CYC1 terminator; (r) a GAL1 promoter; (s) a gene that expresses UGT76G1$_{His155Leu}$, (t) a CYC1 terminator, (u) a GAL1 promoter, and (v) a gene that expresses 1-deoxy-D-xylulose-5-phosphate synthase.

In another aspect, the construct is a pYES2 plasmid having from 5' to 3' the following genetic components in the following order: (a) a gene that expresses mevalonate-5-kinase having SEQ ID NO. 6 or at least 70% homology thereto; (b) a CYC1 terminator; (c) a GAL1 promoter; (d) a gene that expresses isopentenyl pyrophosphate isomerase having SEQ ID NO. 7 or at least 70% homology thereto; (e) a CYC1 terminator; (f) a GAL1 promoter, (g) a gene that expresses mevalonate pyrophosphate decarboxylase having SEQ ID NO. 8 or at least 70% homology thereto; (h) a CYC1 terminator; (i) a GAL1 promoter; (j) a gene that expresses hexokinase having SEQ ID NO. 2 or at least 70% homology thereto; (k) a CYC1 terminator; (l) a GAL1 promoter; (m) a gene that expresses HSP70 having SEQ ID NO. 3 or at least 70% homology thereto; (n) a CYC1 terminator; (o) a GAL1 promoter; (p) a gene that expresses geranylgeranyl pyrophosphate synthase 2 having SEQ ID NO. 4 or at least 70% homology thereto; (q) a CYC1 terminator; (r) a GAL1 promoter; (s) a gene that expresses UGT76G1$_{His155Leu}$ having SEQ ID NO. 12 or at least 70% homology thereto; (t) a CYC1 terminator, (u) a GAL1 promoter, and (v) a gene that expresses 1-deoxy-D-xylulose-5-phosphate synthase having SEQ ID NO. 5 or at least 70% homology thereto.

In another aspect, the construct is a pYES2 plasmid having from 5' to 3' the following genetic components in the following order: (a) a gene that expresses mevalonate-5-kinase having SEQ ID NO. 6 or at least 70% homology thereto; (b) a gene that expresses isopentenyl pyrophosphate isomerase having SEQ ID NO. 7 or at least 70% homology thereto; (c) a gene that expresses mevalonate pyrophosphate decarboxylase having SEQ ID NO. 8 or at least 70% homology thereto; (d) a gene that expresses hexokinase having SEQ ID NO. 2 or at least 70% homology thereto; (e) a gene that expresses HSP70 having SEQ ID NO. 3 or at least 70% homology thereto; (f) a gene that expresses geranylgeranyl pyrophosphate synthase 2 having SEQ ID NO. 4 or at least 70% homology thereto; (g) a gene that expresses an O-linked acetylglucosamine transferase having SEQ ID NO. 13 or at least 70% homology thereto; and (h) a gene that expresses 1-deoxy-D-xylulose-5-phosphate synthase having SEQ ID NO. 5 or at least 70% homology thereto.

In another aspect, the construct is a pYES2 plasmid having from 5' to 3' the following genetic components in the following order: (a) a gene that expresses mevalonate-5-kinase; (b) a CYC1 terminator; (c) a GAL1 promoter; (d) a gene that expresses isopentenyl pyrophosphate isomerase; (e) a CYC1 terminator; (f) a GAL1 promoter, (g) a gene that expresses mevalonate pyrophosphate decarboxylase; (h) a CYC1 terminator; (i) a GAL1 promoter; (j) a gene that expresses hexokinase; (k) a CYC1 terminator; (l) a GAL1 promoter; (m) a gene that expresses HSP70; (n) a CYC1 terminator; (o) a GAL1 promoter; (p) a gene that expresses geranylgeranyl pyrophosphate synthase 2; (q) a CYC1 terminator; (r) a GAL1 promoter; (s) a gene that expresses an O-linked acetylglucosamine transferase; (t) a CYC1 terminator; (u) a GAL1 promoter; and (v) a gene that expresses 1-deoxy-D-xylulose-5-phosphate synthase.

In another aspect, the construct is a pYES2 plasmid having from 5' to 3' the following genetic components in the following order: (a) a gene that expresses mevalonate-5-kinase having SEQ ID NO. 6 or at least 70% homology thereto; (b) a CYC1 terminator; (c) a GAL1 promoter; (d) a gene that expresses isopentenyl pyrophosphate isomerase having SEQ ID NO. 7 or at least 70% homology thereto; (e) a CYC1 terminator; (f) a GAL1 promoter, (g) a gene that expresses mevalonate pyrophosphate decarboxylase having SEQ ID NO. 8 or at least 70% homology thereto; (h) a CYC1 terminator; (i) a GAL1 promoter; (j) a gene that expresses hexokinase having SEQ ID NO. 2 or at least 70% homology thereto; (k) a CYC1 terminator; (l) a GAL1 promoter; (m) a gene that expresses HSP70 having SEQ ID NO. 3 or at least 70% homology thereto; (n) a CYC1 terminator; (o) a GAL1 promoter; (p) a gene that expresses geranylgeranyl pyrophosphate synthase 2 having SEQ ID NO. 4 or at least 70% homology thereto; (q) a CYC1 terminator; (r) a GAL1 promoter; (s) a gene that expresses an O-linked acetylglucosamine transferase having SEQ ID NO. 13 or at least 70% homology thereto; (t) a CYC1 terminator; (u) a GAL1 promoter; and (v) a gene that expresses 1-deoxy-D-xylulose-5-phosphate synthase having SEQ ID NO. 5 or at least 70% homology thereto.

In another aspect, the construct is a pYES2 plasmid having from 5' to 3' the following genetic components in the following order: (a) a gene that expresses mevalonate-5-kinase having SEQ ID NO. 6 or at least 70% homology thereto; (b) a gene that expresses isopentenyl pyrophosphate isomerase having SEQ ID NO. 7 or at least 70% homology thereto; (c) a gene that expresses mevalonate pyrophosphate decarboxylase having SEQ ID NO. 8 or at least 70% homology thereto; (d) a gene that expresses hexokinase having SEQ ID NO. 2 or at least 70% homology thereto; (e) a gene that expresses an O-linked acetylglucosamine transferase having SEQ ID NO. 13 or at least 70% homology thereto; (f) a gene that expresses geranylgeranyl pyrophosphate synthase 2 having SEQ ID NO. 4 or at least 70% homology thereto; (g) a gene that expresses UGT76G1$_{His155Leu}$ having SEQ ID NO. 12 or at least 70% homology thereto; and (h) a gene that expresses 1-deoxy-D-xylulose-5-phosphate synthase having SEQ ID NO. 5 or at least 70% homology thereto.

In another aspect, the construct is a pYES2 plasmid having from 5' to 3' the following genetic components in the following order: (a) a gene that expresses mevalonate-5-kinase; (b) a CYC1 terminator; (c) a GAL1 promoter; (d) a gene that expresses isopentenyl pyrophosphate isomerase; (e) a CYC1 terminator; (f) a GAL1 promoter, (g) a gene that expresses mevalonate pyrophosphate decarboxylase; (h) a CYC1 terminator; (i) a GAL1 promoter; (j) a gene that expresses hexokinase; (k) a CYC1 terminator; (l) a GAL1 promoter; (m) a gene that expresses an O-linked acetylglucosamine transferase; (n) a CYC1 terminator; (o) a GAL1 promoter; (p) a gene that expresses geranylgeranyl pyrophosphate synthase 2; (q) a CYC1 terminator; (r) a GAL1 promoter; (s) a gene that expresses UGT76G1$_{His155Leu}$; (t) a CYC1 terminator; (u) a GAL1 promoter; and (v) a gene that expresses 1-deoxy-D-xylulose-5-phosphate synthase.

In another aspect, the construct is a pYES2 plasmid having from 5' to 3' the following genetic components in the following order: (a) a gene that expresses mevalonate-5-kinase having SEQ ID NO. 6 or at least 70% homology thereto; (b) a CYC1 terminator; (c) a GAL1 promoter; (d) a gene that expresses isopentenyl pyrophosphate isomerase having SEQ ID NO. 7 or at least 70% homology thereto; (e) a CYC1 terminator; (f) a GAL1 promoter, (g) a gene that expresses mevalonate pyrophosphate decarboxylase having SEQ ID NO. 8 or at least 70% homology thereto; (h) a CYC1 terminator; (i) a GAL1 promoter; (j) a gene that expresses hexokinase having SEQ ID NO. 2 or at least 70% homology thereto; (k) a CYC1 terminator; (l) a GAL1 promoter; (m) a gene that expresses an O-linked acetylglucosamine transferase having SEQ ID NO. 13 or at least 70% homology thereto; (n) a CYC1 terminator; (o) a GAL1 promoter; (p) a gene that expresses geranylgeranyl pyrophosphate synthase 2 having SEQ ID NO. 4 or at least 70% homology thereto; (q) a CYC1 terminator; (r) a GAL1 promoter; (s) a gene that expresses UGT76G1$_{His155Leu}$ having SEQ ID NO. 12 or at least 70% homology thereto; (t) a CYC1 terminator; (u) a GAL1 promoter; and (v) a gene that expresses 1-deoxy-D-xylulose-5-phosphate synthase having SEQ ID NO. 5 or at least 70% homology thereto.

In one aspect, the DNA construct has SEQ ID NO. 10 (FIGS. 1A and 1B). In another aspect, the DNA construct has SEQ ID NO. 11 (FIGS. 2A and 2B). In yet another aspect, the DNA construct has SEQ ID NO. 14 (FIGS. 3A and 3B). In still another aspect, the DNA construct has SEQ ID NO. 15 (FIGS. 4A and 4B). In a further aspect, the DNA construct has SEQ ID NO. 16 (FIGS. 5A and 5B).

Exemplary methods for producing the DNA constructs described herein are provided in the Examples. Restriction enzymes and purification techniques known in the art can be used to assemble the DNA constructs. Backbone plasmids and synthetic inserts can be mixed together for ligation purposes at different ratios ranging from 1:1, 1:2, 1:3, 1:4, and up to 1:5. In one aspect, the ratio of backbone plasmid to synthetic insert is 1:4. After the vector comprising the DNA construct has been produced, the resulting vector can be incorporated into the host cells using the methods described below.

II. Biological Devices

In one aspect, a "biological device" is formed when a microbial cell is transfected with the DNA construct described herein. The biological devices are generally composed of microbial host cells, where the host cells are transformed with a DNA construct described herein.

In one aspect, the DNA construct is carried by the expression vector into the cell and is separate from the host cell's genome. In another aspect, the DNA construct is incorporated into the host cell's genome. In still another aspect, incorporation of the DNA construct into the host cell enables the host cell to produce steviol glycosides. "Heterologous" genes and proteins are genes and proteins that have been experimentally inserted into a cell that are not normally expressed by the cell. A heterologous gene may be cloned or derived from a different cell type or species than the recipient cell or organism. Heterologous genes may be introduced into cells by transduction or transformation.

An "isolated" nucleic acid is one that has been separated from other nucleic acid molecules and/or cellular material (peptides, proteins, lipids, saccharides, and the like) normally present in the natural source of the nucleic acid. An "isolated" nucleic acid may optionally be free of the flanking sequences found on either side of the nucleic acid as it naturally occurs. An isolated nucleic acid can be naturally occurring, can be chemically synthesized, or can be a cDNA molecule (i.e., is synthesized from an mRNA template using reverse transcriptase and DNA polymerase enzymes).

"Transformation" or "transfection" as used herein refers to a process for introducing heterologous DNA into a host cell. Transformation can occur under natural conditions or may be induced using various methods known in the art. Many methods for transformation are known in the art and the skilled practitioner will know how to choose the best transformation method based on the type of cells being transformed. Methods for transformation include, for example, viral infection, electroporation, lipofection, chemical transformation, and particle bombardment. Cells may be stably transformed (i.e., the heterologous DNA is capable of replicating as an autonomous plasmid or as part of the host chromosome) or may be transiently transformed (i.e., the heterologous DNA is expressed only for a limited period of time).

"Competent cells" refers to microbial cells capable of taking up heterologous DNA. Competent cells can be purchased from a commercial source, or cells can be made competent using procedures known in the art. Exemplary procedures for producing competent cells are provided in the Examples.

The host cells as referred to herein include their progeny, which are any and all subsequent generations formed by cell division. It is understood that not all progeny may be identical due to deliberate or inadvertent mutations. A host cell may be "transfected" or "transformed," which refers to a process by which exogenous nucleic acid is transferred or introduced into the host cell.

A transformed cell includes the primary subject cell and its progeny. The host cells can be naturally-occurring cells or "recombinant" cells. Recombinant cells are distinguishable from naturally-occurring cells in that naturally-occurring cells do not contain heterologous DNA introduced through molecular cloning procedures. In one aspect, the host cell is a prokaryotic cell such as, for example, *Escherichia coli*. In other aspects, the host cell is a eukaryotic cell such as, for example, the yeast *Saccharomyces cerevisiae*. Host cells transformed with the DNA construct described herein are referred to as "biological devices."

The DNA construct is first delivered into the host cell. In one aspect, the host cells are naturally competent (i.e., able to take up exogenous DNA from the surrounding environment). In another aspect, cells must be treated to induce artificial competence. This delivery may be accomplished in vitro, using well-developed laboratory procedures for transforming cell lines. Transformation of bacterial cell lines can be achieved using a variety of techniques. One method involves calcium chloride. The exposure to the calcium ions renders the cells able to take up the DNA construct. Another method is electroporation. In this technique, a high-voltage electric field is applied briefly to cells, producing transient holes in the membranes of the cells through which the vector containing the DNA construct enters. Another method involves exposing intact yeast cells to alkali cations such as, for example, lithium. In one aspect, this method includes exposing yeast to lithium acetate, polyethylene glycol, and single-stranded DNA such as, for example, salmon sperm DNA. Without wishing to be bound by theory, the single-stranded DNA is thought to bind to the cell wall of the yeast, thereby blocking plasmids from binding. The plasmids are then free to enter the yeast cell. Enzymatic and/or electromagnetic techniques can also be used alone, or in combination with other methods, to transform microbial cells. Exemplary procedures for transforming yeast and bacteria with specific DNA constructs are provided in the Examples. In certain aspects, two or more types of DNA can be incorporated into the host cells. Thus, different metabolites can be produced from the same host cells at enhanced rates.

III. Preparation of Steviol Glycosides

The biological devices described herein are useful in the production of steviol glycosides. Once the DNA construct has been incorporated into the host cell, the cells are cultured such that the cells multiply. A satisfactory microbiological culture contains available sources of hydrogen donors and acceptors, carbon, nitrogen, sulfur, phosphorus, inorganic salts, and, in certain cases, vitamins or other growth-promoting substances. For example, the addition of peptone provides a readily-available source of nitrogen and carbon. Furthermore, the use of different types of media results in different growth rates and different stationary phase densities; stationary phase is where secondary metabolite production occurs most frequently. A rich media results in a short doubling time and higher cell density at stationary phase. Minimal media results in slow growth and low final cell densities. Efficient agitation and aeration increase final cell densities.

In one aspect, host cells can be cultured or fermented by any method known in the art. The skilled practitioner will be able to select a culture medium based on the species and/or strain of host cell selected. In certain aspects, the culture medium will contain a carbon source. A variety of carbon sources are contemplated, including, but not limited to: monosaccharides such as glucose and fructose, disaccharides such as lactose or sucrose, oligosaccharides, polysaccharides such as starch, or mixtures thereof. In one aspect, the biological devices described herein are cultured with a medium composed of raffinose, galactose, or a combination thereof. Unpurified mixtures extracted from feedstocks are also contemplated and include molasses, barley malt, and related compounds and compositions. Other glycolytic and tricarboxylic acid cycle intermediates are also contemplated as carbon sources, as are one-carbon substrates such as carbon dioxide and/or methanol in the cases of compatible organisms. The carbon source utilized is limited only by the particular organism being cultured.

Culturing or fermenting of host cells can be accomplished by any technique known in the art. In one aspect, batch fermentation can be conducted. In batch fermentation, the composition of the culture medium is set at the beginning and the system is closed to future alterations. In some aspects, a limited form of batch fermentation may be carried out, wherein factors such as oxygen concentration and pH are manipulated, but additional carbon is not added. Continuous fermentation methods are also contemplated. In continuous fermentation, equal amounts of a defined medium are continuously added to and removed from a bioreactor. In other aspects, microbial host cells are immobilized on a substrate. Fermentation may be carried out on any scale and may include methods in which literal "fermentation" is carried out as well as other culture methods that are non-fermentative.

In one aspect, the method involves growing the biological devices described herein for a sufficient time to produce steviol glycosides. The ordinary artisan will be able to choose a culture medium and optimum culture conditions based on the biological identity of the host cells.

In certain aspects, after culturing the biological device to produce the steviol glycoside, the host cells of the device can be lysed with one or more enzymes. For example, when the host cells are yeast, the yeast cells can be lysed with lyticase. In one aspect, the lyticase concentration can be 500, 600, 700, 800, 900, or 1000 µL per liter of culture, where any value can be the lower and upper end-point of a range (e.g., 500 to 900 µL, 600 to 800 µL, etc.).

In addition to enzymes, other components can be used to facilitate lysis of the host cells. In one aspect, chitosan can be used in combination with an enzyme to lyse the host cells. Chitosan is generally composed of glucosamine units and N-acetylglucosamine units and can be chemically or enzymatically extracted from chitin, which is a component of arthropod exoskeletons and fungal and microbial cell walls. In certain aspects, the chitosan can be acetylated to a specific degree of acetylation in order to enhance tissue growth during culturing as well as metabolite production. In one aspect, the chitosan is from 60% to about 100%, 70% to 90%, 75% to 80%, or about 80% acetylated. The molecular weight of the chitosan can vary, as well. For example, the chitosan can comprise about 3, 4, 5, 6, 7, 8, 9, 10, 11, 12, 13, 14, 15, 16, 17, 18, 19, or 20 glucosamine units and/or N-acetylglucosamine units. In another aspect, the chitosan includes 5 to 7 glucosamine units and/or N-acetylglucosamine units. In one aspect, chitosan can be added until a concentration of 0.0015, 0.0025, 0.005, 0.0075, 0.01, 0.015, 0.02, 0.03, 0.04, or 0.05 (where any value can be a lower and upper end-point of a range, e.g., 0.005 to 0.02, 0.0075 to 0.015, etc.) is achieved in the culture. Still further in this aspect, the chitosan is present at a concentration of 0.01%.

In a further aspect, the steviol glycoside can be collected, separated from the microbial cells (lysed or intact), and/or purified through any technique known in the art such as, for example, precipitation, centrifugation, filtration, and the like. In one aspect, the steviol glycoside can be purified via microfiltration to remove impurities. In one aspect, the microfilter has a pore size of 0.3, 0.35, 0.4, 0.45, 0.5, 0.55, 0.6, 0.65, 0.7, or 0.8 µm, where any value can be a lower and/or upper end-point of a range (e.g., 0.3 µm to 0.5 µm).

In another aspect, the steviol glycoside can be chemically-modified to produce additional desirable properties. Alternatively, compositions composed of the steviol glycosides with lysed and/or intact host cells (e.g., yeast) can be used herein, where it is not necessary to separate the host cells and other components from the steviol glycosides.

The steviol glycoside produced from the devices herein can be a mixture of two or more compounds. Examples of steviol glycosides produced herein include, but are not limited to, stevioside, steviol, rubusoside, steviol-13-O-glucoside, steviol-19-O-glucoside, rebaudioside A, rebaudioside B, rebaudioside C, rebaudioside D, rebaudioside E, rebaudioside F, rebaudioside M, and dulcoside A. Individual compounds can be isolated and purified or, in the alternative, mixtures of tow or more compounds can be used.

The biological devices described herein in addition to producing steviol glycosides produce other sugars. In one aspect, the biological devices produced increased amounts of sucrose. Certain steviol glycosides possess a bitter taste. The biological devices described herein produce sucrose in a sufficient amount to mask the bitter taste of the steviol glycosides.

IV. Methods for Enhancing the Physiological Properties of Plants

In one aspect, provided herein is a method for producing one or more steviol glycosides from plant cells, where the method involves contacting the plant cells with the biological device disclosed herein.

The selection of the plant used in the methods described herein can vary depending on the application. For example, a specific plant can be selected that produces certain desirable metabolites. An example of one such metabolite is rebaudioside A, or rebA. RebA is 200 times sweeter than sugar and has numerous applications in the food industry (e.g., natural non-caloric sweeteners), pharmaceuticals (e.g., improving the flavor of medications), and dietary supplements. Current techniques for producing steviol glycosides are expensive. For example, large amounts of fresh plant biomass must be cultivated and harvested and expensive and time-consuming extraction methods must be used. The biological devices and methods described herein enhance the production of steviol glycosides from plants that naturally produce steviol glycosides. In one aspect, the plant can include, but is not limited to, *Stevia rebaudiana, Stevia phlebophylla*, or *Rubus chingii*.

In another aspect, other steviol glycosides in addition to rebA can have the same or similar food, pharmaceutical, and dietary supplement applications described above with respect to rebA.

In one aspect, plant cells when contacted with the biological devices described above exhibit enhanced production of rebA and/or other steviol glycosides. Recipient cell targets include, but are not limited to, meristem cells, Type I, Type II, and Type III callus, immature embryos and gametic cells such as microspores, pollen, sperm, and egg cells. It is contemplated that any cell from which a fertile plant may be regenerated is useful as a recipient cell. Type I, Type II, and Type III callus may be initiated from tissue sources including, but not limited to, immature embryos, immature inflorescences, seedling apical meristems, microspores, and the like. Those cells that are capable of proliferating as callus are also useful herein. Methods for growing plant cells are known in the art (see U.S. Pat. No. 7,919,679). Exemplary procedures for growing plant calluses are also provided in the Examples. In one aspect, plant calluses grown from 2 to 4 weeks can be used herein. The plant cells can also be derived from plants varying in age. For example, plants that are 80 days to 120 days old after pollination can be used to produce calluses useful herein.

The plant cells can be contacted with the biological device in a number of different ways. In one aspect, the device can be added to media containing the plant cells. In another aspect, the device can be injected into the plant cells via syringe. The amount of device and the duration of exposure to the device can vary as well. In one aspect, the concentration of the device is about $10^3$, $10^4$, $10^5$, $10^6$, $10^7$, $10^8$, or $10^9$ cells/mL of water. In one aspect, when the host cell is a bacterium, the concentration of the device is $10^6$. In another aspect, when the host cell is yeast, the concentration of the device is $10^9$. Different volumes of the biological device can be used as well, ranging from 5 µL to 500 µL.

Once the plant cells have been in contact with the biological device for a sufficient time to produce the metabolite (e.g., rebA or another steviol glycoside), the metabolite is isolated. In one aspect, the metabolite is extracted from the media containing the biological device and the plant cells. The selection of the extraction solvent can vary depending upon the solubility of the metabolite.

With current techniques, the extraction of metabolites produced from plants usually requires high initial amounts of plant biomass or material, which in turn requires larger amounts of extraction solvents. The use of higher amounts of extraction solvents adds to the expense of metabolite production. The use of higher amounts of organic solvents presents environmental risks as well. However, the use of the biological devices described herein produces significantly higher amounts of metabolites such as rebA and other steviol glycosides, which means smaller amounts of biomass are required in order to produce and isolate the metabolites when compared with existing techniques. The extraction of plant metabolites using current techniques also requires fresh biomass, which entails agronomic practices, the use of chemicals, and time-consuming extraction methods. Therefore, the use of the biological devices described herein is more cost-effective and safer for the environment than traditional methods for producing and synthesizing steviol glycosides.

In certain aspects, any of the biological devices described above can be used in combination with a polysaccharide. In one aspect, the plant cells are first contacted with the biological device then subsequently contacted with the polysaccharide. In another aspect, the plant cells are first contacted with the polysaccharide then subsequently contacted with the biological device. In a further aspect, the plant cells are only contacted with a polysaccharide and not contacted with the biological device. In a still further aspect, the plant cells are contacted simultaneously with the polysaccharide and the biological device.

In one aspect, the polysaccharide includes chitosan, glucosamine (GlcN), N-acetylglucosamine (NAG), or any combination thereof. Chitosan is generally composed of GlcN and NAG units and can be chemically or enzymatically extracted from chitin, which is a component of arthropod exoskeletons and fungal and microbial cell walls. In certain aspects, the chitosan can be acetylated to a specific degree of acetylation in order to enhance tissue growth during culturing as well as metabolite production. In one aspect, the chitosan is from about 60% to about 100%, 70% to 90%, 75% to 85%, or about 80% acetylated. Exemplary procedures for producing and isolating the chitosan are provided in the Examples. In one aspect, chitosan isolated from shells of crab, shrimp, lobster, and/or krill is useful herein.

The molecular weight of the chitosan can vary, as well. For example, the chitosan comprises about 3, 4, 5, 6, 7, 8, 9, 10, 11, 12, 13, 14, 15, 16, 17, 18, 19, or 20 GlcN and/or NAG units. In another aspect, the chitosan includes 5 to 7 GlcN and/or NAG units. In one aspect, the chitosan is in a solution of water and acetic acid at less than 1% by weight, less than 0.75% by weight, less than 0.5% by weight, less than 0.25% by weight, or less than 0.1% by weight. In another aspect, the amount of chitosan that is applied to the plant cells is from 0.1% to 0.01% by weight, from 0.075% to 0.025% by weight, or is about 0.05% by weight. The polysaccharides used herein are generally natural polymers and thus present no environmental concerns. Additionally, the polysaccharide can be used in acceptably low concentrations. In certain aspects, the polysaccharide can be used in combination with one or more growth regulators.

In one aspect, the plant growth regulator is an auxin, a cytokinin, a gibberellin, abscisic acid, or a polyamine. In a further aspect, the auxin is a natural or synthetic auxin. In a still further aspect, the auxin is indole-3-acetic acid (IAA), 4-chloroindole-3-acetic acid (4-CI-IAA), 2-phenylacetic acid (PAA), indole-3-butyric acid (IBA), 2,4-dichlorophenoxyacetic acid (2,4-D), α-naphthalene acetic acid (α-NAA), 2-methoxy-3,6-dichlorobenzoic acid (dicamba), 4-amino-3,5,6-trichloropicolinic acid (torden or picloram), 2,4,5-trichloropicolinic acid (2,4,5-T), or a combination thereof. In another aspect, the cytokinin is zeatin, kinetin, 6-benzylaminopurine, diphenylurea, thidizuron (TDZ), 6-(γ, γ-dimethylallylamino) purine, or a combination thereof. In another aspect, the gibberellins is gibberellins A1 (GA1), gibberellic acid (GA3), ent-gibberellane, ent-kaurene, or a combination thereof. In yet another aspect, the polyamine is putrescine, spermidine, or a combination thereof.

In one aspect, the plant cell or callus is first contacted with a polysaccharide and subsequently contacted with a plant growth regulator. In another aspect, the plant cell or callus is first contacted with a plant growth regulator and subsequently contacted with a polysaccharide. In an alternative aspect, the plant cell or callus is simultaneously contacted with a polysaccharide and a plant growth regulator. In a further aspect, the plant cell or callus is only contacted with a polysaccharide and is not contacted with a plant growth regulator.

The plant cells can be contacted with the polysaccharide using a number of techniques. In one aspect, the plant cells or reproductive organs (e.g., a plant embryo) can be cultured in agar and medium with a solution of the polysaccharide. In other aspects, the polysaccharide can be applied to a plant callus by techniques such as, for example, coating the callus or injecting the polysaccharide into the callus. In this aspect, the age of the callus can vary depending on the type of plant. The amount of polysaccharide can vary depending upon, among other things, the selection and number of plant cells. The use of the polysaccharide in the methods described herein permits rapid tissue culturing at room temperature. Due to the ability of the polysaccharide to prevent microbial contamination, the tissue culture can grow for extended periods of time ranging from days to several weeks. Moreover, tissue culturing with the polysaccharide can occur in the dark and/or light. As discussed above, the plant cells can optionally be contacted with any of the biological devices described above. Thus, the use of the polysaccharides and biological devices described herein is a versatile way to culture and grow plant cells—and, ultimately, plants of interest—with enhanced physiological properties.

In other aspects, the plant cells can be cultured in a liquid medium on a larger scale in a bioreactor. For example, plant cells can be cultured in agar and medium, then subsequently contacted with (e.g., injected) a biological device described herein. After a sufficient culturing time (e.g., two to four weeks), the plant cells are introduced into a container with the same medium used above and, additionally, the polysaccharide. In certain aspects, the polysaccharide can be introduced with anionic polysaccharides including, but not limited to, alginates (e.g., sodium, calcium, potassium, etc.). After the introduction of the polysaccharide, the solution is mixed for a sufficient time to produce a desired result (e.g., production of a desired metabolite).

In one aspect, provided herein is a plant grown by the process consisting of contacting plant gamete cells or a plant reproductive organ with the biological devices disclosed herein. In a further aspect, the plant is produced by the following method:

(a) contacting a plant callus with the biological device;

(b) culturing the plant callus; and (c) growing the plant from the plant callus.

In one aspect, the plant is *Stevia rebaudiana, Stevia phlebophylla*, or *Rubus chingii*. In a further aspect, the method of growing the plant described above includes an additional step (d), wherein the plant callus is cultured with chitosan.

In one aspect, provided herein is a method for producing one or more steviol glycosides from plant cells, the method including the steps of:

(a) contacting a plant callus of *Stevia rebaudiana, Stevia phlebophylla*, or *Rubus chingii* with a biological device described herein;

(b) culturing the plant callus; and (c) removing the steviol glycoside from the plant callus.

In an alternative aspect, provided herein is a method for producing one or more steviol glycosides from leaves, the method including the steps of:

(a) contacting a plant callus of *Stevia rebaudiana, Stevia phlebophylla*, or *Rubus chingii* with a biological device described herein;

(b) culturing the plant callus;

(c) growing a plant from the plant callus, where the plant grows one or more leaves; and (d) removing the steviol glycoside from the leaves.

In a further aspect, the same method can be applied to other plant parts including fruits, stems, roots, tubers, corms, bulbs, flowers, buds, seeds, and the like. In a still further aspect, the same method can be applied to an entire plant.

In one aspect, the plant callus is immersed in a solution of polysaccharide (e.g., chitosan) then inoculated with the device. In one aspect, the plant callus is that of *Stevia rebaudiana, Stevia phlebophylla*, or *Rubus chingii*. The plant callus can be from 2 days up to 20 days old prior to inoculation with the device. The plant callus is then allowed to grow until it is of sufficient weight and size. In one aspect, the plant callus is allowed to grow (i.e., culture) for 1 to 10 weeks after inoculation. The next step involves removal of the rebA or other steviol glycoside from the callus.

In another aspect, a plant callus described above can be planted and allowed to grow and mature into a plant bearing fruit and leaves. In one aspect, rebA or another steviol glycoside can be isolated from a plant that has been grown from a plant callus inoculated with a device described herein and optionally contacted with a polysaccharide (e.g., chitosan). In one aspect, the steviol glycoside can be removed from the leaves of a plant grown with the devices described herein. In one aspect, the leaves of *Stevia rebaudiana* grown from calluses inoculated with the devices described herein provide a rich source of rebA.

The ordinarily-skilled artisan will be able to use established procedures for culturing and providing nutrients to the calluses. In one aspect, calluses ranging in age from one to four weeks, or about 7, 14, 15, 20, 21, 25, or 28 days can be used in the procedures described herein. Further in this aspect, calluses can be inoculated with biological devices and, optionally, chitosan at the start of steviol glycoside production. In one aspect, 15-day-old calluses (e.g., 15 days post-inoculation) are used. In a further aspect, the calluses can be placed under an artificial light source in a chamber where conditions such as temperature and humidity are controlled. At various points during callus culture, calluses can be transferred to trays with fresh nutrients or can be directly sprayed with fresh nutrients.

In one aspect, calluses can be grown in trays for a period of time ranging from 1 to 6 months, or can be grown for 1, 2, 3, 4, 5, or 6 months. In one aspect, the calluses are grown for 3 months. Further in this aspect, the calluses have generally sprouted small plants after 3 months of growth.

Several procedures have been established for extraction of hydrophobic compounds such as steviol glycosides from calluses, or the following procedures can be used. In one aspect, callus samples are lyophilized and weighed. Further in this aspect, the samples are placed in ethyl acetate at a ratio of from 1:50 to 1:200 of callus:ethyl acetate (w:v) and macerated. In one aspect, the ratio is 1:100. In a further aspect, callus samples that have been homogenized can be sealed and placed in a water bath with shaking.

Alternatively, steviol glycosides can be extracted from leaves. In a further aspect, the procedure for extracting steviol glycosides from leaves is the same for extracting from calluses, with the exception of the leaf:solvent ratio, which can be from 1:1 to 1:20. In one aspect, the leaf:ethyl acetate ratio is 1:10.

In a further aspect, any solvent in which rebA or the desired steviol glycoside is soluble in can be used in place of a portion or all of the ethyl acetate in the procedure described above. In a further aspect, the solvent can be hexane, methanol, acetone, dichloromethane, chloroform, ethanol, diethyl ether, DMSO, toluene, isopropyl alcohol, n-butane, heptanes, acetonitrile, THF, or a combination thereof.

In one aspect, steviol glycosides such as, for example, rebA, stevioside, and other steviol glycosides produced by the devices and methods described above can be quantified and/or purified using high pressure liquid chromatography (HPLC). Exemplary methods for quantifying steviol glycosides are provided in the examples.

V. Food Products

The extracts composed of steviol glycosides produced herein can be used to make food products, dietary supplements and sweetener compositions. For example, the steviol glycoside can be included in food products such as ice cream, beverages, (e.g., carbonated fruit juices, energy drinks), yogurts, baked goods, chewing gums, hard and soft candies, sauces, and tabletop sweeteners. The extracts can also be included in non-food products such as pharmaceutical products, medicinal products, dietary supplements and nutritional supplements. The extracts can also be included in animal feed products for both the agriculture industry and the companion animal industry.

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperatures, etc.) but some errors and deviations should be accounted for.

Unless indicated otherwise, parts are parts by weight, temperature is in ° C. or is at ambient temperature, and pressure is at or near atmospheric. Numerous variations and combinations of reaction conditions, e.g., component concentrations, desired solvents, solvent mixtures, temperatures, pressures, and other reaction ranges and conditions can be used to optimize the produce purity and yield obtained from the described process. Only reasonable and routine experimentation will be required to optimize such processes and conditions.

Example 1: Preparation of DNA Construct

The DNA construct was composed of genetic components described herein and assembled in plasmid vectors (e.g., pYES2 and pBSK). Sequences of genes and/or proteins with desired properties were identified in GenBank; these included a DXP synthase gene, a beta-carotene hydroxylase gene, and a lycopene epsilon-cyclase gene. Other genetic parts were also obtained for inclusion in the DNA constructs including, for example, promoter genes (e.g., GAL1 promoter), reporter genes (e.g., yellow fluorescent reporter protein), and terminator sequences (e.g., CYC1 terminator). These genetic parts included restriction sites for ease of insertion into plasmid vectors.

The cloning of the DNA construct into the biological devices was performed as follows. Sequences of individual genes were amplified by polymerase chain reaction using primers that incorporated restriction sites at their 5' ends to facilitate construction of the full sequence to be inserted into the plasmid. Genes were then ligated using standard protocols to form an insert. The plasmid was then digested with restriction enzymes according to directions and using reagents provided by the enzyme's supplier (Promega). The complete insert, containing restriction sites on each end, was then ligated into the plasmid. Successful construction of the insert and ligation of the insert into the plasmid were confirmed by gel electrophoresis.

PCR was used to enhance DNA concentration using a Mastercycler Personal 5332 ThermoCycler (Eppendorf North America) with specific sequence primers and the standard method for amplification (Sambrook, J., E. F. Fritsch, and T. Maniatis, 1989, *Molecular Cloning: A Laboratory Manual, 2^{nd} ed.*, Vol. 1, Cold Spring Harbor Laboratory Press: Cold Spring Harbor, NY). Digestion and ligation were used to ensure assembly of DNA synthesized parts using restriction enzymes and reagents (PCR master mix of restriction enzymes: XhoI, KpnI, XbaI, EcoRI, BamHI, and HindIII, with alkaline phosphatase and quick ligation kit, all from Promega). DNA was quantified using a Nano Vue spectrophotometer (GE Life Sciences) and a standard UV/Visible spectrophotometer using the ratio of absorbances at 260 nm versus 280 nm. In order to verify final ligations, DNA was visualized and purified via electrophoresis using a Thermo EC-150 power supply.

The DNA construct was made with gene parts fundamental for expression of sequences such as, for example, ribosomal binding sites, native and constitutive promoters, reporter genes, and transcriptional terminators or stops. Backbone plasmids and synthetic inserts can be mixed together for ligation purposes at different ratios ranging from 1:1, 1:2, 1:3, 1:4, and up to 1:5. In one aspect, the ratio of backbone plasmid to synthetic insert is 1:4. The DNA constructs in FIGS. 1 and 2 were assembled using the techniques above.

After the vector comprising the DNA construct has been produced, the resulting vector can be incorporated into the host cells using the methods known in the art (e.g., Gietz, R. D. and R. H. Schiestl, 2007, *Nature Protocols, "Quick and easy yeast transformation using the LiAc/SS carrier DNA/PEG method," Vol.* 2, 35-37, doi:10.1038/nprot.2007.14).

Example 2: Quantification of Steviol Glycosides in Extracts by HPLC

The steviol glycosides rebaudioside A (rebA) and stevioside produced by yeast transformed independently with SEQ ID NOs. 15 and 16 using the procedure in Example 1 were quantified using HPLC. Chromatographic separations were carried out on a Thermo Scientific Dionex Ultimate 3000 UHPLC system, using a Thermo Scientific variable wavelength detector. Results were analyzed using Chromeleon™ 7 software.

HPLC method parameters are provided in Table 11. The method was run 10 minutes for calibration curve samples and 15 minutes for experimental samples.

TABLE 11

| HPLC Method Parameters | |
| --- | --- |
| Column | ODS Hypersil 100 × 4.6 mm, C18 Reverse Phase, Particle Size 5 μm |
| Mobile phase | Isocratic, 68:32 Phosphate buffer (10 mM): ACN, pH 2.9 |
| Flow rate | 1 mL/min |
| Column temperature | 40° C. |
| Detection wavelength | 210 nm |
| Injection volume | 5 μL |

All solvents and diluents were HPLC grade and all standard dilutions were made using 70:30 10 mM phosphate buffer:ACN. Rebaudioside A standards were obtained from Sigma-Aldrich and stevioside hydrate standards were obtained from Adipo Gen Life Sciences. Stock solutions of 1000 ppm standards were prepared and used to make serial dilutions, as shown in Table 12.

TABLE 12

| Stock Solution Preparation | | | | |
| --- | --- | --- | --- | --- |
| | Mass (mg) | Purity | Volume | Real Concentration (ppm) |
| Rebaudioside A | 26.3 | 96% | 25 mL | 1009.92 |
| Stevioside | 10.4 | 98% | 10 mL | 1019.2 |

Figure 6A:
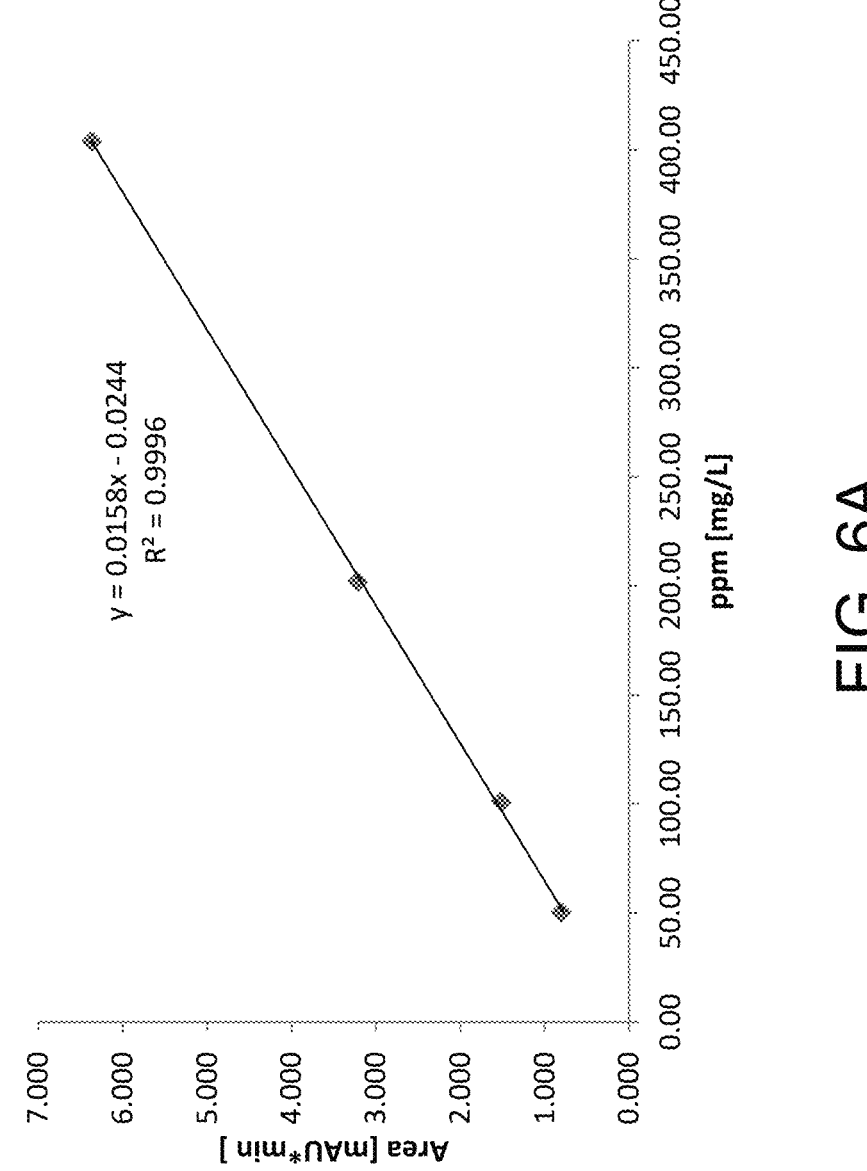
FIGS. 6A and 6B show, respectively, calibration curves obtained from HPLC analysis of rebaudioside A and stevioside.
Figure 6B:
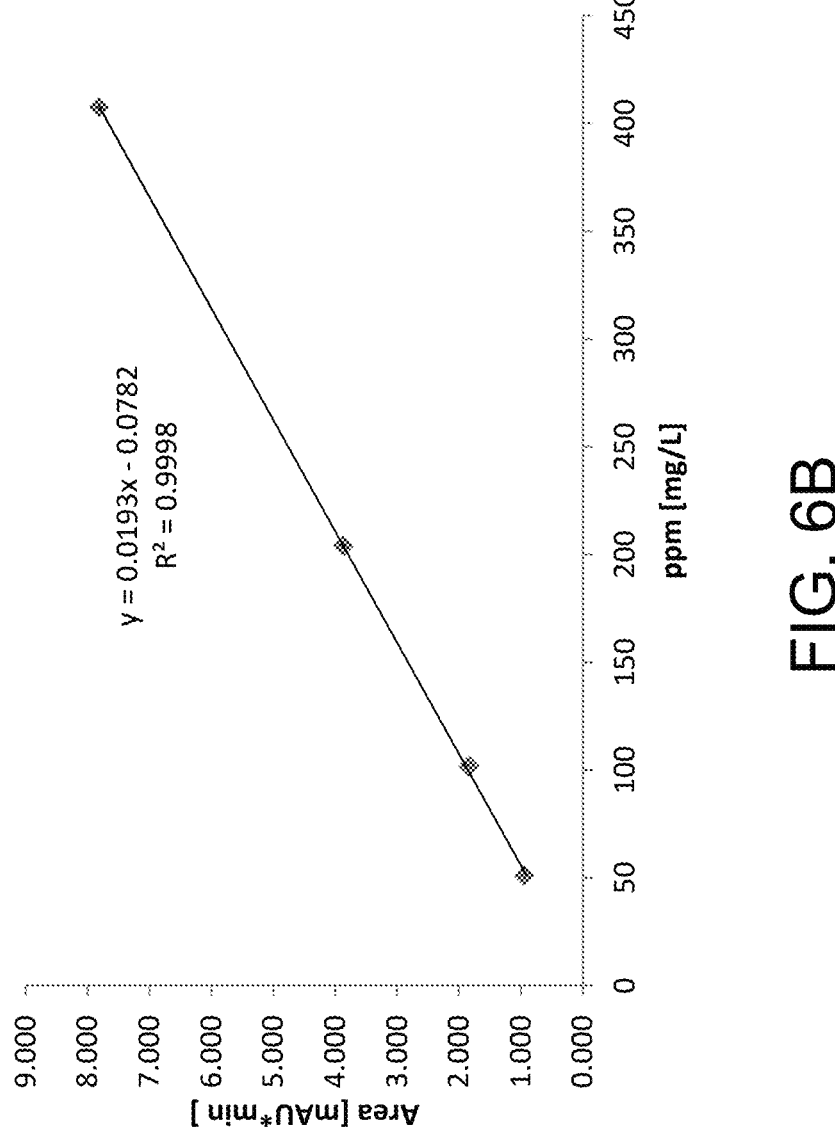
Figure 7:
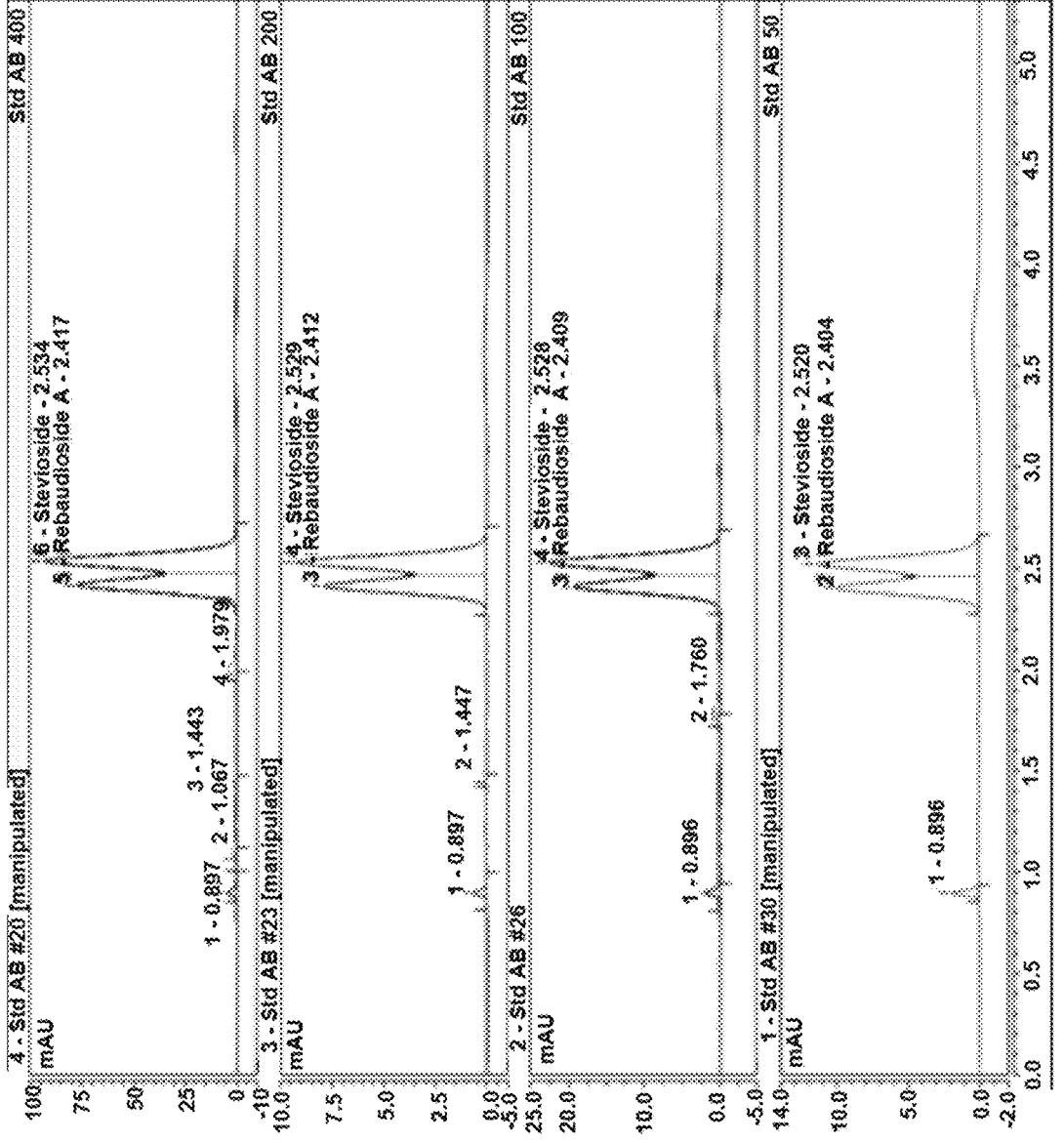
FIG. 7 shows HPLC chromatograms used in generating calibration curves useful in quantifying stevioside and rebaudioside A. Stevioside has a retention time of 2.527 minutes and rebA has a retention time of 2.410 minutes under the conditions used for these experiments.

Standard samples of rebA and stevioside were run separately and together in order to determine the order of elution. Areas of chromatogram peaks were determined by software provided by the HPLC manufacturer and used to construct calibration curves. Repeated injections revealed low standard deviations and low variation coefficients. Calibration curves for rebA and stevioside are shown in FIGS. 6A and 6B, respectively. Sample chromatograms for calibration curve samples are shown in FIG. 7, with rebA peaks at 2.410 and stevioside peaks at 2.527 minutes, respectively. Retention times were consistent over a wide range of concentrations (e.g., 50, 100, 200, and 400 ppm).

Following the development of calibration curves, steviol glycosides were produced and extracted as follows. Yeast transformed independently with SEQ ID NOs. 15 and 16 according to the protocols described above were incubated, separately, in yeast malt medium with 2% raffinose and induction with galactose at 30° C. for 72 hours. Samples were centrifuged at 9,000 rpm for 15 min to produce a pellet. The pellet was resuspended at 1 g/50 mL in sterile deionized water and sonicated 3 times for a total of 2 min, 30 s. Samples were again centrifuged at 9,000 rpm for 15 min and the supernatant was filtered with a 0.45 μm filter. RebA and stevioside were then quantified using HPLC and the calibration curves described above.

HPLC samples were prepared using 1 mL of extracts prepared as described above, brought to a final volume of 5 mL with 70:30 10 mM phosphate buffer:ACN. Samples were analyzed in duplicant. A small shift in retention times for rebA and stevioside was observed in experimental samples as compared to standard samples, with rebA having a peak at 2.514 min and stevioside having a peak at 2.667 min.

Figure 8:
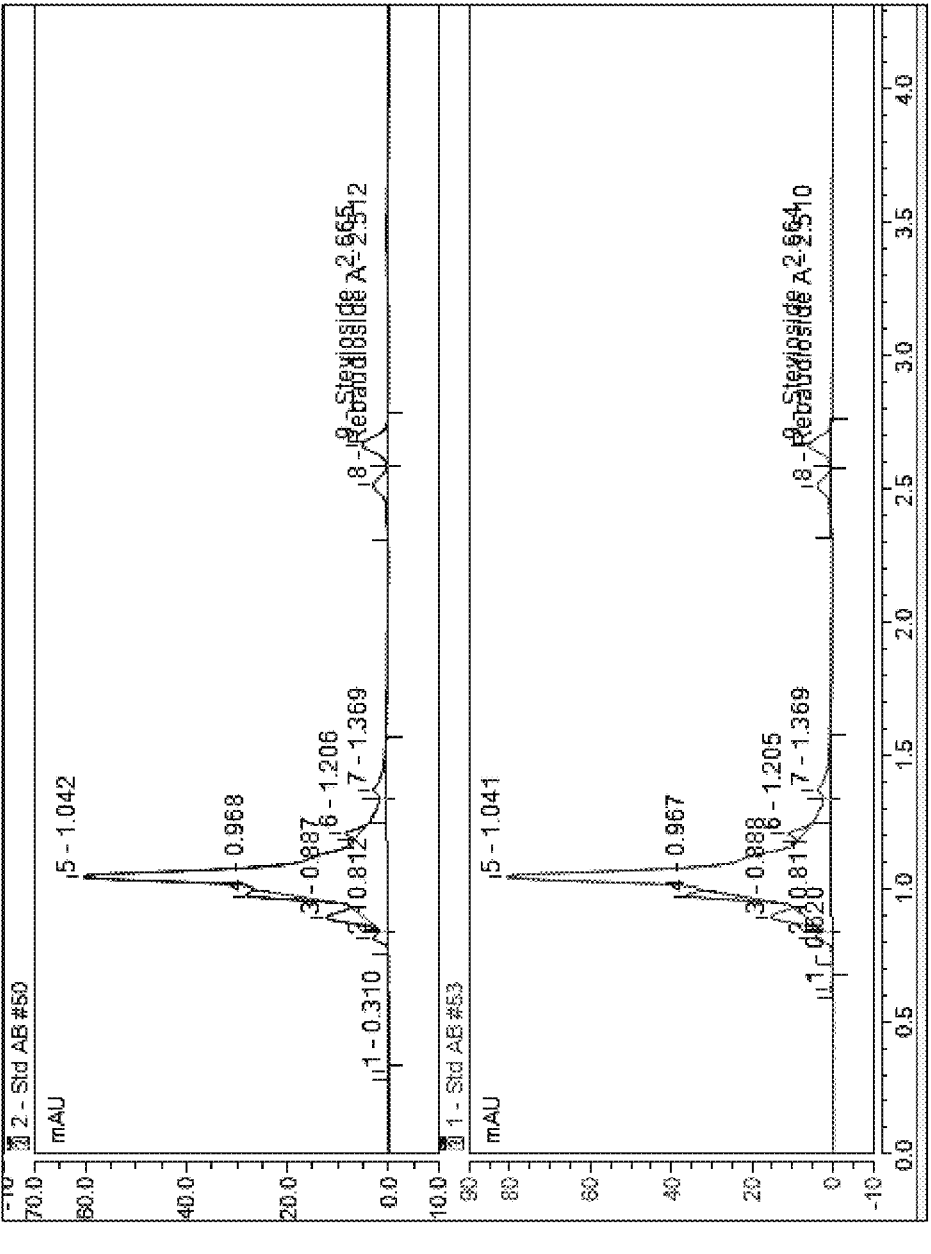
FIG. 8 shows chromatograms of extracts produced using the devices and methods disclosed herein.
Figure 9A:
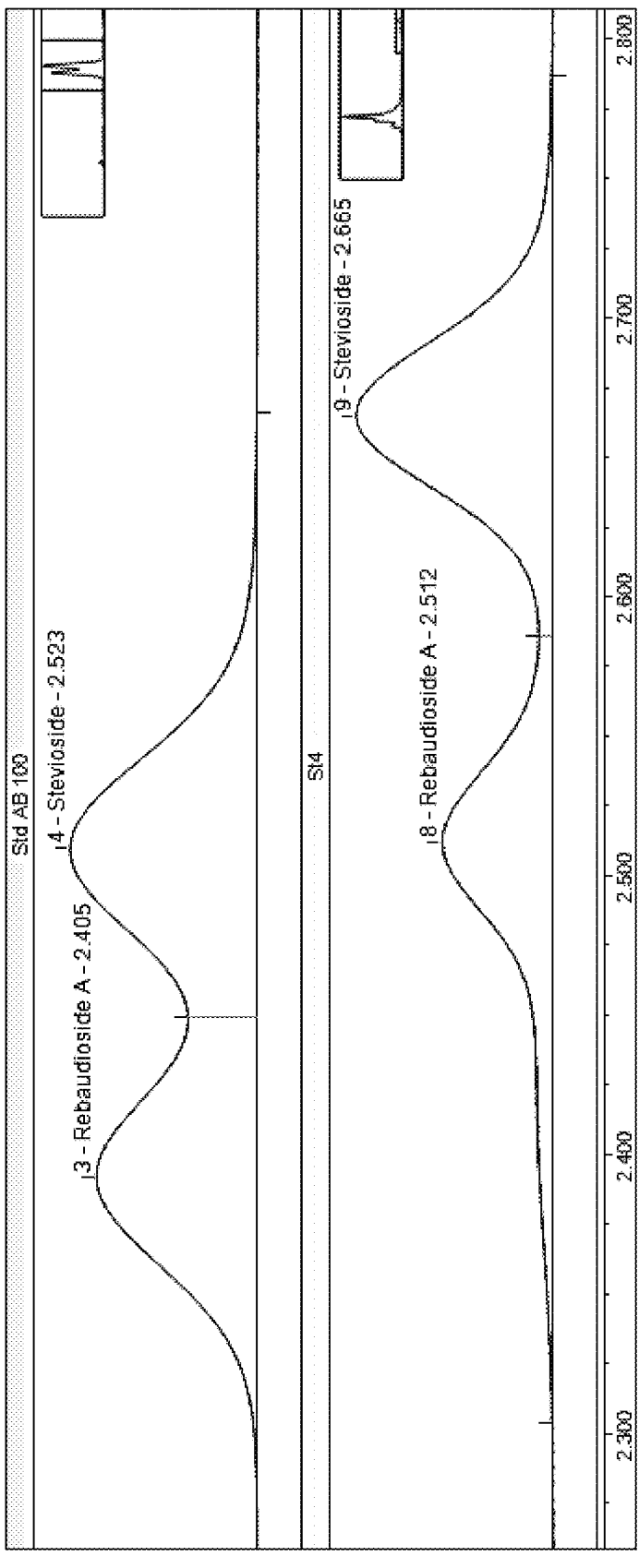
FIGS. 9A and 9B show close views of the rebaudioside A and stevioside peaks from standard solutions (top chromatograms) and extracts from the devices disclosed herein (bottom chromatograms).
Figure 9B:
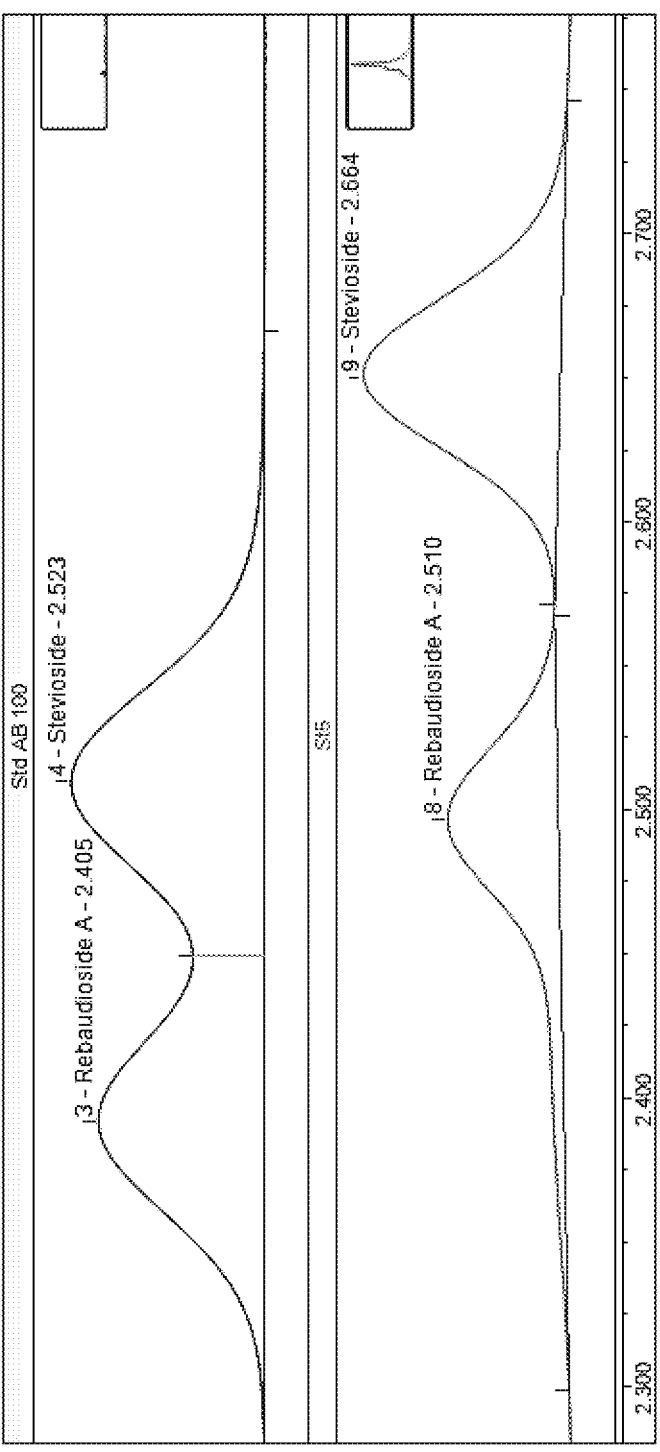

Chromatograms of experimental samples extracted from devices having SEQ ID NO. 15 and SEQ ID NO. 16 are shown in FIG. 8 (top and bottom chromatograms, respectively). FIGS. 9A and 9B show 1000 ppm standards in their top chromatograms and close views of experimental samples for SEQ ID NO. 15 and SEQ ID NO. 16, respectively, in their bottom chromatograms. Concentrations were determined using the calibration curves of FIGS. 6A and 6B, with the extracts from the device having SEQ ID NO. 15 containing 15.01 mg rebA/L sample and 22.00 mg/stevioside/L sample and the device having SEQ ID NO. 16 containing 18.76 mg rebA/L sample and 25.06 mg stevioside/L sample.

Extracts from the device having SEQ ID NO. 16 showed a higher ratio of rebA to stevioside, indicating a sweeter flavor, since stevioside is responsible for the bitter taste associated with *stevia*-based sweeteners.

Example 3: Production of Sucrose

Growth of Device

DNA *stevia* yeast device (FIGS. 4A and 4B) and non-transformed yeast (*Saccharomyces cerevisiae*) were independently grown at 30° C. at 150 RPM for 10 days. The cultures were treated with 2% raffinose, 1% galactose, and 1% glucosamine, to facilitate the induction of *stevia* production. The growth of the cultures was determined by standard optical density using an UV-VIS Spectrophotometer Model Lambda 365 (PerkinElmer CT, USA) measured as different times.

Extraction of Steviol Glycosides from DNA Device

Extraction of steviol glycosides was achieved by adding lyticase to the culture for 4 hours and then centrifuging the culture at 10,000 RPM for 10 minutes to produce a pellet (6.1 g). The pellet was resuspended in distilled deionized water and sonicated with 4 pulses of 30 seconds each. Sonication was repeated. The solution was then centrifuged again, and the supernatant was filtrated with different pore sizes (i.e. 3, 2, 0.8, 0.6, 0.4 μm), with 0.45 μm the preferred size.

Concentration of Steviol Glycosides

The concentration of steviol glycosides produced by the device was determined using the standard curves based on rebaudioside A or stevioside. Different dilutions solutions (i.e. 6-7) were used and measured using an UV-VIS Spectrophotometer Model Lambda 365 (PerkinElmer CT, USA) set at 203 nm and 210 nm wavelengths. Standard curves based on stevioside and rebaudioside A were used as a reference to determine the concentration of the steviol glycosides present in the extract produced from the device. The concentration measurement was performed after 10 days growth of the device culture (see above). The steviol glycoside concentration based on stevioside and rebaudioside A was 100 mg/ml and 89 mg/ml, respectively.

Sweetness Determination

The sugar concentration produced by the cultures of yeast transformed with the construct in FIGS. 4A and 4B and non-transformed yeast was also monitored using a refractometer (VEE GEE Scientific USA/Canada), which measures the refractive index of a solution in a sample, converts it to sugar concentration in units of percent by weight (% Brix), and displays the results. A liquid has one-degree Brix (1% Brix) if it has the same refractive index as a solution of 1 g sucrose in 100 g of sucrose water solution. Aliquots of three-four drops were taken from the device culture and from the non-transformed control culture and placed on the refractometer in order to determine the sweetness of each sample. Three replicates were used at each sampling time. Results are provided in Tables 13 and 14.

TABLE 13

Growth and percentage of sweetness at different times by non-transformed yeast (*Saccharomyces cerviceae*)
Non-transformed Yeast

| Time (hrs) | OD Growth | % Sweetness |
|---|---|---|
| 0 | 0.002 | 2.2 |
| 19 | 0.980 | 3.1 |
| 26 | 1.032 | 3.2 |
| 43 | 1.392 | 3.5 |
| 50 | 1.392 | 3.7 |
| 67 | 1.360 | 3.7 |
| 74 | 1.341 | 3.6 |
| 98 | 1.378 | 3.5 |
| 145 | 1.402 | 3.6 |
| 169 | 1.648 | 3.6 |
| 192 | 1.640 | 3.4 |
| 215 | 1.620 | 3.4 |

TABLE 14

Growth and percentage of sweetness at different times by the stevia device (*Saccharomyces cerviceae*)
Stevia Device

| Time (hrs) | OD Growth | % Sweetness |
|---|---|---|
| 0 | 0.003 | 2.2 |
| 7 | 0.028 | 2.2 |
| 22 | 1.9755 | 2.7 |
| 48 | 2.151 | 3.3 |
| 50 | 2.0835 | 3.9 |
| 70 | 2.078 | 4.3 |
| 94 | 2.07 | 4.3 |
| 168 | 2.064 | 4.5 |
| 192 | 1.91 | 4.5 |

Based on the results above, the *stevia* device produced more sucrose compared to yeast not transformed with the construct based on the increased % sweetness results. Moreover, the yeast transformed with the construct grew quicker and produced a higher population of cells compared to the non-transformed yeast.

Throughout this application, various publications are referenced. The disclosures of these publications in their entireties are hereby incorporated by reference into this application in order to more fully describe the compounds, compositions, and methods described herein.

Various modifications and variations can be made to the compounds, compositions, and methods described herein. Other aspects of the compounds, compositions, and methods described herein will be apparent from consideration of the specification and practice of the compounds, compositions, and methods disclosed herein. It is intended that the specification and examples be considered as exemplary.

What is claimed:

1. A vector comprising a DNA construct comprising the following genetic components:
   a) a gene that expresses hexokinase having SEQ ID NO: 2 or at least 90% homology thereto;
   b) a gene that expresses geranylgeranyl pyrophosphate synthase 2 having SEQ ID NO: 4 or at least 90% homology thereto;
   c) a gene that expresses 1-deoxy-D-xylulose-5-phosphate synthase having SEQ ID NO: 5 or at least 90% homology thereto;
   d) a gene that expresses mevalonate-5-kinase having SEQ ID NO: 6 or at least 90% homology thereto;
   e) a gene that expresses isopentenyl pyrophosphate isomerase having SEQ ID NO: 7 or at least 90% homology thereto;
   f) a gene that expresses mevalonate pyrophosphate decarboxylase having SEQ ID NO: 8 or at least 90% homology thereto; and
   g) a gene that expresses UDP-glycosyltransferase 76G1 having a His 155Leu mutation and SEQ ID NO: 12 or at least 90% homology thereto;
   wherein the vector is a plasmid.

2. The vector of claim 1, wherein the DNA construct further comprises a gene that expresses a heat shock protein.

3. The vector of claim 2, wherein the gene that expresses a heat shock protein expresses HSP70.

4. The vector of claim 3, wherein the gene that expresses HSP70 is SEQ ID NO: 3 or at least 70% homology thereto.

5. The vector of claim 1, wherein the DNA construct comprises from 5' to 3' the following genetic components in the following order: (a) the gene that expresses mevalonate-5-kinase; (b) the gene that expresses isopentenyl pyrophosphate isomerase; (c) the gene that expresses mevalonate pyrophosphate decarboxylase; (d) the gene that expresses hexokinase; (e) a gene that expresses HSP70; (f) the gene that expresses geranylgeranyl pyrophosphate synthase 2; (g) the gene that expresses a UDP-glycosyltransferase; and (h) the gene that expresses 1-deoxy-D-xylulose-5-phosphate synthase.

6. The vector of claim 1, wherein the vector has SEQ ID NO: 14.

7. The vector of claim 1, wherein the plasmid is pWLneo, pSV2cat, pOG44, pXT1, pSG, pSVK3, pBSK, pBSKII, pYES, pYES2, pUC, or pUC19.

8. A biological device comprising host cells transformed with the vector of claim 1.

9. A method for producing one or more steviol glycosides comprising growing the biological device of claim 8 for a time sufficient to produce the steviol glycoside.

10. A method for producing one or more steviol glycosides from plant cells, the method comprising contacting the plant cells with the biological device claim 8.

* * * * *

SEQUENCE LISTING

<160> NUMBER OF SEQ ID NOS: 16

<210> SEQ ID NO 1
<211> LENGTH: 1420
<212> TYPE: DNA
<213> ORGANISM: Arabidopsis thaliana

<400> SEQUENCE: 1
cctaggccac catggctgtt gcgctccaat tcagccgatt atgcgttcga ccggatactt        60
tcgtgcggga gaatcatctc tctggatctg gatctctccg ccgccggaaa gctttatcag       120
tccggtgctc gtctggcgat gagaacgctc cttcgccatc ggtggtgatg gactccgatt       180
tcgacgccaa ggtgttccgt aagaacttga cgagaagcga taattacaat cgtaaagggt       240
tcggtcataa ggaggagaca ctcaagctca tgaatcgaga gtacaccagt gatatattgg       300
agacactgaa aacaaatggg tatacttatt cttggggaga tgttactgtg aaactcgcta       360
aagcatatgg tttttgctgg ggtgttgagc gtgctgttca gattgcatat gaagcacgaa       420
agcagtttcc agaggagagg ctttggatta ctaacgaaat cattcataac ccgaccgtca       480
ataagaggtt ggaagatatg gatgttaaaa ttattccggt tgaggattca aagaaacagt       540
ttgatgtagt agagaaagat gatgtggtta tccttcctgc gtttggagct ggtgttgacg       600
agatgtatgt tcttaatgat aaaaaggtgc aaattgttga cacgacttgt ccttgggtga       660
caaaggtctg gaacacggtt gagaagcaca agaagggga atacacatca gtaatccatg       720
gtaaatataa tcatgaagag acgattgcaa ctgcgtcttt tgcaggaaag tacatcattg       780
taaagaacat gaaagaggca aattacgttt gtgattacat tctcggtggc caatacgatg       840
gatctagctc cacaaaagag gagttcatgg agaaattcaa atacgcaatt tcgaagggtt       900
tcgatcccga caatgacctt gtcaaagttg gtattgcaaa ccaaacaacg atgctaaagg       960
gagaaacaga ggagatagga agattactgg agacaacaat gatgcgcaag tatggagtgg      1020
aaaatgtaag cggacatttc atcagcttca acacaatatg cgacgctact caagagcgac      1080
aagacgcaat ctatgagcta gtggaagaga agattgacct catgctagtg gttggcggat      1140
ggaattcaag taacacctct caccttcagg aaatctcaga ggcacgggga atcccatctt      1200
actggatcga tagtgagaaa cggataggac ctgggaataa aatagcctat aagctccact      1260
atggagaact ggtcgagaag gaaaactttc tcccaaaggg accaataaca atcggtgtga      1320
catcaggtgc atcaaccccg gataaggtcg tggaagatgc tttggtgaag gtgttcgaca      1380
ttaaacgtga agagttattg cagctggctt gattaattaa                            1420

<210> SEQ ID NO 2
<211> LENGTH: 1470
<212> TYPE: DNA
<213> ORGANISM: Saccharomyces cerevisiae

<400> SEQUENCE: 2
gagctcatgg ttcatttagg tccaaagaaa ccacaggcta gaaagggttc catggctgat        60
gtgcccaagg aattgatgga tgaaattcat cagttggaag atatgtttac agttgacagc       120
gagaccttga gaaaggttgt taagcacttt atcgacgaat tgaataaagg tttgacaaag       180
aagggaggta acattccaat gattcccggt tgggtcatgg aattcccaac aggtaaagaa       240
tctggtaact atttggccat tgatttgggt ggtactaact taagagtcgt gttggtcaag       300
ttgagcggta accataccct tgacaccact caatccaagt ataaactacc acatgacatg       360
agaaccacta agcaccaaga ggagttatgg tcctttattg ccgactcttt gaaggacttt       420

-continued

```
atggtcgagc aagaattgct aaacaccaag gacaccttac cattaggttt caccttctcg      480
tacccagctt cccaaaacaa gattaacgaa ggtattttgc aaagatggac caagggtttc      540
gatattccaa atgtcgaagg ccacgatgtc gtcccattgc tacaaaacga aatttccaag      600
agagagttgc ctattgaaat tgtagcgttg attaatgata ctgttggtac tttaattgcc      660
tcatactaca ctgacccaga gactaagatg ggtgtgattt cggtactgg tgtcaacggt        720 gctttctatg atgttgtttc cgatatcgaa aagttggagg gcaaattagc agacgatatt      780
ccaagtaact ctccaatggc tatcaattgt gaatatggtt ccttcgataa tgaacatttg      840
gtcttgccaa gaaccaagta cgatgttgct gtcgacgaac aatctccaag acctggtcaa      900
caagcttttg aaaagatgac ctccggttac tacttgggtg aattgttgcg tctagtgtta      960
cttgaattaa acgagaaggg cttgatgttg aaggatcaag atctaagcaa gttgaaacaa     1020
ccatacatca tggatacctc ctacccagca agaatcgagg atgatccatt tgtttcttg      1080 gaagatactg atgacatctt ccaaaaggac tttggtgtca agaccactct gccagaacgt     1140
aagttgatta aagactttg tgaattgact ggtaccagag ctgctagatt agctgtttgt     1200
ggtattgccg ctatttgcca aaagagaggt tacaagactg gtcacattgc cgctgacggt     1260
tctgtctata acaaataccc aggtttcaag gaagccgccg ctaagggttt gagagatatc     1320
tatggatgga ctggtgacgc aagcaaagat ccaattacga ttgttccagc tgaggatggt     1380
tcaggtgcag gtgctgctgt tattgctgca ttgtccgaaa aaagaattgc cgaaggtaag     1440
tctcttggta tcattggcgc ttaactcgag                                       1470
```

```
<210> SEQ ID NO 3
<211> LENGTH: 1854
<212> TYPE: DNA
<213> ORGANISM: Saccharomyces cerevisiae

<400> SEQUENCE: 3
ggtaccatgg ctgaaggtgt tttccaaggt gctatcggta tcgatttagg tacaacctac       60
tcttgtgttg ctacttacga atcctccgtt gaaattattg ccaacgaaca aggtaacaga      120
gtcaccccat ctttcgttgc tttcactcca gaagaaagat tgattggtga tgctgccaag      180
aaccaagctg ctttgaaccc aagaaacact gtcttcgatg ctaagcgttt gattggtaga      240
agattcgacg acgaatctgt tcaaaaggac atgaagacct ggcctttcaa ggttatcgac      300
gtcgatggta acccagtcat cgaagtccaa tacttggaag aaaccaagac tttctcccca      360
caagaaattt ccgctatggt tttgaccaag atgaaggaaa ttgctgaagc taagattggt      420
aagaaggttg aaaaggccgt cattactgtc ccagcttact ttaacgacgc tcaaagacaa      480
gctaccaagg atgccggtgc catttctggt ttgaacgttt gcgtatcat caacgaacct       540 actgccgctg ctattgctta cggtctaggt gctggtaagt ccgaaaagga aagacatgtt      600
ttgattttcg atttgggtgg tggtactttc gatgtttcct tgttgcacat tgctggtggt      660
gtttacactg ttaaatctac ttccggtaac actcacttgg gtggtcaaga tttcgacacc      720
aacttgttgg aacacttcaa ggctgaattc aagaagaaga ctggttttgga catctccgac      780 gatgccagag ctttgagaag attgagaact gctgctgaaa gagctaagag aaccttatct      840
tctgtcactc aaactaccgt tgaagttgac tctttgtttg acggtgaaga tttcgaatcc      900
tctttgacta gagctagatt tgaagacttg aacgccgcat gttcaagtc tactttggaa       960 cctgttgaac aagtttttgaa ggatgctaag atctctaagt ctcaaatcga cgaagttgtc     1020
```

```
ttggttggtg gttccaccag aattccaaag gtccaaaagt tgttgtctga cttctttgac        1080
ggtaagcaat tggaaaaatc tattaaccca gatgaagctg ttgcttacgg tgctgctgtt        1140
caaggtgcta tcttgaccgg ccaatccaca tctgacgaaa ccaaggactt gttgttgtta        1200
gatgttgctc cattatctct aggtgttggt atgcaaggtg acatgttcgg tatcgttgtt        1260
ccaagaaaca ctactgttcc aaccatcaag agaagaacct ttactacatg tgctgacaac        1320
caaaccaccg ttcaattccc agtctaccaa ggtgaacgtg ttaactgtaa agaaaacact        1380
ttgttgggtg aattcgactt gaagaacatc ccaatgatgc cagctggtga accagtcttg        1440
gaagctatct tcgaagttga tgctaacggt atcttgaagg ttactgccgt cgaaaagtct        1500
accggtaagt cttctaacat cactatctct aacgctgttg gtagattgtc ttctgaagaa        1560
attgaaaaga tggttaacca agctgaagag ttcaaggctg ccgatgaagc ttttgccaag        1620
aagcacgaag ctagacaaag attggaatcc tacgttgcct ccatcgaaca aactgtcact        1680
gacccagtct tgtcttctaa attgaagaga ggttccaagt ccaagattga agctgctttg        1740
tccgatgctt tggctgcttt gcaaatcgaa gacccatctg ctgatgaatt gagaaaggct        1800
gaagttggtt tgaagagagt tgtcaccaag gccatgtctt ctcgttaact cgag             1854
```

```
<210> SEQ ID NO 4
<211> LENGTH: 1149
<212> TYPE: DNA
<213> ORGANISM: Arabidopsis thaliana

<400> SEQUENCE: 4
```

```
ggatccgcca ccatggaacc acaaattctt tttctctatc tctcactctt cattctctcc          60
ctaaacttct tcttcacgaa tcttaaacca aggctagtcc gcctcttcca gccttcttta         120
gaatctcgtg tcaagaccgc tcttttatcc cgaaaggaag tagccgcgtt tcttgattct         180
cccattgtcg aagacgaaga aggcgaagaa agagaagagg aagaagaagg aggtatcgtt         240
tcaaatgcca actttacgtt tgagtttgat ccatacatga tgagcaaagc cgaatcagtg         300
aacaaagctc tggaagaagc aattccagtc ggagagccac tcaagattca tgaagccatg         360
cgatacgcga ttcttgcggc tggaaaacgt gttaggccaa tactctgcct tgcttcttgc         420
gagctagtag gtggccaaga aaatgcggca atgcccgccg cttgtgcggt tgagatgatc         480
cacacgatgt ctctaatcaa agacgatttg ccttgtatgg acaacgacga tttgcgtcgt         540
ggaaagccca cgacgcacaa agtctacggc gaaggagttg ccattctctc tggtgggggct         600 ctcttgtctc ttgcctttga gcacatgacc accgctgaaa tatcctcgga gagaatggtt         660
tgggcggtga gagaattggc taggtctatt gggacaagag gtttagtcgc gggacaagcg         720
atggatataa gcagtgaagg tttggactta aacgaggtcg gattagagca tttggagttt         780
atccatgttc ataaaaccgc ggttttgttg gaaactgccg cggttcttgg cgccataatt         840
ggtggtggat ctgatgaaga gattgaaagt gtgagaaagt ttgcaaggtg cattggattg         900
ttgtttcagg tggtggatga tattttggac gagacgaagt cgtcggagga attgggaaaa         960
accgccggga aagatcagct cgccggaaag ctaacgtatc caaagttgat agggttggag        1020
aaatcgaaag aatttgttaa gagattgacg aaagatgcac ggcaacatct tcaagggttt        1080
agttctgaaa aggttgctcc tttagtagct cttactactt ttattgctaa tagaaataag        1140
tgagaattc                                                              1149
```

```
<210> SEQ ID NO 5
<211> LENGTH: 2160
```

-continued

```
<212> TYPE: DNA
<213> ORGANISM: Arabidopsis thaliana

<400> SEQUENCE: 5
gccaccatgg cggttgcagg atcgaccatg aacctgcatc tcacttcatc tccatacaag      60
acagttccat cactctgtaa attcaccaga aaacagttcc gattaaaggc ctctgcaacg     120
aatccagacg ctgaagatgg gaagatgatg tttaaaaacg ataaacccaa tttgaaggtc     180
gaattcgctg gggagaaacc ggtgacacca ttactggata ccattaatta ccctgtgcac     240
atgaaaaacc tcaccactca ggatcttgag caattagcag cagaacttag acaagatatt     300
gtatattcag tagcgaatac aggtggtcat ttgagttcaa gtttaggtgt tgttgaattg     360
tctgttgctt tacaccatgt tttcaacacc ccagatgaca agatcatttg ggacgttggt     420
caccaggcat acccacataa gattttgacc ggaagaaggt caaagatgca caccataaga     480
aaaacttctg gtttagctgg tttttcctaaa cgagatgaaa gtgctcatga tgcttttggt     540
gctggacata gttctacaag catctctgct ggactaggta tggctgtcgg tagagattta     600
ttagggaaaa ccaacaacgt gatatcggtg atcggagatg cgcgccatgac ggccggacga     660 gcatatgagg cgataaataa tgcaggattt cttgattcaa atctaatcgt cgttttaaac     720
gacaacaagc aagtttcatt accgactgcc acgttggacg gacctgcaac tcccgtcggg     780
gctctcagcg gcgctttatc caaattgcaa gccagtacca agttccgtaa gcttcgtgaa     840
gccgccaaga gcattactaa acaaattgga cctcaagcac atgaagtggc ggcgaaagtc     900
gacgaatacg caagaggtat gattagtgct agcgggtcga cttttattcga ggaactcgga     960 ttatactaca tcggtcccgt cgatggtcac aatgttgaag atttagtcaa cattttttgaa    1020 aaagtcaagt caatgcccgc acccggaccg gttctaatcc acatcgtgac cgaaaaaggc    1080
aaaggttacc ctcctgctga agccgctgct gaccgtatgc acggagttgt gaagtttgat    1140
gttccaactg aaaacaatt caagacaaaa tcaccgacac tttcgtatac tcagtatttt    1200
gctgaatcac ttataaaaga agctgaagct gataacaaga ttgtcgcgat acacgccgcc    1260
atgggaggcg gtaccggact caattacttc cagaagaagt gtcctgaacg ttgtttttgat    1320 gtcggtatcg cggaacaaca cgcagttact ttcgccgcgg gtttagccac cgaaggtctt    1380
aaaccatttt gcgcgatcta ttcgtcgttt ttgcaacgag gatacgatca agtggtgcat    1440
gacgttgatc tacaaaagtt accggttcgg tttgcgatgg accgagctgg tttagtcggg    1500
gctgatggac cgacacattg tggtgcgttt gacataacct acatggcgtg tctaccaaac    1560
atggtggtga tggctccagc cgatgaagcc gaattgatgc acatggttgc aacggctgca    1620
gccattgacg acagaccgag ttgctttcgg ttcccaagag gcaatggcat tggtgcacca    1680
cttcctccta ataacaaagg gattcccata gaggttggta aaggaagaat attacttgaa    1740
ggaactcgtg ttgcgatatt gggatacggt tcgatagttc aagaatgtct aggtgcggct    1800
agcttgcttc aagcccataa cgtgtctgca accgtagccg atgcgcggtt ctgcaaaccg    1860
ttagacaccg gactgattag acgattagcc aacgagcatg aagtcttact taccgtagag    1920
gaaggctcga ttggtggatt tggatcacac gttgctcact ttctaagctt aaatggtctc    1980
ttagatggaa aacttaagct tagagcaatg actcttcctg ataaatacat tgatcatggt    2040
gcaccacaag atcagcttga agaagccggt cttcttcaa aacatatttg ttcatctctt     2100
ttatcacttt tgggaaaacc taaagaagca cttcaataca aatcaataat gtaatctaga    2160
```

<210> SEQ ID NO 6

```
<211> LENGTH: 1349
<212> TYPE: DNA
<213> ORGANISM: Saccharomyces cerevisiae

<400> SEQUENCE: 6
cctaggccac catgtcatta ccgttcttaa cttctgcacc gggaaaggtt attattttg      60 gtgaacactc tgctgtgtac aacaagcctg ccgtcgctgc tagtgtgtct gcgttgagaa     120
cctacctgct aataagcgag tcatctgcac cagatactat tgaattggac ttcccggaca     180
ttagctttaa tcataagtgg tccatcaatg atttcaatgc catcaccgag gatcaagtaa     240
actcccaaaa attggccaag gctcaacaag ccaccgatgg cttgtctcag gaactcgtta     300
gtcttcttga tccgttgtta gctcaactat ccgaatcctt ccactaccat gcagcgtttt     360
gtttcctgta tatgtttgtt tgcctatgcc cccatgccaa gaatattaag ttttctttaa     420
agtctacttt acccatcggt gctgggttgg gctcaagcgc ctctatttct gtatcactgg     480
ccttagctat ggcctacttg ggggggttaa taggatctaa tgacttggaa aagctgtcag     540
aaaacgataa gcatatagtg aatcaatggg ccttcatagg tgaaaagtgt attcacggta     600 cccccttcagg aatagataac gctgtggcca cttatggtaa tgccctgcta tttgaaaaag     660
actcacataa tggaacaata aacacaaaca attttaagtt cttagatgat ttcccagcca     720
ttccaatgat cctaacctat actagaattc caaggtctac aaaagatctt gttgctcgcg     780
ttcgtgtgtt ggtcaccgag aaatttcctg aagttatgaa gccaattctg gatgccatgg     840
gtgaatgtgc cctacaaggc ttagagatca tgactaagtt aagtaaatgt aaaggcaccg     900
atgacgaggc tgtagaaact aataatgaac tgtatgaaca actattggaa ttgataagaa     960
taaatcatgg actgcttgtc tcaatcggtg tttctcatcc tggattagaa cttattaaaa    1020
atctgagcga tgatttgaga attggctcca caaaacttac cggtgctggt ggcggcggtt    1080
gctctttgac tttgttacga agagacatta ctcaagagca aattgacagc ttcaaaaaga    1140
aattgcaaga tgattttagt tacgagacat ttgaaacaga cttgggtggg actggctgct    1200
gtttgttaag cgcaaaaaat ttgaataaag atcttaaaat caaatccta gtattccaat    1260 tatttgaaaa taaaactacc acaaagcaac aaattgacga tctattattg ccaggaaaca    1320
cgaatttacc atggacttca taactcgag                                       1349

<210> SEQ ID NO 7
<211> LENGTH: 1067
<212> TYPE: DNA
<213> ORGANISM: Bacillus thuringiensis serovar konkukian str. 97-27

<400> SEQUENCE: 7
ggccggccac catggtaagg gcaaaacgta aattagatca tattgaatac gctctttcta      60
ctggtcagtc tcgtacgcat ggctttcatg atattgattt tgtgcatcaa agcttgccaa     120
attcaagtta tgaaacaata acatgtgaaa caaaaatcgg cgaactttca ctaagttcgc     180 cgattttat caatgcgatg actggtggtg gaggagagaa aacgttacat attaatgagc     240
aattagcata tgtagcgaaa catcataacc ttgctatggc tgtaggatcg caaatggcag     300
cgttaaaaga tgaaagtgaa gctgcttctt ataagattat tagaaaggta aatccaaatg     360
gtattttctt tgctaattta ggtagtgagg caactgttga acaggcagag cgtgctgttg     420
atatggttga agcgaatgca ttgcaaattc atttaaatgt catacaagag ttaacgatgc     480
cagaaggaga ccgtgacttt actggtgtac ttcagcgtat tgagaaaatt gttttaaata     540
gtaaagttcc tgtcattgta aaagaagttg gatttgggat gagtaaggaa acaatgcaac     600
```

```
agttggcgag cgtaggtgta acggcaattg atattggcgg acaagggggt acgaattttg      660
ctgctgttga aaatgaaaga agacagcgaa tgctttctta ttttaataac tggggcatac      720
aaacagctac ctcgattatt gaagcaacct ctacaaataa taacctctct tttattgcat      780
ctgggggtat acaaacagcg cttgacgtag cgaaagcaat cgcattaggg gcgaatacca      840
ctgcgtttgc tggatacttt ttacgcattt taatggaaga tggtatcgag aagttggtgg      900
acgaaattga cctttacat acagatttga aatttattat gacagctctc ggtgcaaaga      960
cgatagaaga gttacagtcc gtacctcttg ttataaaggg tgaaacgtat cattggttaa     1020
cgcagcgtgg aattgatacg acgcattata gtagaagata atccgga                  1067
```

<210> SEQ ID NO 8
<211> LENGTH: 1024
<212> TYPE: DNA
<213> ORGANISM: Lactobacillus paracasei

<400> SEQUENCE: 8

```
cccgggccac catgacgact tatgcacgcg cgcacacaaa tattgcgctg attaaatatt       60
ggggaaaagc caatcgcaag ttgatgctgc cagccacaag cagcatttct ttaactttaa      120
atgactttta tactgacaca gcagtgacat ttgatcctag tctaaatgat gatcgcttca      180
tgcttaacgg tgaagaacaa aacccggttg cggtcagccg cttttttggat cgggttcggc      240 acttaggaaa aattagcacg tacgcccaag tcacttcctt gaatcacgtg ccgactgctg      300
ccgggctggc aagttcagcc tctgcttttg ctgccttggc cactgctgcc agccgcgcgg      360
caggtctaaa cctttctccg actgaactat caagattagc gcgccgcgga tcaggttcag      420
caacgcgctc tatctttggt ggtgccgtta tctggcatcg cggccatgac gacgcctctt      480
cattcgctga accactcgcg attcaaccta gtttgccatt acgaatgctt gtggtcacgg      540
tatctgctga aaaaaaggcg gtcagttcac gaaaaggcat ggccaacaca gtggccacaa      600
gtccctacta tgatgcctgg gtggcctcaa atgaaagttt aattgaacca atgattaccg      660
cgttggctga agacgactta gcgctgatcg gcaaattgac agaattgtcc agtatgcgca      720
tgcatgcggc gattatggcc gaggaaccgc cattcaccta ctttctgccg gaaacattac      780
gggcgtggca attagtgcaa gaacaacggg ctttgggtat tcccgcgttt gccacgatgg      840
atgcaggacc aaatgtcaaa attctgacta ctgaacctta cgtggacatt ttattaaccg      900
ccttgcgccc tgtgttcggt gatcggattt tgagcacacg ccttggtcct gatgccagca      960
tcatcacaaa ggagcaattt gatgacacaa agtcagcaat cgcatcgcaa ggatgattaa     1020
ttaa                                                                   1024
```

<210> SEQ ID NO 9
<211> LENGTH: 890
<212> TYPE: DNA
<213> ORGANISM: Artificial sequence
<220> FEATURE:
<223> OTHER INFORMATION: Synthetic construct

<400> SEQUENCE: 9

```
ggattcaaag aggagaaata ctagatggtg agcaagggcg aggagctgtt caccggggtg       60
gtgcccatcc tggtcgagct ggacggcgac gtaaacggcc acaagttcag cgtgtccggc      120
gagggcgagg gcgatgccac ctacggcaag ctgaccctga agttcatctg caccaccggc      180
aagctgcccg tgccctggcc caccctcgtg accaccttcg gctacggcct gcaatgcttc      240
```

```
gcccgctacc ccgaccacat gaagctgcac gacttcttca agtccgccat gcccgaaggc      300
tacgtccagg agcgcaccat cttcttcaag gacgacggca actacaagac ccgcgccgag      360
gtgaagttcg agggcgacac cctggtgaac cgcatcgagc tgaagggcat cgacttcaag      420
gaggacggca acatcctggg gcacaagctg gagtacaact acaacagcca caacgtctat      480
atcatggccg acaagcagaa gaacggcatc aaggtgaact tcaagatccg ccacaacatc      540
gaggacggca gcgtgcagct cgccgaccac taccagcaga acacccccat cggcgacggc      600
cccgtgctgc tgcccgacaa ccactacctg agctaccagt ccgccctgag caaagacccc      660
aacgagaagc gcgatcacat ggtcctgctg gagttcgtga ccgccgccgg gatcactctc      720
ggcatggacg agctgtacaa gtaataatac tagagccagg catcaaataa aacgaaaggc      780
tcagtcgaaa gactgggcct ttcgttttat ctgttgtttg tcggtgaacg ctctctacta      840
gagtcacact ggctcacctt cgggtgggcc tttctgcgtt tataaagctt      890
```

```
<210> SEQ ID NO 10
<211> LENGTH: 18019
<212> TYPE: DNA
<213> ORGANISM: Artificial sequence
<220> FEATURE:
<223> OTHER INFORMATION: Synthetic construct

<400> SEQUENCE: 10
acggattaga agccgccgag cgggtgacag ccctccgaag gaagactctc ctccgtgcgt       60
cctcgtcttc accggtcgcg ttcctgaaac gcagatgtgc ctcgcgccgc actgctccga      120
acaataaaga ttctacaata ctagctttta tggttatgaa gaggaaaaat tggcagtaac      180
ctggccccac aaaccttcaa atgaacgaat caaattaaca accataggat gataatgcga      240
ttagtttttt agccttattt ctggggtaat taatcagcga agcgatgatt tttgatctat      300
taacagatat ataaatgcaa aaactgcata accactttaa ctaatacttt caacattttc      360
ggtttgtatt acttcttatt caaatgtaat aaaagtatca acaaaaaatt gttaatatac      420
ctctatactt taacgtcaag gagaaaaaac cccggatcgg actactagca gctgtaatac      480
gactcactat aggggaatatt aagcttccta ggccaccatg gctgttgcgc tccaattcag      540
ccgattatgc gttcgaccgg atactttcgt gcgggagaat catctctctg gatctggatc      600
tctccgccgc cggaaagctt tatcagtccg gtgctcgtct ggcgatgaga acgtccttc       660 gccatcggtg gtgatggact ccgatttcga cgccaaggtg ttccgtaaga acttgacgag      720
aagcgataat tacaatcgta aagggttcgg tcataaggag gagacactca agctcatgaa      780
tcgagagtac accagtgata tattggagac actgaaaaca aatgggtata cttattcttg      840
gggagatgtt actgtgaaac tcgctaaagc atatggtttt tgctggggtg ttgagcgtgc      900
tgttcagatt gcatatgaag cacgaaagca gtttccagag gagaggcttt ggattactaa      960
cgaaatcatt cataacccga ccgtcaataa gaggttggaa gatatggatg ttaaaattat     1020
tccggttgag gattcaaaga aacagtttga tgtagtagag aaagatgatg tggttatcct     1080
tcctgcgttt ggagctggtg ttgacgagat gtatgttctt aatgataaaa aggtgcaaat     1140
tgttgacacg acttgtcctt gggtgacaaa ggtctggaac acggttgaga agcacaagaa     1200
gggggaatac acatcagtaa tccatggtaa atataatcat gaagagacga ttgcaactgc     1260
gtcttttgca ggaaagtaca tcattgtaaa gaacatgaaa gaggcaaatt acgtttgtga     1320
ttacattctc ggtggccaat acgatggatc tagctccaca aaagaggagt tcatggaaa      1380 attcaaatac gcaatttcga agggtttcga tcccgacaat gaccttgtca aagttggtat     1440
```

-continued

```
tgcaaaccaa acaacgatgc taaagggaga aacagaggag ataggaagat tactggagac    1500
aacaatgatg cgcaagtatg gagtggaaaa tgtaagcgga catttcatca gcttcaacac    1560
aatatgcgac gctactcaag agcgacaaga cgcaatctat gagctagtgg aagagaagat    1620
tgacctcatg ctagtggttg gcggatggaa ttcaagtaac acctctcacc ttcaggaaat    1680
ctcagaggca cggggaatcc catcttactg gatcgatagt gagaaacgga taggacctgg    1740
gaataaaata gcctataagc tccactatgg agaactggtc gagaaggaaa actttctccc    1800
aaagggacca ataacaatcg gtgtgacatc aggtgcatca accccggata aggtcgtgga    1860
agatgctttg gtgaaggtgt tcgacattaa acgtgaagag ttattgcagc tggcttgatt    1920
aattaatcat gtaattagtt atgtcacgct tacattcacg ccctcccccc acatccgctc    1980
taaccgaaaa ggaaggagtt agacaacctg aagtctaggt ccctatttat tttttttatag    2040 ttatgttagt attaagaacg ttatttatat ttcaaatttt tcttttttttt ctgtacagac    2100 gcgtgtacgc atgtaacatt atactgaaaa ccttgcttga gaaggttttg ggacgctcga    2160
aggctttaat ttgccggatt agaagccgcc gagcgggtga cagccctccg aaggaagact    2220
ctcctccgtg cgtcctcgtc ttcaccggtc gcgttcctga aacgcagatg tgcctcgcgc    2280
cgcactgctc cgaacaataa agattctaca atactagctt ttatggttat gaagaggaaa    2340
aattggcagt aacctggccc cacaaacctt caaatgaacg aatcaaatta acaaccatag    2400
gatgataatg cgattagttt tttagcctta tttctggggt aattaatcag cgaagcgatg    2460
atttttgatc tattaacaga tatataaatg caaaaactgc ataaccactt taactaatac    2520
tttcaacatt ttcggtttgt attacttctt attcaaatgt aataaaagta tcaacaaaaa    2580
attgttaata tacctctata ctttaacgtc aaggagggcg cgccatggtt catttaggtc    2640
caaagaaacc acaggctaga aagggttcca tggctgatgt gcccaaggaa ttgatggatg    2700
aaattcatca gttggaagat atgtttacag ttgacagcga gaccttgaga aaggttgtta    2760
agcactttat cgacgaattg aataaaggtt tgacaaagaa gggaggtaac attccaatga    2820
ttcccggttg ggtcatggaa ttcccaacag gtaaagaatc tggtaactat ttggccattg    2880
atttgggtgg tactaactta agagtcgtgt tggtcaagtt gagcggtaac catacctttg    2940
acaccactca atccaagtat aaactaccac atgacatgag aaccactaag caccaagagg    3000
agttatggtc ctttattgcc gactctttga aggactttat ggtcgagcaa gaattgctaa    3060
acaccaagga caccttacca ttaggtttca ccttctcgta cccagcttcc caaaacaaga    3120
ttaacgaagg tattttgcaa agatggacca agggtttcga tattccaaat gtcgaaggcc    3180
acgatgtcgt cccattgcta caaaacgaaa tttccaagag agagttgcct attgaaattg    3240
tagcattgat taatgatact gttggtactt taattgcctc atactacact gacccagaga    3300
ctaagatggg tgtgattttc ggtactggtg tcaacggtgc tttctatgat gttgtttccg    3360
atatcgaaaa gttggagggc aaaattagcag acgatattcc aagtaactct ccaatggcta    3420
tcaattgtga atatggttcc ttcgataatg aacatttggt cttgccaaga accaagtacg    3480
atgttgctgt cgacgaacaa tctccaagac ctggtcaaca agcttttgaa aagatgacct    3540
ccggttacta cttgggtgaa ttgttgcgtc tagtgttact tgaattaaac gagaagggct    3600
tgatgttgaa ggatcaagat ctaagcaagt tgaaacaacc atacatcatg gatacctcct    3660
acccagcaag aatcgaggat gatccatttg aaaaacttgga agatactgat gacatcttcc    3720
aaaaggactt tggtgtcaag accactctgc cagaacgtaa gttgattaga agactttgtg    3780
```

-continued

```
aattgatcgg taccagagct gctagattag ctgtttgtgg tattgccgct atttgccaaa    3840
agagaggtta caagactggt cacattgccg ctgacggttc tgtctataac aaatacccag    3900
gtttcaagga agccgccgct aagggtttga gagatatcta tggatggact ggtgacgcaa    3960
gcaaagatcc aattacgatt gttccagctg aggatggttc aggtgcaggt gctgctgtta    4020
ttgctgcatt gtccgaaaaa agaattgccg aaggtaagtc tcttggtatc attggcgctt    4080
aagtttaaac tcatgtaatt agttatgtca cgcttacatt cacgccctcc ccccacatcc    4140
gctctaaccg aaaaggaagg agttagacaa cctgaagtct aggtccctat ttattttttt    4200
atagttatgt tagtattaag aacgttattt atatttcaaa tttttctttt ttttctgtac    4260
agacgcgtgt acgcatgtaa cattatactg aaaaccttgc ttgagaaggt tttgggacgc    4320
tcgaaggctt taatttgccg gattagaagc cgccgagcgg gtgacagccc tccgaaggaa    4380
gactctcctc cgtgcgtcct cgtcttcacc ggtcgcgttc ctgaaacgca gatgtgcctc    4440
gcgccgcact gctccgaaca ataaagattc tacaatacta gctttttatgg ttatgaagag    4500 gaaaaattgg cagtaacctg gccccacaaa ccttcaaatg aacgaatcaa attaacaacc    4560
ataggatgat aatgcgatta gttttttttagc cttatttctg gggtaattaa tcagcgaagc    4620
gatgattttt gatctattaa cagatatata aatgcaaaaa ctgcataacc actttaacta    4680
atactttcaa cattttcggt ttgtattact tcttattcaa atgtaataaa agtatcaaca    4740
aaaaattgtt aatatacctc tatactttaa cgtcaaggag gagctcacca tggctgaagg    4800
tgttttccaa ggtgctatcg gtatcgattt aggtacaacc tactcttgtg ttgctactta    4860
cgaatcctcc gttgaaatta ttgccaacga acaaggtaac agagtcaccc catctttcgt    4920
tgctttcact ccagaagaaa gattgattgg tgatgctgcc aagaaccaag ctgctttgaa    4980
cccaagaaac actgtcttcg atgctaagcg tttgattggt agaagattcg acgacgaatc    5040
tgttcaaaag gacatgaaga cctggccttt caaggttatc gacgtcgatg gtaacccagt    5100
catcgaagtc caatacttgg aagaaaccaa gactttctcc ccacaagaaa tttccgctat    5160
ggttttgacc aagatgaagg aaattgctga agctaagatt ggtaagaagg ttgaaaaggc    5220
cgtcattact gtcccagctt actttaacga cgctcaaaga caagctacca aggatgccgg    5280
tgccatttct ggtttgaacg ttttgcgtat catcaacgaa cctactgccg ctgctattgc    5340
ttacggtcta ggtgctggta agtccgaaaa ggaaagacat gttttgattt tcgatttggg    5400
tggtggtact ttcgatgttt ccttgttgca cattgctggt ggtgtttaca ctgttaaatc    5460
tacttccggt aacactcact ggggtggtca agatttcgac accaacttgt tggaacactt    5520
caaggctgaa ttcaagaaga gactggtttt ggacatctcc gacgatgcca gagctttgag    5580
aagattgaga actgctgctg aaagagctaa gagaaccttg tcttctgtca ctcaaactac    5640
cgttgaagtt gactctttgt ttgacggtga agatttcgaa tcctcttttga ctagagctag    5700 atttgaagac ttgaacgccg cattgttcaa gtctactttg gaacctgttg aacaagtttt    5760
gaaggatgct aagatctcta agtctcaaat cgacgaagtt gtcttggttg gtggttccac    5820
cagaattcca aaggtccaaa agttgttgtc tgacttcttt gacggtaagc aattggaaaa    5880
atctattaac ccagatgaag ctgttgctta cggtgctgct gttcaaggtg ctatcttgac    5940
cggccaatcc acatctgacg aaaccaagga cttgttgttg ttagatgttg ctccattatc    6000
tctaggtgtt ggtatgcaag gtgacatgtt cggtatcgtt gttccaagaa acactactgt    6060
tccaaccatc aagagaagaa cctttactac atgtgctgac aaccaaacca ccgttcaatt    6120
cccagtctac caaggtgaac gtgttaactg taaagaaaac actttgttgg gtgaattcga    6180
```

```
cttgaagaac atcccaatga tgccagctgg tgaaccagtc ttggaagcta tcttcgaagt   6240
tgatgctaac ggtatcttga aggttactgc cgtcgaaag tctaccggta agtcttctaa    6300
catcactatc tctaacgctg ttggtagatt gtcttctgaa gaaattgaaa agatggttaa   6360
ccaagctgaa gagttcaagg ctgccgatga agcttttgcc aagaagcacg aagctagaca   6420
aagattggaa tcctacgttg cctccatcga acaaactgtc actgacccag tcttgtcttc   6480
taaattgaag agaggttcca agtccaagat tgaagctgct ttgtccgatg ctttggctgc   6540
tttgcaaatc gaagacccat ctgctgatga attgagaaag gctgaagttg gtttgaagag   6600
agttgtcacc aaggccatgt cttctcgtta aggtacctca tgtaattagt tatgtcacgc   6660
ttacattcac gccctccccc cacatccgct ctaaccgaaa aggaaggagt tagacaacct   6720
gaagtctagg tccctatta tttttttata gttatgttag tattaagaac gttatttata    6780
tttcaaattt ttcttttttt tctgtacaga cgcgtgtacg catgtaacat tatactgaaa   6840
accttgcttg agaaggtttt gggacgctcg aaggctttaa tttgccggat tagaagccgc   6900
cgagcgggtg acagccctcc gaaggaagac tctcctccgt gcgtcctcgt cttcaccggt   6960
cgcgttcctg aaacgcagat gtgcctcgcg ccgcactgct ccgaacaata aagattctac   7020
aatactagct tttatggtta tgaagaggaa aaattggcag taacctggcc ccacaaacct   7080
tcaaatgaac gaatcaaatt aacaaccata ggatgataat gcgattagtt ttttagcctt   7140
atttctgggg taattaatca gcgaagcgat gatttttgat ctattaacag atatataaat   7200
gcaaaaactg cataaccact ttaactaata ctttcaacat tttcggtttg tattacttct   7260
tattcaaatg taataaaagt atcaacaaaa aattgttaat atacctctat actttaacgt   7320
caaggaggga tccgccacca tggaaccaca aattcttttt ctctatctct cactcttcat   7380
tctctcccta aacttcttct tcacgaatct taaaccaagg ctagtccgcc tcttccagcc   7440
ttctttagaa tctcgtgtca agaccgctct tttatcccga aaggaagtag ccgcgtttct   7500
tgattctccc attgtcgaag acgaagaagg cgaagaaaga gaagaggaag aagaaggagg   7560
tatcgtttca aatgccaact ttacgtttga gtttgatcca tacatgatga gcaaagccga   7620
atcagtgaac aaagctctgg aagaagcaat tccagtcgga gagccactca agattcatga   7680
agccatgcga tacgcgattc ttgcggctgg aaaacgtgtt aggccaatac tctgccttgc   7740
ttcttgcgag ctagtaggtg gccaagaaaa tgcggcaatg cccgccgctt gtgcggttga   7800
gatgatccac acgatgtctc taatcaaaga cgatttgcct tgtatggaca acgacgattt   7860
gcgtcgtgga aagcccacga cgcacaaagt ctacggcgaa ggagttgcca ttctctctgg   7920
tggggctctc ttgtctcttg cctttgagca catgaccacc gctgaaatat cctcggagag   7980
aatggtttgg gcggtgagag aattggctag gtctattggg acaagaggtt tagtcgcggg   8040
acaagcgatg gatataagca gtgaaggttt ggacttaaac gaggtcggat tagagcattt   8100
ggagtttatc catgttcata aaaccgcggt tttgttggaa actgccgcgg ttcttggcgc   8160
cataattggt ggtggatctg atgaagagat tgaaagtgtg agaaagtttg caaggtgcat   8220
tggattgttg tttcaggtgg tggatgatat tttggacgag acgaagtcgt cggaggaatt   8280
gggaaaaacc gccgggaaag atcagctcgc cggaaagcta acgtatccaa agttgatagg   8340
gttggagaaa tcgaaagaat ttgttaagag attgacgaaa gatgcacggc aacatcttca   8400
agggtttagt tctgaaaagg ttgctccttt agtagctctt actactttta ttgctaatag   8460
aaataagtga gaattctcat gtaattagtt atgtcacgct tacattcacg ccctcccccc   8520
```

-continued

```
acatccgctc taaccgaaaa ggaaggagtt agacaacctg aagtctaggt ccctatttat   8580
ttttttatag ttatgttagt attaagaacg ttatttatat ttcaaatttt tcttttttttt  8640 ctgtacagac gcgtgtacgc atgtaacatt atactgaaaa ccttgcttga gaaggttttg   8700
ggacgctcga aggctttaat ttgccggatt agaagccgcc gagcgggtga cagccctccg   8760
aaggaagact ctcctccgtg cgtcctcgtc ttcaccggtc gcgttcctga aacgcagatg   8820
tgcctcgcgc cgcactgctc cgaacaataa agattctaca atactagctt ttatggttat   8880
gaagaggaaa aattggcagt aacctggccc cacaaacctt caaatgaacg aatcaaatta   8940
acaaccatag gatgataatg cgattagttt tttagcctta tttctggggt aattaatcag   9000
cgaagcgatg attttttgatc tattaacaga tatataaatg caaaaactgc ataaccactt  9060
taactaatac tttcaacatt ttcggtttgt attacttctt attcaaatgt aataaaagta   9120
tcaacaaaaa attgttaata tacctctata ctttaacgtc aaggaggcgg ccgccatggt   9180
gagcaagggc gaggagctgt tcaccggggt ggtgcccatc ctggtcgagc tggacggcga   9240
cgtaaacggc cacaagttca gcgtgtccgg cgagggcgag ggcgatgcca cctacggcaa   9300
gctgaccctg aagttcatct gcaccaccgg caagctgccc gtgccctggc ccaccctcgt   9360
gaccaccttc ggctacggcc tgcaatgctt cgcccgctac cccgaccaca tgaagctgca   9420
cgacttcttc aagtccgcca tgcccgaagg ctacgtccag gagcgcacca tcttcttcaa   9480
ggacgacggc aactacaaga cccgcgccga ggtgaagttc gagggcgaca ccctggtgaa   9540
ccgcatcgag ctgaagggca tcgacttcaa ggaggacggc aacatcctgg ggcacaagct   9600
ggagtacaac tacaacagcc acaacgtcta tatcatggcc gacaagcaga agaacggcat   9660
caaggtgaac ttcaagatcc gccacaacat cgaggacggc agcgtgcagc tcgccgacca   9720
ctaccagcag aacacccca tcggcgacg ccccgtgctg ctgcccgaca ccactacct    9780 gagctaccag tccgccctga gcaaagaccc caacgagaag cgcgatcaca tggtcctgct   9840
ggagttcgtg accgccgccg ggatcactct cggcatggac gagctgtaca gtaataatc    9900 gtacgcatca tgtaattagt tatgtcacgc ttacattcac gccctccccc cacatccgct   9960
ctaaccgaaa aggaaggagt tagacaacct gaagtctagg tccctatttta ttttttttata  10020 gttatgttag tattaagaac gttatttata tttcaaattt ttcttttttt tctgtacaga   10080
cgcgtgtacg catgtaacat tatactgaaa accttgcttg agaaggtttt gggacgctcg   10140
aaggctttaa tttgcatgct acggattaga agccgccgag cgggtgacag ccctccgaag   10200
gaagactctc ctccgtgcgt cctcgtcttc accggtcgcg ttcctgaaac gcagatgtgc   10260
ctcgcgccgc actgctccga acaataaaga ttctacaata ctagctttta tggttatgaa   10320
gaggaaaaat tggcagtaac ctggccccac aaaccttcaa atgaacgaat caaattaaca   10380
accataggat gataatgcga ttagtttttt agccttattt ctggggtaat taatcagcga   10440
agcgatgatt tttgatctat aacagatat ataaatgcaa aaactgcata accactttaa   10500
ctaatacttt caacattttc ggtttgtatt acttcttatt caaatgtaat aaaagtatca   10560
acaaaaaatt gttaatatac ctctatactt taacgtcaag gaggccacca tggcggttgc   10620
aggatcgacc atgaacctgc atctcacttc atctccatac aagacagttc catcactctg   10680
taaattcacc agaaaacagt tccgattaaa ggcctctgca acgaatccag acgctgaaga   10740
tgggaagatg atgtttaaaa acgataaacc caatttgaag gtcgaattcg ctggggagaa   10800
accggtgaca ccattactgg ataccattaa ttaccctgtg cacatgaaaa acctcaccac   10860
tcaggatctt gagcaattag cagcagaact tagacaagat attgtatatt cagtagcgaa   10920
```

-continued

```
tacaggtggt catttgagtt caagtttagg tgttgttgaa ttgtctgttg ctttacacca   10980
tgttttcaac accccagatg acaagatcat ttgggacgtt ggtcaccagg catacccaca   11040
taagattttg accggaagaa ggtcaaagat gcacaccata agaaaaactt ctggtttagc   11100
tggttttcct aaacgagatg aaagtgctca tgatgctttt ggtgctggac atagttctac   11160
aagcatctct gctggactag gtatggctgt cggtagagat ttattaggga aaaccaacaa   11220
cgtgatatcg gtgatcggag atggcgccat gacggccgga cgagcatatg aggcgataaa   11280
taatgcagga tttcttgatt caaatctaat cgtcgtttta aacgacaaca agcaagtttc   11340
attaccgact gccacgttgg acggacctgc aactcccgtc ggggctctca gcggcgcttt   11400
atccaaattg caagccagta ccaagttccg taagcttcgt gaagccgcca agagcattac   11460
taaacaaatt ggacctcaag cacatgaagt ggcggcgaaa gtcgacgaat acgcaagagg   11520
tatgattagt gctagcgggt cgactttatt cgaggaactc ggattatact acatcggtcc   11580
cgtcgatggt cacaatgttg aagatttagt caacattttt gaaaaagtca agtcaatgcc   11640
cgcacccgga ccggttctaa tccacatcgt gaccgaaaaa ggcaaaggtt accctcctgc   11700
tgaagccgct gctgaccgta tgcacggagt tgtgaagttt gatgttccaa ctggaaaaca   11760
attcaagaca aaatcaccga cactttcgta tactcagtat tttgctgaat cacttataaa   11820
agaagctgaa gctgataaca agattgtcgc gatacacgcc gccatgggag gcggtaccgg   11880
actcaattac ttccagaaga agtgtcctga acgttgtttt gatgtcggta tcgcggaaca   11940
acacgcagtt actttcgccg cgggtttagc caccgaaggt cttaaaccat tttgcgcgat   12000
ctattcgtcg tttttgcaac gaggatacga tcaagtggtg catgacgttg atctacaaaa   12060
gttaccggtt cggtttgcga tggaccgagc tggtttagtc ggggctgatg gaccgacaca   12120
ttgtggtgcg tttgacataa cctacatggc gtgtctacca aacatggtgg tgatggctcc   12180
agccgatgaa gccgaattga tgcacatggt tgcaacggct gcagccattg acgacagacc   12240
gagttgcttt cggttcccaa gaggcaatgg cattggtgca ccacttcctc ctaataacaa   12300
agggattccc atagaggttg gtaaaggaag aatattactt gaaggaactc gtgttgcgat   12360
attgggatac ggttcgatag ttcaagaatg tctaggtgcg gctagcttgc ttcaagccca   12420
taacgtgtct gcaaccgtag ccgatgcgcg gttctgcaaa ccgttagaca ccggactgat   12480
tagacgatta gccaacgagc atgaagtctt acttaccgta gaggaaggct cgattggtgg   12540
atttggatca cacgttgctc actttctaag cttaaatggt ctcttagatg gaaaacttaa   12600
gcttagagca atgactcttc ctgataaata cattgatcat ggtgcaccac aagatcagct   12660
tgaagaagcc ggtctttctt caaaacatat ttgttcatct cttttatcac tttttgggaaa   12720 acctaaagaa gcacttcaat acaaatcaat aatgtaatct agagggccgc atcatgtaat   12780
tagttatgtc acgcttacat tcacgccctc cccccacatc cgctctaacc gaaaaggaag   12840
gagttagaca acctgaagtc taggtcccta tttattttt tatagttatg ttagtattaa   12900
gaacgttatt tatatttcaa attttttcttt ttttctgtta cagacgcgtg tacgcatgta   12960
acattatact gaaaaccttg cttgagaagg ttttgggacg ctcgaaggct ttaatttgcg   13020
gccctgcatt aatgaatcgg ccaacgcgcg gggagaggcg gtttgcgtat tgggcgctct   13080
tccgcttcct cgctcactga ctcgctgcgc tcggtcgttc ggctgcggcg agcggtatca   13140
gctcactcaa aggcggtaat acggttatcc acagaatcag gggataacgc aggaaagaac   13200
atgtgagcaa aaggccagca aaagcccagg aaccgtaaaa aggccgcgtt gctggcgttt   13260
```

```
ttccataggc tccgcccccc tgacgagcat cacaaaaatc gacgctcaag tcagaggtgg    13320
cgaaacccga caggactata aagataccag gcgtttcccc ctggaagctc cctcgtgcgc    13380
tctcctgttc cgaccctgcc gcttaccgga tacctgtccg cctttctccc ttcgggaagc    13440
gtggcgcttt ctcatagctc acgctgtagg tatctcagtt cggtgtaggt cgttcgctcc    13500
aagctgggct gtgtgcacga acccccgtt cagcccgacc gctgcgcctt atccggtaac      13560
tatcgtcttg agtccaaccc ggtaagacac gacttatcgc cactggcagc agccactggt    13620
aacaggatta gcagagcgag gtatgtaggc ggtgctacag agttcttgaa gtggtggcct    13680
aactacggct acactagaag gacagtattt ggtatctgcg ctctgctgaa gccagttacc    13740
ttcggaaaaa gagttggtag ctcttgatcc ggcaaacaaa ccaccgctgg tagcggtggt    13800
ttttttgttt gcaagcagca gattacgcgc agaaaaaaag gatctcaaga agatcctttg    13860 atctttteta cggggtctga cgctcagtgg aacgaaaact cacgttaagg gattttggtc    13920
atgagattat caaaaaggat cttcacctag atccttttaa attaaaaatg aagttttaaa    13980
tcaatctaaa gtatatatga gtaaacttgg tctgacagtt accaatgctt aatcagtgag    14040
gcacctatct cagcgatctg tctatttcgt tcatccatag ttgcctgact ccccgtcgtg    14100
tagataacta cgatacggga gcgcttacca tctggcccca gtgctgcaat gataccgcga    14160
gacccacgct caccggctcc agatttatca gcaataaacc agccagccgg aagggccgag    14220
cgcagaagtg gtcctgcaac tttatccgcc tccatccagt ctattaattg ttgccgggaa    14280
gctagagtaa gtagttcgcc agttaatagt ttgcgcaacg ttgttggcat tgctacaggc    14340
atcgtggtgt cactctcgtc gtttggtatg gcttcattca gctccggttc ccaacgatca    14400
aggcgagtta catgatcccc catgttgtgc aaaaaagcgg ttagctcctt cggtcctccg    14460
atcgttgtca gaagtaagtt ggccgcagtg ttatcactca tggttatggc agcactgcat    14520
aattctctta ctgtcatgcc atccgtaaga tgcttttctg tgactggtga gtactcaacc    14580
aagtcattct gagaatagtg tatgcggcga ccgagttgct cttgcccggc gtcaatacgg    14640
gataatagtg tatcacatag cagaacttta aaagtgctca tcattggaaa acgttcttcg    14700
gggcgaaaac tctcaaggat cttaccgctg ttgagatcca gttcgatgta acccactcgt    14760
gcacccaact gatcttcagc atcttttact ttcaccagcg tttctgggtg agcaaaaaca    14820
ggaaggcaaa atgccgcaaa aaagggaata agggcgacac ggaaatgttg aatactcata    14880
ctcttccttt ttcaatgggt aataactgat ataattaaat tgaagctcta atttgtgagt    14940
ttagtataca tgcatttact tataatacag ttttttagtt ttgctggccg catcttctca    15000
aatatgcttc ccagcctgct tttctgtaac gttcaccctc taccttagca tcccttccct    15060
ttgcaaatag tcctcttcca acaataataa tgtcagatcc tgtagagacc acatcatcca    15120
cggttctata ctgttgaccc aatgcgtctc ccttgtcatc taaacccaca ccgggtgtca    15180
taatcaacca atcgtaacct tcatctcttc cacccatgtc tctttgagca ataaagccga    15240
taacaaaatc tttgtcgctc ttcgcaatgt caacagtacc cttagtatat tctccagtag    15300 ataggagcc cttgcatgac aattctgcta acatcaaaag gcctctaggt tcctttgtta      15360
cttcttctgc cgcctgcttc aaaccgctaa caatacctgg gccaccaca ccgtgtgcat       15420 tcgtaatgtc tgcccattct gctattctgt atacacccgc agagtactgc aatttgactg    15480
tattaccaat gtcagcaaat tttctgtctt cgaagagtaa aaaattgtac ttggcggata    15540
atgcctttag cggcttaact gtgccctcca tggaaaaatc agtcaagata tccacatgtg    15600 ttttttagtaa acaaattttg ggacctaatg cttcaactaa ctccagtaat tccttggtgg    15660
```

-continued

```
tacgaacatc caatgaagca cacaagtttg tttgcttttc gtgcatgata ttaaatagct   15720
tggcagcaac aggactagga tgagtagcag cacgttcctt atatgtagct ttcgacatga   15780
tttatcttcg tttcctgcag gtttttgttc tgtgcagttg ggttaagaat actgggcaat   15840
ttcatgtttc ttcaacacta catatgcgta tatataccaa tctaagtctg tgctccttcc   15900
ttcgttcttc cttctgttcg gagattaccg aatcaaaaaa atttcaaaga aaccgaaatc   15960
aaaaaaaaga ataaaaaaaa aatgatgaat tgaattgaaa agctagctta tcgatgataa   16020
gctgtcaaag atgagaatta attccacgga ctatagacta tactagatac tccgtctact   16080
gtacgataca cttccgctca ggtccttgtc ctttaacgag gccttaccac tcttttgtta   16140
ctctattgat ccagctcagc aaaggcagtg tgatctaaga ttctatcttc gcgatgtagt   16200
aaaactagct agaccgagaa agagactaga aatgcaaaag gcacttctac aatggctgcc   16260
atcattatta tccgatgtga cgctgcagct tctcaatgat attcgaatac gctttgagga   16320
gatacagcct aatatccgac aaactgtttt acagatttac gatcgtactt gttacccatc   16380
attgaatttt gaacatccga acctgggagt tttccctgaa acagatagta tatttgaacc   16440
tgtataataa tatatagtct agcgctttac ggaagacaat gtatgtattt cggttcctgg   16500
agaaactatt gcatctattg cataggtaat cttgcacgtc gcatccccgg ttcattttct   16560
gcgtttccat cttgcacttc aatagcatat cttttgttaac gaagcatctg tgcttcattt   16620
tgtagaacaa aaatgcaacg cgagagcgct aatttttcaa acaaagaatc tgagctgcat   16680
ttttacagaa cagaaatgca acgcgaaagc gctattttac caacgaagaa tctgtgcttc   16740
atttttgtaa aacaaaaatg caacgcgacg agagcgctaa ttttttcaaac aaagaatctg   16800 agctgcatt tttacgaaca gaaatgcaac gcgagagcgc tattttacca acaaagaatc   16860
tatacttctt ttttgttcta caaaaatgca tcccgagagc gctatttttc taacaaagca   16920
tcttagatta ctttttttct cctttgtgcg ctctataatg cagtctcttg ataacttttt   16980
gcactgtagg tccgttaagg ttagaagaag gctactttgg tgtctatttt ctcttccata   17040
aaaaaagcct gactccactt cccgcgttta ctgattacta gcgaagctgc gggtgcattt   17100
tttcaagata aaggcatccc cgattatatt ctataccgat gtggattgcg catactttgt   17160
gaacagaaag tgatagcgtt gatgattctt cattggtcag aaaattatga acggtttctt   17220
ctattttgtc tctatatact acgtatagga aatgtttaca ttttcgtatt gttttcgatt   17280
cactctatga atagttctta ctacaatttt tttgtctaaa gagtaatact agagataaac   17340
ataaaaaatg tagaggtcga gtttagatgc aagttcaagg agcgaaaggt ggatgggtag   17400
gttatatagg gatatagcac agagatatat agcaaagaga tacttttgag caatgtttgt   17460
ggaagcggta ttcgcaatgg gaagctccac cccggttgat aatcagaaaa gccccaaaaa   17520
caggaagatt gtataagcaa atatttaaat tgtaaacgtt aatattttgt taaaattcgc   17580
gttaaatttt tgttaaatca gctcattttt taacgaatag cccgaaatcg gcaaaatccc   17640
ttataaatca aaagaataga ccgagatagg gttgagtgtt gttccagttt ccaacaagag   17700
tccactatta aagaacgtgg actccaacgt caaagggcga aaaagggtct atcagggcga   17760
tggcccacta cgtgaaccat caccctaatc aagttttttg gggtcgaggt gccgtaaagc   17820
agtaaatcgg aagggtaaac ggatgccccc atttagagct tgacggggaa agccggcgaa   17880
cgtggcgaga aggaaggga agaaagcgaa aggagcgggg gctagggcgg tgggaagtgt   17940
aggggtcacg ctgggcgtaa ccaccacacc cgccgcgctt aatggggcgc tacagggcgc   18000
```

-continued

```
gtggggatga tccactagt                                          18019
```

```
<210> SEQ ID NO 11
<211> LENGTH: 21419
<212> TYPE: DNA
<213> ORGANISM: Artificial sequence
<220> FEATURE:
<223> OTHER INFORMATION: Synthetic construct

<400> SEQUENCE: 11
acggattaga agccgccgag cgggtgacag ccctccgaag gaagactctc ctccgtgcgt         60
cctcgtcttc accggtcgcg ttcctgaaac gcagatgtgc ctcgcgccgc actgctccga        120
acaataaaga ttctacaata ctagctttta tggttatgaa gaggaaaaat tggcagtaac        180
ctggccccac aaaccttcaa atgaacgaat caaattaaca accataggat gataatgcga        240
ttagtttttt agccttattt ctggggtaat taatcagcga agcgatgatt tttgatctat        300
taacagatat ataaatgcaa aaactgcata accactttaa ctaatacttt caacattttc        360
ggtttgtatt acttcttatt caaatgtaat aaaagtatca acaaaaaatt gttaatatac        420
ctctatactt taacgtcaag gagaaaaaac cccggatcgg actactagca gctgtaatac        480
gactcactat agggaatatt aagcttccta ggccaccatg tcattaccgt tcttaacttc        540
tgcaccggga aaggttatta tttttggtga acactctgct gtgtacaaca agcctgccgt        600
cgctgctagt gtgtctgcgt tgagaaccta cctgctaata agcgagtcat ctgcaccaga        660
tactattgaa ttggacttcc cggacattag ctttaatcat aagtggtcca tcaatgattt        720
caatgccatc accgaggatc aagtaaactc ccaaaaattg gccaaggctc aacaagccac        780
cgatggcttg tctcaggaac tcgttagtct tcttgatccg ttgttagctc aactatccga        840
atccttccac taccatgcag cgttttgttt cctgtatatg tttgtttgcc tatgccccca        900
tgccaagaat attaagtttt ctttaaagtc tactttaccc atcggtgctg ggttgggctc        960
aagcgcctct atttctgtat cactggcctt agctatggcc tacttggggg ggttaatagg       1020
atctaatgac ttggaaaagc tgtcagaaaa cgataagcat atagtgaatc aatgggcctt       1080
cataggtgaa aagtgtattc acggtacccc ttcaggaata gataacgctg tggccactta       1140
tggtaatgcc ctgctatttg aaaaagactc acataatgga acaataaaca caaacaattt       1200
taagttctta gatgatttcc cagccattcc aatgatccta acctatacta gaattccaag       1260
gtctacaaaa gatcttgttg ctcgcgttcg tgtgttggtc accgagaaat ttcctgaagt       1320
tatgaagcca attctggatg ccatgggtga atgtgcccta caaggcttag agatcatgac       1380
taagttaagt aaatgtaaag gcaccgatga cgaggctgta gaaactaata atgaactgta       1440
tgaacaacta ttggaattga taagaataaa tcatggactg cttgtctcaa tcggtgtttc       1500
tcatcctgga ttagaactta ttaaaaatct gagcgatgat ttgagaattg gctccacaaa       1560
acttaccggt gctggtggcg gcggttgctc tttgactttg ttacgaagag acattactca       1620
agagcaaatt gacagcttca aaaagaaatt gcaagatgat tttagttacg agacatttga       1680
aacagacttg ggtgggactg gctgctgttt gttaagcgca aaaaatttga ataaagatct       1740
taaaatcaaa tccctagtat tccaattatt tgaaaataaa actaccacaa agcaacaaat       1800
tgacgatcta ttattgccag gaaacacgaa tttaccatgg acttcataac tcgagtcatg       1860
taattagtta tgtcacgctt acattcacgc cctcccccca catccgctct aaccgaaaag       1920
gaaggagtta gacaacctga agtctaggtc cctatttatt tttttatagt tatgttagta       1980
ttaagaacgt tatttatatt tcaaattttt cttttttttc tgtacagacg cgtgtacgca       2040
```

-continued

```
tgtaacatta tactgaaaac cttgcttgag aaggttttgg gacgctcgaa ggctttaatt   2100
tgccggatta gaagccgccg agcgggtgac agccctccga aggaagactc tcctccgtgc   2160
gtcctcgtct tcaccggtcg cgttcctgaa acgcagatgt gcctcgcgcc gcactgctcc   2220
gaacaataaa gattctacaa tactagcttt tatggttatg aagaggaaaa attggcagta   2280
acctggcccc acaaaccttc aaatgaacga atcaaattaa caaccatagg atgataatgc   2340
gattagtttt ttagccttat ttctggggta attaatcagc gaagcgatga ttttttgatct   2400 attaacagat atataaatgc aaaaactgca taaccacttt aactaatact ttcaacattt   2460
tcggtttgta ttacttctta ttcaaatgta ataaagtat caacaaaaaa ttgttaatat   2520
acctctatac tttaacgtca aggaggccgg ccaccatggt aagggcaaaa cgtaaattag   2580
atcatattga atacgctctt tctactggtc agtctcgtac gcatggcttt catgatattg   2640
attttgtgca tcaaagcttg ccaaattcaa gttatgaaac aataacatgt gaaacaaaaa   2700
tcggcgaact ttcactaagt tcgccgattt ttatcaatgc gatgactggt ggtggaggag   2760
agaaaacgtt acatattaat gagcaattag catatgtagc gaaacatcat aaccttgcta   2820
tggctgtagg atcgcaaatg gcagcgttaa aagatgaaag tgaagctgct tcttataaga   2880
ttattagaaa ggtaaatcca aatggtattt tctttgctaa tttaggtagt gaggcaactg   2940
ttgaacaggc agagcgtgct gttgatatgg ttgaagcgaa tgcattgcaa attcatttaa   3000
atgtcataca agagttaacg atgccagaag gagaccgtga ctttactggt gtacttcagc   3060
gtattgagaa aattgtttta aatagtaaag ttcctgtcat tgtaaaagaa gttggatttg   3120
ggatgagtaa ggaaacaatg caacagttgg cgagcgtagg tgtaacggca attgatattg   3180
gcggacaagg gggtacgaat tttgctgctg ttgaaaatga aagaagacag cgaatgcttt   3240
cttattttaa taactggggc atacaaacag ctacctcgat tattgaagca acctctacaa   3300
ataataacct ctcttttatt gcatctgggg gtatacaaac agcgcttgac gtagcgaaag   3360
caatcgcatt aggggcgaat accactgcgt ttgctggata cttttacgc atttttaatgg   3420 aagatggtat cgagaagttg gtggacgaaa ttgacctttt acatacagat ttgaaattta   3480
ttatgacagc tctcggtgca aagacgatag aagagttaca gtccgtacct cttgttataa   3540
agggtgaaac gtatcattgg ttaacgcagc gtggaattga tacgacgcat tatagtagaa   3600
gataatccgg aatcatgtaa ttagttatgt cacgcttaca ttcacgccct ccccccacat   3660
ccgctctaac cgaaaaggaa ggagttagac aacctgaagt ctaggtccct atttattttt   3720
ttatagttat gttagtatta agaacgttat ttatatttca aatttttctt ttttttctgt   3780
acagacgcgt gtacgcatgt aacattatac tgaaaacctt gcttgagaag gttttgggac   3840
gctcgaaggc tttaatttgc cggattagaa gccgccgagc gggtgacagc cctccgaagg   3900
aagactctcc tccgtgcgtc ctcgtcttca ccggtcgcgt tcctgaaacg cagatgtgcc   3960
tcgcgccgca ctgctccgaa caataaagat tctacaatac tagctttat ggttatgaag   4020 aggaaaaatt ggcagtaacc tggccccaca aaccttcaaa tgaacgaatc aaattaacaa   4080
ccataggatg ataatgcgat tagttttttta gccttattc tggggtaatt aatcagcgaa   4140
gcgatgattt ttgatctatt aacagatata aaatgcaaa aactgcataa ccactttaac   4200
taatactttc aacattttcg gtttgtatta cttcttattc aaatgtaata aagtatcaa   4260 caaaaaattg ttaatatacc tctatacttt aacgtcaagg agcccgggcc accatgacga   4320
cttatgcacg cgcgcacaca aatattgcgc tgattaaata ttggggaaaa gccaatcgca   4380
```

-continued

```
agttgatgct gccagccaca agcagcattt ctttaacttt aaatgacttt tatactgaca      4440
cagcagtgac atttgatcct agtctaaatg atgatcgctt catgcttaac ggtgaagaac      4500
aaaacccggt tgcggtcagc cgcttttttgg atcgggttcg gcacttagga aaaattagca     4560
cgtacgccca agtcacttcc ttgaatcacg tgccgactgc tgccgggctg gcaagttcag      4620
cctctgcttt tgctgccttg gccactgctg ccagccgcgc ggcaggtcta aacctttctc      4680
cgactgaact atcaagatta gcgcgccgcg gatcaggttc agcaacgcgc tctatctttg      4740
gtggtgccgt tatctggcat cgcggccatg acgacgcctc ttcattcgct gaaccactcg      4800
cgattcaacc tagtttgcca ttacgaatgc ttgtggtcac ggtatctgct gaaaaaaagg      4860
cggtcagttc acgaaaaggc atggccaaca cagtggccac aagtccctac tatgatgcct      4920
gggtggcctc aaatgaaagt ttaattgaac caatgattac cgcgttggct gaagacgact      4980
tagcgctgat cggcaaattg acagaattgt ccagtatgcg catgcatgcg gcgattatgg      5040
ccgaggaacc gccattcacc tactttctgc cggaaacatt acgggcgtgg caattagtgc      5100
aagaacaacg ggctttgggt attcccgcgt ttgccacgat ggatgcagga ccaaatgtca      5160
aaattctgac tactgaacct tacgtggaca tttttattaac cgccttgcgc cctgtgttcg      5220
gtgatcggat tttgagcaca cgccttggtc ctgatgccag catcatcaca aaggagcaat      5280
ttgatgacac aaagtcagca atcgcatcgc aaggatgatt aattaatcat gtaattagtt      5340
atgtcacgct tacattcacg ccctccccc acatccgctc taaccgaaaa ggaaggagtt        5400
agacaacctg aagtctaggt ccctatttat tttttatag ttatgttagt attaagaacg        5460
ttatttatat ttcaaatttt tcttttttttt ctgtacagac gcgtgtacgc atgtaacatt      5520
atactgaaaa ccttgcttga gaaggttttg ggacgctcga aggctttaat ttgccggatt       5580
agaagccgcc gagcgggtga cagccctccg aaggaagact ctcctccgtg cgtcctcgtc       5640
ttcaccggtc gcgttcctga aacgcagatg tgcctcgcgc cgcactgctc cgaacaataa       5700
agattctaca atactagctt ttatggttat gaagaggaaa aattggcagt aacctggccc       5760
cacaaacctt caaatgaacg aatcaaatta acaaccatag gatgataatg cgattagttt       5820
tttagcctta tttctggggt aattaatcag cgaagcgatg attttttgatc tattaacaga     5880 tatataaatg caaaaactgc ataaccactt taactaatac tttcaacatt ttcggtttgt      5940
attacttctt attcaaatgt aataaaagta tcaacaaaaa attgttaata tacctctata      6000
ctttaacgtc aaggagggcg cgccatggtt catttaggtc caaagaaacc acaggctaga      6060
aagggttcca tggctgatgt gcccaaggaa ttgatggatg aaattcatca gttggaagat      6120
atgtttacag ttgacagcga gaccttgaga aaggttgtta agcactttat cgacgaattg      6180
aataaaggtt tgacaaagaa gggaggtaac attccaatga ttcccggttg ggtcatggaa      6240
ttcccaacag gtaaagaatc tggtaactat ttggccattg atttgggtgg tactaactta      6300
agagtcgtgt tggtcaagtt gagcggtaac catacctttg acaccactca atccaagtat      6360
aaactaccac atgacatgag aaccactaag caccaagagg agttatggtc ctttattgcc       6420
gactctttga aggactttat ggtcgagcaa gaattgctaa acaccaagga caccttacca      6480
ttaggtttca ccttctcgta cccagcttcc caaaacaaga ttaacgaagg tattttgcaa      6540
agatggacca agggtttcga tattccaaat gtcgaaggcc acgatgtcgt cccattgcta      6600
caaaacgaaa tttccaagag agagttgcct attgaaattg tagcattgat taatgatact      6660
gttggtactt taattgcctc atactacact gacccagaga ctaagatggg tgtgatttte      6720 ggtactggtg tcaacggtgc tttctatgat gttgtttccg atatcgaaaa gttggagggc      6780
```

-continued

```
aaattagcag acgatattcc aagtaactct ccaatggcta tcaattgtga atatggttcc    6840
ttcgataatg aacatttggt cttgccaaga accaagtacg atgttgctgt cgacgaacaa    6900
tctccaagac ctggtcaaca agcttttgaa aagatgacct ccggttacta cttgggtgaa    6960
ttgttgcgtc tagtgttact tgaattaaac gagaagggct tgatgttgaa ggatcaagat    7020
ctaagcaagt tgaaacaacc atacatcatg gatacctcct acccagcaag aatcgaggat    7080
gatccatttg aaaacttgga agatactgat gacatcttcc aaaaggactt tggtgtcaag    7140
accactctgc cagaacgtaa gttgattaga agactttgtg aattgatcgg taccagagct    7200
gctagattag ctgtttgtgg tattgccgct atttgccaaa agagaggtta caagactggt    7260
cacattgccg ctgacggttc tgtctataac aaatacccag gtttcaagga agccgccgct    7320
aagggtttga gagatatcta tggatggact ggtgacgcaa gcaaagatcc aattacgatt    7380
gttccagctg aggatggttc aggtgcaggt gctgctgtta ttgctgcatt gtccgaaaaa    7440
agaattgccg aaggtaagtc tcttggtatc attggcgctt aagtttaaac tcatgtaatt    7500
agttatgtca cgcttacatt cacgccctcc ccccacatcc gctctaaccg aaaaggaagg    7560
agttagacaa cctgaagtct aggtccctat ttattttttt atagttatgt tagtattaag    7620
aacgttattt atatttcaaa ttttttcttt ttttctgtac agacgcgtgt acgcatgtaa    7680
cattatactg aaaaccttgc ttgagaaggt tttgggacgc tcgaaggctt taatttgccg    7740
gattagaagc cgccgagcgg gtgacagccc tccgaaggaa gactctcctc cgtgcgtcct    7800
cgtcttcacc ggtcgcgttc ctgaaacgca gatgtgcctc gcgccgcact gctccgaaca    7860
ataaagattc tacaatacta gctttttatgg ttatgaagag gaaaaattgg cagtaacctg    7920
gccccacaaa ccttcaaatg aacgaatcaa attaacaacc ataggatgat aatgcgatta    7980 gtttttttagc cttatttctg gggtaattaa tcagcgaagc gatgattttt gatctattaa    8040
cagatatata aatgcaaaaa ctgcataacc actttaacta atactttcaa cattttcggt    8100
ttgtattact tcttattcaa atgtaataaa agtatcaaca aaaaattgtt aatatacctc    8160
tatactttaa cgtcaaggag gagctcacca tggctgaagg tgttttccaa ggtgctatcg    8220
gtatcgattt aggtacaacc tactcttgtg ttgctactta cgaatcctcc gttgaaatta    8280
ttgccaacga acaaggtaac agagtcaccc catctttcgt tgctttcact ccagaagaaa    8340
gattgattgg tgatgctgcc aagaaccaag ctgctttgaa cccaagaaac actgtcttcg    8400
atgctaagcg tttgattggt agaagattcg acgacgaatc tgttcaaaag gacatgaaga    8460
cctggccttt caaggttatc gacgtcgatg gtaacccagt catcgaagtc caatacttgg    8520
aagaaaccaa gacttttctcc ccacaagaaa tttccgctat ggttttgacc aagatgaagg    8580
aaattgctga agctaagatt ggtaagaagg ttgaaaaggc cgtcattact gtcccagctt    8640
actttaacga cgctcaaaga caagctacca aggatgccgg tgccatttct ggtttgaacg    8700
ttttgcgtat catcaacgaa cctactgccg ctgctattgc ttacggtcta ggtgctggta    8760
agtccgaaaa ggaaagacat gttttgattt tcgatttggg tggtggtact ttcgatgttt    8820
ccttgttgca cattgctggt ggtgtttaca ctgttaaatc tacttccggt aacactcact    8880
tgggtggtca agatttcgac accaacttgt tggaacactt caaggctgaa ttcaagaaga    8940
agactggttt ggacatctcc gacgatgcca gagctttgag aagattgaga actgctgctg    9000
aaagagctaa gagaacctta tcttctgtca ctcaaactac cgttgaagtt gactctttgt    9060
ttgacggtga agatttcgaa tcctctttga ctagagctag atttgaagac ttgaacgccg    9120
```

-continued

```
cattgttcaa gtctactttg gaacctgttg aacaagtttt gaaggatgct aagatctcta      9180
agtctcaaat cgacgaagtt gtcttggttg gtggttccac cagaattcca aaggtccaaa      9240
agttgttgtc tgacttcttt gacggtaagc aattggaaaa atctattaac ccagatgaag      9300
ctgttgctta cggtgctgct gttcaaggtg ctatcttgac cggccaatcc acatctgacg      9360
aaaccaagga cttgttgttg ttagatgttg ctccattatc tctaggtgtt ggtatgcaag      9420
gtgacatgtt cggtatcgtt gttccaagaa acactactgt tccaaccatc aagagaagaa      9480
cctttactac atgtgctgac aaccaaacca ccgttcaatt cccagtctac caaggtgaac      9540
gtgttaactg taaagaaaac actttgttgg gtgaattcga cttgaagaac atcccaatga      9600
tgccagctgg tgaaccagtc ttggaagcta tcttcgaagt tgatgctaac ggtatcttga      9660
aggttactgc cgtcgaaaag tctaccggta agtcttctaa catcactatc tctaacgctg      9720
ttggtagatt gtcttctgaa gaaattgaaa agatggttaa ccaagctgaa gagttcaagg      9780
ctgccgatga agcttttgcc aagaagcacg aagctagaca aagattggaa tcctacgttg      9840
cctccatcga acaaactgtc actgacccag tcttgtcttc taaattgaag agaggttcca      9900
agtccaagat tgaagctgct ttgtccgatg cttttggctgc tttgcaaatc gaagacccat      9960
ctgctgatga attgagaaag gctgaagttg gtttgaagag agttgtcacc aaggccatgt     10020
cttctcgtta aggtacctca tgtaattagt tatgtcacgc ttacattcac gccctccccc     10080
cacatccgct ctaaccgaaa aggaaggagt tagacaacct gaagtctagg tccctattta     10140 ttttttata gttatgttag tattaagaac gttatttata tttcaaattt ttcttttttt      10200
tctgtacaga cgcgtgtacg catgtaacat tatactgaaa accttgcttg agaaggtttt     10260
gggacgctcg aaggctttaa tttgccggat tagaagccgc cgagcgggtg acagccctcc     10320
gaaggaagac tctcctccgt gcgtcctcgt cttcaccggt cgcgttcctg aaacgcagat     10380
gtgcctcgcg ccgcactgct ccgaacaata aagattctac aatactagct tttatggtta     10440
tgaagaggaa aaattggcag taacctggcc ccacaaacct tcaaatgaac gaatcaaatt     10500
aacaaccata ggatgataat gcgattagtt ttttagcctt atttctgggg taattaatca     10560
gcgaagcgat gatttttgat ctattaacag atatataaat gcaaaaactg cataaccact     10620
ttaactaata ctttcaacat tttcggtttg tattacttct tattcaaatg taataaaagt     10680
atcaacaaaa aattgttaat atacctctat actttaacgt caaggaggga tccgccacca     10740
tggaaccaca aattctttt ctctatctct cactcttcat tctctcccta aacttcttct       10800
tcacgaatct taaaccaagg ctagtccgcc tcttccagcc ttctttagaa tctcgtgtca     10860
agaccgctct tttatcccga aaggaagtag ccgcgtttct tgattctccc attgtcgaag     10920
acgaagaagg cgaagaaaga gaagaggaag aagaaggagg tatcgtttca aatgccaact     10980
ttacgtttga gtttgatcca tacatgatga gcaaagccga atcagtgaac aaagctctgg     11040
aagaagcaat tccagtcgga gagccactca agattcatga agccatgcga tacgcgattc     11100
ttgcggctgg aaaacgtgtt aggccaatac tctgccttgc ttcttgcgag ctagtaggtg     11160
gccaagaaaa tgcggcaatg cccgccgctt gtgcggttga gatgatccac acgatgtctc     11220
taatcaaaga cgatttgcct tgtatggaca acgacgattt cgtcgtggga aagcccacga     11280
cgcacaaagt ctacggcgaa ggagttgcca ttctctctgg tggggctctc ttgtctcttg     11340
cctttgagca catgaccacc gctgaaatat cctcggagag aatggtttgg gcggtgagag     11400
aattggctag gtctattggg acaagaggtt tagtcgcggg acaagcgatg gatataagca     11460
gtgaaggttt ggacttaaac gaggtcggat tagagcattt ggagtttatc catgttcata     11520
```

-continued

```
aaaccgcggt tttgttggaa actgccgcgg ttcttggcgc cataattggt ggtggatctg   11580
atgaagagat tgaaagtgtg agaaagtttg caaggtgcat tggattgttg tttcaggtgg   11640
tggatgatat tttggacgag acgaagtcgt cggaggaatt gggaaaaacc gccgggaaag   11700
atcagctcgc cggaaagcta acgtatccaa agttgatagg gttggagaaa tcgaaagaat   11760
ttgttaagag attgacgaaa gatgcacggc aacatcttca agggtttagt tctgaaaagg   11820
ttgctccttt agtagctctt actactttta ttgctaatag aaataagtga gaattctcat   11880
gtaattagtt atgtcacgct tacattcacg ccctcccccc acatccgctc taaccgaaaa   11940
ggaaggagtt agacaacctg aagtctaggt ccctatttat tttttatag ttatgttagt   12000 attaagaacg ttatttatat ttcaaatttt tcttttttt ctgtacagac gcgtgtacgc   12060
atgtaacatt atactgaaaa ccttgcttga gaaggttttg ggacgctcga aggctttaat   12120
ttgccggatt agaagccgcc gagcgggtga cagccctccg aaggaagact ctcctccgtg   12180
cgtcctcgtc ttcaccggtc gcgttcctga aacgcagatg tgcctcgcgc cgcactgctc   12240
cgaacaataa agattctaca atactagctt ttatggttat gaagaggaaa aattggcagt   12300
aacctggccc cacaaacctt caaatgaacg aatcaaatta acaaccatag gatgataatg   12360
cgattagttt tttagcctta tttctggggt aattaatcag cgaagcgatg atttttgatc   12420
tattaacaga tatataaatg caaaaactgc ataaccactt taactaatac tttcaacatt   12480
ttcggtttgt attacttctt attcaaatgt aataaaagta tcaacaaaaa attgttaata   12540
tacctctata ctttaacgtc aaggaggcgg ccgccatggt gagcaagggc gaggagctgt   12600
tcaccggggt ggtgcccatc ctggtcgagc tggacggcga cgtaaacggc cacaagttca   12660
gcgtgtccgg cgagggcgag ggcgatgcca cctacggcaa gctgaccctg aagttcatct   12720
gcaccaccgg caagctgccc gtgccctggc ccaccctcgt gaccaccttc ggctacggcc   12780
tgcaatgctt cgcccgctac cccgaccaca tgaagctgca cgacttcttc aagtccgcca   12840
tgcccgaagg ctacgtccag gagcgcacca tcttcttcaa ggacgacggc aactacaaga   12900
cccgcgccga ggtgaagttc gagggcgaca ccctggtgaa ccgcatcgag ctgaagggca   12960
tcgacttcaa ggaggacggc aacatcctgg ggcacaagct ggagtacaac tacaacagcc   13020
acaacgtcta tatcatggcc gacaagcaga agaacggcat caaggtgaac ttcaagatcc   13080
gccacaacat cgaggacggc agcgtgcagc tcgccgacca ctaccagcag aacacccca   13140 tcggcgacgg ccccgtgctg ctgcccgaca accactacct gagctaccag tccgccctga   13200
gcaaagaccc caacgagaag cgcgatcaca tggtcctgct ggagttcgtg accgccgccg   13260
ggatcactct cggcatggac gagctgtaca agtaataatc gtacgcatca tgtaattagt   13320
tatgtcacgt ttacattcac gccctccccc cacatccgct ctaaccgaaa aggaaggagt   13380
tagacaacct gaagtctagg tccctattta tttttttata gttatgttag tattaagaac   13440
gttatttata tttcaaattt ttctttttt tctgtacaga cgcgtgtacg catgtaacat   13500
tatactgaaa accttgcttg agaaggtttt gggacgctcg aaggctttaa tttgcatgct   13560
acggattaga agccgccgag cgggtgacag ccctccgaag gaagactctc ctccgtgcgt   13620
cctcgtcttc accggtcgcg ttcctgaaac gcagatgtgc ctcgcgccgc actgctccga   13680
acaataaaga ttctacaata ctagctttta tggttatgaa gaggaaaaat tggcagtaac   13740
ctggccccac aaaccttcaa atgaacgaat caaattaaca accataggat gataatgcga   13800
ttagtttttt agccttattt ctggggtaat taatcagcga agcgatgatt tttgatctat   13860
```

-continued

```
taacagatat ataaatgcaa aaactgcata accactttaa ctaatacttt caacattttc   13920
ggtttgtatt acttcttatt caaatgtaat aaaagtatca acaaaaaatt gttaatatac   13980
ctctatactt taacgtcaag gaggccacca tggcggttgc aggatcgacc atgaacctgc   14040
atctcacttc atctccatac aagacagttc catcactctg taaattcacc agaaaacagt   14100
tccgattaaa ggcctctgca acgaatccag acgctgaaga tgggaagatg atgtttaaaa   14160
acgataaacc caatttgaag gtcgaattcg ctggggagaa accggtgaca ccattactgg   14220
ataccattaa ttaccctgtg cacatgaaaa acctcaccac tcaggatctt gagcaattag   14280
cagcagaact tagacaagat attgtatatt cagtagcgaa tacagtggt catttgagtt    14340 caagtttagg tgttgttgaa ttgtctgttg ctttacacca tgttttcaac accccagatg   14400
acaagatcat ttgggacgtt ggtcaccagg catacccaca taagattttg accggaagaa   14460
ggtcaaagat gcacaccata agaaaaactt ctggtttagc tggttttcct aaacgagatg   14520
aaagtgctca tgatgctttt ggtgctggac atagttctac aagcatctct gctggactag   14580
gtatggctgt cggtagagat ttattaggga aaaccaacaa cgtgatatcg gtgatcggag   14640
atggcgccat gacggccgga cgagcatatg aggcgataaa taatgcagga tttcttgatt   14700
caaatctaat cgtcgtttta aacgacaaca agcaagtttc attaccgact gccacgttgg   14760
acggacctgc aactcccgtc ggggctctca gcggcgcttt atccaaattg caagccagta   14820
ccaagttccg taagcttcgt gaagccgcca agagcattac taaacaaatt ggacctcaag   14880
cacatgaagt ggcggcgaaa gtcgacgaat acgcaagagg tatgattagt gctagcgggt   14940
cgactttatt cgaggaactc ggattatact acatcggtcc cgtcgatggt cacaatgttg   15000
aagatttagt caacattttt gaaaaagtca agtcaatgcc cgcacccgga ccggttctaa   15060
tccacatcgt gaccgaaaaa ggcaaaggtt accctcctgc tgaagccgct gctgaccgta   15120
tgcacggagt tgtgaagttt gatgttccaa ctggaaaaca attcaagaca aaatcaccga   15180
cactttcgta tactcagtat tttgctgaat cacttataaa agaagctgaa gctgataaca   15240
agattgtcgc gatacacgcc gccatgggag gcggtaccgg actcaattac ttccagaaga   15300
agtgtcctga acgttgtttt gatgtcggta tcgcggaaca acacgcagtt actttcgccg   15360
cgggtttagc caccgaaggt cttaaaccat tttgcgcgat ctattcgtcg tttttgcaac   15420
gaggatacga tcaagtggtg catgacgttg atctacaaaa gttaccggtt cggtttgcga   15480
tggaccgagc tggtttagtc ggggctgatg gaccgacaca ttgtggtgcg tttgacataa   15540
cctacatggc gtgtctacca aacatggtgg tgatggctcc agccgatgaa gccgaattga   15600
tgcacatggt tgcaacggct gcagccattg acgacagacc gagttgcttt cggttcccaa   15660
gaggcaatgg cattggtgca ccacttcctc ctaataacaa agggattccc atagaggttg   15720
gtaaaggaag aatattactt gaaggaactc gtgttgcgat attgggatac ggttcgatag   15780
ttcaagaatg tctaggtgcg gctagcttgc ttcaagccca taacgtgtct gcaaccgtag   15840
ccgatgcgcg gttctgcaaa ccgttagaca ccggactgat tagacgatta gccaacgagc   15900
atgaagtctt acttaccgta gaggaaggct cgattggtgg atttggatca cacgttgctc   15960
actttctaag cttaaatggt ctcttagatg gaaaacttaa gcttagagca atgactcttc   16020 ctgataaaata cattgatcat ggtgcaccac aagatcagct tgaagaagcc ggtctttctt   16080
caaaacatat ttgttcatct cttttatcac ttttgggaaa acctaaagaa gcacttcaat   16140
acaaatcaat aatgtaatct agagggccgc atcatgtaat tagttatgtc acgcttacat   16200
tcacgccctc cccccacatc cgctctaacc gaaaaggaag gagttagaca acctgaagtc   16260
```

-continued

```
taggtcccta tttatttttt tatagttatg ttagtattaa gaacgttatt tatatttcaa    16320 attttttcttt tttttctgta cagacgcgtg tacgcatgta acattatact gaaaaccttg    16380
cttgagaagg ttttgggacg ctcgaaggct ttaatttgcg gccctgcatt aatgaatcgg    16440
ccaacgcgcg gggagaggcg gtttgcgtat tgggcgctct tccgcttcct cgctcactga    16500
ctcgctgcgc tcggtcgttc ggctgcggcg agcggtatca gctcactcaa aggcggtaat    16560
acggttatcc acagaatcag gggataacgc aggaaagaac atgtgagcaa aaggccagca    16620
aaagcccagg aaccgtaaaa aggccgcgtt gctggcgttt ttccataggc tccgcccccc    16680
tgacgagcat cacaaaaatc gacgctcaag tcagaggtgg cgaaacccga caggactata    16740
aagataccag gcgtttcccc ctggaagctc cctcgtgcgc tctcctgttc cgaccctgcc    16800
gcttaccgga tacctgtccg cctttctccc ttcgggaagc gtggcgcttt ctcatagctc    16860
acgctgtagg tatctcagtt cggtgtaggt cgttcgctcc aagctgggct gtgtgcacga    16920
accccccgtt cagcccgacc gctgcgcctt atccggtaac tatcgtcttg agtccaaccc    16980
ggtaagacac gacttatcgc cactggcagc agccactggt aacaggatta gcagagcgag    17040
gtatgtaggc ggtgctacag agttcttgaa gtggtggcct aactacggct acactagaag    17100
gacagtattt ggtatctgcg ctctgctgaa gccagttacc ttcggaaaaa gagttggtag    17160
ctcttgatcc ggcaaacaaa ccaccgctgg tagcggtggt ttttttgttt gcaagcagca    17220
gattacgcgc agaaaaaaag gatctcaaga agatcctttg atcttttcta cggggtctga    17280
cgctcagtgg aacgaaaact cacgttaagg gattttggtc atgagattat caaaaaggat    17340
cttcacctag atccttttaa attaaaaatg aagttttaaa tcaatctaaa gtatatatga    17400
gtaaacttgg tctgacagtt accaatgctt aatcagtgag gcacctatct cagcgatctg    17460
tctatttcgt tcatccatag ttgcctgact ccccgtcgtg tagataacta cgatacggga    17520
gcgcttacca tctggcccca gtgctgcaat gataccgcga cccacgct caccggctcc    17580 agatttatca gcaataaacc agccagccgg aagggccgag cgcagaagtg gtcctgcaac    17640
tttatccgcc tccatccagt ctattaattg ttgccgggaa gctagagtaa gtagttcgcc    17700
agttaatagt ttgcgcaacg ttgttggcat tgctacaggc atcgtggtgt cactctcgtc    17760
gtttggtatg gcttcattca gctccggttc ccaacgatca aggcgagtta catgatcccc    17820
catgttgtgc aaaaaagcgg ttagctcctt cggtcctccg atcgttgtca gaagtaagtt    17880
ggccgcagtg ttatcactca tggttatggc agcactgcat aattctctta ctgtcatgcc    17940
atccgtaaga tgcttttctg tgactggtga gtactcaacc aagtcattct gagaatagtg    18000
tatgcggcga ccgagttgct cttgcccggc gtcaatacgg gataatagtg tatcacatag    18060
cagaacttta aaagtgctca tcattggaaa acgttcttcg gggcgaaaac tctcaaggat    18120
cttaccgctg ttgagatcca gttcgatgta acccactcgt gcacccaact gatcttcagc    18180
atcttttact ttcaccagcg tttctgggtg agcaaaaaca ggaaggcaaa atgccgcaaa    18240
aaagggaata agggcgacac ggaaatgttg aatactcata ctcttccttt ttcaatgggt    18300
aataactgat ataattaaat tgaagctcta atttgtgagt ttagtataca tgcatttact    18360
tataatacag ttttttttagtt ttgctggccg catcttctca atatgcttc ccagcctgct    18420 tttctgtaac gttcaccctc taccttagca tcccttccct ttgcaaatag tcctcttcca    18480
acaataataa tgtcagatcc tgtagagacc acatcatcca cggttctata ctgttgaccc    18540
aatgcgtctc ccttgtcatc taaacccaca ccgggtgtca taatcaacca atcgtaacct    18600
```

```
tcatctcttc cacccatgtc tctttgagca ataaagccga taacaaaatc tttgtcgctc   18660
ttcgcaatgt caacagtacc cttagtatat tctccagtag atagggagcc cttgcatgac   18720
aattctgcta acatcaaaag gcctctaggt tcctttgtta cttcttctgc cgcctgcttc   18780
aaaccgctaa caatacctgg gcccaccaca ccgtgtgcat tcgtaatgtc tgcccattct   18840
gctattctgt atacacccgc agagtactgc aatttgactg tattaccaat gtcagcaaat   18900
tttctgtctt cgaagagtaa aaaattgtac ttggcggata atgcctttag cggcttaact   18960
gtgccctcca tggaaaaatc agtcaagata tccacatgtg tttttagtaa acaaattttg   19020
ggacctaatg cttcaactaa ctccagtaat tccttggtgg tacgaacatc caatgaagca   19080
cacaagtttg tttgcttttc gtgcatgata ttaaatagct tggcagcaac aggactagga   19140
tgagtagcag cacgttcctt atatgtagct ttcgacatga tttatcttcg tttcctgcag   19200
gtttttgttc tgtgcagttg ggttaagaat actgggcaat ttcatgtttc ttcaacacta   19260
catatgcgta tatataccaa tctaagtctg tgctccttcc ttcgttcttc cttctgttcg   19320
gagattaccg aatcaaaaaa atttcaaaga aaccgaaatc aaaaaaaaga ataaaaaaaa   19380
aatgatgaat tgaattgaaa agctagctta tcgatgataa gctgtcaaag atgagaatta   19440
attccacgga ctatagacta tactagatac tccgtctact gtacgataca cttccgctca   19500
ggtccttgtc ctttaacgag gccttaccac tcttttgtta ctctattgat ccagctcagc   19560
aaaggcagtg tgatctaaga ttctatcttc gcgatgtagt aaaactagct agaccgagaa   19620
agagactaga aatgcaaaag gcacttctac aatggctgcc atcattatta tccgatgtga   19680
cgctgcagct tctcaatgat attcgaatac gctttgagga gatacagcct aatatccgac   19740
aaactgtttt acagatttac gatcgtactt gttacccatc attgaatttt gaacatccga   19800
acctgggagt tttccctgaa acagatagta tatttgaacc tgtataataa tatatagtct   19860
agcgctttac ggaagacaat gtatgtattt cggttcctgg agaaactatt gcatctattg   19920
cataggtaat cttgcacgtc gcatccccgg ttcattttct gcgtttccat cttgcacttc   19980
aatagcatat cttttgttaac gaagcatctg tgcttcattt tgtagaacaa aaatgcaacg   20040
cgagagcgct aatttttcaa acaaagaatc tgagctgcat ttttacagaa cagaaatgca   20100
acgcgaaagc gctattttac caacgaagaa tctgtgcttc atttttgtaa aacaaaaatg   20160
caacgcgacg agagcgctaa tttttcaaac aaagaatctg agctgcattt ttacagaaca   20220
gaaatgcaac gcgagagcgc tatttttacca acaaagaatc tatacttctt ttttgttcta   20280
caaaaatgca tcccgagagc gctatttttc taacaaagca tcttagatta cttttttttct   20340 cctttgtgcg ctctataatg cagtctcttg ataacttttt gcactgtagg tccgttaagg   20400
ttagaagaag gctactttgg tgtctatttt ctcttccata aaaaaagcct gactccactt   20460
cccgcgttta ctgattacta gcgaagctgc gggtgcattt tttcaagata aaggcatccc   20520
cgattatatt ctataccgat gtggattgcg catactttgt gaacagaaag tgatagcgtt   20580
gatgattctt cattggtcag aaaattatga acggtttctt ctattttgtc tctatatact   20640
acgtatagga aatgtttaca ttttcgtatt gttttcgatt cactctatga atagttctta   20700
ctacaatttt tttgtctaaa gagtaatact agagataaac ataaaaaatg tagaggtcga   20760
gtttagatgc aagttcaagg agcgaaaggt ggatgggtag gttatatagg atatagcac   20820 agagatatat agcaaagaga tacttttgag caatgtttgt ggaagcggta ttcgcaatgg   20880
gaagctccac cccggttgat aatcagaaaa gccccaaaaa caggaagatt gtataagcaa   20940
atatttaaat tgtaaacgtt aatattttgt taaaattcgc gttaaatttt tgttaaatca   21000
```

```
gctcattttt taacgaatag cccgaaatcg gcaaaatccc ttataaatca aaagaataga    21060
ccgagatagg gttgagtgtt gttccagttt ccaacaagag tccactatta aagaacgtgg    21120
actccaacgt caaagggcga aaaagggtct atcagggcga tggcccacta cgtgaaccat    21180
caccctaatc aagttttttg gggtcgaggt gccgtaaagc agtaaatcgg aagggtaaac    21240
ggatgccccc atttagagct tgacggggaa agccggcgaa cgtggcgaga aaggaaggga    21300
agaaagcgaa aggagcgggg gctagggcgg tgggaagtgt aggggtcacg ctgggcgtaa    21360
ccaccacacc cgccgcgctt aatggggcgc tacagggcgc gtggggatga tccactagt    21419
```

<210> SEQ ID NO 12
<211> LENGTH: 1387
<212> TYPE: DNA
<213> ORGANISM: Artificial sequence
<220> FEATURE:
<223> OTHER INFORMATION: Synthetic construct

<400> SEQUENCE: 12

```
ggccgccacc atggagaaca agacagaaac taccgtgaga cgtagaagga ggataatctt      60
attcccagtt ccctttcaag gtcatatcaa tcccatattg caattggcca acgtcttgta     120
ttctaaagga ttctcaatca caatcttcca taccaacttt aacaaaccta agacatccaa     180
ttaccctcat ttcactttca ggttcatctt agacaatgat ccacaagatg aaaggatttc     240
taacttgcca actcatggtc ctttggctgg catgaggata cctatcatca tgaacatgg      300 tgcagacgaa ttgagaagag aattggagtt attgatgttg gcttcagaag aagacgaaga     360
agtgtcttgc ttaatcactg atgccttgtg gtatttcgct caatccgttg ccgactcctt     420
gaatttgaga aggttagtct tgatgacttc atccttgttt aacttccacg ctttggtgtc     480
tttacctcaa tttgacgaat taggatactt ggacccagat gataagacaa ggttggaaga     540
gcaggcttca ggtttcccaa tgttgaaagt aaaggacatc aaatccgcat atagtaattg     600
gcaaatcttg aaagagatat tgggaaagat gataaagcaa actagagctt cttctggagt     660
catttggaac tcattcaagg aattagagga gtccgaatta gaaacagtta tcagggaaat     720
tcctgctcct tccttcttga ttcctttacc caaaacactta accgcatcat cttctagttt     780
gttggaccat gatagaacag tatttcagtg gttggatcag cagccaccct cctctgtgtt     840
gtacgtttca tttggttcaa cttcagaagt tgatgagaaa gacttcttag aaatagcacg     900
tggcttagtc gattccaagc agtccttctt gtgggtcgtt agaccaggtt tcgtaaaggg     960
ttctacatgg gtcgaaccat taccagatgg tttcttgggt gaaagaggta gaatagtaaa    1020
gtgggtccct caacaagaag tgttggctca cggtgccata ggtgcattct ggactcactc    1080
tggctggaac tcaactttag aatctgtttg tgaaggagtt ccaatgatat tcagtgattt    1140
cggtttggac caaccattga acgcaaggta tatgagtgac gtgttgaaag tgggtgttta    1200
cttggagaac ggctgggagc gtggagagat agctaatgca atccgtagag tgatggtaga    1260
cgaagaaggt gaatacataa ggcagaacgc cagggtctta aagcagaaag ctgatgtttc    1320
cttaatgaaa ggtggttcct cttatgaaag tttagaatct ttggtttcct acatttcttc    1380
tttataa                                                             1387
```

<210> SEQ ID NO 13
<211> LENGTH: 3141
<212> TYPE: DNA
<213> ORGANISM: Artificial sequence
<220> FEATURE:

<223> OTHER INFORMATION: Synthetic construct

<400> SEQUENCE: 13

```
atggcttcat ctgttggaaa tgttgccgat tctactgaac ctaccaagag aatgttatca      60
tttcaaggat tagctgaatt agcccatagg gaataccaag ccggtgactt tgaagctgcc     120
gaaagacact gtatgcaatt gtggagacag gagccagaca atacaggcgt gttattgttg     180
ttgtcatcta ttcatttcca atgtagaagg ttggatagat ctgctcactt tagtactttg     240
gcaatcaaac agaatccatt gttagctgaa gcatattcca acttaggtaa cgtctataag     300
gaaagaggtc aattgcagga agccatcgag cattaccgtc atgcattaag attgaagccc     360
gatttcatcg atggttacat taacttagca gcagccttgg ttgcagcagg agatatggaa     420
ggtgcagtcc aagcctatgt ctccgcatta cagtataacc ctgacttgta ctgtgttaga     480
tctgatttgg gaaacttatt gaaggcattg ggaaggttgg aagaggcaaa ggcttgctac     540
ttgaaggcca tagaaactca accaaacttc gcagtcgcat ggtcaaactt gggttgcgtg     600
ttcaacgcac aaggtgaaat ctggttagct atccaccatt cgagaaagc agttacttta      660 gatcccaatt tcttggatgc ctacatcaat ttgggaaatg tgttaaagga ggcaaggatc     720
ttcgaccgtg ctgtcgcagc atacttaagg gctttgtctt taagtccaaa ccacgcagtt     780
gtacatggca acttggcttg tgtctactat gagcaaggat tgattgactt agctattgat     840
acctatcgta gggccattga attacagcca cactttcctg acgcttactg caacttggct     900
aatgccttga aggagaaggg atctgtggca gaggctgagg attgctacaa caccgcattg     960
aggttatgtc caacacatgc agattcctta aacaatttgg ccaatatcaa gcgtgaacag    1020
ggtaacatcg aagaagccgt cagattgtat agaaaggcct tagaggtctt tcctgaattt    1080
gctgctgccc attccaactt agcaagtgtg ttacagcagc aaggcaagtt gcaagaagcc    1140
ttaatgcact ataaggaagc aatcagaata agtcctacct ttgccgatgc ttattccaat    1200
atgggtaata ctttgaagga aatgcaggat gtccaaggtg ccttacaatg ttataccagg    1260
gcaattcaaa tcaatcctgc tttcgcagat gctcattcta acttggcatc catccataaa    1320
gattcaggca acataccaga ggccatcgcc tcttatcgta cagccttgaa gttgaagcct    1380
gatttcccag atgcctattg caacttggcc cattgtttgc aaattgtatg tgattggaca    1440
gattacgatg aaagaatgaa gaagttggtg agtatcgttg ctgaccaatt agagaagaac    1500
agattgccat cagttcaccc tcatcactct atgttgtacc cattgagtca tggtttcaga    1560
aaggcaattg ctgaaaggca tggcaatttg tgtttggaca agatcaatgt cttacataag    1620
cctccatacg aacatcctaa ggatttgaaa ttgtcagatg gaaggttgcg tgtcggatat    1680
gtttcttctg atttcggtaa tcatccaacc agtcacttaa tgcagagtat ccctggtatg    1740
cataatcccg acaaattcga agtcttctgt tatgccttaa gtccagatga cggcaccaat    1800
ttcagagtga aagttatggc tgaagctaat catttcattg atttgagtca aattccttgt    1860
aacggtaaag ccgcagatag gatacaccaa gacggcattc atatcttggt caatatgaac    1920
ggatacacaa agggtgctag aaacgagttg tttgctttaa gaccagcacc tatacaagca    1980
atgtggttag gctatccagg cacttcaggt gctttgttca tggactacat cataaccgac    2040
caagaaactt ctcccgcaga ggttgctgaa caatacagtg agaagttggc ttacatgcca    2100
catactttct tcattggtga tcatgccaat atgttcccac atttgaagaa gaaagcagtc    2160
atagatttca aatctaatgg acatatctat gataacagaa tagtgttaaa cggtattgat    2220
ttgaaagcat tcttggattc cttacctgat gttaagattg ttaagatgaa gtgtccagat    2280
```

```
ggtggcgaca acgctgattc ttctaatacc gctttgaata tgcctgtgat cccaatgaat    2340
actatcgccg aggcagttat cgaaatgatc aatagaggcc aaattcaaat cacaatcaat    2400
ggattctcta tttctaacgg tttagcaaca acacagataa acaacaaagc tgctaccgga    2460
gaagaggtgc ctaggaccat tatcgttact acaagatccc agtatggttt acctgaggac    2520
gctatcgtgt actgcaactt caatcagtta tacaagatcg atccttcaac cttacagatg    2580
tgggctaaca tcttgaagag ggttcccaat tcagtattgt ggttgttaag atttcccgca    2640
gtcggtgagc ctaacattca acagtacgct cagaatatgg gcttacctca gaatagaatc    2700
atattctctc ctgtagctcc aaaggaagaa catgtcagac gtggtcaatt ggccgatgtg    2760
tgtttggaca ctcccttgtg caacggacac accactggta tggatgtctt gtgggcaggc    2820
actcctatgg taactatgcc tggcgaaaca ttggctagta gagttgcagc tagtcaattg    2880
acatgcttag gttgcttaga gttgattgca aagaacagac aagaatacga agatattgct    2940
gtcaagttag gtactgattt ggagtacttg aagaaggtta gaggtaaggt ctggaaacaa    3000
agaattagta gtccattgtt caacaccaaa caatacacaa tggaattaga aagattgtac    3060
ttacaaatgt gggagcacta tgccgcaggt aacaaacctg accacatgat caaaccagtt    3120
gaagtaaccg aatccgctta a                                              3141
```

```
<210> SEQ ID NO 14
<211> LENGTH: 22076
<212> TYPE: DNA
<213> ORGANISM: Artificial sequence
<220> FEATURE:
<223> OTHER INFORMATION: Synthetic construct

<400> SEQUENCE: 14
```

```
acggattaga agccgccgag cgggtgacag ccctccgaag gaagactctc ctccgtgcgt      60
cctcgtcttc accggtcgcg ttcctgaaac gcagatgtgc ctcgcgccgc actgctccga     120
acaataaaga ttctacaata ctagctttta tggttatgaa gaggaaaaat tggcagtaac     180
ctggccccac aaaccttcaa atgaacgaat caaattaaca accataggat gataatgcga     240
ttagtttttt agccttattt ctggggtaat taatcagcga agcgatgatt tttgatctat     300
taacagatat ataaatgcaa aaactgcata accactttaa ctaatacttt caacattttc     360
ggtttgtatt acttcttatt caaatgtaat aaaagtatca acaaaaaatt gttaatatac     420
ctctatactt taacgtcaag gagaaaaaac cccggatcgg actactagca gctgtaatac     480
gactcactat agggaatatt aagcttccta ggccaccatg tcattaccgt tcttaacttc     540
tgcaccggga aaggttatta tttttggtga acactctgct gtgtacaaca agcctgccgt     600
cgctgctagt gtgtctgcgt tgagaaccta cctgctaata agcgagtcat ctgcaccaga     660
tactattgaa ttggacttcc cggacattag ctttaatcat aagtggtcca tcaatgattt     720
caatgccatc accgaggatc aagtaaactc ccaaaaattg gccaaggctc aacaagccac     780
cgatggcttg tctcaggaac tcgttagtct tcttgatccg ttgttagctc aactatccga     840
atccttccac taccatgcag cgttttgttt cctgtatatg tttgtttgcc tatgcccca     900 tgccaagaat attaagtttt ctttaaagtc tactttaccc atcggtgctg ggttgggctc     960
aagcgcctct atttctgtat cactggcctt agctatggcc tacttggggg ggttaatagg    1020
atctaatgac ttggaaaagc tgtcagaaaa cgataagcat atagtgaatc aatgggcctt    1080
cataggtgaa aagtgtattc acggtacccc ttcaggaata gataacgctg tggccactta    1140
```

-continued

```
tggtaatgcc ctgctatttg aaaaagactc acataatgga acaataaaca caaacaattt   1200
taagttctta gatgatttcc cagccattcc aatgatccta acctatacta gaattccaag   1260
gtctacaaaa gatcttgttg ctcgcgttcg tgtgttggtc accgagaaat ttcctgaagt   1320
tatgaagcca attctggatg ccatgggtga atgtgcccta caaggcttag agatcatgac   1380
taagttaagt aaatgtaaag gcaccgatga cgaggctgta gaaactaata atgaactgta   1440
tgaacaacta ttggaattga taagaataaa tcatggactg cttgtctcaa tcggtgtttc   1500
tcatcctgga ttagaactta ttaaaaatct gagcgatgat ttgagaattg gctccacaaa   1560
acttaccggt gctggtggcg gcggttgctc tttgactttg ttacgaagag acattactca   1620
agagcaaatt gacagcttca aaaagaaatt gcaagatgat tttagttacg agacatttga   1680
aacagacttg ggtgggactg gctgctgttt gttaagcgca aaaaatttga ataaagatct   1740
taaaatcaaa tccctagtat tccaattatt tgaaaataaa actaccacaa agcaacaaat   1800
tgacgatcta ttattgccag gaaacacgaa tttaccatgg acttcataac tcgagtcatg   1860
taattagtta tgtcacgctt acattcacgc cctcccccca catccgctct aaccgaaaag   1920
gaaggagtta gacaacctga agtctaggtc cctatttatt tttttatagt tatgttagta   1980
ttaagaacgt tatttatatt tcaaattttt cttttttttc tgtacagacg cgtgtacgca   2040
tgtaacatta tactgaaaac cttgcttgag aaggtttttgg gacgctcgaa ggctttaatt   2100
tgccggatta gaagccgccg agcgggtgac agccctccga aggaagactc tcctccgtgc   2160
gtcctcgtct tcaccggtcg cgttcctgaa acgcagatgt gcctcgcgcc gcactgctcc   2220
gaacaataaa gattctacaa tactagcttt tatggttatg aagaggaaaa attggcagta   2280
acctggcccc acaaaccttc aaatgaacga atcaaattaa caaccatagg atgataatgc   2340
gattagtttt ttagccttat ttctggggta attaatcagc gaagcgatga ttttgatct   2400 attaacagat atataaatgc aaaaactgca taaccacttt aactaatact ttcaacattt   2460
tcggtttgta ttacttctta ttcaaatgta ataaagtat caacaaaaaa ttgttaatat   2520
acctctatac tttaacgtca aggaggccgg ccaccatggt aagggcaaaa cgtaaattag   2580
atcatattga atacgctctt tctactggtc agtctcgtac gcatggcttt catgatattg   2640
attttgtgca tcaaagcttg ccaaattcaa gttatgaaac aataacatgt gaaacaaaaa   2700
tcggcgaact ttcactaagt tcgccgattt ttatcaatgc gatgactggt ggtggaggag   2760
agaaaacgtt acatattaat gagcaattag catatgtagc gaaacatcat aaccttgcta   2820
tggctgtagg atcgcaaatg gcagcgttaa aagatgaaag tgaagctgct tcttataaga   2880
ttattagaaa ggtaaatcca aatggtattt tctttgctaa tttaggtagt gaggcaactg   2940
ttgaacaggc agagcgtgct gttgatatgg ttgaagcgaa tgcattgcaa attcatttaa   3000
atgtcataca agagttaacg atgccagaag gagaccgtga ctttactggt gtacttcagc   3060
gtattgagaa aattgtttta aatagtaaag ttcctgtcat tgtaaaagaa gttggatttg   3120
ggatgagtaa ggaaacaatg caacagttgg cgagcgtagg tgtaacggca attgatattg   3180
gcggacaagg gggtacgaat tttgctgctg ttgaaaatga agaagacag cgaatgcttt   3240 cttattttaa taactggggc atacaaacag ctacctcgat tattgaagca acctctacaa   3300
ataataacct ctctttatt gcatctgggg gtatacaaac agcgcttgac gtagcgaaag   3360
caatcgcatt aggggcgaat accactgcgt ttgctggata cttttacgc attttaatgg   3420 aagatggtat cgagaagttg gtggacgaaa ttgacctttt acatacagat ttgaaattta   3480
ttatgacagc tctcggtgca aagacgatag aagagttaca gtccgtacct cttgttataa   3540
```

```
agggtgaaac gtatcattgg ttaacgcagc gtggaattga tacgacgcat tatagtagaa      3600
gataatccgg aatcatgtaa ttagttatgt cacgcttaca ttcacgccct cccccccacat     3660 ccgctctaac cgaaaaggaa ggagttagac aacctgaagt ctaggtccct atttattttt      3720
ttatagttat gttagtatta agaacgttat ttatatttca aatttttctt ttttttctgt      3780
acagacgcgt gtacgcatgt aacattatac tgaaaacctt gcttgagaag gtttttgggac    3840 gctcgaaggc tttaatttgc cggattagaa gccgccgagc gggtgacagc cctccgaagg      3900
aagactctcc tccgtgcgtc ctcgtcttca ccggtcgcgt tcctgaaacg cagatgtgcc      3960
tcgcgccgca ctgctccgaa caataaagat tctacaatac tagctttat ggttatgaag       4020 aggaaaaatt ggcagtaacc tggccccaca aaccttcaaa tgaacgaatc aaattaacaa      4080
ccataggatg ataatgcgat tagtttttta gccttatttc tggggtaatt aatcagcgaa      4140
gcgatgattt ttgatctatt aacagatata taaatgcaaa aactgcataa ccactttaac      4200
taatactttc aacattttcg gtttgtatta cttcttattc aaatgtaata aaagtatcaa      4260
caaaaaattg ttaatatacc tctatacttt aacgtcaagg agcccgggcc accatgacga      4320
cttatgcacg cgcgcacaca aatattgcgc tgattaaata ttggggaaaa gccaatcgca      4380
agttgatgct gccagccaca agcagcattt ctttaacttt aaatgacttt tatactgaca      4440
cagcagtgac atttgatcct agtctaaatg atgatcgctt catgcttaac ggtgaagaac      4500
aaaacccggt tgcggtcagc cgcttttttgg atcgggttcg gcacttagga aaaattagca     4560
cgtacgccca agtcacttcc ttgaatcacg tgccgactgc tgccgggctg gcaagttcag      4620
cctctgcttt tgctgccttg gccactgctg ccagccgcgc ggcaggtcta aacctttctc      4680
cgactgaact atcaagatta gcgcgccgcg gatcaggttc agcaacgcgc tctatctttg      4740
gtggtgccgt tatctggcat cgcggccatg acgacgcctc ttcattcgct gaaccactcg      4800
cgattcaacc tagtttgcca ttacgaatgc ttgtggtcac ggtatctgct gaaaaaaagg      4860
cggtcagttc acgaaaaggc atggccaaca cagtggccac aagtccctac tatgatgcct      4920
gggtggcctc aaatgaaagt ttaattgaac caatgattac cgcgttggct gaagacgact      4980
tagcgctgat cggcaaattg acagaattgt ccagtatgcg catgcatgcg gcgattatgg      5040
ccgaggaacc gccattcacc tactttctgc cggaaacatt acgggcgtgg caattagtgc      5100
aagaacaacg ggctttgggt attcccgcgt ttgccacgat ggatgcagga ccaaatgtca      5160
aaattctgac tactgaacct tacgtggaca ttttattaac cgccttgcgc cctgtgttcg      5220
gtgatcggat tttgagcaca cgccttggtc ctgatgccag catcatcaca aaggagcaat      5280
ttgatgacac aaagtcagca atcgcatcgc aaggatgatt aattaatcat gtaattagtt      5340
atgtcacgct tacattcacg ccctcccccc acatccgctc taaccgaaaa ggaaggagtt      5400
agacaacctg aagtctaggt ccctatttat tttttatag ttatgttagt attaagaacg       5460
ttatttatat ttcaaatttt tctttttttt ctgtacagac gcgtgtacgc atgtaacatt      5520
atactgaaaa ccttgcttga gaaggttttg ggacgctcga aggctttaat ttgccggatt      5580
agaagccgcc gagcgggtga cagccctccg aaggaagact ctcctccgtg cgtcctcgtc      5640
ttcaccggtc gcgttcctga aacgcagatg tgcctcgcgc cgcactgctc cgaacaataa      5700
agattctaca atactagctt ttatggttat gaagaggaaa aattggcagt aacctggccc       5760
cacaaacctt caaatgaacg aatcaaatta acaaccatag gatgataatg cgattagttt      5820
tttagcctta tttctggggt aattaatcag cgaagcgatg attttttgatc tattaacaga     5880
```

-continued

```
tatataaatg caaaaactgc ataaccactt taactaatac tttcaacatt ttcggtttgt   5940
attacttctt attcaaatgt aataaaagta tcaacaaaaa attgttaata tacctctata   6000 cttttaacgtc aaggagggcg cgccatggtt catttaggtc caaagaaacc acaggctaga   6060
aagggttcca tggctgatgt gcccaaggaa ttgatggatg aaattcatca gttggaagat   6120
atgtttacag ttgacagcga gaccttgaga aaggttgtta agcactttat cgacgaattg   6180
aataaaggtt tgacaaagaa gggaggtaac attccaatga ttcccggttg ggtcatggaa   6240
ttcccaacag gtaaagaatc tggtaactat ttggccattg atttgggtgg tactaactta   6300
agagtcgtgt tggtcaagtt gagcggtaac catacctttg acaccactca atccaagtat   6360
aaactaccac atgacatgag aaccactaag caccaagagg agttatggtc ctttattgcc   6420
gactctttga aggactttat ggtcgagcaa gaattgctaa acaccaagga caccttacca   6480
ttaggtttca ccttctcgta cccagcttcc caaaacaaga ttaacgaagg tattttgcaa   6540
agatggacca agggtttcga tattccaaat gtcgaaggcc acgatgtcgt cccattgcta   6600
caaaacgaaa tttccaagag agagttgcct attgaaattg tagcattgat taatgatact   6660
gttggtactt taattgcctc atactacact gacccagaga ctaagatggg tgtgattttc   6720
ggtactggtg tcaacggtgc tttctatgat gttgtttccg atatcgaaaa gttggagggc   6780
aaattagcag acgatattcc aagtaactct ccaatggcta tcaattgtga atatggttcc   6840
ttcgataatg aacatttggt cttgccaaga accaagtacg atgttgctgt cgacgaacaa   6900
tctccaagac ctggtcaaca agcttttgaa aagatgacct ccggttacta cttgggtgaa   6960
ttgttgcgtc tagtgttact tgaattaaac gagaagggct tgatgttgaa ggatcaagat   7020
ctaagcaagt tgaaacaacc atacatcatg gatacctcct acccagcaag aatcgaggat   7080
gatccatttg aaaacttgga agatactgat gacatcttcc aaaaggactt tggtgtcaag   7140
accactctgc cagaacgtaa gttgattaga agactttgtg aattgatcgg taccagagct   7200
gctagattag ctgtttgtgg tattgccgct atttgccaaa agagaggtta caagactggt   7260
cacattgccg ctgacggttc tgtctataac aaatacccag gtttcaagga agccgccgct   7320
aagggtttga gagatatcta tggatggact ggtgacgcaa gcaaagatcc aattacgatt   7380
gttccagctg aggatggttc aggtgcaggt gctgctgtta ttgctgcatt gtccgaaaaa   7440
agaattgccg aaggtaagtc tcttggtatc attggcgctt aagtttaaac tcatgtaatt   7500
agttatgtca cgcttacatt cacgccctcc ccccacatcc gctctaaccg aaaaggaagg   7560
agttagacaa cctgaagtct aggtccctat ttattttttt atagttatgt tagtattaag   7620
aacgttattt atatttcaaa ttttttcttt ttttctgtac agacgcgtgt acgcatgtaa   7680
cattatactg aaaaccttgc ttgagaaggt tttgggacgc tcgaaggctt taatttgccg   7740
gattagaagc cgccgagcgg gtgacagccc tccgaaggaa gactctcctc cgtgcgtcct   7800
cgtcttcacc ggtcgcgttc ctgaaacgca gatgtgcctc gcgccgcact gctccgaaca   7860
ataaagattc tacaatacta gcttttatgg ttatgaagag gaaaaattgg cagtaacctg   7920
gccccacaaa ccttcaaatg aacgaatcaa attaacaacc ataggatgat aatgcgatta   7980
gttttttagc cttatttctg gggtaattaa tcagcgaagc gatgattttt gatctattaa   8040
cagatatata aatgcaaaaa ctgcataacc actttaacta atactttcaa cattttcggt   8100
ttgtattact tcttattcaa atgtaataaa agtatcaaca aaaaattgtt aatatacctc   8160
tatactttaa cgtcaaggag gagctcacca tggctgaagg tgttttccaa ggtgctatcg   8220
gtatcgattt aggtacaacc tactcttgtg ttgctactta cgaatcctcc gttgaaatta   8280
```

```
ttgccaacga acaaggtaac agagtcaccc catctttcgt tgctttcact ccagaagaaa   8340
gattgattgg tgatgctgcc aagaaccaag ctgctttgaa cccaagaaac actgtcttcg   8400
atgctaagcg tttgattggt agaagattcg acgacgaatc tgttcaaaag gacatgaaga   8460
cctggccttt caaggttatc gacgtcgatg gtaacccagt catcgaagtc caatacttgg   8520
aagaaaccaa gactttctcc ccacaagaaa tttccgctat ggttttgacc aagatgaagg   8580
aaattgctga agctaagatt ggtaagaagg ttgaaaaggc cgtcattact gtcccagctt   8640
actttaacga cgctcaaaga caagctacca aggatgccgg tgccatttct ggtttgaacg   8700
ttttgcgtat catcaacgaa cctactgccg ctgctattgc ttacggtcta ggtgctggta   8760
agtccgaaaa ggaaagacat gttttgattt tcgatttggg tggtggtact ttcgatgttt   8820
ccttgttgca cattgctggt ggtgtttaca ctgttaaatc tacttccggt aacactcact   8880
tgggtggtca agatttcgac accaacttgt tggaacactt caaggctgaa ttcaagaaga   8940
agactggttt ggacatctcc gacgatgcca gagctttgag aagattgaga actgctgctg   9000
aaagagctaa gagaacctta tcttctgtca ctcaaactac cgttgaagtt gactctttgt   9060
ttgacggtta agatttcgaa tcctctttga ctagagctag atttgaagac ttgaacgccg   9120
cattgttcaa gtctactttg gaacctgttg aacaagtttt gaaggatgct aagatctcta   9180
agtctcaaat cgacgaagtt gtcttggttg gtggttccac cagaattcca aaggtccaaa   9240
agttgttgtc tgacttcttt gacggtaagc aattggaaaa atctattaac ccagatgaag   9300
ctgttgctta cggtgctgct gttcaaggtg ctatcttgac cggccaatcc acatctgacg   9360
aaaccaagga cttgttgttg ttagatgttg ctccattatc tctaggtgtt ggtatgcaag   9420
gtgacatgtt cggtatcgtt gttccaagaa acactactgt tccaaccatc aagagaagaa   9480
cctttactac atgtgctgac aaccaaacca ccgttcaatt cccagtctac caaggtgaac   9540
gtgttaactg taaagaaaac actttgttgg gtgaattcga cttgaagaac atcccaatga   9600
tgccagctgg tgaaccagtc ttggaagcta tcttcgaagt tgatgctaac ggtatcttga   9660
aggttactgc cgtcgaaaag tctaccggta agtcttctaa catcactatc tctaacgctg   9720
ttggtagatt gtcttctgaa gaaattgaaa agatggttaa ccaagctgaa gagttcaagg   9780
ctgccgatga agcttttgcc aagaagcacg aagctagaca aagattggaa tcctacgttg   9840
cctccatcga acaaactgtc actgacccag tcttgtcttc taaattgaag agaggttcca   9900
agtccaagat tgaagctgct ttgtccgatg ctttggctgc tttgcaaatc gaagacccat   9960
ctgctgatga attgagaaag gctgaagttg gtttgaagag agttgtcacc aaggccatgt   10020
cttctcgtta aggtacctca tgtaattagt tatgtcacgc ttacattcac gccctcccc   10080 cacatccgct ctaaccgaaa aggaaggagt tagacaacct gaagtctagg tccctattta   10140 ttttttata gttatgttag tattaagaac gttatttata tttcaaattt ttcttttttt   10200
tctgtacaga cgcgtgtacg catgtaacat tatactgaaa accttgcttg agaaggtttt   10260
gggacgctcg aaggctttaa tttgccggat tagaagccgc cgagcgggtg acagccctcc   10320
gaaggaagac tctcctccgt gcgtcctcgt cttcaccggt cgcgttcctg aaacgcagat   10380
gtgcctcgcg ccgcactgct ccgaacaata aagattctac aatactagct tttatggtta   10440
tgaagaggaa aaattggcag taacctggcc ccacaaacct tcaaatgaac gaatcaaatt   10500
aacaaccata ggatgataat gcgattagtt ttttagcctt atttctgggg taattaatca   10560
gcgaagcgat gattttttgat ctattaacag atatataaat gcaaaaactg cataaccact   10620
```

-continued

```
ttaactaata ctttcaacat tttcggtttg tattacttct tattcaaatg taataaaagt   10680
atcaacaaaa aattgttaat atacctctat actttaacgt caaggaggga tccgccacca   10740
tggaaccaca aattcttttt ctctatctct cactcttcat tctctcccta aacttcttct   10800
tcacgaatct taaaccaagg ctagtccgcc tcttccagcc ttctttagaa tctcgtgtca   10860
agaccgctct tttatcccga aaggaagtag ccgcgtttct tgattctccc attgtcgaag   10920
acgaagaagg cgaagaaaga gaagaggaag aagaaggagg tatcgtttca aatgccaact   10980
ttacgtttga gtttgatcca tacatgatga gcaaagccga atcagtgaac aaagctctgg   11040
aagaagcaat tccagtcgga gagccactca agattcatga agccatgcga tacgcgattc   11100
ttgcggctgg aaaacgtgtt aggccaatac tctgccttgc ttcttgcgag ctagtaggtg   11160
gccaagaaaa tgcggcaatg cccgccgctt gtgcggttga gatgatccac acgatgtctc   11220
taatcaaaga cgatttgcct tgtatggaca acgacgattt gcgtcgtgga aagcccacga   11280
cgcacaaagt ctacggcgaa ggagttgcca ttctctctgg tggggctctc ttgtctcttg   11340
cctttgagca catgaccacc gctgaaatat cctcggagag aatggtttgg gcggtgagag   11400
aattggctag gtctattggg acaagaggtt tagtcgcggg acaagcgatg gatataagca   11460
gtgaaggttt ggacttaaac gaggtcggat tagagcattt ggagtttatc catgttcata   11520
aaaccgcggt tttgttggaa actgccgcgg ttcttggcgc cataattggt ggtggatctg   11580
atgaagagat tgaaagtgtg agaaagtttg caaggtgcat tggattgttg tttcaggtgg   11640
tggatgatat tttggacgag acgaagtcgt cggaggaatt gggaaaaacc gccgggaaag   11700
atcagctcgc cggaaagcta acgtatccaa agttgatagg gttggagaaa tcgaaagaat   11760
ttgttaagag attgacgaaa gatgcacggc aacatcttca agggtttagt tctgaaaagg   11820
ttgctccttt agtagctctt actactttta ttgctaatag aaataagtga gaattctcat   11880
gtaattagtt atgtcacgct tacattcacg ccctcccccc acatccgctc taaccgaaaa   11940
ggaaggagtt agacaacctg aagtctaggt ccctatttat tttttttatag ttatgttagt   12000 attaagaacg ttatttatat ttcaaatttt tctttttttt ctgtacagac gcgtgtacgc   12060
atgtaacatt atactgaaaa ccttgcttga gaaggttttg ggacgctcga aggctttaat   12120
ttgccggatt agaagccgcc gagcgggtga cagccctccg aaggaagact ctcctccgtg   12180
cgtcctcgtc ttcaccggtc gcgttcctga aacgcagatg tgcctcgcgc cgcactgctc   12240
cgaacaataa agattctaca atactagctt ttatggttat gaagaggaaa aattggcagt   12300
aacctggccc cacaaacctt caaatgaacg aatcaaatta acaaccatag gatgataatg   12360
cgattagttt tttagcctta tttctggggt aattaatcag cgaagcgatg atttttgatc   12420
tattaacaga tatataaatg caaaaactgc ataaccactt taactaatac tttcaacatt   12480
ttcggtttgt attacttctt attcaaatgt aataaaagta tcaacaaaaa attgttaata   12540
tacctctata ctttaacgtc aaggaggcgg ccgccaccat ggagaacaag acagaaacta   12600
ccgtgagacg tagaaggagg ataatcttat tcccagttcc ctttcaaggt catatcaatc   12660
ccatattgca attggccaac gtcttgtatt ctaaaggatt ctcaatcaca atcttccata   12720
ccaactttaa caaacctaag acatccaatt accctcattt cactttcagg ttcatcttag   12780
acaatgatcc acaagatgaa aggatttcta acttgccaac tcatggtcct ttggctggca   12840
tgaggatacc tatcatcaat gaacatggtg cagacgaatt gagaagagaa ttggagttat   12900
tgatgttggc ttcagaagaa gacgaagaag tgtcttgctt aatcactgat gccttgtggt   12960
atttcgctca atccgttgcc gactccttga atttgagaag gttagtcttg atgacttcat   13020
```

```
ccttgtttaa cttccacgct ttggtgtctt tacctcaatt tgacgaatta ggatacttgg   13080
acccagatga taagacaagg ttggaagagc aggcttcagg tttcccaatg ttgaaagtaa   13140
aggacatcaa atccgcatat agtaattggc aaatcttgaa agagatattg ggaaagatga   13200
taaagcaaac tagagcttct tctggagtca tttggaactc attcaaggaa ttagaggagt   13260
ccgaattaga aacagttatc agggaaattc ctgctccttc cttcttgatt cctttaccca   13320
aacacttaac cgcatcatct tctagtttgt tggaccatga tagaacagta tttcagtggt   13380
tggatcagca gccaccctcc tctgtgttgt acgtttcatt tggttcaact tcagaagttg   13440
atgagaaaga cttcttagaa atagcacgtg gcttagtcga ttccaagcag tccttcttgt   13500
gggtcgttag accaggtttc gtaaagggtt ctacatgggt cgaaccatta ccagatggtt   13560
tcttgggtga aagaggtaga atagtaaagt gggtccctca acaagaagtg ttggctcacg   13620
gtgccatagg tgcattctgg actcactctg gctggaactc aactttagaa tctgtttgtg   13680
aaggagttcc aatgatattc agtgatttcg gtttggacca accattgaac gcaaggtata   13740
tgagtgacgt gttgaaagtg ggtgtttact tggagaacgg ctgggagcgt ggagagatag   13800
ctaatgcaat ccgtagagtg atggtagacg aagaaggtga atacataagg cagaacgcca   13860
gggtcttaaa gcagaaagct gatgtttcct taatgaaagg tggttcctct tatgaaagtt   13920
tagaatcttt ggtttcctac atttcttctt tataatcgta cgcatcatgt aattagttat   13980
gtcacgctta cattcacgcc ctcccccac atccgctcta accgaaaagg aaggagttag    14040
acaacctgaa gtctaggtcc ctatttattt ttttatagtt atgttagtat taagaacgtt   14100
atttatattt caaatttttc tttttttct gtacagacgc gtgtacgcat gtaacattat    14160
actgaaaacc ttgcttgaga aggttttggg acgctcgaag gctttaattt gcatgctacg   14220
gattagaagc cgccgagcgg gtgacagccc tccgaaggaa gactctcctc cgtgcgtcct   14280
cgtcttcacc ggtcgcgttc ctgaaacgca gatgtgcctc gcgccgcact gctccgaaca   14340
ataaagattc tacaatacta gctttatgg ttatgaagag gaaaaattgg cagtaacctg    14400
gccccacaaa ccttcaaatg aacgaatcaa attaacaacc ataggatgat aatgcgatta   14460
gttttttagc cttatttctg gggtaattaa tcagcgaagc gatgattttt gatctattaa   14520
cagatatata aatgcaaaaa ctgcataacc actttaacta atactttcaa cattttcggt   14580
ttgtattact tcttattcaa atgtaataaa agtatcaaca aaaaattgtt aatatacctc   14640
tatactttaa cgtcaaggag gccaccatgg cggttgcagg atcgaccatg aacctgcatc   14700
tcacttcatc tccatacaag acagttccat cactctgtaa attcaccaga aaacagttcc   14760
gattaaaggc ctctgcaacg aatccagacg ctgaagatgg gaagatgatg tttaaaaacg   14820
ataaacccaa tttgaaggtc gaattcgctg gggagaaacc ggtgacacca ttactggata   14880
ccattaatta ccctgtgcac atgaaaaacc tcaccactca ggatcttgag caattagcag   14940
cagaacttag acaagatatt gtatattcag tagcgaatac aggtggtcat ttgagttcaa   15000
gtttaggtgt tgttgaattg tctgttgctt tacaccatgt tttcaacacc ccagatgaca   15060
agatcatttg ggacgttggt caccaggcat acccacataa gattttgacc ggaagaaggt   15120
caaagatgca caccataaga aaaacttctg gtttagctgg ttttcctaaa cgagatgaaa   15180
gtgctcatga tgcttttggt gctggacata gttctacaag catctctgct ggactaggta   15240
tggctgtcgg tagagattta ttagggaaaa ccaacaacgt gatatcggtg atcggagatg   15300
gcgccatgac ggccggacga gcatatgagg cgataaataa tgcaggattt cttgattcaa   15360
```

-continued

```
atctaatcgt cgttttaaac gacaacaagc aagtttcatt accgactgcc acgttggacg   15420
gacctgcaac tcccgtcggg gctctcagcg gcgctttatc caaattgcaa gccagtacca   15480
agttccgtaa gcttcgtgaa gccgccaaga gcattactaa acaaattgga cctcaagcac   15540
atgaagtggc ggcgaaagtc gacgaatacg caagaggtat gattagtgct agcgggtcga   15600
ctttattcga ggaactcgga ttatactaca tcggtcccgt cgatggtcac aatgttgaag   15660
atttagtcaa cattttttgaa aaagtcaagt caatgcccgc acccggaccg gttctaatcc   15720
acatcgtgac cgaaaaaggc aaaggttacc ctcctgctga agccgctgct gaccgtatgc   15780
acggagttgt gaagtttgat gttccaactg gaaaacaatt caagacaaaa tcaccgacac   15840
tttcgtatac tcagtatttt gctgaatcac ttataaaaga agctgaagct gataacaaga   15900
ttgtcgcgat acacgccgcc atgggaggcg gtaccggact caattacttc cagaagaagt   15960
gtcctgaacg ttgtttttgat gtcggtatcg cggaacaaca cgcagttact ttcgccgcgg   16020
gtttagccac cgaaggtctt aaaccatttt gcgcgatcta ttcgtcgttt ttgcaacgag   16080
gatacgatca agtggtgcat gacgttgatc tacaaaagtt accggttcgg tttgcgatgg   16140
accgagctgg tttagtcggg gctgatggac cgacacattg tggtgcgttt gacataacct   16200
acatggcgtg tctaccaaac atggtggtga tggctccagc cgatgaagcc gaattgatgc   16260
acatggttgc aacggctgca gccattgacg acagaccgag ttgctttcgg ttcccaagag   16320
gcaatggcat tggtgcacca cttcctccta ataacaaagg gattcccata gaggttggta   16380
aaggaagaat attacttgaa ggaactcgtg ttgcgatatt gggatacggt tcgatagttc   16440
aagaatgtct aggtgcggct agcttgcttc aagcccataa cgtgtctgca accgtagccg   16500
atgcgcggtt ctgcaaaccg ttagacaccg gactgattag acgattagcc aacgagcatg   16560
aagtcttact taccgtagag gaaggctcga ttggtggatt tggatcacac gttgctcact   16620
ttctaagctt aaatggtctc ttagatggaa aacttaagct tagagcaatg actcttcctg   16680
ataaatacat tgatcatggt gcaccacaag atcagcttga agaagccggt ctttcttcaa   16740
aacatatttg ttcatctctt ttatcacttt tgggaaaacc taaagaagca cttcaataca   16800
aatcaataat gtaatctaga gggccgcatc atgtaattag ttatgtcacg cttacattca   16860
cgccctcccc ccacatccgc tctaaccgaa aaggaaggag ttagacaacc tgaagtctag   16920
gtccctattt attttttat agttatgtta gtattaagaa cgttatttat atttcaaatt   16980 tttcttttttt ttctgtacag acgcgtgtac gcatgtaaca ttatactgaa aaccttgctt   17040
gagaaggttt tgggacgctc gaaggcttta atttgcggcc ctgcattaat gaatcggcca   17100
acgcgcgggg agaggcggtt tgcgtattgg gcgctcttcc gcttcctcgc tcactgactc   17160
gctgcgctcg tcgttcggc tgcggcgagc ggtatcagct cactcaaagg cggtaatacg   17220
gttatccaca gaatcagggg ataacgcagg aaagaacatg tgagcaaaag gccagcaaaa   17280
gcccaggaac cgtaaaaagg ccgcgttgct ggcgtttttc cataggctcc gcccccctga   17340
cgagcatcac aaaaatcgac gctcaagtca gaggtggcga aacccgacag gactataaag   17400
ataccaggcg tttccccctg gaagctccct cgtgcgctct cctgttccga ccctgccgct   17460
taccggatac ctgtccgcct ttctcccttc gggaagcgtg gcgctttctc atagctcacg   17520
ctgtaggtat ctcagttcgg tgtaggtcgt tcgctccaag ctgggctgtg tgcacgaacc   17580
ccccgttcag cccgaccgct gcgccttatc cggtaactat cgtcttgagt ccaacccggt   17640
aagacacgac ttatcgccac tggcagcagc cactggtaac aggattagca gagcgaggta   17700
tgtaggcggt gctacagagt tcttgaagtg gtggcctaac tacggctaca ctagaaggac   17760
```

-continued

```
agtatttggt atctgcgctc tgctgaagcc agttaccttc ggaaaaagag ttggtagctc   17820
ttgatccggc aaacaaacca ccgctggtag cggtggtttt tttgtttgca agcagcagat   17880
tacgcgcaga aaaaaggat  ctcaagaaga tcctttgatc ttttctacgg ggtctgacgc   17940
tcagtggaac gaaaactcac gttaagggat tttggtcatg agattatcaa aaaggatctt   18000
cacctagatc cttttaaatt aaaaatgaag ttttaaatca atctaaagta tatatgagta   18060
aacttggtct gacagttacc aatgcttaat cagtgaggca cctatctcag cgatctgtct   18120
atttcgttca tccatagttg cctgactccc cgtcgtgtag ataactacga tacgggagcg   18180
cttaccatct ggccccagtg ctgcaatgat accgcgagac ccacgctcac cggctccaga   18240
tttatcagca ataaaccagc cagccggaag ggccgagcgc agaagtggtc ctgcaacttt   18300
atccgcctcc atccagtcta ttaattgttg ccgggaagct agagtaagta gttcgccagt   18360
taatagtttg cgcaacgttg ttggcattgc tacaggcatc gtggtgtcac tctcgtcgtt   18420
tggtatggct tcattcagct ccggttccca acgatcaagg cgagttacat gatcccccat   18480
gttgtgcaaa aaagcggtta gctccttcgg tcctccgatc gttgtcagaa gtaagttggc   18540
cgcagtgtta tcactcatgg ttatggcagc actgcataat tctcttactg tcatgccatc   18600
cgtaagatgc ttttctgtga ctggtgagta ctcaaccaag tcattctgag aatagtgtat   18660
gcggcgaccg agttgctctt gcccggcgtc aatacgggat aatagtgtat cacatagcag   18720
aactttaaaa gtgctcatca ttggaaaacg ttcttcgggg cgaaaactct caaggatctt   18780
accgctgttg agatccagtt cgatgtaacc cactcgtgca cccaactgat cttcagcatc   18840
ttttactttc accagcgttt ctgggtgagc aaaaacagga aggcaaaatg ccgcaaaaaa   18900
gggaataagg cgacacgga  aatgttgaat actcatactc ttcctttttc aatgggtaat   18960
aactgatata attaaattga agctctaatt tgtgagttta gtatacatgc atttacttat   19020
aatacagttt tttagttttg ctggccgcat cttctcaaat atgcttccca gcctgctttt   19080
ctgtaacgtt caccctctac cttagcatcc cttccctttg caaatagtcc tcttccaaca   19140
ataataatgt cagatcctgt agagaccaca tcatccacgg ttctatactg ttgacccaat   19200
gcgtctccct tgtcatctaa acccacaccg ggtgtcataa tcaaccaatc gtaaccttca   19260
tctcttccac ccatgtctct ttgagcaata aagccgataa caaaatcttt gtcgctcttc   19320
gcaatgtcaa cagtaccctt agtatattct ccagtagata gggagcccct gcatgacaat   19380
tctgctaaca tcaaaaggcc tctaggttcc tttgttactt cttctgccgc ctgcttcaaa   19440
ccgctaacaa tacctgggcc caccacaccg tgtgcattcg taatgtctgc ccattctgct   19500
attctgtata cacccgcaga gtactgcaat ttgactgtat taccaatgtc agcaaatttt   19560
ctgtcttcga agagtaaaaa attgtacttg gcggataatg cctttagcgg cttaactgtg   19620
ccctccatgg aaaaatcagt caagatatcc acatgtgttt ttagtaaaca attttggga   19680 cctaatgctt caactaactc cagtaattcc ttggtggtac gaacatccaa tgaagcacac   19740
aagtttgttt gcttttcgtg catgatatta aatagcttgg cagcaacagg actaggatga   19800
gtagcagcac gttccttata tgtagctttc gacatgattt atcttcgttt cctgcaggtt   19860
tttgttctgt gcagttgggt taagaatact gggcaatttc atgtttcttc aacactacat   19920
atgcgtatat ataccaatct aagtctgtgc tccttccttc gttcttcctt ctgttcggag   19980
attaccgaat caaaaaaatt tcaaagaaac cgaaatcaaa aaaagaata  aaaaaaaat    20040 gatgaattga attgaaaagc tagcttatcg atgataagct gtcaaagatg agaattaatt   20100
```

-continued

```
ccacggacta tagactatac tagatactcc gtctactgta cgatacactt ccgctcaggt   20160
ccttgtcctt taacgaggcc ttaccactct tttgttactc tattgatcca gctcagcaaa   20220
ggcagtgtga tctaagattc tatcttcgcg atgtagtaaa actagctaga ccgagaaaga   20280
gactagaaat gcaaaaggca cttctacaat ggctgccatc attattatcc gatgtgacgc   20340
tgcagcttct caatgatatt cgaatacgct ttgaggagat acagcctaat atccgacaaa   20400
ctgttttaca gatttacgat cgtacttgtt acccatcatt gaattttgaa catccgaacc   20460
tgggagtttt ccctgaaaca gatagtatat ttgaacctgt ataataatat atagtctagc   20520
gctttacgga agacaatgta tgtatttcgg ttcctggaga aactattgca tctattgcat   20580
aggtaatctt gcacgtcgca tccccggttc attttctgcg tttccatctt gcacttcaat   20640
agcatatctt tgttaacgaa gcatctgtgc ttcattttgt agaacaaaaa tgcaacgcga   20700
gagcgctaat ttttcaaaca aagaatctga gctgcatttt tacagaacag aaatgcaacg   20760
cgaaagcgct attttaccaa cgaagaatct gtgcttcatt tttgtaaaac aaaaatgcaa   20820
cgcgacgaga gcgctaattt ttcaaacaaa gaatctgagc tgcattttta cagaacagaa   20880
atgcaacgcg agagcgctat tttaccaaca aagaatctat acttcttttt tgttctacaa   20940
aaatgcatcc cgagagcgct attttttctaa caaagcatct tagattactt tttttctcct   21000
ttgtgcgctc tataatgcag tctcttgata acttttttgca ctgtaggtcc gttaaggtta   21060
gaagaaggct actttggtgt ctattttctc ttccataaaa aaagcctgac tccacttccc   21120
gcgtttactg attactagcg aagctgcggg tgcatttttt caagataaag gcatccccga   21180
ttatattcta taccgatgtg gattgcgcat actttgtgaa cagaaagtga tagcgttgat   21240
gattcttcat tggtcagaaa attatgaacg gtttcttcta ttttgtctct atatactacg   21300
tataggaaat gtttacattt tcgtattgtt ttcgattcac tctatgaata gttcttacta   21360 caatttttt gtctaaagag taatactaga gataaacata aaaaatgtag aggtcgagtt   21420
tagatgcaag ttcaaggagc gaaaggtgga tgggtaggtt atatagggat atagcacaga   21480
gatatatagc aaagagatac ttttgagcaa tgtttgtgga agcggtattc gcaatgggaa   21540
gctccacccc ggttgataat cagaaaagcc ccaaaaacag gaagattgta taagcaaata   21600
tttaaattgt aaacgttaat attttgttaa aattcgcgtt aaattttttgt taaatcagct   21660 catttttttaa cgaatagccc gaaatcggca aaatccctta taaatcaaaa gaatagaccg   21720
agatagggtt gagtgttgtt ccagtttcca acaagagtcc actattaaag aacgtggact   21780
ccaacgtcaa agggcgaaaa agggtctatc agggcgatgg cccactacgt gaaccatcac   21840
cctaatcaag ttttttgggg tcgaggtgcc gtaaagcagt aaatcggaag ggtaaacgga   21900
tgcccccatt tagagcttga cggggaaagc cggcgaacgt ggcgagaaag gaagggaaga   21960
aagcgaaagg agcgggggct agggcggtgg gaagtgtagg ggtcacgctg gccgtaacca   22020
ccacacccgc cgcgcttaat ggggcgctac agggcgcgtg gggatgatcc actagt      22076
```

<210> SEQ ID NO 15
<211> LENGTH: 23844
<212> TYPE: DNA
<213> ORGANISM: Artificial sequence
<220> FEATURE:
<223> OTHER INFORMATION: Synthetic construct

<400> SEQUENCE: 15

```
acggattaga agccgccgag cgggtgacag ccctccgaag gaagactctc ctccgtgcgt      60
cctcgtcttc accggtcgcg ttcctgaaac gcagatgtgc ctcgcgccgc actgctccga     120
```

```
acaataaaga ttctacaata ctagctttta tggttatgaa gaggaaaaat tggcagtaac    180
ctggccccac aaaccttcaa atgaacgaat caaattaaca accataggat gataatgcga    240
ttagtttttt agccttattt ctggggtaat taatcagcga agcgatgatt tttgatctat    300
taacagatat ataaatgcaa aaactgcata accactttaa ctaatacttt caacattttc    360
ggtttgtatt acttcttatt caaatgtaat aaaagtatca acaaaaaatt gttaatatac    420
ctctatactt taacgtcaag gagaaaaaac cccggatcgg actactagca gctgtaatac    480
gactcactat agggaatatt aagcttccta ggccaccatg tcattaccgt tcttaacttc    540
tgcaccggga aaggttatta ttttggtga acactctgct gtgtacaaca agcctgccgt     600
cgctgctagt gtgtctgcgt tgagaaccta cctgctaata agcgagtcat ctgcaccaga    660
tactattgaa ttggacttcc cggacattag ctttaatcat aagtggtcca tcaatgattt    720
caatgccatc accgaggatc aagtaaactc ccaaaaattg gccaaggctc aacaagccac    780
cgatggcttg tctcaggaac tcgttagtct tcttgatccg ttgttagctc aactatccga    840
atccttccac taccatgcag cgtttttgttt cctgtatatg tttgtttgcc tatgccccca    900
tgccaagaat attaagtttt cttaaagtc tactttaccc atcggtgctg ggttgggctc     960
aagcgcctct atttctgtat cactggcctt agctatggcc tacttggggg ggttaatagg    1020
atctaatgac ttggaaaagc tgtcagaaaa cgataagcat atagtgaatc aatgggcctt    1080
cataggtgaa aagtgtattc acggtacccc ttcaggaata gataacgctg tggccactta    1140
tggtaatgcc ctgctatttg aaaaagactc acataatgga acaataaaca caaacaattt    1200
taagttctta gatgatttcc cagccattcc aatgatccta acctatacta gaattccaag    1260
gtctacaaaa gatcttgttg ctcgcgttcg tgtgttggtc accgagaaat ttcctgaagt    1320
tatgaagcca attctggatg ccatgggtga atgtgcccta caaggcttag agatcatgac    1380
taagttaagt aaatgtaaag gcaccgatga cgaggctgta gaaactaata atgaactgta    1440
tgaacaacta ttggaattga taagaataaa tcatggactg cttgtctcaa tcggtgtttc    1500
tcatcctgga ttagaactta ttaaaaatct gagcgatgat ttgagaattg gctccacaaa    1560
acttaccggt gctggtggcg gcggttgctc tttgactttg ttacgaagag acattactca    1620
agagcaaatt gacagcttca aaaagaaatt gcaagatgat tttagttacg agacatttga    1680
aacagacttg ggtgggactg gctgctgttt gttaagcgca aaaaatttga ataaagatct    1740
taaaatcaaa tccctagtat tccaattatt tgaaaataaa actaccacaa agcaacaaat    1800
tgacgatcta ttattgccag gaaacacgaa tttaccatgg acttcataac tcgagtcatg    1860
taattagtta tgtcacgctt acattcacgc cctcccccca catccgctct aaccgaaaag    1920
gaaggagtta gacaacctga gtctaggtc cctatttatt tttttatagt tatgttagta    1980
ttaagaacgt tatttatatt tcaaattttt cttttttttc tgtacagacg cgtgtacgca    2040
tgtaacatta tactgaaaac cttgcttgag aaggttttgg gacgctcgaa ggctttaatt    2100
tgccggatta gaagccgccg agcgggtgac agccctccga aggaagactc tcctccgtgc    2160
gtcctcgtct tcaccggtcg cgttcctgaa acgcagatgt gcctcgcgcc gcactgctcc    2220
gaacaataaa gattctacaa tactagcttt tatggttatg aagaggaaaa attggcagta    2280
acctggcccc acaaaccttc aaatgaacga atcaaattaa caaccatagg atgataatgc    2340
gattagtttt ttagccttat ttctgggggta attaatcagc gaagcgatga tttttgatct    2400
attaacagat atataaatgc aaaaactgca taaccacttt aactaatact ttcaacattt    2460
```

```
tcggtttgta ttacttctta ttcaaatgta ataaaagtat caacaaaaaa ttgttaatat        2520
acctctatac tttaacgtca aggaggccgg ccaccatggt aagggcaaaa cgtaaattag        2580
atcatattga atacgctctt tctactggtc agtctcgtac gcatggcttt catgatattg        2640
attttgtgca tcaaagcttg ccaaattcaa gttatgaaac aataacatgt gaaacaaaaa        2700
tcggcgaact ttcactaagt tcgccgattt ttatcaatgc gatgactggt ggtggaggag        2760
agaaaacgtt acatattaat gagcaattag catatgtagc gaaacatcat aaccttgcta        2820
tggctgtagg atcgcaaatg gcagcgttaa aagatgaaag tgaagctgct tcttataaga        2880
ttattagaaa ggtaaatcca aatggtattt tctttgctaa tttaggtagt gaggcaactg        2940
ttgaacaggc agagcgtgct gttgatatgg ttgaagcgaa tgcattgcaa attcatttaa        3000
atgtcataca agagttaacg atgccagaag gagaccgtga ctttactggt gtacttcagc        3060
gtattgagaa aattgtttta aatagtaaag ttcctgtcat tgtaaaagaa gttggatttg        3120
ggatgagtaa ggaaacaatg caacagttgg cgagcgtagg tgtaacggca attgatattg        3180
gcggacaagg gggtacgaat tttgctgctg ttgaaaatga aagaagacag cgaatgcttt        3240
cttattttaa taactggggc atacaaacag ctacctcgat tattgaagca acctctacaa        3300
ataataacct ctcttttatt gcatctgggg gtatacaaac agcgcttgac gtagcgaaag        3360
caatcgcatt aggggcgaat accactgcgt ttgctggata cttttttacgc attttaatgg        3420 aagatggtat cgagaagttg gtggacgaaa ttgacctttt acatacagat ttgaaattta        3480
ttatgacagc tctcggtgca aagacgatag aagagttaca gtccgtacct cttgttataa        3540
agggtgaaac gtatcattgg ttaacgcagc gtggaattga tacgacgcat tatagtagaa        3600
gataatccgg aatcatgtaa ttagttatgt cacgcttaca ttcacgccct ccccccacat        3660
ccgctctaac cgaaaaggaa ggagttagac aacctgaagt ctaggtccct atttattttt        3720
ttatagttat gttagtatta agaacgttat ttatatttca aatttttctt tttttttctgt        3780 acagacgcgt gtacgcatgt aacattatac tgaaaacctt gcttgagaag gttttgggac        3840
gctcgaaggc tttaatttgc cggattagaa gccgccgagc gggtgacagc cctccgaagg        3900
aagactctcc tccgtgcgtc ctcgtcttca ccggtcgcgt tcctgaaacg cagatgtgcc        3960
tcgcgccgca ctgctccgaa caataaagat tctacaatac tagcttttat ggttatgaag        4020
aggaaaaatt ggcagtaacc tggccccaca aaccttcaaa tgaacgaatc aaattaacaa        4080
ccataggatg ataatgcgat tagttttttta gccttatttc tggggtaatt aatcagcgaa        4140
gcgatgattt ttgatctatt aacagatata taaatgcaaa aactgcataa ccactttaac        4200
taatactttc aacattttcg gtttgtatta cttcttattc aaatgtaata aaagtatcaa        4260
caaaaaattg ttaatatacc tctatacttt aacgtcaagg agcccgggcc accatgacga        4320
cttatgcacg cgcgcacaca aatattgcgc tgattaaata ttggggaaaa gccaatcgca        4380
agttgatgct gccagccaca agcagcattt ctttaacttt aaatgacttt tatactgaca        4440
cagcagtgac atttgatcct agtctaaatg atgatcgctt catgcttaac ggtgaagaac        4500
aaaacccggt tgcggtcagc cgcttttttgg atcgggttcg gcacttagga aaaattagca        4560
cgtacgccca agtcacttcc ttgaatcacg tgccgactgc tgccgggctg gcaagttcag        4620
cctctgcttt tgctgccttg gccactgctg ccagccgcgc ggcaggtcta aacctttctc        4680
cgactgaact atcaagatta gcgcgccgcg gatcaggttc agcaacgcgc tctatctttg        4740
gtggtgccgt tatctggcat cgcggccatg acgacgcctc ttcattcgct gaaccactcg        4800
cgattcaacc tagtttgcca ttacgaatgc ttgtggtcac ggtatctgct gaaaaaaagg        4860
```

-continued

```
cggtcagttc acgaaaaggc atggccaaca cagtggccac aagtccctac tatgatgcct    4920
gggtggcctc aaatgaaagt ttaattgaac caatgattac cgcgttggct gaagacgact    4980
tagcgctgat cggcaaattg acagaattgt ccagtatgcg catgcatgcg gcgattatgg    5040
ccgaggaacc gccattcacc tactttctgc cggaaacatt acgggcgtgg caattagtgc    5100
aagaacaacg ggctttgggt attcccgcgt ttgccacgat ggatgcagga ccaaatgtca    5160
aaattctgac tactgaacct tacgtggaca ttttattaac cgccttgcgc cctgtgttcg    5220
gtgatcggat tttgagcaca cgccttggtc ctgatgccag catcatcaca aaggagcaat    5280
ttgatgacac aaagtcagca atcgcatcgc aaggatgatt aattaatcat gtaattagtt    5340
atgtcacgct tacattcacg ccctccccc acatccgctc taaccgaaaa ggaaggagtt    5400
agacaacctg aagtctaggt ccctatttat ttttttatag ttatgttagt attaagaacg    5460
ttatttatat ttcaaatttt tctttttttt ctgtacagac gcgtgtacgc atgtaacatt    5520
atactgaaaa ccttgcttga gaaggttttg ggacgctcga aggctttaat ttgccggatt    5580
agaagccgcc gagcgggtga cagccctccg aaggaagact ctcctccgtg cgtcctcgtc    5640
ttcaccggtc gcgttcctga aacgcagatg tgcctcgcgc cgcactgctc cgaacaataa    5700
agattctaca atactagctt ttatggttat gaagaggaaa aattggcagt aacctggccc    5760
cacaaacctt caaatgaacg aatcaaatta acaaccatag gatgataatg cgattagttt    5820
tttagcctta tttctggggt aattaatcag cgaagcgatg attttttgatc tattaacaga    5880 tatataaatg caaaaactgc ataaccactt taactaatac tttcaacatt ttcggtttgt    5940
attacttctt attcaaatgt aataaaagta tcaacaaaaa attgttaata tacctctata    6000
ctttaacgtc aaggagggcg cgccatggtt catttaggtc caaagaaacc acaggctaga    6060
aagggttcca tggctgatgt gcccaaggaa ttgatggatg aaattcatca gttggaagat    6120
atgtttacag ttgacagcga gaccttgaga aaggttgtta agcactttat cgacgaattg    6180
aataaaggtt tgacaaagaa gggaggtaac attccaatga ttcccggttg ggtcatggaa    6240
ttcccaacag gtaaagaatc tggtaactat ttggccattg atttgggtgg tactaactta    6300
agagtcgtgt tggtcaagtt gagcggtaac catacctttg acaccactca atccaagtat    6360
aaactaccac atgacatgag aaccactaag caccaagagg agttatggtc ctttattgcc    6420
gactctttga aggactttat ggtcgagcaa gaattgctaa acaccaagga caccttacca    6480
ttaggtttca ccttctcgta cccagcttcc caaaacaaga ttaacgaagg tattttgcaa    6540
agatggacca agggtttcga tattccaaat gtcgaaggcc acgatgtcgt cccattgcta    6600
caaaacgaaa tttccaagag agagttgcct attgaaattg tagcattgat taatgatact    6660
gttggtactt taattgcctc atactacact gacccagaga ctaagatggg tgtgattttc    6720
ggtactggtg tcaacggtgc tttctatgat gttgtttccg atatcgaaaa gttggagggc    6780
aaattagcag acgatattcc aagtaactct ccaatggcta tcaattgtga atatggttcc    6840
ttcgataatg aacatttggt cttgccaaga accaagtacg atgttgctgt cgacgaacaa    6900
tctccaagac ctggtcaaca agcttttgaa aagatgacct ccggttacta cttgggtgaa    6960
ttgttgcgtc tagtgttact tgaattaaac gagaagggct tgatgttgaa ggatcaagat    7020
ctaagcaagt tgaaacaacc atacatcatg gatacctcct acccagcaag aatcgaggat    7080
gatccatttg aaaacttgga agatactgat gacatcttcc aaaaggactt tggtgtcaag    7140
accactctgc cagaacgtaa gttgattaga agactttgtg aattgatcgg taccagagct    7200
```

-continued

```
gctagattag ctgtttgtgg tattgccgct atttgccaaa agagaggtta caagactggt      7260
cacattgccg ctgacggttc tgtctataac aaatacccag gtttcaagga agccgccgct      7320
aagggtttga gagatatcta tggatggact ggtgacgcaa gcaaagatcc aattacgatt      7380
gttccagctg aggatggttc aggtgcaggt gctgctgtta ttgctgcatt gtccgaaaaa      7440
agaattgccg aaggtaagtc tcttggtatc attggcgctt aagtttaaac tcatgtaatt      7500
agttatgtca cgcttacatt cacgccctcc ccccacatcc gctctaaccg aaaaggaagg      7560
agttagacaa cctgaagtct aggtccctat ttatttttt atagttatgt tagtattaag      7620
aacgttattt atatttcaaa tttttctttt ttttctgtac agacgcgtgt acgcatgtaa      7680
cattatactg aaaaccttgc ttgagaaggt tttgggacgc tcgaaggctt taatttgccg      7740
gattagaagc cgccgagcgg gtgacagccc tccgaaggaa gactctcctc cgtgcgtcct      7800
cgtcttcacc ggtcgcgttc ctgaaacgca gatgtgcctc gcgccgcact gctccgaaca      7860
ataaagattc tacaatacta gcttttatgg ttatgaagag gaaaaattgg cagtaacctg      7920
gccccacaaa ccttcaaatg aacgaatcaa attaacaacc ataggatgat aatgcgatta      7980
gttttttagc cttatttctg gggtaattaa tcagcgaagc gatgattttt gatctattaa      8040
cagatatata aatgcaaaaa ctgcataacc actttaacta atactttcaa cattttcggt      8100
ttgtattact tcttattcaa atgtaataaa agtatcaaca aaaaattgtt aatatacctc      8160
tatactttaa cgtcaaggag gagctcacca tggctgaagg tgtttccaa ggtgctatcg      8220 gtatcgattt aggtacaacc tactcttgtg ttgctactta cgaatcctcc gttgaaatta      8280
ttgccaacga acaaggtaac agagtcaccc catctttcgt tgctttcact ccagaagaaa      8340
gattgattgg tgatgctgcc aagaaccaag ctgctttgaa cccaagaaac actgtcttcg      8400
atgctaagcg tttgattggt agaagattcg acgacgaatc tgttcaaaag gacatgaaga      8460
cctggccttt caaggttatc gacgtcgatg gtaacccagt catcgaagtc caatacttgg      8520
aagaaaccaa gacttctcc ccacaagaaa tttccgctat ggttttgacc aagatgaagg      8580
aaattgctga agctaagatt ggtaagaagg ttgaaaaggc cgtcattact gtcccagctt      8640
actttaacga cgctcaaaga caagctacca aggatgccgg tgccatttct ggtttgaacg      8700
ttttgcgtat catcaacgaa cctactgccg ctgctattgc ttacggtcta ggtgctggta      8760
agtccgaaaa ggaaagacat gttttgattt cgatttggg tggtggtact ttcgatgttt      8820
ccttgttgca cattgctggt ggtgtttaca ctgttaaatc tacttccggt aacactcact      8880
tgggtggtca agatttcgac accaacttgt tggaacactt caaggctgaa ttcaagaaga      8940
agactggttt ggacatctcc gacgatgcca gagctttgag aagattgaga actgctgctg      9000
aaagagctaa gagaacctta tcttctgtca ctcaaactac cgttgaagtt gactctttgt      9060
ttgacggtga agatttcgaa tcctctttga ctagagctag atttgaagac ttgaacgccg      9120
cattgttcaa gtctactttg gaacctgttg aacaagtttt gaaggatgct aagatctcta      9180
agtctcaaat cgacgaagtt gtcttggttg gtggttccac cagaattcca aaggtccaaa      9240
agttgttgtc tgacttcttt gacggtaagc aattggaaaa atctattaac ccagatgaag      9300
ctgttgctta cggtgctgct gttcaaggtg ctatcttgac cggccaatcc acatctgacg      9360
aaaccaagga cttgttgttg ttagatgttg ctccattatc tctaggtgtt ggtatgcaag      9420
gtgacatgtt cggtatcgtt gttccaagaa acactactgt tccaaccatc aagagaagaa      9480
cctttactac atgtgctgac aaccaaacca ccgttcaatt cccagtctac caaggtgaac      9540
gtgttaactg taaagaaaac actttgttgg gtgaattcga cttgaagaac atcccaatga      9600
```

```
tgccagctgg tgaaccagtc ttggaagcta tcttcgaagt tgatgctaac ggtatcttga     9660
aggttactgc cgtcgaaaag tctaccggta agtcttctaa catcactatc tctaacgctg     9720
ttggtagatt gtcttctgaa gaaattgaaa agatggttaa ccaagctgaa gagttcaagg     9780
ctgccgatga agcttttgcc aagaagcacg aagctagaca aagattggaa tcctacgttg     9840
cctccatcga acaaactgtc actgacccag tcttgtcttc taaattgaag agaggttcca     9900
agtccaagat tgaagctgct ttgtccgatg ctttggctgc tttgcaaatc gaagacccat     9960
ctgctgatga attgagaaag gctgaagttg gtttgaagag agttgtcacc aaggccatgt     10020
cttctcgtta aggtacctca tgtaattagt tatgtcacgc ttacattcac gccctccccc     10080
cacatccgct ctaaccgaaa aggaaggagt tagacaacct gaagtctagg tccctattta     10140 ttttttata gttatgttag tattaagaac gttatttata tttcaaattt ttctttttt     10200 tctgtacaga cgcgtgtacg catgtaacat tatactgaaa accttgcttg agaaggtttt     10260
gggacgctcg aaggctttaa tttgccggat tagaagccgc cgagcgggtg acagccctcc     10320
gaaggaagac tctcctccgt gcgtcctcgt cttcaccggt cgcgttcctg aaacgcagat     10380
gtgcctcgcg ccgcactgct ccgaacaata aagattctac aatactagct tttatggtta     10440
tgaagaggaa aaattggcag taacctggcc ccacaaacct tcaaatgaac gaatcaaatt     10500
aacaaccata ggatgataat gcgattagtt ttttagcctt atttctgggg taattaatca     10560
gcgaagcgat gatttttgat ctattaacag atatataaat gcaaaaactg cataaccact     10620
ttaactaata ctttcaacat tttcggtttg tattacttct tattcaaatg taataaaagt     10680
atcaacaaaa aattgttaat atacctctat actttaacgt caaggaggga tccgccacca     10740
tggaaccaca aattctttt ctctatctct cactcttcat tctctcccta aacttcttct     10800
tcacgaatct taaaccaagg ctagtccgcc tcttccagcc ttctttagaa tctcgtgtca     10860
agaccgctct tttatcccga aaggaagtag ccgcgtttct tgattctccc attgtcgaag     10920
acgaagaagg cgaagaaaga gaagaggaag aagaaggagg tatcgtttca aatgccaact     10980
ttacgtttga gtttgatcca tacatgatga gcaaagccga atcagtgaac aaagctctgg     11040
aagaagcaat tccagtcgga gagccactca agattcatga agccatgcga tacgcgattc     11100
ttgcggctgg aaaacgtgtt aggccaatac tctgccttgc ttcttgcgag ctagtaggtg     11160
gccaagaaaa tgcggcaatg cccgccgctt gtgcggttga gatgatccac acgatgtctc     11220
taatcaaaga cgatttgcct tgtatggaca cgacgattt gcgtcgtgga aagcccacga     11280
cgcacaaagt ctacggcgaa ggagttgcca ttctctctgg tggggctctc ttgtctcttg     11340
cctttgagca catgaccacc gctgaaatat cctcggagag aatggtttgg gcggtgagag     11400
aattggctag gtctattggg acaagaggtt tagtcgcggg acaagcgatg gatataagca     11460
gtgaaggttt ggacttaaac gaggtcggat tagagcattt ggagtttatc catgttcata     11520
aaaccgcggt tttgttggaa actgccgcgg ttccttggcgc cataattggt ggtggatctg     11580
atgaagagat tgaaagtgtg agaaagtttg caaggtgcat tggattgttg tttcaggtgg     11640
tggatgatat tttggacgag acgaagtcgt cggaggaatt gggaaaaacc gccgggaaag     11700
atcagctcgc cggaaagcta acgtatccaa agttgatagg gttggagaaa tcgaaagaat     11760
ttgttaagag attgacgaaa gatgcacggc aacatcttca agggtttagt tctgaaaagg     11820
ttgctccttt agtagctctt actactttta ttgctaatag aaataagtga gaattctcat     11880
gtaattagtt atgtcacgct tacattcacg ccctccccc acatccgctc taaccgaaaa     11940
```

-continued

```
ggaaggagtt agacaacctg aagtctaggt ccctatttat ttttttatag ttatgttagt   12000
attaagaacg ttatttatat ttcaaatttt tctttttttt ctgtacagac gcgtgtacgc   12060
atgtaacatt atactgaaaa ccttgcttga gaaggttttg ggacgctcga aggctttaat   12120
ttgccggatt agaagccgcc gagcgggtga cagccctccg aaggaagact ctcctccgtg   12180
cgtcctcgtc ttcaccggtc gcgttcctga aacgcagatg tgcctcgcgc cgcactgctc   12240
cgaacaataa agattctaca atactagctt ttatggttat gaagaggaaa aattggcagt   12300
aacctggccc cacaaacctt caaatgaacg aatcaaatta acaaccatag gatgataatg   12360
cgattagttt tttagcctta tttctggggt aattaatcag cgaagcgatg atttttgatc   12420
tattaacaga tatataaatg caaaaactgc ataaccactt taactaatac tttcaacatt   12480
ttcggtttgt attacttctt attcaaatgt aataaaagta tcaacaaaaa attgttaata   12540
tacctctata ctttaacgtc aaggaggcgg ccgccaccat ggcttcatct gttggaaatg   12600
ttgccgattc tactgaacct accaagagaa tgttatcatt tcaaggatta gctgaattag   12660
cccataggga ataccaagcc ggtgactttg aagctgccga aagacactgt atgcaattgt   12720
ggagacagga gccagacaat acaggcgtgt tattgttgtt gtcatctatt catttccaat   12780
gtagaaggtt ggatagatct gctcacttta gtactttggc aatcaaacag aatccattgt   12840
tagctgaagc atattccaac ttaggtaacg tctataagga aagaggtcaa ttgcaggaag   12900
ccatcgagca ttaccgtcat gcattaagat tgaagcccga tttcatcgat ggttacatta   12960
acttagcagc agccttggtt gcagcaggag atatggaagg tgcagtccaa gcctatgtct   13020
ccgcattaca gtataaccct gacttgtact gtgttagatc tgatttggga aacttattga   13080
aggcattggg aaggttggaa gaggcaaagg cttgctactt gaaggccata gaaactcaac   13140
caaacttcgc agtcgcatgg tcaaacttgg gttgcgtgtt caacgcacaa ggtgaaatct   13200
ggttagctat ccaccatttc gagaaagcag ttactttaga tcccaatttc ttggatgcct   13260
acatcaattt gggaaatgtg ttaaaggagg caaggatctt cgaccgtgct gtcgcagcat   13320
acttaagggc tttgtcttta agtccaaacc acgcagttgt acatggcaac ttggcttgtg   13380
tctactatga gcaaggattg attgacttag ctattgatac ctatcgtagg gccattgaat   13440
tacagccaca ctttcctgac gcttactgca acttggctaa tgccttgaag gagaagggat   13500
ctgtggcaga ggctgaggat tgctacaaca ccgcattgag gttatgtcca acacatgcag   13560
attccttaaa caatttggcc aatatcaagc gtgaacaggg taacatcgaa gaagccgtca   13620
gattgtatag aaaggcctta gaggtctttc ctgaatttgc tgctgcccat tccaacttag   13680
caagtgtgtt acagcagcaa ggcaagttgc aagaagcctt aatgcactat aaggaagcaa   13740
tcagaataag tcctaccttt gccgatgctt attccaatat gggtaatact ttgaaggaaa   13800
tgcaggatgt ccaaggtgcc ttacaatgtt ataccagggc aattcaaatc aatcctgctt   13860
tcgcagatgc tcattctaac ttggcatcca tccataaaga ttcaggcaac ataccagagg   13920
ccatcgcctc ttatcgtaca gccttgaagt tgaagcctga tttcccagat gcctattgca   13980
acttggccca ttgtttgcaa attgtatgtg attggacaga ttacgatgaa agaatgaaga   14040
agttggtgag tatcgttgct gaccaattag agaagaacag attgccatca gttcaccctc   14100
atcactctat gttgtaccca ttgagtcatg gtttcagaaa ggcaattgct gaaaggcatg   14160
gcaatttgtg tttggacaag atcaatgtct acataagcc tccatacgaa catcctaagg   14220
atttgaaatt gtcagatgga aggttgcgtg tcggatatgt ttcttctgat ttcggtaatc   14280
atccaaccag tcacttaatg cagagtatcc ctggtatgca taatcccgac aaaattcgaag  14340
```

```
tcttctgtta tgccttaagt ccagatgacg gcaccaattt cagagtgaaa gttatggctg   14400
aagctaatca ttttcattgat ttgagtcaaa ttccttgtaa cggtaaagcc gcagatagga   14460
tacaccaaga cggcattcat atcttggtca atatgaacgg atacacaaag ggtgctagaa   14520
acgagttgtt tgctttaaga ccagcaccta tacaagcaat gtggttaggc tatccaggca   14580
cttcaggtgc tttgttcatg gactacatca taaccgacca agaaacttct cccgcagagg   14640
ttgctgaaca atacagtgag aagttggctt acatgccaca tactttcttc attggtgatc   14700
atgccaatat gttcccacat ttgaagaaga aagcagtcat agatttcaaa tctaatggac   14760
atatctatga taacagaata gtgttaaacg gtattgattt gaaagcattc ttggattcct   14820
tacctgatgt taagattgtt aagatgaagt gtccagatgg tggcgacaac gctgattctt   14880
ctaataccgc tttgaatatg cctgtgatcc caatgaatac tatcgccgag gcagttatcg   14940
aaatgatcaa tagaggccaa attcaaatca caatcaatgg attctctatt tctaacggtt   15000
tagcaacaac acagataaac aacaaagctg ctaccggaga agaggtgcct aggaccatta   15060
tcgttactac aagatcccag tatggtttac ctgaggacgc tatcgtgtac tgcaacttca   15120
atcagttata caagatcgat ccttcaacct tacagatgtg ggctaacatc ttgaagaggg   15180
ttcccaattc agtattgtgg ttgttaagat ttcccgcagt cggtgagcct aacattcaac   15240
agtacgctca gaatatgggc ttacctcaga atagaatcat attctctcct gtagctccaa   15300
aggaagaaca tgtcagacgt ggtcaattgg ccgatgtgtg tttggacact cccttgtgca   15360
acggacacac cactggtatg gatgtcttgt gggcaggcac tcctatggta actatgcctg   15420
gcgaaacatt ggctagtaga gttgcagcta gtcaattgac atgcttaggt tgcttagagt   15480
tgattgcaaa gaacagacaa gaatacgaag atattgctgt caagttaggt actgatttgg   15540
agtacttgaa gaaggttaga ggtaaggtct ggaaacaaag aattagtagt ccattgttca   15600
acaccaaaca atacacaatg gaattagaaa gattgtactt acaaatgtgg gagcactatg   15660
ccgcaggtaa caaacctgac cacatgatca aaccagttga agtaaccgaa tccgcttaat   15720
taatcgtacg catcatgtaa ttagttatgt cacgcttaca ttcacgccct ccccccacat   15780
ccgctctaac cgaaaaggaa ggagttagac aacctgaagt ctaggtccct atttatttt   15840 ttatagttat gttagtatta agaacgttat ttatatttca aattttctt ttttttctgt   15900 acagacgcgt gtacgcatgt aacattatac tgaaaacctt gcttgagaag gttttgggac   15960
gctcgaaggc tttaatttgc atgctacgga ttagaagccg ccgagcgggt gacagccctc   16020
cgaaggaaga ctctcctccg tgcgtcctcg tcttcaccgg tcgcgttcct gaaacgcaga   16080
tgtgcctcgc gccgcactgc tccgaacaat aaagattcta caatactagc ttttatggtt   16140
atgaagagga aaaattggca gtaacctggc cccacaaacc ttcaaatgaa cgaatcaaat   16200
taacaaccat aggatgataa tgcgattagt ttttttagcct tatttctggg gtaattaatc   16260
agcgaagcga tgatttttga tctattaaca gatatataaa tgcaaaaact gcataaccac   16320
tttaactaat actttcaaca ttttcggttt gtattacttc ttattcaaat gtaataaaag   16380
tatcaacaaa aaattgttaa tatacctcta tactttaacg tcaaggaggc caccatggcg   16440
gttgcaggat cgaccatgaa cctgcatctc acttcatctc catacaagac agttccatca   16500
ctctgtaaat tcaccagaaa acagttccga ttaaaggcct ctgcaacgaa tccagacgct   16560
gaagatggga agatgatgtt taaaaacgat aaacccaatt tgaaggtcga attcgctggg   16620
gagaaaccgg tgacaccatt actggatacc attaattacc ctgtgcacat gaaaaacctc   16680
```

-continued

```
accactcagg atcttgagca attagcagca gaacttagac aagatattgt atattcagta   16740
gcgaatacag gtggtcattt gagttcaagt ttaggtgttg ttgaattgtc tgttgcttta   16800
caccatgttt tcaacacccc agatgacaag atcatttggg acgttggtca ccaggcatac   16860
ccacataaga tttttgaccgg aagaaggtca aagatgcaca ccataagaaa aacttctggt   16920
ttagctggtt ttcctaaacg agatgaaagt gctcatgatg cttttggtgc tggacatagt   16980
tctacaagca tctctgctgg actaggtatg gctgtcggta gagatttatt agggaaaacc   17040
aacaacgtga tatcggtgat cggagatggc gccatgacgg ccggacgagc atatgaggcg   17100
ataaataatg caggatttct tgattcaaat ctaatcgtcg ttttaaacga caacaagcaa   17160
gtttcattac cgactgccac gttggacgga cctgcaactc ccgtcggggc tctcagcggc   17220
gctttatcca aattgcaagc cagtaccaag ttccgtaagc ttcgtgaagc cgccaagagc   17280
attactaaac aaattggacc tcaagcacat gaagtggcgg cgaaagtcga cgaatacgca   17340
agaggtatga ttagtgctag cgggtcgact ttattcgagg aactcggatt atactacatc   17400
ggtcccgtcg atggtcacaa tgttgaagat ttagtcaaca tttttgaaaa agtcaagtca   17460
atgcccgcac ccggaccggt tctaatccac atcgtgaccg aaaaaggcaa aggttaccct   17520
cctgctgaag ccgctgctga ccgtatgcac ggagttgtga agtttgatgt tccaactgga   17580
aaacaattca agacaaaatc accgacactt tcgtatactc agtattttgc tgaatcactt   17640 ataaagaag ctgaagctga taacaagatt gtcgcgatac acgccgccat gggaggcggt   17700
accggactca attacttcca gaagaagtgt cctgaacgtt gttttgatgt cggtatcgcg   17760
gaacaacacg cagttacttt cgccgcgggt ttagccaccg aaggtcttaa accattttgc   17820
gcgatctatt cgtcgttttt gcaacgagga tacgatcaag tggtgcatga cgttgatcta   17880
caaaagttac cggttcggtt tgcgatggac cgagctggtt tagtcggggc tgatggaccg   17940
acacattgtg gtgcgtttga cataacctac atggcgtgtc taccaaacat ggtggtgatg   18000
gctccagccg atgaagccga attgatgcac atggttgcaa cggctgcagc cattgacgac   18060
agaccgagtt gctttcggtt cccaagaggc aatggcattg gtgcaccact tcctcctaat   18120
aacaaaggga ttcccataga ggttggtaaa ggaagaatat tacttgaagg aactcgtgtt   18180
gcgatattgg gatacggttc gatagttcaa gaatgtctag gtgcggctag cttgcttcaa   18240
gcccataacg tgtctgcaac cgtagccgat gcgcggttct gcaaaccgtt agacaccgga   18300
ctgattagac gattagccaa cgagcatgaa gtcttactta ccgtagagga aggctcgatt   18360
ggtggatttg gatcacacgt tgctcacttt ctaagcttaa atggtctctt agatggaaaa   18420
cttaagctta gagcaatgac tcttcctgat aaatacattg atcatggtgc accacaagat   18480
cagcttgaag aagccggtct ttcttcaaaa catatttgtt catctctttt atcacttttg   18540
ggaaaaccta agaagcact tcaatacaaa tcaataatgt aatctagagg gccgcatcat   18600
gtaattagtt atgtcacgct tacattcacg ccctcccccc acatccgctc taaccgaaaa   18660
ggaaggagtt agacaacctg aagtctaggt ccctatttat tttttatag ttatgttagt   18720 attaagaacg ttatttatat ttcaaatttt tctttttttt ctgtacagac gcgtgtacgc   18780
atgtaacatt atactgaaaa ccttgcttga gaaggttttg ggacgctcga aggctttaat   18840
ttgcggccct gcattaatga atcggccaac gcgcggggag aggcggtttg cgtattgggc   18900
gctcttccgc ttcctcgctc actgactcgc tgcgctcggt cgttcggctg cggcgagcgg   18960
tatcagctca ctcaaaggcg gtaatacggt tatccacaga atcaggggat aacgcaggaa   19020
agaacatgtg agcaaaaggc cagcaaaagc ccaggaaccg taaaaaggcc gcgttgctgg   19080
```

US 12,692,502 B2

```
cgttttccca taggctccgc ccccctgacg agcatcacaa aaatcgacgc tcaagtcaga  19140
ggtggcgaaa cccgacagga ctataaagat accaggcgtt tccccctgga agctccctcg  19200
tgcgctctcc tgttccgacc ctgccgctta ccggatacct gtccgccttt ctcccttcgg  19260
gaagcgtggc gctttctcat agctcacgct gtaggtatct cagttcggtg taggtcgttc  19320
gctccaagct gggctgtgtg cacgaacccc ccgttcagcc cgaccgctgc gccttatccg  19380
gtaactatcg tcttgagtcc aacccggtaa gacacgactt atcgccactg gcagcagcca  19440
ctggtaacag gattagcaga gcgaggtatg taggcggtgc tacagagttc ttgaagtggt  19500
ggcctaacta cggctacact agaaggacag tatttggtat ctgcgctctg ctgaagccag  19560
ttaccttcgg aaaaagagtt ggtagctctt gatccggcaa acaaaccacc gctggtagcg  19620
gtggtttttt tgtttgcaag cagcagatta cgcgcagaaa aaaaggatct caagaagatc  19680
ctttgatctt ttctacgggg tctgacgctc agtggaacga aaactcacgt taagggattt  19740
tggtcatgag attatcaaaa aggatcttca cctagatcct tttaaattaa aaatgaagtt  19800
ttaaatcaat ctaaagtata tatgagtaaa cttggtctga cagttaccaa tgcttaatca  19860
gtgaggcacc tatctcagcg atctgtctat ttcgttcatc catagttgcc tgactccccg  19920
tcgtgtagat aactacgata cgggagcgct taccatctgg ccccagtgct gcaatgatac  19980
cgcgagaccc acgctcaccg gctccagatt tatcagcaat aaaccagcca gccggaaggg  20040
ccgagcgcag aagtggtcct gcaactttat ccgcctccat ccagtctatt aattgttgcc  20100
gggaagctag agtaagtagt tcgccagtta atagtttgcg caacgttgtt ggcattgcta  20160
caggcatcgt ggtgtcactc tcgtcgtttg gtatggcttc attcagctcc ggttcccaac  20220
gatcaaggcg agttacatga tcccccatgt tgtgcaaaaa agcggttagc tccttcggtc  20280
ctccgatcgt tgtcagaagt aagttggccg cagtgttatc actcatggtt atggcagcac  20340
tgcataattc tcttactgtc atgccatccg taagatgctt ttctgtgact ggtgagtact  20400
caaccaagtc attctgagaa tagtgtatgc ggcgaccgag ttgctcttgc ccggcgtcaa  20460
tacgggataa tagtgtatca catagcagaa ctttaaaagt gctcatcatt ggaaaacgtt  20520
cttcggggcg aaaactctca aggatcttac cgctgttgag atccagttcg atgtaaccca  20580
ctcgtgcacc caactgatct tcagcatctt ttactttcac cagcgtttct gggtgagcaa  20640
aaacaggaag gcaaaatgcc gcaaaaaagg aataagggc gacacggaaa tgttgaatac  20700
tcatactctt cctttttcaa tgggtaataa ctgatataat taaattgaag ctctaatttg  20760
tgagtttagt atacatgcat ttacttataa tacagttttt tagttttgct ggccgcatct  20820
tctcaaatat gcttcccagc ctgcttttct gtaacgttca ccctctacct tagcatccct  20880 tcccttttgca aatagtcctc ttccaacaat aataatgtca gatcctgtag agaccacatc  20940
atccacggtt ctatactgtt gacccaatgc gtctcccttg tcatctaaac ccacaccggg  21000
tgtcataatc aaccaatcgt aaccttcatc tcttccaccc atgtctcttt gagcaataaa  21060
gccgataaca aaatctttgt cgctcttcgc aatgtcaaca gtacccttag tatattctcc  21120
agtagatagg gagcccttgc atgacaattc tgctaacatc aaaaggcctc taggttcctt  21180
tgttacttct tctgccgcct gcttcaaacc gctaacaata cctgggccca ccaccgtg  21240 tgcattcgta atgtctgccc attctgctat tctgtataca cccgcagagt actgcaattt  21300
gactgtatta ccaatgtcag caaattttct gtcttcgaag agtaaaaaat tgtacttggc  21360
ggataatgcc tttagcggct taactgtgcc ctccatggaa aaatcagtca agatatccac  21420
```

-continued

```
atgtgttttt agtaaacaaa tttttgggacc taatgcttca actaactcca gtaattcctt   21480
ggtggtacga acatccaatg aagcacacaa gtttgtttgc ttttcgtgca tgatattaaa   21540
tagcttggca gcaacaggac taggatgagt agcagcacgt tccttatatg tagctttcga   21600
catgatttat cttcgtttcc tgcaggtttt tgttctgtgc agttgggtta agaatactgg   21660
gcaatttcat gtttcttcaa cactacatat gcgtatatat accaatctaa gtctgtgctc   21720
cttccttcgt tcttccttct gttcggagat taccgaatca aaaaaatttc aaagaaaccg   21780
aaatcaaaaa aaagaataaa aaaaaaatga tgaattgaat tgaaaagcta gcttatcgat   21840
gataagctgt caaagatgag aattaattcc acggactata gactatacta gatactccgt   21900
ctactgtacg atacacttcc gctcaggtcc ttgtccttta acgaggcctt accactcttt   21960
tgttactcta ttgatccagc tcagcaaagg cagtgtgatc taagattcta tcttcgcgat   22020
gtagtaaaac tagctagacc gagaaagaga ctagaaatgc aaaaggcact tctacaatgg   22080
ctgccatcat tattatccga tgtgacgctg cagcttctca atgatattcg aatacgcttt   22140
gaggagatac agcctaatat ccgacaaact gttttacaga tttacgatcg tacttgttac   22200
ccatcattga attttgaaca tccgaacctg ggagttttcc ctgaaacaga tagtatattt   22260
gaacctgtat aataatatat agtctagcgc tttacggaag acaatgtatg tatttcggtt   22320
cctggagaaa ctattgcatc tattgcatag gtaatcttgc acgtcgcatc cccggttcat   22380
tttctgcgtt tccatcttgc acttcaatag catatctttg ttaacgaagc atctgtgctt   22440
cattttgtag aacaaaaatg caacgcgaga gcgctaattt ttcaaacaaa gaatctgagc   22500 tgcatttttta cagaacagaa atgcaacgcg aaagcgctat tttaccaacg aagaatctgt   22560
gcttcatttt tgtaaaacaa aaatgcaacg cgacgagagc gctaattttt caaacaaaga   22620
atctgagctg cattttttaca gaacagaaat gcaacgcgag agcgctattt taccaacaaa   22680
gaatctatac ttctttttttg ttctacaaaa atgcatcccg agagcgctat ttttctaaca   22740
aagcatctta gattacttttt tttctcctttt gtgcgctcta taatgcagtc tcttgataac   22800
tttttgcact gtaggtccgt taaggttaga agaaggctac tttggtgtct atttttctctt   22860 ccataaaaaa agcctgactc cacttcccgc gtttactgat tactagcgaa gctgcgggtg   22920 catttttttca agataaaggc atccccgatt atattctata ccgatgtgga ttgcgcatac   22980
tttgtgaaca gaaagtgata gcgttgatga ttcttcattg gtcagaaaat tatgaacggt   23040
ttcttctatt ttgtctctat atactacgta taggaaatgt ttacatttttc gtattgtttt   23100 cgattcactc tatgaatagt tcttactaca attttttttgt ctaaagagta atactagaga   23160
taaacataaa aaatgtagag gtcgagttta gatgcaagtt caaggagcga aggtggatg    23220 ggtaggttat atagggatat agcacagaga tatatagcaa agagatactt ttgagcaatg   23280
tttgtggaag cggtattcgc aatgggaagc tccaccccgg ttgataatca gaaaagcccc   23340
aaaaacagga agattgtata agcaaatatt taaattgtaa acgttaatat tttgttaaaa   23400
ttcgcgttaa attttttgtta aatcagctca ttttttaacg aatagcccga aatcggcaaa   23460
atcccttata aatcaaaaga atagaccgag atagggttga gtgttgttcc agtttccaac   23520
aagagtccac tattaaagaa cgtggactcc aacgtcaaag ggcgaaaaag ggtctatcag   23580
ggcgatggcc cactacgtga accatcaccc taatcaagtt ttttgggggtc gaggtgccgt   23640 aaagcagtaa atcggaaggg taaacggatg cccccatttta gagcttgacg gggaaagccg   23700
gcgaacgtgg cgagaaagga agggaagaaa gcgaaaggag cggggctag ggcggtggga   23760 agtgtagggg tcacgctggg cgtaaccacc acacccgccg cgcttaatgg ggcgctacag   23820
```

-continued

```
ggcgcgtggg gatgatccac tagt                                     23844

<210> SEQ ID NO 16
<211> LENGTH: 23379
<212> TYPE: DNA
<213> ORGANISM: Artificial sequence
<220> FEATURE:
<223> OTHER INFORMATION: Synthetic construct

<400> SEQUENCE: 16
acggattaga agccgccgag cgggtgacag ccctccgaag gaagactctc ctccgtgcgt      60
cctcgtcttc accggtcgcg ttcctgaaac gcagatgtgc ctcgcgccgc actgctccga     120
acaataaaga ttctacaata ctagctttta tggttatgaa gaggaaaaat tggcagtaac     180
ctggccccac aaaccttcaa atgaacgaat caaattaaca accataggat gataatgcga     240
ttagtttttt agccttattt ctggggtaat taatcagcga agcgatgatt tttgatctat     300
taacagatat ataaatgcaa aaactgcata accactttaa ctaatacttt caacattttc     360
ggtttgtatt acttcttatt caaatgtaat aaaagtatca acaaaaaatt gttaatatac     420
ctctatactt taacgtcaag gagaaaaaac cccggatcgg actactagca gctgtaatac     480
gactcactat agggaatatt aagcttccta ggccaccatg tcattaccgt tcttaacttc     540
tgcaccggga aaggttatta tttttggtga acactctgct gtgtacaaca agcctgccgt     600
cgctgctagt gtgtctgcgt tgagaaccta cctgctaata agcgagtcat ctgcaccaga     660
tactattgaa ttggacttcc cggacattag ctttaatcat aagtggtcca tcaatgattt     720
caatgccatc accgaggatc aagtaaactc ccaaaaattg gccaaggctc aacaagccac     780
cgatggcttg tctcaggaac tcgttagtct tcttgatccg ttgttagctc aactatccga     840
atccttccac taccatgcag cgttttgttt cctgtatatg tttgtttgcc tatgccccca     900
tgccaagaat attaagtttt ctttaaagtc tactttaccc atcggtgctg ggttgggctc     960
aagcgcctct atttctgtat cactggcctt agctatggcc tacttggggg ggttaatagg    1020
atctaatgac ttggaaaagc tgtcagaaaa cgataagcat atagtgaatc aatgggcctt    1080
cataggtgaa aagtgtattc acggtacccc ttcaggaata gataacgctg tggccactta    1140
tggtaatgcc ctgctatttg aaaaagactc acataatgga acaataaaca caaacaattt    1200
taagttctta gatgatttcc cagccattcc aatgatccta acctatacta gaattccaag    1260
gtctacaaaa gatcttgttg ctcgcgttcg tgtgttggtc accgagaaat ttcctgaagt    1320
tatgaagcca attctggatg ccatgggtga atgtgcccta caaggcttag agatcatgac    1380
taagttaagt aaatgtaaag gcaccgatga cgaggctgta gaaactaata atgaactgta    1440
tgaacaacta ttggaattga taagaataaa tcatggactc cttgtctcaa tcggtgtttc    1500
tcatcctgga ttagaactta ttaaaaatct gagcgatgat ttgagaattg ctccacaaa     1560 acttaccggt gctggtggcg gcggttgctc tttgactttg ttacgaagag acattactca    1620
agagcaaatt gacagcttca aaaagaaatt gcaagatgat tttagttacg agacatttga    1680
aacagacttg ggtgggactg gctgctgttt gttaagcgca aaaaatttga ataaagatct    1740
taaaatcaaa tccctagtat tccaattatt tgaaaataaa actaccacaa agcaacaaat    1800
tgacgatcta ttattgccag gaaacacgaa tttaccatgg acttcataac tcgagtcatg    1860
taattagtta tgtcacgctt acattcacgc cctcccccca catccgctct aaccgaaaag    1920
gaaggagtta gacaacctga agtctaggtc cctatttatt tttttatagt tatgttagta    1980
```

-continued

```
ttaagaacgt tatttatatt tcaaattttt cttttttttc tgtacagacg cgtgtacgca    2040
tgtaacatta tactgaaaac cttgcttgag aaggttttgg gacgctcgaa ggctttaatt    2100
tgccggatta gaagccgccg agcgggtgac agccctccga aggaagactc tcctccgtgc    2160
gtcctcgtct tcaccggtcg cgttcctgaa acgcagatgt gcctcgcgcc gcactgctcc    2220
gaacaataaa gattctacaa tactagcttt tatggttatg aagaggaaaa attggcagta    2280
acctggcccc acaaaccttc aaatgaacga atcaaattaa caaccatagg atgataatgc    2340
gattagtttt ttagccttat ttctggggta attaatcagc gaagcgatga ttttttgatct   2400 attaacagat atataaatgc aaaaactgca taaccacttt aactaatact ttcaacattt    2460
tcggtttgta ttacttctta ttcaaatgta ataaaagtat caacaaaaaa ttgttaatat    2520
acctctatac tttaacgtca aggaggccgg ccaccatggt aagggcaaaa cgtaaattag    2580
atcatattga atacgctctt tctactggtc agtctcgtac gcatggcttt catgatattg    2640
attttgtgca tcaaagcttg ccaaattcaa gttatgaaac aataacatgt gaaacaaaaa    2700
tcggcgaact ttcactaagt tcgccgattt ttatcaatgc gatgactggt ggtggaggag    2760
agaaaacgtt acatattaat gagcaattag catatgtagc gaaacatcat aaccttgcta    2820
tggctgtagg atcgcaaatg gcagcgttaa aagatgaaag tgaagctgct tcttataaga    2880
ttattagaaa ggtaaatcca aatggtattt tctttgctaa tttaggtagt gaggcaactg    2940
ttgaacaggc agagcgtgct gttgatatgg ttgaagcgaa tgcattgcaa attcatttaa    3000
atgtcataca agagttaacg atgccagaag gagaccgtga ctttactggt gtacttcagc    3060
gtattgagaa aattgtttta aatagtaaag ttcctgtcat tgtaaaagaa gttggatttg    3120
ggatgagtaa ggaaacaatg caacagttgg cgagcgtagg tgtaacggca attgatattg    3180
gcggacaagg gggtacgaat tttgctgctg ttgaaaatga aagaagacag cgaatgcttt    3240
cttattttaa taactggggc atacaaacag ctacctcgat tattgaagca acctctacaa    3300
ataataacct ctcttttatt gcatctgggg gtatacaaac agcgcttgac gtagcgaaag    3360
caatcgcatt aggggcgaat accactgcgt ttgctggata cttttttacgc attttaatgg    3420 aagatggtat cgagaagttg gtggacgaaa ttgacctttt acatacagat ttgaaattta    3480
ttatgacagc tctcggtgca aagacgatag aagagttaca gtccgtacct cttgttataa    3540
agggtgaaac gtatcattgg ttaacgcagc gtggaattga tacgacgcat tatagtagaa    3600
gataatccgg aatcatgtaa ttagttatgt cacgcttaca ttcacgccct ccccccacat    3660
ccgctctaac cgaaaaggaa ggagttagac aacctgaagt ctaggtccct atttattttt    3720
ttatagttat gttagtatta agaacgttat ttatatttca aatttttctt tttttctgt     3780 acagacgcgt gtacgcatgt aacattatac tgaaaacctt gcttgagaag gttttgggac    3840
gctcgaaggc tttaatttgc cggattagaa gccgccgagc gggtgacagc cctccgaagg    3900
aagactctcc tccgtgcgtc ctcgtcttca ccggtcgcgt tcctgaaacg cagatgtgcc    3960
tcgcgccgca ctgctccgaa caataaagat tctacaatac tagcttttat ggttatgaag    4020
aggaaaaatt ggcagtaacc tggccccaca accttcaaa tgaacgaatc aaattaacaa     4080
ccataggatg ataatgcgat tagtttttta gccttatttc tggggtaatt aatcagcgaa    4140
gcgatgattt ttgatctatt aacagatata aaatgcaaa aactgcataa ccactttaac     4200
taatactttc aacattttcg gtttgtatta cttcttattc aaatgtaata aaagtatcaa    4260
caaaaaattg ttaatatacc tctatacttt aacgtcaagg agcccgggcc accatgacga    4320
cttatgcacg cgcgcacaca aatattgcgc tgattaaata ttggggaaaa gccaatcgca    4380
```

-continued

```
agttgatgct gccagccaca agcagcattt cttttaacttt aaatgacttt tatactgaca   4440
cagcagtgac atttgatcct agtctaaatg atgatcgctt catgcttaac ggtgaagaac   4500
aaaacccggt tgcggtcagc cgcttttttgg atcgggttcg gcacttagga aaaattagca   4560
cgtacgccca agtcacttcc ttgaatcacg tgccgactgc tgccgggctg gcaagttcag   4620
cctctgcttt tgctgccttg gccactgctg ccagccgcgc ggcaggtcta aacctttctc   4680
cgactgaact atcaagatta gcgcgccgcg gatcaggttc agcaacgcgc tctatctttg   4740
gtggtgccgt tatctggcat cgcggccatg acgacgcctc ttcattcgct gaaccactcg   4800
cgattcaacc tagtttgcca ttacgaatgc ttgtggtcac ggtatctgct gaaaaaaagg   4860
cggtcagttc acgaaaaggc atggccaaca cagtggccac aagtccctac tatgatgcct   4920
gggtggcctc aaatgaaagt ttaattgaac caatgattac cgcgttggct gaagacgact   4980
tagcgctgat cggcaaattg acagaattgt ccagtatgcg catgcatgcg gcgattatgg   5040
ccgaggaacc gccattcacc tactttctgc cggaaacatt acgggcgtgg caattagtgc   5100
aagaacaacg ggctttgggt attcccgcgt ttgccacgat ggatgcagga ccaaatgtca   5160
aaattctgac tactgaacct tacgtggaca ttttattaac cgccttgcgc cctgtgttcg   5220
gtgatcggat tttgagcaca cgccttggtc ctgatgccag catcatcaca aaggagcaat   5280
ttgatgacac aaagtcagca atcgcatcgc aaggatgatt aattaatcat gtaattagtt   5340
atgtcacgct tacattcacg ccctcccccc acatccgctc taaccgaaaa ggaaggagtt   5400
agacaacctg aagtctaggt ccctatttat tttttttatag ttatgttagt attaagaacg   5460
ttatttatat ttcaaatttt tctttttttt ctgtacagac gcgtgtacgc atgtaacatt   5520
atactgaaaa ccttgcttga gaaggttttg ggacgctcga aggctttaat ttgccggatt   5580
agaagccgcc gagcgggtga cagccctccg aaggaagact ctcctccgtg cgtcctcgtc   5640
ttcaccggtc gcgttcctga aacgcagatg tgcctcgcgc cgcactgctc cgaacaataa   5700
agattctaca atactagctt ttatggttat gaagaggaaa aattggcagt aacctggccc   5760
cacaaacctt caaatgaacg aatcaaatta acaaccatag gatgataatg cgattagttt   5820
tttagcctta tttctggggt aattaatcag cgaagcgatg attttttgatc tattaacaga   5880 tatataaatg caaaaactgc ataaccactt aactaatac tttcaacatt ttcggttttgt   5940 attacttctt attcaaatgt aataaaagta tcaacaaaaa attgttaata tacctctata   6000
ctttaacgtc aaggagggcg cgccatggtt catttaggtc caaagaaacc acaggctaga   6060
aagggttcca tggctgatgt gcccaaggaa ttgatggatg aaattcatca gttggaagat   6120
atgtttacag ttgacagcga gaccttgaga aaggttgtta agcactttat cgacgaattg   6180
aataaaggtt tgacaaagaa gggaggtaac attccaatga ttcccggttg ggtcatggaa   6240
ttcccaacag gtaaagaatc tggtaactat ttggccattg atttgggtgg tactaactta   6300
agagtcgtgt tggtcaagtt gagcggtaac catacctttg acaccactca atccaagtat   6360
aaactaccac atgacatgag aaccactaag caccaagagg agttatggtc ctttattgcc   6420
gactctttga aggactttat ggtcgagcaa gaattgctaa acaccaagga caccttacca   6480
ttaggtttca ccttctcgta cccagcttcc caaaacaaga ttaacgaagg tattttgcaa   6540
agatggacca agggtttcga tattccaaat gtcgaaggcc acgatgtcgt cccattgcta   6600
caaaacgaaa tttccaagag agagttgcct attgaaattg tagcattgat taatgatact   6660
gttggtactt taattgcctc atactacact gacccagaga ctaagatggg tgtgatttc   6720
```

-continued

```
ggtactggtg tcaacggtgc tttctatgat gttgtttccg atatcgaaaa gttggagggc    6780
aaattagcag acgatattcc aagtaactct ccaatggcta tcaattgtga atatggttcc    6840
ttcgataatg aacatttggt cttgccaaga accaagtacg atgttgctgt cgacgaacaa    6900
tctccaagac ctggtcaaca agcttttgaa aagatgacct ccggttacta cttgggtgaa    6960
ttgttgcgtc tagtgttact tgaattaaac gagaagggct tgatgttgaa ggatcaagat    7020
ctaagcaagt tgaaacaacc atacatcatg gatacctcct acccagcaag aatcgaggat    7080
gatccatttg aaaacttgga agatactgat gacatcttcc aaaaggactt tggtgtcaag    7140
accactctgc cagaacgtaa gttgattaga agactttgtg aattgatcgg taccagagct    7200
gctagattag ctgtttgtgg tattgccgct atttgccaaa agagaggtta caagactggt    7260
cacattgccg ctgacggttc tgtctataac aaatacccag gtttcaagga agccgccgct    7320
aagggtttga gagatatcta tggatggact ggtgacgcaa gcaaagatcc aattacgatt    7380
gttccagctg aggatggttc aggtgcaggt gctgctgtta ttgctgcatt gtccgaaaaa    7440
agaattgccg aaggtaagtc tcttggtatc attggcgctt aagtttaaac tcatgtaatt    7500
agttatgtca cgcttacatt cacgccctcc ccccacatcc gctctaaccg aaaaggaagg    7560
agttagacaa cctgaagtct aggtccctat ttattttttt atagttatgt tagtattaag    7620
aacgttattt atatttcaaa tttttctttt ttttctgtac agacgcgtgt acgcatgtaa    7680
cattatactg aaaaccttgc ttgagaaggt tttgggacgc tcgaaggctt taatttgccg    7740
gattagaagc cgccgagcgg gtgacagccc tccgaaggaa gactctcctc cgtgcgtcct    7800
cgtcttcacc ggtcgcgttc ctgaaacgca gatgtgcctc gcgccgcact gctccgaaca    7860
ataaagattc tacaatacta gcttttatgg ttatgaagag gaaaaattgg cagtaacctg    7920
gccccacaaa ccttcaaatg aacgaatcaa attaacaacc ataggatgat aatgcgatta    7980
gttttttagc cttatttctg gggtaattaa tcagcgaagc gatgattttt gatctattaa    8040
cagatatata aatgcaaaaa ctgcataacc actttaacta atactttcaa catttتcggt    8100 ttgtattact tcttattcaa atgtaataaa agtatcaaca aaaaattgtt aatatacctc    8160
tatactttaa cgtcaaggag gagctcacca tggcttcatc tgttggaaat gttgccgatt    8220
ctactgaacc taccaagaga atgttatcat ttcaaggatt agctgaatta gcccataggg    8280
aataccaagc cggtgacttt gaagctgccg aaagacactg tatgcaattg tggagacagg    8340
agccagacaa tacaggcgtg ttattgttgt tgtcatctat tcatttccaa tgtagaaggt    8400
tggatagatc tgctcacttt agtactttgg caatcaaaca gaatccattg ttagctgaag    8460
catattccaa cttaggtaac gtctataagg aaagaggtca attgcaggaa gccatcgagc    8520
attaccgtca tgcattaaga ttgaagcccg atttcatcga tggttacatt aacttagcag    8580
cagccttggt tgcagcagga gatatggaag gtgcagtcca agcctatgtc tccgcattac    8640
agtataaccc tgacttgtac tgtgttagat ctgatttggg aaacttattg aaggcattgg    8700
gaaggttgga agaggcaaag gcttgctact tgaaggccat agaaactcaa ccaaacttcg    8760
cagtcgcatg gtcaaacttg ggttgcgtgt tcaacgcaca aggtgaaatc tggttagcta    8820
tccaccattt cgagaaagca gttactttag atcccaattt cttggatgcc tacatcaatt    8880
tgggaaatgt gttaaaggag gcaaggatct tcgaccgtgc tgtcgcagca tacttaaggg    8940
ctttgtcttt aagtccaaac cacgcagttg tacatggcaa cttggcttgt gtctactatg    9000
agcaaggatt gattgactta gctattgata cctatcgtag ggccattgaa ttacagccac    9060
actttcctga cgcttactgc aacttggcta atgccttgaa ggagaaggga tctgtggcag    9120
```

-continued

```
aggctgagga ttgctacaac accgcattga ggttatgtcc aacacatgca gattccttaa   9180
acaatttggc caatatcaag cgtgaacagg gtaacatcga agaagccgtc agattgtata   9240
gaaaggcctt agaggtcttt cctgaatttg ctgctgccca ttccaactta gcaagtgtgt   9300
tacagcagca aggcaagttg caagaagcct taatgcacta taaggaagca atcagaataa   9360
gtcctacctt tgccgatgct tattccaata tgggtaatac tttgaaggaa atgcaggatg   9420
tccaaggtgc cttacaatgt tataccaggg caattcaaat caatcctgct ttcgcagatg   9480
ctcattctaa cttggcatcc atccataaag attcaggcaa cataccagag gccatcgcct   9540
cttatcgtac agccttgaag ttgaagcctg atttcccaga tgcctattgc aacttggccc   9600
attgtttgca aattgtatgt gattggacag attacgatga aagaatgaag aagttggtga   9660
gtatcgttgc tgaccaatta gagaagaaca gattgccatc agttcaccct catcactcta   9720
tgttgtaccc attgagtcat ggtttcagaa aggcaattgc tgaaaggcat ggcaatttgt   9780
gtttggacaa gatcaatgtc ttacataagc ctccatacga acatcctaag gatttgaaat   9840
tgtcagatgg aaggttgcgt gtcggatatg tttcttctga tttcggtaat catccaacca   9900
gtcacttaat gcagagtatc cctggtatgc ataatcccga caaattcgaa gtcttctgtt   9960
atgccttaag tccagatgac ggcaccaatt tcagagtgaa agttatggct gaagctaatc   10020
atttcattga tttgagtcaa attccttgta acggtaaagc cgcagatagg atacaccaag   10080
acggcattca tatcttggtc aatatgaacg gatacacaaa gggtgctaga aacgagttgt   10140
ttgctttaag accagcacct atacaagcaa tgtggttagg ctatccaggc acttcaggtg   10200
ctttgttcat ggactacatc ataaccgacc aagaaacttc tcccgcagag gttgctgaac   10260
aatacagtga gaagttggct tacatgccac atactttctt cattggtgat catgccaata   10320
tgttcccaca tttgaagaag aaagcagtca tagatttcaa atctaatgga catatctatg   10380
ataacagaat agtgttaaac ggtattgatt tgaaagcatt cttggattcc ttacctgatg   10440
ttaagattgt taagatgaag tgtccagatg gtggcgacaa cgctgattct tctaataccg   10500
ctttgaatat gcctgtgatc ccaatgaata ctatcgccga ggcagttatc gaaatgatca   10560
atagaggcca aattcaaatc acaatcaatg gattctctat ttctaacggt ttagcaacaa   10620
cacagataaa caacaaagct gctaccggag aagaggtgcc taggaccatt atcgttacta   10680
caagatccca gtatggttta cctgaggacg ctatcgtgta ctgcaacttc aatcagttat   10740
acaagatcga tccttcaacc ttacagatgt gggctaacat cttgaagagg gttcccaatt   10800
cagtattgtg gttgttaaga tttcccgcag tcggtgagcc taacattcaa cagtacgctc   10860
agaatatggg cttacctcag aatagaatca tattctctcc tgtagctcca aaggaagaac   10920
atgtcagacg tggtcaattg gccgatgtgt gtttggacac tcccttgtgc aacggacaca   10980
ccactggtat ggatgtcttg tgggcaggca ctcctatggt aactatgcct ggcgaaacat   11040
tggctagtag agttgcagct agtcaattga catgcttagg ttgcttagag ttgattgcaa   11100
agaacagaca agaatacgaa gatattgctg tcaagttagg tactgatttg gagtacttga   11160
agaaggttag aggtaaggtc tggaaacaaa gaattagtag tccattgttc aacaccaaac   11220
aatacacaat ggaattagaa agattgtact acaaatgtg ggagcactat gccgcaggta   11280
acaaacctga ccacatgatc aaaccagttg aagtaaccga atccgcttaa ttaaggtacc   11340
tcatgtaatt agttatgtca cgcttacatt cacgccctcc ccccacatcc gctctaaccg   11400
aaaaggaagg agttagacaa cctgaagtct aggtccctat ttatttttt atagttatgt   11460
```

-continued

```
tagtattaag aacgttattt atatttcaaa tttttctttt ttttctgtac agacgcgtgt   11520
acgcatgtaa cattatactg aaaaccttgc ttgagaaggt tttgggacgc tcgaaggctt   11580
taatttgccg gattagaagc cgccgagcgg gtgacagccc tccgaaggaa gactctcctc   11640
cgtgcgtcct cgtcttcacc ggtcgcgttc ctgaaacgca gatgtgcctc gcgccgcact   11700
gctccgaaca ataaagattc tacaatacta gcttttatgg ttatgaagag gaaaaattgg   11760
cagtaacctg gccccacaaa ccttcaaatg aacgaatcaa attaacaacc ataggatgat   11820
aatgcgatta gttttttagc cttatttctg gggtaattaa tcagcgaagc gatgattttt   11880
gatctattaa cagatatata aatgcaaaaa ctgcataacc actttaacta atactttcaa   11940
cattttcggt ttgtattact tcttattcaa atgtaataaa agtatcaaca aaaaattgtt   12000
aatatacctc tatactttaa cgtcaaggag ggatccgcca ccatggaacc acaaattctt   12060
tttctctatc tctcactctt cattctctcc ctaaacttct tcttcacgaa tcttaaacca   12120
aggctagtcc gcctcttcca gccttcttta gaatctcgtg tcaagaccgc tcttttatcc   12180
cgaaaggaag tagccgcgtt tcttgattct cccattgtcg aagacgaaga aggcgaagaa   12240
agagaagagg aagaagaagg aggtatcgtt tcaaatgcca actttacgtt tgagtttgat   12300
ccatacatga tgagcaaagc cgaatcagtg aacaaagctc tggaagaagc aattccagtc   12360
ggagagccac tcaagattca tgaagccatg cgatacgcga ttcttgcggc tggaaaacgt   12420
gttaggccaa tactctgcct tgcttcttgc gagctagtag gtggccaaga aaatgcggca   12480
atgcccgccg cttgtgcggt tgagatgatc cacacgatgt ctctaatcaa agacgatttg   12540
ccttgtatgg acaacgacga tttgcgtcgt ggaaagccca cgacgcacaa agtctacggc   12600
gaaggagttg ccattctctc tggtggggct ctcttgtctc ttgcctttga gcacatgacc   12660
accgctgaaa tatcctcgga gagaatggtt tgggcggtga gagaattggc taggtctatt   12720
gggacaagag gtttagtcgc gggacaagcg atggatataa gcagtgaagg tttggactta   12780
aacgaggtcg gattagagca tttggagttt atccatgttc ataaaaccgc ggttttgttg   12840
gaaactgccg cggttcttgg cgccataatt ggtggtggat ctgatgaaga gattgaaagt   12900
gtgagaaagt ttgcaaggtg cattggattg ttgtttcagg tggtggatga tatttttggac   12960 gagacgaagt cgtcggagga attgggaaaa accgccggga aagatcagct cgccggaaag   13020
ctaacgtatc caaagttgat agggttggag aaatcgaaag aatttgttaa gagattgacg   13080
aaagatgcac ggcaacatct tcaagggttt agttctgaaa aggttgctcc tttagtagct   13140
cttactactt ttattgctaa tagaaataag tgagaattct catgtaatta gttatgtcac   13200
gcttacattc acgccctccc cccacatccg ctctaaccga aaaggaagga gttagacaac   13260
ctgaagtcta ggtccctatt tattttttta tagttatgtt agtattaaga acgttattta   13320
tatttcaaat ttttcttttt tttctgtaca gacgcgtgta cgcatgtaac attatactga   13380
aaaccttgct tgagaaggtt ttgggacgct cgaaggcttt aatttgccgg attagaagcc   13440
gccgagcggg tgacagccct ccgaaggaag actctcctcc gtgcgtcctc gtcttcaccg   13500
gtcgcgttcc tgaaacgcag atgtgcctcg cgccgcactg ctccgaacaa taaagattct   13560
acaatactag cttttatggt tatgaagagg aaaaattggc agtaacctgg ccccacaaac   13620
cttcaaatga acgaatcaaa ttaacaacca taggatgata atgcgattag ttttttagcc   13680
ttatttctgg ggtaattaat cagcgaagcg atgatttttg atctattaac agatatataa   13740
atgcaaaaac tgcataacca ctttaactaa tactttcaac attttcggtt tgtattactt   13800
cttattcaaa tgtaataaaa gtatcaacaa aaaattgtta atatacctct atactttaac   13860
```

-continued

```
gtcaaggagg cggccgccac catggagaac aagacagaaa ctaccgtgag acgtagaagg   13920
aggataatct tattcccagt tccctttcaa ggtcatatca atcccatatt gcaattggcc   13980
aacgtcttgt attctaaagg attctcaatc acaatcttcc ataccaactt taacaaacct   14040
aagacatcca attaccctca tttcactttc aggttcatct tagacaatga tccacaagat   14100
gaaaggattt ctaacttgcc aactcatggt cctttggctg gcatgaggat acctatcatc   14160
aatgaacatg gtgcagacga attgagaaga gaattggagt tattgatgtt ggcttcagaa   14220
gaagacgaag aagtgtcttg cttaatcact gatgccttgt ggtatttcgc tcaatccgtt   14280
gccgactcct tgaatttgag aaggttagtc ttgatgactt catccttgtt taacttccac   14340
gctttggtgt ctttacctca atttgacgaa ttaggatact tggacccaga tgataagaca   14400
aggttggaag agcaggcttc aggtttccca atgttgaaag taaaggacat caaatccgca   14460
tatagtaatt ggcaaatctt gaaagagata ttgggaaaga tgataaagca aactagagct   14520
tcttctggag tcatttggaa ctcattcaag gaattagagg agtccgaatt agaaacagtt   14580
atcagggaaa ttcctgctcc ttccttcttg attcctttac ccaaacactt aaccgcatca   14640
tcttctagtt tgttggacca tgatagaaca gtatttcagt ggttggatca gcagccaccc   14700
tcctctgtgt tgtacgtttc atttggttca acttcagaag ttgatgagaa agacttctta   14760
gaaatagcac gtggcttagt cgattccaag cagtccttct tgtgggtcgt tagaccaggt   14820
ttcgtaaagg gttctacatg ggtcgaacca ttaccagatg gtttcttggg tgaaagaggt   14880
agaatagtaa agtgggtccc tcaacaagaa gtgttggctc acggtgccat aggtgcattc   14940
tggactcact ctggctggaa ctcaacttta gaatctgttt gtgaaggagt tccaatgata   15000
ttcagtgatt tcggtttgga ccaaccattg aacgcaaggt atatgagtga cgtgttgaaa   15060
gtgggtgttt acttggagaa cggctgggag cgtggagaga tagctaatgc aatccgtaga   15120
gtgatggtag acgaagaagg tgaatacata aggcagaacg ccagggtctt aaagcagaaa   15180
gctgatgttt ccttaatgaa aggtggttcc tcttatgaaa gtttagaatc tttggtttcc   15240
tacatttctt ctttataatc gtacgcatca tgtaattagt tatgtcacgc ttacattcac   15300
gccctccccc cacatccgct ctaaccgaaa aggaaggagt tagacaacct gaagtctagg   15360
tccctattta ttttttttata gttatgttag tattaagaac gttatttata tttcaaattt   15420 ttctttttttt tctgtacaga cgcgtgtacg catgtaacat tatactgaaa accttgcttg   15480
agaaggtttt gggacgctcg aaggctttaa tttgcatgct acggattaga agccgccgag   15540
cgggtgacag ccctccgaag gaagactctc ctccgtgcgt cctcgtcttc accggtcgcg   15600
ttcctgaaac gcagatgtgc ctcgcgccgc actgctccga acaataaaga ttctacaata   15660
ctagctttta tggttatgaa gaggaaaaat tggcagtaac ctggccccac aaaccttcaa   15720
atgaacgaat caaattaaca accataggat gataatgcga ttagtttttt agccttattt   15780
ctggggtaat taatcagcga agcgatgatt tttgatctat taacagatat ataaatgcaa   15840
aaactgcata accactttaa ctaatacttt caacattttc ggtttgtatt acttcttatt   15900
caaatgtaat aaaagtatca acaaaaaatt gttaatatac ctctatactt taacgtcaag   15960
gaggccacca tggcggttgc aggatcgacc atgaacctgc atctcacttc atctccatac   16020
aagacagttc catcactctg taaattcacc agaaaacagt tccgattaaa ggcctctgca   16080
acgaatccag acgctgaaga tgggaagatg atgtttaaaa acgataaacc caatttgaag   16140
gtcgaattcg ctggggagaa accggtgaca ccattactgg ataccattaa ttaccctgtg   16200
```

-continued

```
cacatgaaaa acctcaccac tcaggatctt gagcaattag cagcagaact tagacaagat  16260
attgtatatt cagtagcgaa tacaggtggt catttgagtt caagtttagg tgttgttgaa  16320
ttgtctgttg ctttacacca tgttttcaac accccagatg acaagatcat ttgggacgtt  16380
ggtcaccagg catacccaca taagattttg accggaagaa ggtcaaagat gcacaccata  16440
agaaaaactt ctggtttagc tggttttcct aaacgagatg aaagtgctca tgatgctttt  16500
ggtgctggac atagttctac aagcatctct gctggactag gtatggctgt cggtagagat  16560
ttattaggga aaaccaacaa cgtgatatcg gtgatcggag atggcgccat gacggccgga  16620
cgagcatatg aggcgataaa taatgcagga tttcttgatt caaatctaat cgtcgtttta  16680
aacgacaaca agcaagtttc attaccgact gccacgttgg acggacctgc aactcccgtc  16740
ggggctctca gcggcgcttt atccaaattg caagccagta ccaagttccg taagcttcgt  16800
gaagccgcca agagcattac taaacaaatt ggacctcaag cacatgaagt ggcggcgaaa  16860
gtcgacgaat acgcaagagg tatgattagt gctagcgggt cgactttatt cgaggaactc  16920
ggattatact acatcggtcc cgtcgatggt cacaatgttg aagatttagt caacattttt  16980
gaaaaagtca agtcaatgcc cgcacccgga ccggttctaa tccacatcgt gaccgaaaaa  17040
ggcaaaggtt accctcctgc tgaagccgct gctgaccgta tgcacggagt tgtgaagttt  17100
gatgttccaa ctggaaaaca attcaagaca aaatcaccga cactttcgta tactcagtat  17160
tttgctgaat cacttataaa agaagctgaa gctgataaca agattgtcgc gatacacgcc  17220
gccatgggag gcggtaccgg actcaattac ttccagaaga agtgtcctga acgttgtttt  17280
gatgtcggta tcgcggaaca acacgcagtt actttcgccg cgggtttagc caccgaaggt  17340
cttaaaccat tttgcgcgat ctattcgtcg tttttgcaac gaggatacga tcaagtggtg  17400
catgacgttg atctacaaaa gttaccggtt cggtttgcga tggaccgagc tggtttagtc  17460
ggggctgatg gaccgacaca ttgtggtgcg tttgacataa cctacatggc gtgtctacca  17520
aacatggtgg tgatggctcc agccgatgaa gccgaattga tgcacatggt tgcaacggct  17580
gcagccattg acgacagacc gagttgcttt cggttcccaa gaggcaatgg cattggtgca  17640
ccacttcctc ctaataacaa agggattccc atagaggttg gtaaaggaag aatattactt  17700
gaaggaactc gtgttgcgat attgggatac ggttcgatag ttcaagaatg tctaggtgcg  17760
gctagcttgc ttcaagccca taacgtgtct gcaaccgtag ccgatgcgcg gttctgcaaa  17820
ccgttagaca ccggactgat tagacgatta gccaacgagc atgaagtctt acttaccgta  17880
gaggaaggct cgattggtgg atttggatca cacgttgctc actttctaag cttaaatggt  17940
ctcttagatg gaaaacttaa gcttagagca atgactcttc ctgataaata cattgatcat  18000
ggtgcaccac aagatcagct tgaagaagcc ggtctttctt caaaacatat ttgttcatct  18060
cttttatcac ttttgggaaa acctaaagaa gcacttcaat acaaatcaat aatgtaatct  18120
agagggccgc atcatgtaat tagttatgtc acgcttacat tcacgccctc cccccacatc  18180
cgctctaacc gaaaaggaag gagttagaca acctgaagtc taggtcccta tttatttttt  18240
tatagttatg ttagtattaa gaacgttatt tatatttcaa attttcttt tttttctgta  18300 cagacgcgtg tacgcatgta acattatact gaaaaccttg cttgagaagg tttttgggacg  18360 ctcgaaggct ttaatttgcg gccctgcatt aatgaatcgg ccaacgcgcg gggagaggcg  18420
gtttgcgtat tgggcgctct tccgcttcct cgctcactga ctcgctgcgc tcggtcgttc  18480
ggctgcggcg agcggtatca gctcactcaa aggcggtaat acggttatcc acagaatcag  18540
gggataacgc aggaaagaac atgtgagcaa aaggccagca aaagcccagg aaccgtaaaa  18600
```

```
aggccgcgtt gctggcgttt ttccataggc tccgcccccc tgacgagcat cacaaaaatc   18660
gacgctcaag tcagaggtgg cgaaacccga caggactata aagataccag gcgtttcccc   18720
ctggaagctc cctcgtgcgc tctcctgttc cgaccctgcc gcttaccgga tacctgtccg   18780
cctttctccc ttcgggaagc gtggcgcttt ctcatagctc acgctgtagg tatctcagtt   18840
cggtgtaggt cgttcgctcc aagctgggct gtgtgcacga acccccgtt cagcccgacc     18900 gctgcgcctt atccggtaac tatcgtcttg agtccaaccc ggtaagacac gacttatcgc   18960
cactggcagc agccactggt aacaggatta gcagagcgag gtatgtaggc ggtgctacag   19020
agttcttgaa gtggtggcct aactacggct acactagaag gacagtattt ggtatctgcg   19080
ctctgctgaa gccagttacc ttcggaaaaa gagttggtag ctcttgatcc ggcaaacaaa   19140
ccaccgctgg tagcggtggt ttttttgttt gcaagcagca gattacgcgc agaaaaaaag   19200
gatctcaaga agatcctttg atcttttcta cggggtctga cgctcagtgg aacgaaaact   19260
cacgttaagg gattttggtc atgagattat caaaaaggat cttcacctag atccttttaa   19320
attaaaaatg aagttttaaa tcaatctaaa gtatatatga gtaaacttgg tctgacagtt   19380
accaatgctt aatcagtgag gcacctatct cagcgatctg tctatttcgt tcatccatag   19440
ttgcctgact ccccgtcgtg tagataacta cgatacggga gcgcttacca tctggcccca   19500
gtgctgcaat gataccgcga gacccacgct caccggctcc agatttatca gcaataaacc   19560
agccagccgg aagggccgag cgcagaagtg gtcctgcaac tttatccgcc tccatccagt   19620
ctattaattg ttgccgggaa gctagagtaa gtagttcgcc agttaatagt ttgcgcaacg   19680
ttgttggcat tgctacaggc atcgtggtgt cactctcgtc gtttggtatg gcttcattca   19740
gctccggttc ccaacgatca aggcgagtta catgatcccc catgttgtgc aaaaaagcgg   19800
ttagctcctt cggtcctccg atcgttgtca gaagtaagtt ggccgcagtg ttatcactca   19860
tggttatggc agcactgcat aattctctta ctgtcatgcc atccgtaaga tgcttttctg   19920
tgactggtga gtactcaacc aagtcattct gagaatagtg tatgcggcga ccgagttgct   19980
cttgcccggc gtcaatacgg gataatagtg tatcacatag cagaacttta aaagtgctca   20040
tcattggaaa acgttcttcg gggcgaaaac tctcaaggat cttaccgctg ttgagatcca   20100
gttcgatgta acccactcgt gcacccaact gatcttcagc atcttttact ttcaccagcg   20160
tttctgggtg agcaaaaaca ggaaggcaaa atgccgcaaa aaagggaata agggcgacac   20220
ggaaatgttg aatactcata ctcttccttt ttcaatgggt aataactgat ataattaaat   20280
tgaagctcta atttgtgagt ttagtataca tgcatttact tataatacag ttttttagtt   20340
ttgctggccg catcttctca aatatgcttc ccagcctgct tttctgtaac gttcaccctc   20400
taccttagca tcccttccct ttgcaaatag tcctcttcca acaataataa tgtcagatcc   20460
tgtagagacc acatcatcca cggttctata ctgttgaccc aatgcgtctc ccttgtcatc   20520
taaacccaca ccgggtgtca taatcaacca atcgtaacct tcatctcttc acccatgtc     20580 tctttgagca ataaagccga taacaaaatc tttgtcgctc ttcgcaatgt caacagtacc   20640
cttagtatat tctccagtag ataggggagcc cttgcatgac aattctgcta acatcaaaag   20700
gcctctaggt tcctttgtta cttcttctgc cgcctgcttc aaaccgctaa caatacctgg   20760
gcccaccaca ccgtgtgcat tcgtaatgtc tgcccattct gctattctgt atacacccgc   20820
agagtactgc aatttgactg tattaccaat gtcagcaaat tttctgtctt cgaagagtaa   20880
aaaattgtac ttggcggata atgcctttag cggcttaact gtgccctcca tggaaaaatc   20940
```

-continued

```
agtcaagata tccacatgtg tttttagtaa acaaattttg ggacctaatg cttcaactaa  21000
ctccagtaat tccttggtgg tacgaacatc caatgaagca cacaagtttg tttgcttttc  21060
gtgcatgata ttaaatagct tggcagcaac aggactagga tgagtagcag cacgttcctt  21120
atatgtagct ttcgacatga tttatcttcg tttcctgcag gtttttgttc tgtgcagttg  21180
ggttaagaat actgggcaat ttcatgtttc ttcaacacta catatgcgta tatataccaa  21240
tctaagtctg tgctccttcc ttcgttcttc cttctgttcg gagattaccg aatcaaaaaa  21300
atttcaaaga aaccgaaatc aaaaaaaaga ataaaaaaaa aatgatgaat tgaattgaaa  21360
agctagctta tcgatgataa gctgtcaaag atgagaatta attccacgga ctatagacta  21420
tactagatac tccgtctact gtacgataca cttccgctca ggtccttgtc ctttaacgag  21480
gccttaccac tcttttgtta ctctattgat ccagctcagc aaaggcagtg tgatctaaga  21540
ttctatcttc gcgatgtagt aaaactagct agaccgagaa agagactaga aatgcaaaag  21600
gcacttctac aatggctgcc atcattatta tccgatgtga cgctgcagct tctcaatgat  21660
attcgaatac gctttgagga gatacagcct aaatatccgac aaactgtttt acagatttac  21720
gatcgtactt gttacccatc attgaatttt gaacatccga acctgggagt tttccctgaa  21780
acagatagta tatttgaacc tgtataataa tatatagtct agcgctttac ggaagacaat  21840
gtatgtattt cggttcctgg agaaactatt gcatctattg cataggtaat cttgcacgtc  21900
gcatccccgg ttcattttct gcgtttccat cttgcacttc aatagcatat ctttgttaac  21960
gaagcatctg tgcttcattt tgtagaacaa aaatgcaacg cgagagcgct aatttttcaa  22020
acaaagaatc tgagctgcat ttttacagaa cagaaatgca acgcgaaagc gctattttac  22080
caacgaagaa tctgtgcttc attttttgtaa aacaaaaatg caacgcgacg agagcgctaa  22140
tttttcaaac aaagaatctg agctgcattt ttacagaaca gaaatgcaac gcgagagcgc  22200
tattttacca acaaagaatc tatacttctt ttttgttcta caaaaatgca tcccgagagc  22260 gctattttc taacaaagca tcttagatta cttttttttct cctttgtgcg ctctataatg  22320
cagtctcttg ataactttt gcactgtagg tccgttaagg ttagaagaag ctactttgg  22380 tgtctatttt ctcttccata aaaaaagcct gactccactt cccgcgttta ctgattacta  22440
gcgaagctgc gggtgcattt tttcaagata aaggcatccc cgattatatt ctataccgat  22500
gtggattgcg catactttgt gaacagaaag tgatagcgtt gatgattctt cattggtcag  22560
aaaattatga acggtttctt ctattttgtc tctatatact acgtatagga aatgtttaca  22620
ttttcgtatt gttttcgatt cactctatga atagttctta ctacaatttt tttgtctaaa  22680
gagtaatact agagataaac ataaaaaatg tagaggtcga gtttagatgc aagttcaagg  22740
agcgaaaggt ggatgggtag gttatatagg atatagcac agagatatat agcaaagaga  22800 tactttgag caatgtttgt ggaagcggta ttcgcaatgg gaagctccac cccggttgat  22860
aatcagaaaa gccccaaaaa caggaagatt gtataagcaa atatttaaat tgtaaacgtt  22920
aatattttgt taaaattcgc gttaaatttt tgttaaatca gctcattttt taacgaatag  22980
cccgaaatcg gcaaaatccc ttataaatca aagaatagac cgagatagg gttgagtgtt  23040 gttccagttt ccaacaagag tccactatta agaacgtgg actccaacgt caaagggcga  23100 aaaaggggtct atcagggcga tggcccacta cgtgaaccat cacccctaatc aagttttttg  23160 gggtcgaggt gccgtaaagc agtaaatcgg aagggtaaac ggatgccccc atttagagct  23220
tgacggggaa agccggcgaa cgtggcgaga aggaaggga agaaagcgaa aggagcgggg  23280
```

```
gctagggcgg tgggaagtgt aggggtcacg ctgggcgtaa ccaccacacc cgccgcgctt  23340
aatggggcgc tacagggcgc gtggggatga tccactagt                          23379
```